US010968462B2

(12) United States Patent
Aponte et al.

(10) Patent No.: US 10,968,462 B2
(45) Date of Patent: Apr. 6, 2021

(54) PLANTS HAVING INCREASED TOLERANCE TO HERBICIDES

(71) Applicant: BASF AGRO B.V., Arnheim (NL)

(72) Inventors: Raphael Aponte, Mannheim (DE); Stefan Tresch, Kirchheim (DE); Matthias Witschel, Bad Duerkheim (DE); Jens Lerchl, Golm (DE); Dario Massa, Mannheim (DE); Tobias Seiser, Mannheim (DE); Thomas Mietzner, Annweiler (DE); Doreen Schachtschabel, Mannheim (DE); Jill Marie Paulik, Cary, NC (US); Chad Brommer, Raleigh, NC (US)

(73) Assignee: BASF AGRO B.V., Arnhem (NL)

(*) Notice: Subject to any disclaimer, the term of this patent is extended or adjusted under 35 U.S.C. 154(b) by 89 days.

(21) Appl. No.: 14/911,805

(22) PCT Filed: Aug. 12, 2014

(86) PCT No.: PCT/IB2014/063876
§ 371 (c)(1),
(2) Date: Feb. 12, 2016

(87) PCT Pub. No.: WO2015/022639
PCT Pub. Date: Feb. 19, 2015

(65) Prior Publication Data
US 2016/0194654 A1 Jul. 7, 2016

Related U.S. Application Data

(60) Provisional application No. 61/866,067, filed on Aug. 15, 2013, provisional application No. 61/864,671, filed on Aug. 12, 2013, provisional application No. 61/864,672, filed on Aug. 12, 2013.

(51) Int. Cl.
C12N 15/82 (2006.01)
C12N 9/02 (2006.01)
A01N 43/54 (2006.01)
A01N 43/84 (2006.01)
A01N 37/48 (2006.01)
A01N 43/653 (2006.01)
A01N 57/16 (2006.01)

(52) U.S. Cl.
CPC ......... C12N 15/8274 (2013.01); A01N 37/48 (2013.01); A01N 43/54 (2013.01); A01N 43/653 (2013.01); A01N 43/84 (2013.01); A01N 57/16 (2013.01); C12N 9/001 (2013.01); C12N 9/0071 (2013.01); C12Y 103/03004 (2013.01)

(58) Field of Classification Search
CPC .............. C12N 15/8274; C12Y 103/03004
See application file for complete search history.

(56) References Cited

U.S. PATENT DOCUMENTS

| 5,169,770 A | 12/1992 | Chee et al. |
| 5,198,013 A | 3/1993 | Hirai et al. |
| 5,322,783 A | 6/1994 | Tomes et al. |
| 5,366,892 A | 11/1994 | Foncerrada et al. |
| 5,376,543 A | 12/1994 | Chee et al. |
| 5,380,831 A | 1/1995 | Adang et al. |
| 5,436,391 A | 7/1995 | Fujimoto et al. |
| 5,485,192 A | 1/1996 | Nagahata et al. |
| 5,593,881 A | 1/1997 | Thompson et al. |
| 5,723,756 A | 3/1998 | Peferoen et al. |
| 5,737,514 A | 4/1998 | Stiffler |
| 5,747,450 A | 5/1998 | Ohba et al. |
| 5,767,373 A | 6/1998 | Ward et al. |
| 5,773,702 A | 6/1998 | Penner et al. |
| 5,859,348 A | 1/1999 | Penner et al. |
| 5,939,360 A | 8/1999 | Adachi et al. |
| 5,939,602 A | 8/1999 | Volrath et al. |
| 5,948,917 A | 9/1999 | Adachi et al. |
| 5,990,387 A | 11/1999 | Tomes et al. |
| 6,018,105 A | 1/2000 | Johnson et al. |
| 6,027,945 A | 2/2000 | Smith et al. |
| 6,084,155 A | 7/2000 | Volrath et al. |
| 6,160,206 A | 12/2000 | Sato et al. |
| 6,308,458 B1 | 10/2001 | Volrath et al. |
| 6,368,800 B1 | 4/2002 | Smith et al. |
| 6,653,529 B2 | 11/2003 | Peng et al. |

(Continued)

FOREIGN PATENT DOCUMENTS

| CA | 2382090 A1 | 2/2001 |
| CA | 2807035 A1 | 2/2012 |

(Continued)

OTHER PUBLICATIONS

Dayan, Franck E., Abigail Barker, and Patrick J. Tranel. "Origins and Structure of Chloroplastic and Mitochondrial Plant Protoporphyrinogen Oxidases: Implications for Evolution of Herbicide Resistance." Pest management science (2017). (Year: 2017).*
Bernhardt, Rita, and Vlada B. Urlacher. "Cytochromes P450 as promising catalysts for biotechnological application: chances and limitations." Applied microbiology and biotechnology 98.14 (2014): 6185-6203. (Year: 2014).*
Tan, Li Rong, et al. "A collection of cytochrome P450 monooxygenase genes involved in modification and detoxification of herbicide atrazine in rice (Oryza sativa) plants." Ecotoxicology and environmental safety 119 (2015): 25-34. (Year: 2015).*
Patzoldt, William L., et al. "A codon deletion confers resistance to herbicides inhibiting protoporphyrinogen oxidase." Proceedings of the National Academy of Sciences103.33 (2006): 12329-12334. (Year: 2006).*

(Continued)

Primary Examiner — Weihua Fan
(74) Attorney, Agent, or Firm — Marshall, Gerstein & Borun LLP

(57) ABSTRACT

The present invention refers to a plant or plant part comprising (i) a recombinant polynucleotide encoding a wild-type or mut-PPO polypeptide, and (ii) a recombinant polynucleotide encoding a CYP450 polypeptide, the expression of said polynucleotides (i) and (ii) confers to the plant or plant part tolerance to PPO-inhibiting herbicides.

21 Claims, 7 Drawing Sheets

Specification includes a Sequence Listing.

(56) References Cited

U.S. PATENT DOCUMENTS

| | | | |
|---|---|---|---|
| 6,905,852 | B1 | 6/2005 | Horikoshi et al. |
| 7,671,254 | B2 * | 3/2010 | Tranel .................. C12N 9/001 |
| | | | 435/320.1 |
| 7,705,200 | B2 * | 4/2010 | Dam .................. C12N 15/8278 |
| | | | 504/116.1 |
| 7,745,699 | B2 | 6/2010 | Nakajima et al. |
| 7,842,856 | B2 | 11/2010 | Tranel et al. |
| 8,097,774 | B2 | 1/2012 | Hawkes et al. |
| 8,129,589 | B2 | 3/2012 | Tanaka et al. |
| 8,338,337 | B2 | 12/2012 | Song et al. |
| 10,041,087 | B2 | 8/2018 | Aponte et al. |
| 10,087,460 | B2 | 10/2018 | Aponte et al. |
| 10,100,329 | B2 | 10/2018 | Lerchl et al. |
| 10,392,630 | B2 | 8/2019 | Aponte et al. |
| 2003/0236208 | A1 | 12/2003 | Kmiec et al. |
| 2004/0082770 | A1 | 4/2004 | Castle et al. |
| 2005/0084859 | A1 | 4/2005 | Nakajima et al. |
| 2007/0021515 | A1 | 1/2007 | Glenn et al. |
| 2007/0039067 | A1 | 2/2007 | Feldmann et al. |
| 2007/0050863 | A1 | 3/2007 | Tranel et al. |
| 2009/0011936 | A1 * | 1/2009 | Hawkes .................. C12N 9/0077 |
| | | | 504/136 |
| 2009/0049567 | A1 | 2/2009 | Olhoft et al. |
| 2010/0100988 | A1 | 4/2010 | Tranel et al. |
| 2011/0201501 | A1 | 8/2011 | Song et al. |
| 2012/0122223 | A1 | 5/2012 | Gocal et al. |
| 2013/0184155 | A1 | 7/2013 | Newton et al. |
| 2014/0123340 | A1 | 5/2014 | Aponte et al. |
| 2014/0189906 | A1 | 7/2014 | Gocal et al. |
| 2015/0299725 | A1 | 10/2015 | Lerchl et al. |
| 2016/0201078 | A1 | 7/2016 | Aponte et al. |
| 2018/0371488 | A1 | 12/2018 | Aponte et al. |

FOREIGN PATENT DOCUMENTS

| | | | |
|---|---|---|---|
| CN | 1150820 A | 5/1997 | |
| CN | 1036571 C | 12/1997 | |
| CN | 1212724 A | 3/1999 | |
| CN | 1175107 C | 11/2004 | |
| CN | 1894408 A | 1/2007 | |
| CN | 101215289 A | 7/2008 | |
| CN | 101437844 A | 5/2009 | |
| CN | 101998988 A | 3/2011 | |
| DE | 19505995 A1 | 8/1996 | |
| EP | 0397687 A1 | 11/1990 | |
| EP | 0424047 A1 | 4/1991 | |
| EP | 0900795 A1 | 3/1999 | |
| WO | WO-93/07256 A1 | 4/1993 | |
| WO | WO-95/34659 A1 | 12/1995 | |
| WO | WO-96/26202 A1 | 8/1996 | |
| WO | WO-1997/004088 A1 | 2/1997 | |
| WO | WO-1997/032011 A1 | 9/1997 | |
| WO | WO-97/41116 A1 | 11/1997 | |
| WO | WO-97/41117 A1 | 11/1997 | |
| WO | WO-97/41118 A1 | 11/1997 | |
| WO | WO-1998/029554 A1 | 7/1998 | |
| WO | WO-1998/033927 A1 | 8/1998 | |
| WO | WO-2001/012815 A1 | 2/2001 | |
| WO | WO-2001/068826 A2 | 9/2001 | |
| WO | WO-01/83459 A2 | 11/2001 | |
| WO | WO-02/068607 A2 | 9/2002 | |
| WO | WO-2005/107437 A2 | 11/2005 | |
| WO | WO-2006/024820 A1 | 3/2006 | |
| WO | WO-2006/037945 A1 | 4/2006 | |
| WO | WO-2007/024739 A2 | 3/2007 | |
| WO | WO-2007/071900 A1 | 6/2007 | |
| WO | WO-2007/096576 A1 | 8/2007 | |
| WO | WO-2008/124495 A2 | 10/2008 | |
| WO | WO-2008/141154 A2 | 11/2008 | |
| WO | WO-2010/049269 A1 | 5/2010 | |
| WO | WO-2010/049270 A1 | 5/2010 | |
| WO | WO-2010/145992 A1 | 12/2010 | |
| WO | WO-2011/018486 A2 | 2/2011 | |
| WO | WO-2011085221 A2 * | 7/2011 | .......... C12N 9/0077 |
| WO | WO-2012/018862 A2 | 2/2012 | |
| WO | WO-2012/041789 A1 | 4/2012 | |
| WO | WO-2012/080975 A1 | 6/2012 | |
| WO | WO-2012080975 A1 * | 6/2012 | .......... C12N 15/8274 |
| WO | WO 2012/080975 A1 * | 7/2012 | ............ C12N 15/82 |
| WO | WO-2013/189984 A2 | 12/2013 | |
| WO | WO-2015/022636 A2 | 2/2015 | |
| WO | WO-2015/022639 A2 | 2/2015 | |
| WO | WO-2015/092706 A1 | 6/2015 | |

OTHER PUBLICATIONS

Ma, Rong, et al. "Distinct detoxification mechanisms confer resistance to mesotrione and atrazine in a population of waterhemp." Plant physiology 163.1 (2013): 363-377. (Year: 2013).*

Dayan, Franck E., Abigail Barker, and Patrick J. Tranel. "Origins and structure of chloroplastic and mitochondrial plant protoporphyrinogen oxidases: implications for the evolution of herbicide resistance." Pest management science 74.10 (2018): 2226-2234 (Year: 2018).*

Bernhardt, Rita, and Vlada B. Urlacher. "Cytochromes P450 as promising catalysts for biotechnological application: chances and limitations." Applied microbiology and biotechnology 98.14 (2014): 6185-6203. (Year: 2014).*

Tan, Li Rong, et al. "A collection of cytochrome P450 monooxygenase genes involved in modification and detoxification of herbicide atrazine in rice (Oryza sativa) plants." Ecotoxicology and environmental safety 119 (2015): 25-34. (Year: 2015).*

Che et al., Localization of target-site of the protoporphyrinogen oxidase-inhibiting herbicide, S-23142, in Spinacia oleracea L., Z. Naturforsch, 48e:350-5 (1992).

Cole-Strauss et al., Targeted gene repair directed by the chimeric RNA/DNA oligonucleotide in a mammalian cell-free extract, Nucleic Acids Res., 27(5):1323-30 (1999).

Dailey et al., Expression of a cloned protoporphyrinogen oxidase, J. Biol. Chem., 289(2):813-15 (1994).

Dayan et al., Biochemical and structural consequences of a glycine deletion in the alpha-8 helix of protoporphyrinogen oxidase, Biochim. Biophys. Acta, 1804(7):1548-56 (2010).

Duke et al., Protoporphyrinogen oxidase-inhibiting herbicides, Weed Sci., 39:465-73 (1991).

Geiser et al., The hypervariable region in the genes coding for entomopathogenic crystal proteins of Bacillus thuringiensis: nucleotide sequence of the kurhd1 gene of subsp. kurstaki HD1, Gene, 48(1):109-18 (1986).

GenBank Accession No. DQ386114, Amaranthus tuberculatus biotype herbicide-susceptible WC mitochrondrial protoporphyrinogen oxidase (PPX2L) mRNA, complete cds; nuclear gene for mitochrondrial product, Aug. 18, 2006.

International Preliminary Report on Patentability, International Application No. PCT/IB2014/063876, dated Feb. 16, 2016.

International Search Report and Written Opinion, International Application No. PCT/IB2014/063876, dated Jan. 28, 2015.

Jacobs et al., Assay for enzymatic protoporphyrinogen oxidation, a late step in heme synthesis, Enzyme, 28)2-3):206-19 (1982).

Kataoka et al., Isolation and partial characterization of mutant Chlamydomonas reinhardtii resistant to herbicide S-23142, J. Pesticide Sci., 15:449-51 (1990).

Lee et al., Cellular localization of protoporphyrinogen-oxidizing activities of etiolated barley (Hordeum vulgare L.) leaves, Plant Physiol., 102:881-9 (1993).

Lewis et al., Interactions between redox partners in various cytochrome P450 systems: functional and structural aspects, Biochim. Biophys. Acta, 1460(2-3):353-74 (2000).

Loppes, A new class of arginine-requiring mutants in Chlamydomonas reinhardi, Mol. Gen. Genet., 104(2):172-7 (1969).

Matringe et al., Protoporphyrinogen oxidase as a molecular target for diphenyl ether herbicides, Biochem. J., 260(1):231-5 (1989).

Matringe et al., Protoporphyrinogen oxidase inhibition by three peroxidizing herbicides: oxadiazon, LS 82-556 and M&B 39279, FEBS Lett., 245(1-20:35-8 (1989).

Murray et al., Codon usage in plant genes, Nucleic Acids Res., 17(2):477-98 (1989).

(56) References Cited

OTHER PUBLICATIONS

Nandihalli et al., Quantative structure-activity relationships of protoporphyrinogen oxidase-inhibiting diphenyl ether herbicides, Pesticide Biochem Physbiol., 43:193-211 (1992).
Oshio et al., Isolation and characterization of a Chlamydomonas reinhardtii mutant resistant to photobleaching herbicides, Z. Naturforsch, 48c:339-44 (1993).
Patzoldt et al., A codon deletion confers resistance to herbicides inhibiting protoporphyrinogen oxidase, Proc. Natl. Acad. Sci. USA, 103(33):12329-34 (2006).
Sasarman et al., Mapping of a new hem gene in *Escherichia coli* K12, J. Gen. Microbiol., 113(2):297-303 (1979).
Sasarman et al., Nucleotide sequence of the hemG gene involved in the protoporphyrinogen oxidase activity of *Escherichia coli* K12, Can. J. Microbiol., 39(12):1155-61 (1993).
Shibata et al., Isolation and characterization of a Chlamydomonas reinhardtii mutant resistant to an experimental herbicide S-23142, which inhibits chlorophyll synthesis, in: Murata (ed.), Research in Photosynthesis, vol. III, pp. 567-570 (1992).
Yanase et al., Porphyrin synthesis involvement in diphenyl ether-like mode of action of TNPP-ethyl, a novel phenylpyrazole herbicide, Pesticide Biochemistry and Physiology, 35:70-80 (1989).
Arnould et al., The domain structure of protoporphyrinogen oxidase, the molecular target of diphenyl ether-type herbicides. *Proc. Natl. Acad. Sci. USA*, 95: 10553-8 (1998).
Che et al., Molecular characterization and subcellular localization of protoporphyrinogen oxidase in spinach chloroplasts. *Plant Physiol.* 124: 59-70 (2000).
Choi et al., Generation of resistance to the diphenyl ether herbicide, oxyfluorfen, via expression of the *Bacillus subtilis* protoporphyrinogen oxidase gene in transgenic tobacco plants. *Biosci. Biotechnol. Biochem.* 62(3): 558-60 (1998).
Corradi et al., Crystal structure of protoporphyrinogen oxidase from *Myxococcus xanthus* and it complex with the inhibitor acifluorfen. *J Biol Chem.* 281(50): 38625-33 (2006).
Dayan et al., Phytotoxicity of Protoporphyrinogen Oxidase Inhibitors: Phenomenology, Mode of Action and Mechanisms of Resistance, *Herbicide Activity: Toxicology, Biochemistry and Molecular Biology*, eds. Roe et al., pp. 11-35 (1997).
Extended European Search Report, issued in co-assigned application No. 11848519.2, dated Apr. 23, 2014.
GenBank Accession No. AX084732, submitted on Mar. 9, 2001.
GenBank Accession No. XP_004976030.1, Predicted: protoporhyrinogen oxidase, mitochondrial [*Setaria italica*] (Nov. 30, 2015).
GenBank Accession No. XM_004975973, Predicted: Setaria italica protoporphyrinogen oxidase, mitochondrial (LOC101781148), mRNA (Nov. 30, 2015).
Ha et al., The plastidic *Arabidopsis* protoporphyrinogen IX oxidase gene, with or without the transit sequence, confers resistance to the diphenyl ether herbicide in rice. *Plant Cell Environ.* 27: 79-88 (2003).
Hanin et al., Gene targeting in *Arabidopsis. Plant J.* 28: 671-7 (2001).
Hao et al., Protoporphyrinogen oxidase inhibitor: An ideal target for herbicide discovery. *Chimia*, 65(12): 961-9 (2011).
Heinemann et al., Functional definition of the tobacco protoporphyrinogen IX oxidase substrate-binding site. *Biochem. J.* 402: 575-80 (2007).
Holmberg, A fine line: New herbicide-tolerant crops blur the fine line between weed control and crop injury. *Successful Farm.* 98(5): 25-7 (2000).
Huang et al., Synthesis and herbicidal activity of isoindoline-1,3-dione substituted benzoxazinone derivatives containing a carboxylic ester group. *J. Agric. Food Chem.* 57: 9585-92 (2009).
International Preliminary Report on Patentability, International Application No. PCT/IB2014/063877, dated Feb. 16, 2016.
International Preliminary Report on Patentability, issued in PCT/IB2011/055701, dated Jun. 27, 2013.

International Search Report and Written Opinion, International Application No. PCT/IB2014/063877, dated Feb. 10, 2015.
International Search Report, corresponding International Application No. PCT/EP2013/062744, dated Dec. 10, 2014.
International Search Report, issued in PCT/IB2011/055701, dated May 3, 2012.
Jung et al., Dual targeting of *Myxococcus xanthus* protoporphyrinogen oxidase into chloroplasts and mitochondria and high level oxyfluorfen resistance. *Plant Cell Environ.* 27: 1436-46 (2004).
Jung et al., Resistance mechanisms in protoporphyrinogen oxidase (PROTOX) inhibitor-resistant transgenic rice. *J. Plant Biol.* 50(3): 586-94 (2007).
Koch et al., Crystal structure of protoporphyrinogen IX oxidase: A key enzyme in Haem and chlorophyll biosynthesis. *EMBO J.* 23: 1720-8 (2004).
Layer et al., Structure and function of enzymes in Heme biosynthesis. *Protein Sci.* 19: 1137-61 (2010).
Lee et al., Expression of human protoporphyrinogen oxidase in transgenic rice induces both a photodynamic response and oxyfluorfen resistance. *Pesticide Biochem. Physiol.* 80: 65-74 (2004).
Lee et al., Transgenic rice plants expressing a *Bacillus subtilis* protoporphyrinogen oxidase gene are resistant to diphenyl ether herbicide oxyfluorfen. *Plant Cell Physiol.* 41(6): 743-9 (2000).
Lermontova et al., Cloning and characterization of a plastidal and a mitochondria' isoform of tobacco protoporphyrinogen IX oxidase. *Proc. Natl. Acad. Sci. USA*, 94: 8895-900 (1997).
Lermontova et al., Overexpression of plastidic protoporphyrinogen IX oxidase leads to resistance to the diphenyl-ether herbicide acifluorfen. *Plant Physiol.* 122: 75-83 (2000).
Li et al., Development of PPO inhibitor-resistant cultures and crops, Pest Management Science, 61(3):277-85 (2005).
Li et al., Development of protoporphyrinogen oxidase as an efficient selection marker for *Agrobacterium* tumefaciens-mediated transformation of maize. *Plant Physiol.* 133: 736-47 (2003).
Lyga et al., Structural replacements for the benzoxazinone protox inhibitors. *Pesticide Sci.* 55: 281-7 (1999).
Macias et al., Optimization of benzoxazinones as natural herbicide models by lipophilicity enhancement. *J. Acric. Food Chem.* 54: 9357-65 (2006).
Mulwa et al., Biotechnology approaches to developing herbicide tolerance/selectivity in crops. *Afr. J. Biotechnol.* 5(5): 396-404 (2006).
Rousonelos, S., Master's Thesis, University of Illinois, published Aug. 2010.
Watanabe et al., Molecular characterization of photomixotrophic tobacco cells resistant to protoporphyrinogen oxidase-inhibiting herbicides. *Plant Physiol.* 118: 751-8 (1998).
Brachypodium distachyon protoporphyrinogen oxidase with UniProt accession No. l1IZ42, published on Jun. 13, 2012.
EBI Accession No. GSP:BBB23069, Amaranthus tuberculatus PPO variant R128A/T208S/F420V #1 (Feb. 13, 2014).
Extended European Search Report, European Patent Application No. 14836899.6, dated Jun. 30, 2017 (4 pp.).
Extended European Search Report, issued in application No. EP 14836729.5, dated Jun. 6, 2017.
Guo et al., Protein tolerance to random amino acid change, Proc. Natl. Acad. Sci. USA, 101(25):9205-10 (Jun. 2004).
Keskin et al., A new, structurally nonredundant, diverse data set of protein-protein interfaces and its implications, Protein Sci., 13(4):1043-55 (Apr. 2004).
Maniatis et al., "Hybridization of DNA or RNA Immobilized on Filters to Radioactive Probes", pp. 324-343 and "Hybridization of Southern Filters", pp. 387-389, in: Molecular Cloning: A Laboratory Manual, Cold Spring Harbor Laboratory (1982).
NCBI Reference Sequence XM_004975973.1, Predicted: Setaria italica protoporphyrinogen oxidase, chloroplastic/mitochrondrial-like (LOC101781148), mRNA, Jun. 26, 2013.
Partial Supplementary European Search Report, European patent application No. 14836729.5, dated Mar. 28, 2017.
Supplemental Partial European Search Report, European patent application No. EP 14836899, dated Mar. 20, 2017.

(56) References Cited

OTHER PUBLICATIONS

Thornton et al., From structure to function: approaches and limitations, Nat. Struct. Biol., 7 Suppl:991-4 (Nov. 2000).

\* cited by examiner

Unsprayed

Tritosulfuron
70 g ai/ha

Flurasulam
2.5 g ai/ha

Rimsulfuro
5 g ai/ha

Metsulfuron
4.2 g ai/ha

A B C D E F

SEQUENCE LISTING

```
<160> NUMBER OF SEQ ID NOS: 32

<210> SEQ ID NO 1
<211> LENGTH: 1605
<212> TYPE: DNA
<213> ORGANISM: Amaranthus tuberculatum

<400> SEQUENCE: 1
atggtaattc aatccattac ccacctttca ccaaaccttg cattgccatc gccattgtca      60
gtttcaacca agaactaccc agtagctgta atgggcaaca tttctgagcg ggaagaaccc     120
acttctgcta aaagggttgc tgttgttggt gctggagtta gtggacttgc tgctgcatat     180
aagctaaaat cccatggttt gagtgtgaca ttgtttgaag ctgattctag agctggaggc     240
aaacttaaaa ctgttaaaaa agatggtttt atttgggatg aggggggcaaa tactatgaca    300 gaaagtgagg cagaggtctc gagtttgatc gatgatcttg ggcttcgtga gaagcaacag    360
ttgccaattt cacaaaataa aagatacata gctagagacg tcttcctgt gctactacct     420 tcaaatcccg ctgcactact cacgagcaat atcctttcag caaaatcaaa gctgcaaatt    480
atgttggaac catttctctg gagaaaacac aatgctactg aactttctga tgagcatgtt    540
caggaaagcg ttggtgaatt ttttgagcga cattttggga aagagtttgt tgattatgtt    600 atcgacccttt ttgttgcggg tacatgtggt ggagatcctc aatcgctttc catgcaccat   660
acatttccag aagtatggaa tattgaaaaa aggtttggct ctgtgtttgc tggactaatt    720
caatcaacat tgttatctaa gaaggaaaag ggtggagaaa atgcttctat taagaagcct   780
cgtgtacgtg gttcattttc atttcaaggt ggaatgcaga cacttgttga cacaatgtgc    840
aaacagcttg gtgaagatga actcaaactc cagtgtgagg tgctgtcctt gtcatataac    900
cagaagggga tcccctcatt agggaattgg tcagtctctt ctatgtcaaa taataccagt    960
gaagatcaat cttatgatgc tgtggttgtc actgctccaa ttcgcaatgt caaagaaatg   1020
aagattatga aatttggaaa tccattttca cttgacttta ttccagaggt gacgtacgta   1080
cccctttccg ttatgattac tgcattcaaa aaggataaag tgaagagacc tcttgagggc   1140
ttcggagttc ttatccctc taaagagcaa cataatggac tgaagactct tggtactta    1200 ttttcctcca tgatgtttcc tgatcgtgct ccatctgaca tgtgtctctt tactacattt   1260
gtcggaggaa gcagaaatag aaaacttgca aacgcttcaa cggatgaatt gaagcaaata   1320
gtttcttctg accttcagca gctgttgggc actgaggacg aaccttcatt tgtcaatcat   1380
ctcttttgga gcaacgcatt cccattgtat ggacacaatt acgattctgt tttgagagcc   1440
atagacaaga tggaaaagga tcttcctgga tttttttatg caggtaacca taagggtgga   1500 cttttcagtgg gaaaagcgat ggcctccgga tgcaaggctg cggaacttgt aatatcctat   1560
ctggactctc atatatacgt gaagatggat gagaagaccg cgtaa                   1605

<210> SEQ ID NO 2
<211> LENGTH: 534
<212> TYPE: PRT
```

<213> ORGANISM: Amaranthus tuberculatum

<400> SEQUENCE: 2

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
                100                 105                 110

Leu Gly Leu Arg Glu Lys Gln Gln Leu Pro Ile Ser Gln Asn Lys Arg
            115                 120                 125

Tyr Ile Ala Arg Asp Gly Leu Pro Val Leu Leu Pro Ser Asn Pro Ala
130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Leu Gly Thr Leu
385                 390                 395                 400
```

```
Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530
```

```
<210> SEQ ID NO 3
<211> LENGTH: 1644
<212> TYPE: DNA
<213> ORGANISM: Alopecurus

<400> SEQUENCE: 3
atgctcactt ccgccaccac cccctcctcc tcctccgctt cgtcccgcgc gtccacccgc      60
ttcgcctcct cgtcccgtcc tcgtcgcacc gcctacgcgc gcgggcgccg gcttcgcccc     120
gtgctcgcca tggccgcctc cgacgaccca cgcgccaggt cggtcgccgt tgtaggcgcc     180
ggcatcagtg ggctcgtggc ggcgtacaga ctgagcaaga gcggcgtgcg ggtcacggtg     240
ttcgaggcgg acgaccgggc aggagggaag atacggacca actccgacag cggattcctc     300
tgggacgaag gagccaacac catgacagaa agtgcgctgg aggcgagtag actaatcgat     360
gatcttggtc ttgaggacag gctgcagtat cctaactccc agcacaagcg gtacactgtt     420
aaagatggag cgccagcact gatcccctca gatcccattg cgctgatgaa agcagtctt     480 ctttctacga aatcaaagtt caagttattt ttggaaccat ttctctacga caagtctagc     540
acaaagagct ccaagaaagt gtctgatgag catataagtg agagtgttgg gagcttcttt     600
gaacgccact ttggaaaaga agttgttgac tatcttattg atccatttgt agctggaaca     660
agtgcaggag atcccgagtc attatctatc cgtcatgcat ttccagggtt atggaattta     720
gaaaagaagt atggttctat cattgttggt gccatcatgt ctaaactaac agctaaggt     780 gataagaaag gaagcgctgt atcaggaaaa ggaaggaata agcgggcgtc atttttcattt    840 catggtggta tgcagacact agtagatgca cttcacaaag aagttggaga tggtaatgtg     900
aaacttggag cacaagtgtt gtcattggca tgtatctgtg atgggctctc tgcatcagat     960
gggtggtcaa tttctgttga ttcaaaagat gctagtaaca aggagctaac aaagaaccat    1020
tcctttgatg ctgttatcat gacagctcca ctgtctaatg tccagaggat gaagtttaca    1080
aaaggtggag ctccatttgt gctagacttt cttcctaagg tggattatct gccgttgtcc    1140
ctcatggtaa cagctttaa gaaggaagat gtcaaaagac ctctggaagg atttggggtg    1200 ttgatacect acaaggaaca gcaaaagcat ggtctgaaaa cccttggaac tctcttctcc    1260
tctatgatgt ttccagatcg agctcctaat gaccaacact tatttacaac attcgttggg    1320
```

-continued

```
ggaagccaca acagggatct tgctggagct ccaacgtcta tcttaaaaca acttgtgacc    1380
tctgaccttg gaaagctcct gggtgtagag ggacagccaa cttttgtgaa acatatacat    1440
tggagaaatg cttttccttt atatggccat gattatgatt cggcattgga agctatagga    1500
aagatggaga gtgatcttcc agggttcttc tatgcaggaa ataacaagga cgggttggct    1560
gttggaaatg ttatagcttc aggaagtaag actgctgatc tggtgatctc gtatcttgag    1620
tcaggcatca agcaagataa ttaa                                           1644
```

<210> SEQ ID NO 4
<211> LENGTH: 547
<212> TYPE: PRT
<213> ORGANISM: Alpecurus myosuroides

<400> SEQUENCE: 4

```
Met Leu Thr Ser Ala Thr Thr Pro Ser Ser Ser Ala Ser Ser Arg
1               5                   10                  15

Ala Ser Thr Arg Phe Ala Ser Ser Arg Pro Arg Arg Thr Ala Tyr
                20                  25                  30

Ala Arg Gly Arg Arg Leu Arg Pro Val Leu Ala Met Ala Ala Ser Asp
            35                  40                  45

Asp Pro Arg Ala Arg Ser Val Ala Val Gly Ala Gly Ile Ser Gly
        50                  55                  60

Leu Val Ala Ala Tyr Arg Leu Ser Lys Ser Gly Val Arg Val Thr Val
65                  70                  75                  80

Phe Glu Ala Asp Asp Arg Ala Gly Gly Lys Ile Arg Thr Asn Ser Asp
                85                  90                  95

Ser Gly Phe Leu Trp Asp Glu Gly Ala Asn Thr Met Thr Glu Ser Ala
                100                 105                 110

Leu Glu Ala Ser Arg Leu Ile Asp Asp Leu Gly Leu Glu Asp Arg Leu
            115                 120                 125

Gln Tyr Pro Asn Ser Gln His Lys Arg Tyr Thr Val Lys Asp Gly Ala
        130                 135                 140

Pro Ala Leu Ile Pro Ser Asp Pro Ile Ala Leu Met Lys Ser Ser Leu
145                 150                 155                 160

Leu Ser Thr Lys Ser Lys Phe Lys Leu Phe Leu Glu Pro Phe Leu Tyr
                165                 170                 175

Asp Lys Ser Ser Thr Lys Ser Ser Lys Lys Val Ser Asp Glu His Ile
                180                 185                 190

Ser Glu Ser Val Gly Ser Phe Phe Glu Arg His Phe Gly Lys Glu Val
            195                 200                 205

Val Asp Tyr Leu Ile Asp Pro Phe Val Ala Gly Thr Ser Ala Gly Asp
        210                 215                 220

Pro Glu Ser Leu Ser Ile Arg His Ala Phe Pro Gly Leu Trp Asn Leu
225                 230                 235                 240

Glu Lys Lys Tyr Gly Ser Ile Ile Val Gly Ala Ile Met Ser Lys Leu
                245                 250                 255

Thr Ala Lys Gly Asp Lys Lys Gly Ser Ala Val Ser Gly Lys Gly Arg
                260                 265                 270

Asn Lys Arg Ala Ser Phe Ser Phe His Gly Gly Met Gln Thr Leu Val
            275                 280                 285

Asp Ala Leu His Lys Glu Val Gly Asp Gly Asn Val Lys Leu Gly Ala
        290                 295                 300

Gln Val Leu Ser Leu Ala Cys Ile Cys Asp Gly Leu Ser Ala Ser Asp
305                 310                 315                 320
```

```
Gly Trp Ser Ile Ser Val Asp Ser Lys Asp Ala Ser Asn Lys Glu Leu
                325                 330                 335

Thr Lys Asn His Ser Phe Asp Ala Val Ile Met Thr Ala Pro Leu Ser
            340                 345                 350

Asn Val Gln Arg Met Lys Phe Thr Lys Gly Gly Ala Pro Phe Val Leu
        355                 360                 365

Asp Phe Leu Pro Lys Val Asp Tyr Leu Pro Leu Ser Leu Met Val Thr
370                 375                 380

Ala Phe Lys Lys Glu Asp Val Lys Arg Pro Leu Gly Phe Gly Val
385                 390                 395                 400

Leu Ile Pro Tyr Lys Glu Gln Gln Lys His Gly Leu Lys Thr Leu Gly
                405                 410                 415

Thr Leu Phe Ser Ser Met Met Phe Pro Asp Arg Ala Pro Asn Asp Gln
            420                 425                 430

His Leu Phe Thr Thr Phe Val Gly Ser His Asn Arg Asp Leu Ala
        435                 440                 445

Gly Ala Pro Thr Ser Ile Leu Lys Gln Leu Val Thr Ser Asp Leu Gly
        450                 455                 460

Lys Leu Leu Gly Val Glu Gly Gln Pro Thr Phe Val Lys His Ile His
465                 470                 475                 480

Trp Arg Asn Ala Phe Pro Leu Tyr Gly His Asp Tyr Asp Ser Ala Leu
                485                 490                 495

Glu Ala Ile Gly Lys Met Glu Ser Asp Leu Pro Gly Phe Phe Tyr Ala
            500                 505                 510

Gly Asn Asn Lys Asp Gly Leu Ala Val Gly Asn Val Ile Ala Ser Gly
        515                 520                 525

Ser Lys Thr Ala Asp Leu Val Ile Ser Tyr Leu Glu Ser Gly Ile Lys
530                 535                 540

Gln Asp Asn
545

<210> SEQ ID NO 5
<211> LENGTH: 1572
<212> TYPE: DNA
<213> ORGANISM: Brachypodium

<400> SEQUENCE: 5
atggataacg cttacattgc cgccctctcc ttggccttcg tcttcctgct ccactacctt      60
ctcaagggca agaggagcaa tggcggcaac tgccgccga gccgcctgc catcccgatc       120 ctgggccacc tccacctggt cgagaagccg ctccacgcgg ccctctggcg cctcgcgggc     180
cgtctcggcc cggtcttctc ccttcgtctc ggctcccggc cagtcgtggt cgtctcctcc     240
ccggagctcg ccaaggagtg cttcacggag cacgacgtga ccttcgccga ccggcccag      300 ttcccgtcgc agctgctcgt gtccttcggc ggcaccgcgc tcgccacggc cagctacggc     360
ccgcactggc gcaacctccg ccgcgtcgcc gccgtgcacc tgctctccgc gcaccgcgtc     420
gccgccatgt cctccggcgt catctccgcc gaggtccgcg ccatggcgcg ccgcctcttc     480
cgcgcctccg ccgacggcag tggcggcgcc agggtgcagc tgaagcggcg gctgttcgag     540
ctgtccctga gcgtgctcat ggaggccatc gcgcagacca aggcgacgcg cccggacgat     600
gccgacggcg acgacacgga catgtccgtg gaggcgcagg agttcaagaa ggtggtggac     660
gagatcatcc gcacctcgg gaccgccaac tctctgggatt acctgccggt cttgcgtgg    720 ttcgacgtgt cgggtgag gaacaagatc ctggctgcgg ttaggagacg ggacgcgttc      780
```

```
ctgggccggc tgattgaagc ggagcgaagg aggcttgagg aggaaggcgg cggagaaggg      840
gatcagcaag gggagaagac gagcatgatc gccgtgctgc tcactttgca aaagacggag      900
ccggaggtgt acaccgatac catgatcacg gctctctgtg cgaatctatt cggggccggg      960
acggagacga cctcgacgac gacggaatgg gccatgtcgc tgctcctgaa ccacccagag     1020
gtcctcaaga aagcgcaggc cgagatggac gcctccgtgg gcacctcccg gctcgtcacc     1080
gccgacgacg tggcccaccg gctcccgtac ctgcagcaca tcgtgagcga gacgctccgg     1140
ctctacccgg cggcgccgat gctgctgccg caccagtcct cggccgactg caagatcggc     1200
ggctacaccg tcccgcgcgg cacgatgctg ctggtgaacg cgtacgccat ccacagggac     1260
cccgccgcct ggggcccggc gccggaggag ttcaggccgg agaggttcga ggacgcgagt     1320
aataagggcg aggagttgcc tttgatgctg ccgttcggga tggggcggcg caagtgcccc     1380
ggcgagacgc tggcgctgcg gacggtgggg atggtgctgg gcacgctggt gcagtgcttc     1440 gagtggggaga gggtgggggg agtggaggtg gacatgacgc aggggaccgg gctcaccatg     1500
cccaaggccg tgccgctcga ggccgtctgc cggccgcgcg ccgccatgcg tgacgtgctt     1560
cagaagctct ag                                                        1572
```

<210> SEQ ID NO 6
<211> LENGTH: 523
<212> TYPE: PRT
<213> ORGANISM: Brachypodium

<400> SEQUENCE: 6

```
Met Asp Asn Ala Tyr Ile Ala Ala Leu Ser Leu Ala Phe Val Phe Leu
1               5                   10                  15

Leu His Tyr Leu Leu Lys Gly Lys Arg Ser Asn Gly Gly Asn Leu Pro
            20                  25                  30

Pro Ser Pro Pro Ala Ile Pro Ile Leu Gly His Leu His Leu Val Glu
        35                  40                  45

Lys Pro Leu His Ala Ala Leu Trp Arg Leu Ala Gly Arg Leu Gly Pro
    50                  55                  60

Val Phe Ser Leu Arg Leu Gly Ser Arg Pro Val Val Val Ser Ser
65                  70                  75                  80

Pro Glu Leu Ala Lys Glu Cys Phe Thr Glu His Asp Val Thr Phe Ala
                85                  90                  95

Asp Arg Pro Gln Phe Pro Ser Gln Leu Leu Val Ser Phe Gly Gly Thr
            100                 105                 110

Ala Leu Ala Thr Ala Ser Tyr Gly Pro His Trp Arg Asn Leu Arg Arg
        115                 120                 125

Val Ala Ala Val His Leu Leu Ser Ala His Arg Val Ala Ala Met Ser
    130                 135                 140

Ser Gly Val Ile Ser Ala Glu Val Arg Ala Met Ala Arg Arg Leu Phe
145                 150                 155                 160

Arg Ala Ser Ala Asp Gly Ser Gly Gly Ala Arg Val Gln Leu Lys Arg
                165                 170                 175

Arg Leu Phe Glu Leu Ser Leu Ser Val Leu Met Glu Ala Ile Ala Gln
            180                 185                 190

Thr Lys Ala Thr Arg Pro Asp Asp Ala Asp Gly Asp Thr Asp Met
        195                 200                 205

Ser Val Glu Ala Gln Glu Phe Lys Val Val Asp Glu Ile Ile Pro
    210                 215                 220
```

```
His Leu Gly Thr Ala Asn Leu Trp Asp Tyr Leu Pro Val Leu Arg Trp
225                 230                 235                 240

Phe Asp Val Phe Gly Val Arg Asn Lys Ile Leu Ala Ala Val Arg Arg
            245                 250                 255

Arg Asp Ala Phe Leu Gly Arg Leu Ile Glu Ala Glu Arg Arg Arg Leu
        260                 265                 270

Glu Glu Glu Gly Gly Gly Glu Gly Asp Gln Gln Gly Glu Lys Thr Ser
    275                 280                 285

Met Ile Ala Val Leu Leu Thr Leu Gln Lys Thr Glu Pro Glu Val Tyr
290                 295                 300

Thr Asp Thr Met Ile Thr Ala Leu Cys Ala Asn Leu Phe Gly Ala Gly
305                 310                 315                 320

Thr Glu Thr Thr Ser Thr Thr Thr Glu Trp Ala Met Ser Leu Leu Leu
            325                 330                 335

Asn His Pro Glu Val Leu Lys Lys Ala Gln Ala Glu Met Asp Ala Ser
        340                 345                 350

Val Gly Thr Ser Arg Leu Val Thr Ala Asp Asp Val Ala His Arg Leu
    355                 360                 365

Pro Tyr Leu Gln His Ile Val Ser Glu Thr Leu Arg Leu Tyr Pro Ala
370                 375                 380

Ala Pro Met Leu Leu Pro His Gln Ser Ser Ala Asp Cys Lys Ile Gly
385                 390                 395                 400

Gly Tyr Thr Val Pro Arg Gly Thr Met Leu Leu Val Asn Ala Tyr Ala
            405                 410                 415

Ile His Arg Asp Pro Ala Ala Trp Gly Pro Ala Pro Glu Glu Phe Arg
        420                 425                 430

Pro Glu Arg Phe Glu Asp Ala Ser Asn Lys Gly Glu Glu Leu Pro Leu
    435                 440                 445

Met Leu Pro Phe Gly Met Gly Arg Arg Lys Cys Pro Gly Glu Thr Leu
450                 455                 460

Ala Leu Arg Thr Val Gly Met Val Leu Gly Thr Leu Val Gln Cys Phe
465                 470                 475                 480

Glu Trp Glu Arg Val Gly Gly Val Glu Val Asp Met Thr Gln Gly Thr
            485                 490                 495

Gly Leu Thr Met Pro Lys Ala Val Pro Leu Glu Ala Val Cys Arg Pro
        500                 505                 510

Arg Ala Ala Met Arg Asp Val Leu Gln Lys Leu
    515                 520

<210> SEQ ID NO 7
<211> LENGTH: 513
<212> TYPE: PRT
<213> ORGANISM: Oryza

<400> SEQUENCE: 7

Met Asp Asn Ala Tyr Ile Ile Ala Ile Leu Ser Val Ala Ile Leu Phe
1               5                   10                  15

Leu Leu His Tyr Tyr Leu Leu Gly Arg Gly Asn Gly Gly Ala Ala Arg
            20                  25                  30

Leu Pro Pro Gly Pro Ala Val Pro Ile Leu Gly His Leu His Leu
        35                  40                  45

Val Lys Lys Pro Met His Ala Thr Met Ser Arg Leu Ala Glu Arg Tyr
    50                  55                  60

Gly Pro Val Phe Ser Leu Arg Leu Gly Ser Arg Arg Ala Val Val Val
65                  70                  75                  80
```

-continued

```
Ser Ser Pro Gly Cys Ala Arg Glu Cys Phe Thr His Asp Val Thr
                85                  90                  95

Phe Ala Asn Arg Pro Arg Phe Glu Ser Gln Leu Leu Val Ser Phe Asn
            100                 105                 110

Gly Ala Ala Leu Ala Thr Ala Ser Tyr Gly Ala His Trp Arg Asn Leu
            115                 120                 125

Arg Arg Ile Val Ala Val Gln Leu Leu Ser Ala His Arg Val Gly Leu
        130                 135                 140

Met Ser Gly Leu Ile Ala Gly Glu Val Arg Ala Met Val Arg Arg Met
145                 150                 155                 160

Tyr Arg Ala Ala Ala Ser Pro Ala Gly Ala Ala Arg Ile Gln Leu
                165                 170                 175

Lys Arg Arg Leu Phe Glu Val Ser Leu Ser Val Leu Met Glu Thr Ile
            180                 185                 190

Ala His Thr Lys Ala Thr Arg Pro Glu Thr Asp Pro Asp Thr Asp Met
        195                 200                 205

Ser Val Glu Ala Gln Glu Phe Lys Gln Val Val Asp Glu Ile Ile Pro
    210                 215                 220

His Ile Gly Ala Ala Asn Leu Trp Asp Tyr Leu Pro Ala Leu Arg Trp
225                 230                 235                 240

Phe Asp Val Phe Gly Val Arg Arg Lys Ile Leu Ala Ala Val Ser Arg
                245                 250                 255

Arg Asp Ala Phe Leu Arg Arg Leu Ile Asp Ala Glu Arg Arg Arg Leu
            260                 265                 270

Asp Asp Gly Asp Glu Gly Glu Lys Lys Ser Met Ile Ala Val Leu Leu
        275                 280                 285

Thr Leu Gln Lys Thr Glu Pro Glu Val Tyr Thr Asp Asn Met Ile Thr
        290                 295                 300

Ala Leu Thr Ala Asn Leu Phe Gly Ala Gly Thr Glu Thr Thr Ser Thr
305                 310                 315                 320

Thr Ser Glu Trp Ala Met Ser Leu Leu Leu Asn His Pro Asp Thr Leu
                325                 330                 335

Lys Lys Ala Gln Ala Glu Ile Asp Ala Ser Val Gly Asn Ser Arg Leu
            340                 345                 350

Ile Thr Ala Asp Asp Val Thr Arg Leu Gly Tyr Leu Gln Cys Ile Val
        355                 360                 365

Arg Glu Thr Leu Arg Leu Tyr Pro Ala Ala Pro Met Leu Leu Pro His
    370                 375                 380

Glu Ser Ser Ala Asp Cys Lys Val Gly Gly Tyr Asn Ile Pro Arg Gly
385                 390                 395                 400

Ser Met Leu Leu Ile Asn Ala Tyr Ala Ile His Arg Asp Pro Ala Val
                405                 410                 415

Trp Glu Glu Pro Glu Lys Phe Met Pro Glu Arg Phe Glu Asp Gly Gly
            420                 425                 430

Cys Asp Gly Asn Leu Leu Met Pro Phe Gly Met Gly Arg Arg Cys
        435                 440                 445

Pro Gly Glu Thr Leu Ala Leu Arg Thr Val Gly Leu Val Leu Gly Thr
    450                 455                 460

Leu Ile Gln Cys Phe Asp Trp Glu Arg Val Asp Gly Val Glu Val Asp
465                 470                 475                 480

Met Thr Glu Gly Gly Gly Leu Thr Ile Pro Lys Val Val Pro Leu Glu
                485                 490                 495
```

```
Ala Met Cys Arg Pro Arg Asp Ala Met Gly Gly Val Leu Arg Glu Leu
            500                 505                 510

Val
```

```
<210> SEQ ID NO 8
<211> LENGTH: 521
<212> TYPE: PRT
<213> ORGANISM: Zea

<400> SEQUENCE: 8

Met Asp Lys Ala Tyr Ile Ala Ala Leu Ser Ala Ala Ala Leu Phe Leu
1               5                   10                  15

Leu His Tyr Leu Leu Gly Arg Arg Ala Gly Gly Glu Gly Lys Ala Lys
            20                  25                  30

Ala Lys Gly Ser Arg Arg Leu Pro Pro Ser Pro Pro Ala Ile Pro
        35                  40                  45

Phe Leu Gly His Leu His Leu Val Lys Ala Pro Phe His Gly Ala Leu
50                  55                  60

Ala Arg Leu Ala Ala Arg His Gly Pro Val Phe Ser Met Arg Leu Gly
65                  70                  75                  80

Thr Arg Arg Ala Val Val Val Ser Ser Pro Asp Cys Ala Arg Glu Cys
                85                  90                  95

Phe Thr Glu His Asp Val Asn Phe Ala Asn Arg Pro Leu Phe Pro Ser
            100                 105                 110

Met Arg Leu Ala Ser Phe Asp Gly Ala Met Leu Ser Val Ser Ser Tyr
        115                 120                 125

Gly Pro Tyr Trp Arg Asn Leu Arg Arg Val Ala Ala Val Gln Leu Leu
130                 135                 140

Ser Ala His Arg Val Gly Cys Met Ala Pro Ala Ile Glu Ala Gln Val
145                 150                 155                 160

Arg Ala Met Val Arg Arg Met Asp Arg Ala Ala Ala Gly Gly Gly
                165                 170                 175

Gly Val Ala Arg Val Gln Leu Lys Arg Arg Leu Phe Glu Leu Ser Leu
            180                 185                 190

Ser Val Leu Met Glu Thr Ile Ala His Thr Lys Thr Ser Arg Ala Glu
        195                 200                 205

Ala Asp Ala Asp Ser Asp Met Ser Thr Glu Ala His Glu Phe Lys Gln
210                 215                 220

Ile Val Asp Glu Leu Val Pro Tyr Ile Gly Thr Ala Asn Arg Trp Asp
225                 230                 235                 240

Tyr Leu Pro Val Leu Arg Trp Phe Asp Val Phe Gly Val Arg Asn Lys
                245                 250                 255

Ile Leu Asp Ala Val Gly Arg Arg Asp Ala Phe Leu Gly Arg Leu Ile
            260                 265                 270

Asp Gly Glu Arg Arg Arg Leu Asp Ala Gly Asp Glu Ser Glu Ser Lys
        275                 280                 285

Ser Met Ile Ala Val Leu Leu Thr Leu Gln Lys Ser Glu Pro Glu Val
290                 295                 300

Tyr Thr Asp Thr Val Ile Thr Ala Leu Cys Ala Asn Leu Phe Gly Ala
305                 310                 315                 320

Gly Thr Glu Thr Thr Ser Thr Thr Thr Glu Trp Ala Met Ser Leu Leu
                325                 330                 335

Leu Asn His Arg Glu Ala Leu Lys Lys Ala Gln Ala Glu Ile Asp Ala
            340                 345                 350
```

```
Ala Val Gly Thr Ser Arg Leu Val Thr Ala Asp Asp Val Pro His Leu
            355                 360                 365

Thr Tyr Leu Gln Cys Ile Val Asp Glu Thr Leu Arg Leu His Pro Ala
370                 375                 380

Ala Pro Leu Leu Leu Pro His Glu Ser Ala Ala Asp Cys Thr Val Gly
385                 390                 395                 400

Gly Tyr Asp Val Pro Arg Gly Thr Met Leu Leu Val Asn Val His Ala
                405                 410                 415

Val His Arg Asp Pro Ala Val Trp Glu Asp Pro Asp Arg Phe Val Pro
            420                 425                 430

Glu Arg Phe Glu Gly Ala Gly Gly Lys Ala Glu Gly Arg Leu Leu Met
        435                 440                 445

Pro Phe Gly Met Gly Arg Arg Lys Cys Pro Gly Glu Thr Leu Ala Leu
    450                 455                 460

Arg Thr Val Gly Leu Val Leu Ala Thr Leu Leu Gln Cys Phe Asp Trp
465                 470                 475                 480

Asp Thr Val Asp Gly Ala Gln Val Asp Met Lys Ala Ser Gly Gly Leu
                485                 490                 495

Thr Met Pro Arg Ala Val Pro Leu Glu Ala Met Cys Arg Pro Arg Thr
            500                 505                 510

Ala Met Arg Gly Val Leu Lys Arg Leu
        515                 520

<210> SEQ ID NO 9
<211> LENGTH: 522
<212> TYPE: PRT
<213> ORGANISM: Sorghum

<400> SEQUENCE: 9

Met Asp Lys Ala Tyr Val Ala Val Leu Ser Phe Ala Phe Leu Phe Val
1               5                   10                  15

Leu His Tyr Leu Val Gly Arg Ala Gly Gly Asn Gly Arg Lys Gly Asn
            20                  25                  30

Asn Gly Lys Gly Asn Ala Ala Gln Gln Arg Leu Pro Pro Ser Pro Pro
        35                  40                  45

Ala Val Pro Phe Leu Gly His Leu His Leu Val Lys Thr Pro Phe His
    50                  55                  60

Glu Ala Leu Ala Gly Leu Ala Ala Arg His Gly Pro Val Phe Ser Met
65                  70                  75                  80

Arg Met Gly Ser Arg Gly Ala Val Val Ser Ser Pro Glu Cys Ala
                85                  90                  95

Lys Glu Cys Phe Thr Glu His Asp Val Ala Phe Ala Asn Arg Pro Arg
            100                 105                 110

Phe Ala Thr Gln Glu Leu Val Ser Phe Gly Gly Ala Leu Ala Thr
        115                 120                 125

Ala Ser Tyr Gly Pro Tyr Trp Arg Asn Leu Arg Arg Val Ala Ala Val
    130                 135                 140

Gln Leu Leu Ser Ala His Arg Val Ala Cys Met Ser Ser Val Ile Ser
145                 150                 155                 160

Ala Glu Val Arg Ala Met Val Arg Met Ser Arg Ala Ala Ala
                165                 170                 175

Ala Pro Asp Gly Ala Arg Val Gln Leu Lys Arg Arg Leu Phe Glu
            180                 185                 190

Val Ser Leu Ser Val Leu Met Glu Thr Ile Ala Gln Thr Lys Thr Ser
        195                 200                 205
```

```
Arg Thr Glu Ala Asp Ala Asp Thr Asp Met Ser Pro Glu Ala His Glu
        210                 215                 220

Phe Lys Gln Ile Val Asp Glu Ile Val Pro His Leu Gly Thr Ala Asn
225                 230                 235                 240

Leu Trp Asp Tyr Leu Pro Val Leu Gln Trp Phe Asp Val Phe Gly Val
                245                 250                 255

Arg Asn Lys Ile Met Ala Ala Val Ser Arg Arg Asp Ala Phe Leu Arg
                260                 265                 270

Arg Leu Ile Asp Ala Glu Arg Arg Met Asp Asp Gly Gly Asp Ser
        275                 280                 285

Asp Lys Lys Ser Met Ile Ala Val Leu Leu Ser Leu Gln Lys Ser Glu
        290                 295                 300

Pro Glu Leu Tyr Thr Asp Thr Met Ile Met Ala Leu Cys Gly Asn Leu
305                 310                 315                 320

Phe Gly Ala Gly Thr Glu Thr Thr Ser Ser Thr Thr Glu Trp Ala Met
                325                 330                 335

Ser Leu Leu Leu Asn His Pro Glu Ala Leu Lys Lys Ala Gln Ala Glu
                340                 345                 350

Ile Asp Ala Val Val Gly Asn Ser Arg Leu Ile Thr Ala Glu Asp Val
        355                 360                 365

Pro Arg Leu Gly Tyr Leu Gln Cys Val Ile Asn Glu Thr Leu Arg Met
370                 375                 380

Tyr Pro Ala Ala Pro Leu Leu Pro His Glu Ser Ala Ala Asp Cys
385                 390                 395                 400

Lys Val Gly Gly Tyr Asp Val Pro Arg Gly Thr Leu Leu Ile Val Asn
                405                 410                 415

Ala Tyr Ala Ile His Arg Asp Pro Ala Val Trp Glu Asp Pro Ala Glu
                420                 425                 430

Phe Arg Pro Glu Arg Phe Glu Asp Gly Lys Ala Glu Gly Arg Leu Leu
                435                 440                 445

Met Pro Phe Gly Met Gly Arg Arg Lys Cys Pro Gly Glu Thr Leu Ala
450                 455                 460

Leu Arg Thr Val Gly Leu Val Leu Gly Thr Leu Ile Gln Cys Ile Asp
465                 470                 475                 480

Trp Asp Arg Val Asp Gly Leu Glu Ile Asp Met Thr Ala Gly Gly
                485                 490                 495

Leu Thr Met Pro Arg Ala Val Pro Leu Glu Ala Thr Cys Lys Pro Arg
                500                 505                 510

Ala Ala Met Arg Asp Val Leu Met Glu Leu
                515                 520

<210> SEQ ID NO 10
<211> LENGTH: 518
<212> TYPE: PRT
<213> ORGANISM: Oryza

<400> SEQUENCE: 10

Met Val Lys Ala Tyr Ile Ala Ile Phe Ser Ile Ala Val Leu Leu Leu
1               5                   10                  15

Ile His Phe Leu Phe Arg Arg Gly Arg Ser Asn Gly Met Pro Leu
                20                  25                  30

Pro Pro Ser Pro Pro Ala Ile Pro Phe Gly His Leu His Leu Ile
                35                  40                  45

Asp Lys Pro Phe His Ala Ala Leu Ser Arg Leu Ala Glu Arg His Gly
```

```
            50                  55                  60
Pro Val Phe Ser Leu Arg Leu Gly Ser Arg Asn Ala Val Val Ser
 65                  70                  75                  80

Ser Pro Glu Cys Ala Arg Glu Cys Phe Thr Asp Asn Asp Val Cys Phe
                     85                  90                  95

Ala Asn Arg Pro Arg Phe Pro Ser Gln Met Leu Ala Thr Phe Asn Gly
                100                 105                 110

Thr Ser Leu Gly Ser Ala Asn Tyr Gly Pro His Trp Arg Asn Leu Arg
                115                 120                 125

Arg Ile Ala Thr Val His Leu Leu Ser Ser His Arg Val Ser Gly Met
130                 135                 140

Ser Gly Ile Ile Ser Gly Gln Ala Arg His Met Val Arg Arg Met Tyr
145                 150                 155                 160

Arg Ala Ala Thr Ala Ser Ala Ala Gly Val Ala Arg Val Gln Leu Asn
                165                 170                 175

Arg Arg Leu Phe Glu Leu Ser Leu Ser Val Leu Met Glu Ala Ile Ala
                180                 185                 190

Gln Ser Lys Thr Thr Arg Arg Glu Ala Pro Asp Ala Asp Thr Asp Met
                195                 200                 205

Ser Met Glu Ala Gln Glu Leu Arg His Val Leu Asp Glu Leu Asn Pro
210                 215                 220

Leu Ile Gly Ala Ala Asn Leu Trp Asp Tyr Leu Pro Ala Leu Arg Trp
225                 230                 235                 240

Phe Asp Val Phe Gly Val Lys Arg Lys Ile Val Ala Ala Val Asn Arg
                245                 250                 255

Arg Asn Ala Phe Met Arg Arg Leu Ile Asp Ala Glu Arg Gln Arg Met
                260                 265                 270

Asp Asn Asn Asp Val Asp Gly Gly Asp Gly Glu Lys Lys Ser Met
                275                 280                 285

Ile Ser Val Leu Leu Thr Leu Gln Lys Thr Gln Pro Glu Val Tyr Thr
290                 295                 300

Asp Thr Leu Ile Met Thr Leu Cys Ala Pro Leu Phe Gly Ala Gly Thr
305                 310                 315                 320

Glu Thr Thr Ser Thr Thr Ile Glu Trp Ala Met Ser Leu Leu Leu Asn
                325                 330                 335

His Pro Glu Ile Leu Lys Lys Ala Gln Ala Glu Ile Asp Met Ser Val
                340                 345                 350

Gly Asn Ser Arg Leu Ile Ser Val Val Asp Val His Arg Leu Gly Tyr
                355                 360                 365

Leu Gln Cys Ile Ile Asn Glu Thr Leu Arg Met Tyr Pro Ala Ala Pro
                370                 375                 380

Leu Leu Leu Pro His Glu Ser Ser Ala Asp Cys Lys Val Gly Gly Tyr
385                 390                 395                 400

His Ile Pro Ser Gly Ala Met Leu Leu Val Asn Val Ala Ala Ile Gln
                405                 410                 415

Arg Asp Pro Val Ile Trp Lys Glu Pro Ser Glu Phe Lys Pro Glu Arg
                420                 425                 430

Phe Glu Asn Gly Arg Phe Glu Gly Leu Phe Met Ile Pro Phe Gly Met
                435                 440                 445

Gly Arg Arg Arg Cys Pro Gly Glu Met Leu Ala Leu Gln Thr Ile Gly
                450                 455                 460

Leu Val Leu Gly Thr Met Ile Gln Cys Phe Asp Trp Gly Arg Val Asp
465                 470                 475                 480
```

```
Asp Ala Met Val Asp Met Thr Gln Ser Asn Gly Leu Thr Ser Leu Lys
            485                 490                 495

Val Ile Pro Leu Glu Ala Met Cys Lys Pro Arg Glu Ala Met Cys Asp
            500                 505                 510

Val Leu Arg Lys Phe Met
        515

<210> SEQ ID NO 11
<211> LENGTH: 520
<212> TYPE: PRT
<213> ORGANISM: Zea

<400> SEQUENCE: 11

Met Glu Arg Phe Tyr Tyr Val Ala Ala Thr Phe Val Leu Val Phe
1               5                   10                  15

Leu Leu His His Leu Leu Thr Arg Lys Lys Gln Gln Arg Leu Pro Pro
                20                  25                  30

Gly Pro Arg Phe Ala Tyr Pro Ile Leu Gly His Leu Pro Leu Val Lys
            35                  40                  45

Lys Pro Leu Gln Thr Ser Phe Ala Asp Leu Val Ser Arg His Gly Pro
50                  55                  60

Ile Ile His Leu Arg Leu Gly Arg Arg His Ala Val Val Gly Ser
65                  70                  75                  80

Ala Ala Val Ala Lys Glu Cys Phe Ser Gly Leu Asp Val Ala Ile
                85                  90                  95

Ala Asn Arg Pro His Phe Pro Ser Ala Arg Glu Val Thr Phe Asp Tyr
            100                 105                 110

Ser Val Leu Thr Ala Val Asn Tyr Gly Ala Leu Trp Arg Thr Met Arg
            115                 120                 125

Arg Val Ser Thr Val His Leu Leu Ser Ala His Arg Val Asn Val Met
130                 135                 140

Ser Asp Thr Val Ile Ala Arg Glu Leu Arg Val Met Val Arg Arg Leu
145                 150                 155                 160

Ala Arg Ala Ser Ala Ser Ala Pro Gly Asp Ala Ala Arg Val Glu Leu
                165                 170                 175

Lys Arg Arg Leu Phe Asp Leu Ser His Ser Val Leu Met Glu Thr Met
            180                 185                 190

Ala Gln Thr Lys Asn Thr Tyr Ser Asp Asp Pro Glu Asp Met Ser
            195                 200                 205

Arg Glu Ala Arg Glu Met Lys Asp Ile Ile Glu Ile Ile Pro Leu
            210                 215                 220

Val Gly Ala Ala Asn Leu Trp Asn Tyr Val Pro Leu Leu Arg Trp Leu
225                 230                 235                 240

Asp Leu Tyr Gly Ala Lys Arg Lys Leu Ala Asp Val Asn Arg Arg
                245                 250                 255

Asp Leu Ile Phe Asp Asn Met Ile Gly Ala Glu Arg Gln Lys Leu Arg
            260                 265                 270

Gln Leu Glu Arg Lys Lys Gly Glu Ala His Ala Ser Glu Ser Asp Lys
            275                 280                 285

Met Gly Met Ile Gly Val Met Leu Ser Leu Gln Lys Thr Glu Pro Asp
            290                 295                 300

Val Tyr Thr Asp Thr Phe Ile Asn Ala Leu Val Ser Asn Leu Leu Ala
305                 310                 315                 320

Ala Gly Thr Glu Thr Thr Ser Thr Thr Leu Glu Trp Ala Met Ser Leu
```

```
                     325                 330                 335

Leu Leu Asn His Pro Asp Val Leu Lys Arg Ala Gln Glu Glu Ile Glu
            340                 345                 350

Ser Asn Val Gly Arg Asp Arg Leu Leu Asp Lys Asn Asp Leu Pro Arg
            355                 360                 365

Leu Pro Tyr Leu His Cys Ile Ile Ser Glu Thr Leu Arg Leu Tyr Pro
370                 375                 380

Pro Thr Pro Met Leu Leu Pro His Glu Ala Ser Thr Asp Cys Lys Ile
385                 390                 395                 400

His Gly Tyr Asp Val Pro Ala Gly Ser Met Val Leu Val Asn Ala Tyr
                405                 410                 415

Ala Ile His Arg Asp Pro Ala Met Trp Glu Asp Pro Glu Glu Phe Arg
                420                 425                 430

Pro Glu Arg Phe Glu Leu Gly Arg Ala Glu Gly Lys Phe Met Met Pro
            435                 440                 445

Phe Gly Met Gly Arg Arg Cys Pro Gly Glu Asn Leu Ala Met Arg
450                 455                 460

Thr Met Gly Leu Val Leu Gly Ala Leu Leu Gln Cys Phe Asp Trp Thr
465                 470                 475                 480

Arg Val Gly Asp Arg Glu Val Asp Met Ala Thr Ala Thr Gly Thr Ile
                485                 490                 495

Met Ser Lys Ala Val Pro Leu Glu Ala Gln Cys Lys Pro Arg Ala Asn
            500                 505                 510

Met Ser Ala Val Leu Gln Lys Ile
            515                 520

<210> SEQ ID NO 12
<211> LENGTH: 515
<212> TYPE: PRT
<213> ORGANISM: Zea

<400> SEQUENCE: 12

Met Val Ala Ala Thr Ala Leu Ser Phe Ser Phe Leu Ser Leu Ala Thr
1               5                   10                  15

Thr Leu Phe Leu Leu Leu Arg Ser Leu Ile Asn Asn Lys Lys Arg
            20                  25                  30

His Cys Arg Leu Pro Pro Ser Pro Ser Ser Leu Pro Val Ile Gly
            35                  40                  45

His Leu His Leu Leu Lys Lys Pro Leu His Arg Thr Leu Ser Ala Leu
        50                  55                  60

Ala Ala Gln His Gly Pro Val Leu Leu Phe Arg Phe Gly Ser Arg Arg
65                  70                  75                  80

Val Val His Val Ala Asp Pro Ala Val Ala Glu Cys Leu Ser Thr
                85                  90                  95

His Asp Val Thr Phe Ala Asn Arg Pro Arg Leu Pro Ser Ala Arg Tyr
            100                 105                 110

Leu Ser Asn Asp Tyr Thr Thr Leu Gly Ser Ser Ser Tyr Gly Pro Asn
            115                 120                 125

Trp Arg Asn Leu Arg Arg Ile Ala Thr Val Asp Val Phe Ser Ser His
130                 135                 140

Arg Val Leu Cys Ser Ala Asp Val Arg Ala Ser Glu Val Arg Asn Met
145                 150                 155                 160

Ala Arg Gln Leu Phe Lys Ala Ala Gly Ala Asp Ala Ser Arg Pro
            165                 170                 175
```

```
Ala Arg Cys Asp Val Lys Ala Arg Ala Phe Glu Ile Ala Leu Asn Thr
            180                 185                 190

Val Ala Arg Val Ile Ala Gly Lys Arg Tyr Tyr Gly Asp Gly Ser Val
        195                 200                 205

Ala Ser Glu Glu Ala Glu Arg Phe Arg Ala Met Val Arg Glu Tyr Leu
    210                 215                 220

Ala Met His Gly Ala Ser Asn Leu Gln Asp Phe Val Pro Val Leu Ala
225                 230                 235                 240

Leu Val Asp Ile Gly Gly Val Asn Lys Arg Ala Ile Arg Leu Ser Lys
                245                 250                 255

Ala Arg Asn Glu Trp Ala Gln Arg Leu Ile Asp Glu His Arg Ala Ala
            260                 265                 270

Ala Ala Ala Gly Arg Glu Gln Gly Lys Thr Met Val Gly Asp Leu Leu
        275                 280                 285

Glu Lys Gln Ala Ser Asp Pro Glu Thr Tyr Ser Asp Lys Val Ile Arg
    290                 295                 300

Ala Leu Cys Leu Ser Ile Leu Gln Ala Gly Thr Asp Thr Ser Ser Ser
305                 310                 315                 320

Thr Ile Glu Trp Gly Met Ala Leu Leu Leu Asn His Pro Ala Ala Met
                325                 330                 335

Ala Lys Ala Lys Ala Glu Ile Asp Glu Val Ile Gly Thr Ala Arg Ile
            340                 345                 350

Leu Glu Glu Ala Asp Leu Pro Asn Leu Pro Tyr Leu Gly Cys Ile Ile
        355                 360                 365

Lys Glu Thr Leu Arg Leu His Pro Val Gly Pro Leu Leu Ala Pro His
    370                 375                 380

Glu Ser Ala Ser Asp Cys Ser Val Gly Gly Tyr Asp Ile Pro Ala Gly
385                 390                 395                 400

Thr Met Leu Leu Val Asn Val His Ala Met His Arg Asp Ala Arg Val
                405                 410                 415

Trp Glu Glu Pro Glu Arg Phe Ser Pro Glu Arg Phe Glu Gly Gly Asn
            420                 425                 430

Ser Asp Gly Lys Trp Met Leu Pro Phe Gly Met Gly Arg Arg Arg Cys
        435                 440                 445

Pro Gly Glu Gly Leu Ala Val Lys Met Val Gly Leu Ala Leu Gly Thr
    450                 455                 460

Leu Leu Gln Cys Phe Glu Trp Arg Arg Thr Gly Asp Glu Val Asp
465                 470                 475                 480

Met Thr Glu Ala Ser Gly Leu Thr Met Pro Lys Ser Val Pro Leu Glu
                485                 490                 495

Ala Phe Tyr Trp Pro Arg Thr Glu Met Met Ser Pro Leu Thr Ala Leu
            500                 505                 510

His Gly Cys
        515

<210> SEQ ID NO 13
<211> LENGTH: 509
<212> TYPE: PRT
<213> ORGANISM: Oryza

<400> SEQUENCE: 13

Met Asp Ala Leu Leu Ile Ala Leu Phe Leu Leu Leu Ile Ala Leu
1               5                   10                  15

Met Glu Thr Ala Arg Val Arg Arg Ser Gly Thr Gln Arg Ala Gly
            20                  25                  30
```

```
Asn Val Pro Pro Pro Pro Glu Pro Ala Gly Leu Pro Leu Val Gly
         35                  40                  45

His Leu His Leu Phe Arg Lys Pro Leu His Arg Thr Leu Ala Arg Leu
 50                  55                  60

Ala Ala Arg His Gly Gly Ala Val Phe Gly Leu Arg Leu Gly Ser Arg
 65                  70                  75                  80

Arg Val Ala Val Val Ser Ser Ala Pro Ala Ala Glu Glu Cys Leu Gly
                 85                  90                  95

Ala His Asp Val Ala Phe Ala Asp Arg Pro Arg Leu Pro Ser Gly Arg
                 100                 105                 110

Ile Leu Ser Tyr Asp Trp Ser Thr Met Gly Thr Ala Ser Tyr Gly Pro
             115                 120                 125

Tyr Trp Arg His Val Arg Arg Val Ala Val Thr Glu Ile Leu Ser Ala
         130                 135                 140

Arg Arg Val Gln His Phe Ala Asp Val His Val Arg Glu Ala Arg Ala
145                 150                 155                 160

Met Ala Arg His Leu His Arg Ala Ala Val Arg His Gly Val Gly Gly
                 165                 170                 175

Ala Ala Arg Val Arg Val Glu Leu Lys Ser Arg Leu Phe Glu Leu Leu
             180                 185                 190

Met Asn Thr Met Met Ala Met Ile Cys Asp Lys Thr Tyr Tyr Gly Asp
         195                 200                 205

Asp Asp Asp Gly Lys Val Ser Lys Glu Ala Arg Trp Phe Arg Glu Met
210                 215                 220

Val Glu Glu Thr Met Ala Leu Ser Gly Ala Ser Thr Val Trp Asp Phe
225                 230                 235                 240

Leu Pro Ala Ala Leu Arg Trp Val Asp Val Gly Gly Val Gly Arg Arg
                 245                 250                 255

Leu Trp Arg Leu Arg Glu Ser Arg Thr Arg Phe Leu Gln Gly Leu Ile
             260                 265                 270

Asn Asp Glu Arg Lys Glu Met Glu Gln Glu Gln Gly Gly Asp Arg Ala
         275                 280                 285

Gln Pro Ala Ala Arg Arg Arg Thr Met Ile Gly Val Leu Leu Ser Val
290                 295                 300

Gln Arg Gln Asp Pro Asp Ala Cys Pro Asp Gln Leu Ile Arg Ser Leu
305                 310                 315                 320

Cys Ile Ser Ser Leu Glu Ala Gly Thr Asp Thr Ser Ala Asp Thr Ile
                 325                 330                 335

Glu Trp Ala Met Ser Leu Leu Leu Asn Asn Pro Asn Val Met Arg Lys
             340                 345                 350

Ala Arg Asp Glu Ile Asp Ala Phe Ile Gly Gln Pro Cys Ile Ile Met
         355                 360                 365

Glu Thr Leu Arg Leu Tyr Pro Pro Ala Pro Leu Leu Val Pro His Glu
370                 375                 380

Ala Ser Thr Asp Cys Ser Ile Ala Gly Phe His Ile Thr Arg Gly Thr
385                 390                 395                 400

Met Leu Leu Val Asn Thr Phe Ala Ile His Arg Asp Pro Gln Val Trp
                 405                 410                 415

Asn Glu Pro Thr Ser Phe Ile Pro Glu Arg Phe Glu Asn Gly Arg Ser
             420                 425                 430

Glu Gly Lys Met Ala Ile Pro Phe Gly Met Gly Arg Cys Lys Cys Pro
         435                 440                 445
```

```
Ala Glu Asn Leu Gly Met Gln Met Val Gly Leu Ala Leu Gly Thr Met
        450                 455                 460

Ile Gln Cys Phe Glu Trp Glu Arg Val Gly Glu Glu Leu Val Asp Met
465                 470                 475                 480

Thr Glu Gly Ser Gly Leu Thr Met Pro Lys Glu Val Pro Leu Gln Ala
                485                 490                 495

Phe Tyr Gln Pro Arg Ala Ser Leu Met His Leu Leu Tyr
                500                 505

<210> SEQ ID NO 14
<211> LENGTH: 524
<212> TYPE: PRT
<213> ORGANISM: Oryza

<400> SEQUENCE: 14

Met Ala Val Asp Ala Met Phe Gly Ser Val Ala Val Ala Leu Leu Ala
1               5                   10                  15

Val Val Val Ala Ala Ala Leu Arg Arg Trp Arg Arg Arg Arg Arg Arg
            20                  25                  30

Arg Gly Gly Gly Arg Pro Leu Pro Gly Pro Val Ala Leu Pro Val Val
        35                  40                  45

Gly His Leu His Leu Phe Arg Arg Pro Leu His Arg Thr Leu Ala Arg
    50                  55                  60

Leu Ala Ala Arg His Gly Ala Val Met Gly Leu Arg Phe Gly Ser
65                  70                  75                  80

Arg Arg Val Ala Val Ser Ser Ala Pro Ala Glu Glu Cys Leu
                85                  90                  95

Gly Pro His Asp Leu Ala Phe Ala Asn Arg Pro Arg Leu Pro Ser Gly
                100                 105                 110

Glu Ile Leu Ala Tyr Glu Trp Ser Thr Met Gly Thr Ala Ser Tyr Gly
            115                 120                 125

Pro Tyr Trp Arg His Ile Arg Arg Ile Ala Val Thr Glu Leu Leu Ser
    130                 135                 140

Ala His Arg Val Gln His Phe Ala Asp Val Asn Val Arg Glu Val Arg
145                 150                 155                 160

Ala Leu Ala Arg Arg Leu Tyr Arg Arg Ala Ala Ala Ala Ala Ala Ala
                165                 170                 175

Gly Ala Arg Thr Arg Val Glu Leu Lys Ser Arg Leu Phe Glu Leu Leu
            180                 185                 190

Met Asn Thr Met Met Ser Met Ile Cys Glu Arg Thr Phe Tyr Gly Ala
        195                 200                 205

Asp Asp Asp Glu Val Ser Glu Glu Ala Arg Trp Phe Arg Ser Val Val
    210                 215                 220

Lys Glu Thr Met Glu Leu Ser Gly Ala Ser Thr Val Trp Asp Phe Leu
225                 230                 235                 240

Pro Ala Pro Ala Arg Trp Leu Asp Ala Gly Arg Met Thr Arg Arg Met
                245                 250                 255

Arg Glu Leu Ser Asp Ser Arg Thr Arg Phe Leu Gln Arg Leu Ile Asp
            260                 265                 270

Asp Gln Arg Lys Asp Met Asp Ala Asp Ser Asp His Ala Pro Ala
        275                 280                 285

Lys Arg Arg Thr Met Ile Gly Val Leu Leu Ser Leu Gln Arg Lys Asp
    290                 295                 300

Pro Asp Ser Cys Pro Asp Gln Leu Ile Arg Ser Leu Cys Ile Gly Ser
305                 310                 315                 320
```

-continued

Leu Gln Ala Gly Thr Asp Thr Ser Ala Ala Thr Val Glu Trp Ala Met
                325                 330                 335

Ser Leu Leu Leu Asn Asn Pro Gly Ala Met Ala Arg Ala Arg Gly Glu
            340                 345                 350

Ile Asp Ala Cys Val Gly Gln Pro Ala Ala Arg Leu Leu Glu Ala Ala
        355                 360                 365

Asp Leu Pro Lys Leu His Tyr Leu Arg Cys Val Val Met Glu Thr Leu
    370                 375                 380

Arg Leu Tyr Pro Pro Val Pro Leu Leu Ala Pro His Glu Ser Ser Ala
385                 390                 395                 400

Asp Cys Val Val Ala Gly Phe His Val Pro Gln Gly Thr Met Leu Leu
                405                 410                 415

Val Asn Thr Phe Ala Ile His Arg Asp Pro Gln Val Trp Asp Glu Pro
            420                 425                 430

Glu Ala Phe Ile Pro Asp Arg Phe Ala Asp Gly Lys Asn Glu Gly Lys
        435                 440                 445

Met Val Ile Pro Phe Gly Met Gly Arg Arg Cys Pro Gly Glu Asn
    450                 455                 460

Leu Gly Met Gln Met Val Gly Leu Ala Leu Gly Thr Leu Ile Gln Cys
465                 470                 475                 480

Phe Asp Trp Glu Arg Val Gly Glu Glu Leu Val Asp Met Arg Glu Cys
                485                 490                 495

Ser Gly Leu Thr Met Pro Lys Glu Leu Pro Leu Glu Ala Leu Tyr Gln
            500                 505                 510

Pro Arg Ala Ser Met Val Asp Leu Leu Thr Lys Ile
        515                 520

<210> SEQ ID NO 15
<211> LENGTH: 526
<212> TYPE: PRT
<213> ORGANISM: Oryza

<400> SEQUENCE: 15

Met His Ile Gly Pro Ala Ala Ser Asp Arg Ala Val Leu Val Leu Pro
1               5                   10                  15

Leu Leu Gly Gly Asp Ser Ala Pro Ala Val Met Val Asp Ala Met Ser
            20                  25                  30

Gly Gly Val Leu Val Ala Leu Met Val Leu Leu Val Ala Ala Pro
        35                  40                  45

Ala Leu Leu Ser Arg Leu Glu Arg Arg Arg Pro Pro Gly Pro
    50                  55                  60

Val Ala Leu Pro Val Val Gly His Leu His Leu Leu Arg Arg Pro Leu
65                  70                  75                  80

His Arg Thr Leu Ala Arg Leu Ala Ala Arg His Gly Ala Ala Val
                85                  90                  95

Met Gly Leu Arg Phe Gly Ser Arg Val Ala Val Ser Ser Ala
            100                 105                 110

Pro Ala Ala Glu Glu Cys Leu Gly Pro His Asp Leu Ala Phe Ala Asp
        115                 120                 125

Lys Pro Arg Leu Pro Ser Gly Glu Ile Leu Ser Tyr Glu Trp Ser Thr
    130                 135                 140

Met Gly Thr Ala Ser Tyr Gly Pro Tyr Trp Arg His Ile Arg Arg Ile
145                 150                 155                 160

Thr Val Thr Glu Leu Leu Ser Ala His Arg Val Gln His Phe Ala Gly

```
            165                 170                 175
Val Asn Ala Arg Glu Leu Lys Ser Arg Leu Phe Glu Leu Phe Met Asn
            180                 185                 190

Ile Met Met Ala Met Ile Cys Asp Arg Thr Phe Tyr Gly Asp Gly Asp
            195                 200                 205

Asp Glu Val Ser Glu Ala Arg Trp Phe Arg Ser Val Val Lys Glu
        210                 215                 220

Thr Met Glu Leu Ser Gly Ala Ser Thr Ala Trp Asp Phe Leu Pro Ala
225                 230                 235                 240

Ala Ala Arg Trp Leu Phe Ala Arg Arg Leu Thr Arg Arg Met Arg Glu
                245                 250                 255

Leu Ser Asp Ser Arg Thr Arg Phe Tyr Gln Arg Leu Ile Thr Asp His
                260                 265                 270

Arg Thr Lys Glu Lys Thr Asp Asp Asn Ala Ala Ala Gly Asp His
            275                 280                 285

Ser Pro Ala Pro Arg Arg Arg Thr Met Ile Gly Val Leu Leu Ser Leu
        290                 295                 300

Gln Ser Lys Asp Pro Asp Ala Cys Pro Asp Gln Leu Ile Arg Ala Leu
305                 310                 315                 320

Cys Ile Gly Ser Leu Gln Ala Gly Thr Glu Thr Ser Ala Ala Val Val
                325                 330                 335

Glu Trp Ala Met Ser Leu Leu Leu Asn Asn Pro Gly Ala Met Ala Arg
                340                 345                 350

Ala Arg Gly Glu Ile Asp Ala Cys Val Gly Gln Pro Ala Ala Arg Leu
                355                 360                 365

Leu Glu Ala Ala Asp Leu Pro Lys Leu His Tyr Leu Arg Cys Val Val
        370                 375                 380

Met Glu Thr Leu Arg Leu Tyr Pro Pro Val Pro Leu Leu Ala His Glu
385                 390                 395                 400

Ser Ser Ala Asp Cys Asp Val Ala Gly Phe His Val Arg Lys Gly Thr
                405                 410                 415

Met Leu Leu Val Asn Thr Phe Ala Ile His Arg Asp Pro Gln Val Trp
                420                 425                 430

Asp Glu Pro Glu Ser Phe Phe Pro Asp Arg Phe Ala Asp Gly Gln Asn
        435                 440                 445

Glu Ala Lys Met Val Ile Pro Phe Gly Met Gly Arg Arg Gly Cys Pro
        450                 455                 460

Gly Glu Asn Leu Ala Met Gln Met Val Gly Leu Thr Leu Gly Thr Leu
465                 470                 475                 480

Ile Gln Cys Phe Asp Trp Glu Arg Val Gly Glu Glu Leu Glu Asp Met
                485                 490                 495

Gly Glu Ser Ser Gly Ile Thr Met Pro Lys Lys Leu Pro Leu Glu Ala
                500                 505                 510

Phe Tyr Gln Pro Arg Ala Cys Met Val His Leu Leu Ser Ser
            515                 520                 525

<210> SEQ ID NO 16
<211> LENGTH: 517
<212> TYPE: PRT
<213> ORGANISM: Lolium

<400> SEQUENCE: 16

Met Asp Lys Ala Tyr Ile Ala Ile Leu Ser Cys Ala Phe Leu Phe Leu
1               5                   10                  15
```

Val His Tyr Val Leu Gly Lys Val Ser Asp Gly Arg Arg Gly Lys Lys
            20                  25                  30

Gly Ala Val Gln Leu Pro Pro Ser Pro Pro Ala Ile Pro Phe Ile Gly
        35                  40                  45

His Leu His Leu Val Glu Lys Pro Ile His Ala Thr Met Cys Arg Leu
    50                  55                  60

Ala Ala Arg Leu Gly Pro Val Phe Ser Leu Arg Leu Gly Ser Arg Arg
65                  70                  75                  80

Ala Val Val Val Pro Ser Ser Glu Cys Ala Arg Glu Cys Phe Thr Glu
                85                  90                  95

His Asp Val Thr Phe Ala Asn Arg Pro Lys Phe Pro Ser Gln Leu Leu
            100                 105                 110

Ala Ser Phe Asn Gly Thr Ala Leu Val Thr Ser Ser Tyr Gly Pro His
        115                 120                 125

Trp Arg Asn Leu Arg Arg Val Ala Thr Val Gln Leu Leu Ser Ala His
    130                 135                 140

Arg Val Ala Cys Met Ser Gly Val Ile Ala Ala Glu Val Arg Ala Met
145                 150                 155                 160

Ala Arg Arg Leu Phe His Ala Ala Glu Ala Ser Pro Asp Gly Ala Ala
                165                 170                 175

Arg Val Gln Leu Lys Arg Arg Leu Phe Glu Leu Ser Leu Ser Val Leu
            180                 185                 190

Met Glu Thr Ile Ala Gln Thr Lys Ala Thr Arg Ser Glu Ala Asp Ala
        195                 200                 205

Asp Thr Asp Met Ser Val Glu Ala Gln Glu Phe Lys Glu Val Val Asp
210                 215                 220

Lys Leu Ile Pro His Leu Gly Ala Ala Asn Met Trp Asp Tyr Leu Pro
225                 230                 235                 240

Val Met Arg Trp Phe Asp Val Phe Gly Val Arg Asn Lys Ile Leu His
                245                 250                 255

Ala Val Ser Arg Arg Asp Ala Phe Leu Arg Arg Leu Ile Asp Ala Glu
            260                 265                 270

Arg Arg Arg Leu Ala Asp Gly Gly Ser Asp Gly Asp Lys Lys Ser Met
        275                 280                 285

Ile Ala Val Leu Leu Thr Leu Gln Lys Thr Glu Pro Lys Val Tyr Thr
290                 295                 300

Asp Thr Met Ile Thr Ala Leu Cys Ala Asn Leu Phe Gly Ala Gly Thr
305                 310                 315                 320

Glu Thr Thr Ser Thr Thr Thr Glu Trp Ala Met Ser Leu Leu Leu Asn
                325                 330                 335

His Pro Ala Ala Leu Lys Lys Ala Gln Ala Glu Ile Asp Ala Ser Val
            340                 345                 350

Gly Thr Ser Arg Leu Val Ser Val Asp Asp Val Pro Ser Leu Ala Tyr
        355                 360                 365

Leu Gln Cys Ile Val Asn Glu Thr Leu Arg Leu Tyr Pro Ala Ala Pro
370                 375                 380

Leu Leu Leu Pro His Glu Ser Ser Ala Asp Cys Lys Val Gly Gly Tyr
385                 390                 395                 400

Asn Val Pro Ala Asp Thr Met Leu Ile Val Asn Ala Tyr Ala Ile His
                405                 410                 415

Arg Asp Pro Ala Ala Trp Glu His Pro Leu Glu Phe Arg Pro Glu Arg
            420                 425                 430

Phe Glu Asp Gly Lys Ala Glu Gly Leu Phe Met Ile Pro Phe Gly Val

```
            435                 440                 445
Gly Arg Arg Arg Cys Pro Gly Glu Thr Leu Ala Leu Arg Thr Ile Ser
    450                 455                 460

Met Val Leu Ala Thr Leu Val Gln Cys Phe Asp Trp Glu Pro Val Asp
465                 470                 475                 480

Gly Val Lys Val Asp Met Thr Glu Gly Gly Phe Thr Ile Pro Lys
                485                 490                 495

Ala Val Pro Leu Glu Ala Val Cys Arg Pro Arg Ala Val Met Arg Asp
                500                 505                 510

Val Leu Gln Asn Leu
        515

<210> SEQ ID NO 17
<211> LENGTH: 521
<212> TYPE: PRT
<213> ORGANISM: Oryza

<400> SEQUENCE: 17

Met Asp Lys Ala Tyr Ile Ala Ala Leu Ser Ala Ala Ala Leu Phe Leu
1               5                   10                  15

Leu His Tyr Leu Leu Gly Arg Arg Ala Gly Gly Glu Gly Lys Ala Lys
            20                  25                  30

Ala Lys Gly Ser Arg Arg Leu Pro Pro Ser Pro Pro Ala Ile Pro
        35                  40                  45

Phe Leu Gly His Leu His Leu Val Lys Ala Pro Phe His Gly Ala Leu
    50                  55                  60

Ala Arg Leu Ala Ala Arg His Gly Pro Val Phe Ser Met Arg Leu Gly
65                  70                  75                  80

Thr Arg Arg Ala Val Val Val Ser Ser Pro Asp Cys Ala Arg Glu Cys
                85                  90                  95

Phe Thr Glu His Asp Val Asn Phe Ala Asn Arg Pro Leu Phe Pro Ser
            100                 105                 110

Met Arg Leu Ala Ser Phe Asp Gly Ala Met Leu Ser Val Ser Ser Tyr
        115                 120                 125

Gly Pro Tyr Trp Arg Asn Leu Arg Arg Val Ala Ala Val Gln Leu Leu
    130                 135                 140

Ser Ala His Arg Val Gly Cys Met Ala Pro Ala Ile Glu Ala Gln Val
145                 150                 155                 160

Arg Ala Met Val Arg Met Asp Arg Ala Ala Ala Gly Gly Gly
                165                 170                 175

Gly Val Ala Arg Val Gln Leu Lys Arg Leu Phe Glu Leu Ser Leu
            180                 185                 190

Ser Val Leu Met Glu Thr Ile Ala His Thr Lys Thr Ser Arg Ala Glu
195                 200                 205

Ala Asp Ala Asp Ser Asp Met Ser Thr Glu Ala His Glu Phe Lys Gln
    210                 215                 220

Ile Val Asp Glu Leu Val Pro Tyr Ile Gly Thr Ala Asn Arg Trp Asp
225                 230                 235                 240

Tyr Leu Pro Val Leu Arg Trp Phe Asp Val Phe Gly Val Arg Asn Lys
            245                 250                 255

Ile Leu Asp Ala Val Gly Arg Arg Asp Ala Phe Leu Gly Arg Leu Ile
        260                 265                 270

Asp Gly Glu Arg Arg Arg Leu Asp Ala Gly Asp Glu Ser Glu Ser Lys
    275                 280                 285
```

```
Ser Met Ile Ala Val Leu Leu Thr Leu Gln Lys Ser Glu Pro Glu Val
    290                 295                 300

Tyr Thr Asp Thr Val Ile Thr Ala Leu Cys Ala Asn Leu Phe Gly Ala
305                 310                 315                 320

Gly Thr Glu Thr Thr Ser Thr Thr Thr Glu Trp Ala Met Ser Leu Leu
                    325                 330                 335

Leu Asn His Arg Glu Ala Leu Lys Lys Ala Gln Ala Glu Ile Asp Ala
                340                 345                 350

Ala Val Gly Thr Ser Arg Leu Val Thr Ala Asp Asp Val Pro His Leu
            355                 360                 365

Thr Tyr Leu Gln Cys Ile Val Asp Glu Thr Leu Arg Leu His Pro Ala
370                 375                 380

Ala Pro Leu Leu Leu Pro His Glu Ser Ala Ala Asp Cys Thr Val Gly
385                 390                 395                 400

Gly Tyr Asp Val Pro Arg Gly Thr Met Leu Leu Val Asn Val His Ala
                    405                 410                 415

Val His Arg Asp Pro Ala Val Trp Glu Asp Pro Asp Arg Phe Val Pro
                420                 425                 430

Glu Arg Phe Glu Gly Ala Gly Gly Lys Ala Glu Gly Arg Leu Leu Met
            435                 440                 445

Pro Phe Gly Met Gly Arg Arg Lys Cys Pro Gly Glu Thr Leu Ala Leu
450                 455                 460

Arg Thr Val Gly Leu Val Leu Ala Thr Leu Leu Gln Cys Phe Asp Trp
465                 470                 475                 480

Asp Thr Val Asp Gly Ala Gln Val Asp Met Lys Ala Ser Gly Gly Leu
                    485                 490                 495

Thr Met Pro Arg Ala Val Pro Leu Glu Ala Met Cys Arg Pro Arg Thr
                500                 505                 510

Ala Met Arg Gly Val Leu Lys Arg Leu
            515                 520

<210> SEQ ID NO 18
<211> LENGTH: 527
<212> TYPE: PRT
<213> ORGANISM: Oryza

<400> SEQUENCE: 18

Met Ala Gly Leu Glu Val Ala Thr Thr Ala Val Thr Gly Gly Asp Ala
1               5                   10                  15

Ser Leu Val Val Val Gly Val Leu Phe Leu Met Val Ala Val Val
                20                  25                  30

Val Met Thr Arg Leu Gly Asp Gly Ala Ala Pro Ser Pro Ala
            35                  40                  45

Met Pro Val Leu Gly His Leu His Leu Ile Lys Lys Pro Leu His Arg
            50                  55                  60

Ser Leu Ala Glu Val Ala Ala Arg Val Gly Ala Ala Pro Val Val Ser
65                  70                  75                  80

Leu Arg Leu Gly Ala Arg Arg Ala Leu Leu Val Ser Thr His Ala Ala
                85                  90                  95

Ala Glu Glu Cys Phe Thr Ala Cys Asp Ala Ala Val Ala Gly Arg Pro
            100                 105                 110

Arg Leu Leu Ala Gly Asp Val Leu Gly Tyr Gly His Thr Thr Val Val
        115                 120                 125

Trp Ala Ser His Gly Asp His Trp Arg Ala Leu Arg Arg Leu Leu Gly
    130                 135                 140
```

```
Val Glu Leu Phe Ser Asn Ala Arg Leu Ala Ala Leu Ala Ala Asp Arg
145                 150                 155                 160

Arg Ala Glu Val Ala Ser Leu Val Asp Ala Val Leu Arg Asp Ala Ala
                165                 170                 175

Ala Gly Gly Gly Gly Gly Thr Val Thr Leu Arg Pro Arg Leu Phe
            180                 185                 190

Glu Leu Val Leu Asn Val Met Leu Arg Ala Val Thr Ala Arg Arg His
                195                 200                 205

Ala Gly Asp Glu Thr Arg Arg Phe Gln Glu Ile Val Glu Glu Thr Phe
210                 215                 220

Ala Ala Ser Gly Ser Pro Thr Val Gly Asp Phe Phe Pro Ala Leu Arg
225                 230                 235                 240

Trp Val Asp Arg Leu Arg Gly Val Val Ala Thr Leu Gln Ser Leu Gln
                245                 250                 255

Lys Arg Arg Asp Ala Phe Val Ala Gly Leu Val Asp Asp His Arg Arg
                260                 265                 270

Thr Arg Arg Ala Ala Ala Ala Ala Asp Lys Asp Gln Lys Lys Asn
                275                 280                 285

Gly Ile Ile Asp Ala Leu Leu Thr Leu Gln Glu Thr Asp Pro Asp His
290                 295                 300

Tyr Thr Asp Asn Val Val Lys Gly Ile Val Leu Val Leu Leu Thr Ala
305                 310                 315                 320

Gly Thr Asp Thr Ser Ala Leu Thr Thr Glu Trp Ala Met Ala Gln Leu
                325                 330                 335

Val Ala His Pro Glu Ala Met Thr Lys Val Arg Ala Glu Ile Asp Ala
                340                 345                 350

Asn Val Gly Ala Ala Arg Leu Val Glu Glu Ala Asp Met Ala Ser Leu
                355                 360                 365

Pro Tyr Leu Gln Cys Val Val Lys Glu Thr Leu Arg Leu Arg Pro Val
370                 375                 380

Gly Pro Val Ile Pro Ala His Glu Ala Met Glu Asp Cys Lys Val Gly
385                 390                 395                 400

Gly Tyr His Val Arg Arg Gly Thr Met Ile Leu Val Asn Ala Trp Ala
                405                 410                 415

Ile His Arg Asp Gly Asp Val Trp Gly Ser Pro Glu Glu Phe Arg Pro
                420                 425                 430

Glu Arg Phe Met Asp Asp Gly Ala Gly Ala Gly Ala Val Thr Ala Val
                435                 440                 445

Thr Ala Pro Met Leu Pro Phe Gly Leu Gly Arg Arg Arg Cys Pro Gly
450                 455                 460

Glu Gly Leu Ala Val Arg Leu Val Gly Leu Thr Val Ala Ala Leu Val
465                 470                 475                 480

Gln Cys Phe Asp Trp Glu Ile Gly Glu Gly Gly Ala Val Asp Met Ala
                485                 490                 495

Glu Gly Gly Gly Leu Thr Met Pro Met Ala Thr Pro Leu Ala Ala Val
                500                 505                 510

Cys Arg Pro Arg Glu Phe Val Lys Thr Val Val Ser Asp Cys Phe
                515                 520                 525
```

<210> SEQ ID NO 19
<211> LENGTH: 530
<212> TYPE: PRT
<213> ORGANISM: Sorghum

```
<400> SEQUENCE: 19

Met Ala Ala Ala Gly Leu Ser Leu Ala Ala Phe Leu Leu Val Leu His
1               5                   10                  15

Arg Leu Val Val Val Gly Arg Val Gly Gly Gly Gly Gly Gly Gly Gly
            20                  25                  30

Lys Gly Asn Ser Asn Ala Ala Ala Arg Arg Leu Pro Pro Ser Pro Pro
        35                  40                  45

Ala Val Pro Phe Leu Gly His Leu Pro Leu Leu Val Ser Gly Arg Ala
    50                  55                  60

Phe His Ser Ser Leu Ala Gly Leu Ala Ala Arg His Gly Pro Val Phe
65                  70                  75                  80

Ser Leu Arg Leu Gly Ser Arg Ala Ala Val Val Ser Ser Pro Ala
                85                  90                  95

Cys Ala Glu Ala Cys Phe Thr Glu His Asp Val Ala Phe Ala Asn Arg
                100                 105                 110

Pro Arg Leu Pro Ser Gln Glu Leu Ala Ser Phe Gly Gly Ala Ala Leu
            115                 120                 125

Ala Val Ser Ser Tyr Gly Pro Tyr Trp Arg Thr Leu Arg Arg Val Ala
    130                 135                 140

Ala Val Arg Leu Leu Ser Thr His Arg Val Ala Ser Ser Met Cys Pro
145                 150                 155                 160

Val Ile Ser Ala Glu Val Arg Ala Met Leu Arg Arg Val Met Ser Arg
                165                 170                 175

Ala Ala Ala Asp Gly Arg Val Gln Leu Lys Asp Ser Leu Phe Glu Leu
            180                 185                 190

Ser Leu Ser Val Leu Met Glu Thr Ile Ala Gln Thr Lys Thr Ser Arg
    195                 200                 205

Thr Asp Ala Asp Asp Gly Val Ser Pro Glu Ala His Glu Phe Arg Arg
210                 215                 220

Ile Val Asp Glu Ile Leu Pro Tyr Leu Gly Ala Thr Asn Pro Trp Asp
225                 230                 235                 240

Tyr Leu Pro Ser Phe Leu Arg Arg Phe Asp Val Leu Gly Val Arg Ser
                245                 250                 255

Lys Ile Arg Asp Val Val Gly Arg Arg Asp Ala Phe Leu Gln Arg Leu
            260                 265                 270

Ile Asp Ala Glu Arg Arg Leu Gln Asp Asp Gly Gly Asp Gly Glu
    275                 280                 285

Gly Glu Lys Lys Ser Met Ile Ala Val Met Leu Ser Leu Gln Lys Ser
290                 295                 300

Glu Pro Asp Val Tyr Thr Asp Thr Met Ile Met Ala Leu Cys Gly Leu
305                 310                 315                 320

Phe Thr Ala Gly Thr Glu Thr Thr Ser Ser Thr Ile Glu Trp Ala Met
                325                 330                 335

Ser Leu Leu Leu Asn His Pro Glu Ala Leu Lys Lys Val Glu Ala Glu
            340                 345                 350

Ile Glu Ala Ala Val Gly Thr Ser Gly Gly Leu Ile Thr Met Asp Asp
    355                 360                 365

Val Ala Gly Leu Ser Tyr Leu Gln Cys Val Ile Ser Glu Thr Leu Arg
370                 375                 380

Leu Tyr Pro Val Ala Pro Leu Leu Pro His Glu Ser Ala Ala Asp
385                 390                 395                 400

Cys Ala Val Gly Gly Tyr Asp Val Pro Arg Gly Thr Leu Leu Phe Val
                405                 410                 415
```

```
Asn Ala Tyr Ala Ile His Arg Asp Pro Ala Val Trp Glu Glu Pro Gly
                420                 425                 430

Glu Phe Arg Pro Glu Arg Phe Arg Asp Gly Gly Lys Ala Ala Glu
            435                 440                 445

Ala Glu Ala Glu Gly Arg Leu Met Leu Pro Phe Gly Met Gly Arg Arg
450                 455                 460

Arg Cys Pro Gly Glu Thr Leu Ala Leu Arg Thr Val Gly Leu Val Leu
465                 470                 475                 480

Ala Thr Leu Ile Gln Cys Phe His Trp Asp Arg Val Asp Gly Ala Glu
                485                 490                 495

Ile Asp Met Thr Glu Ser Gly Gly Leu Thr Met Pro Arg Ala Val Pro
            500                 505                 510

Leu Glu Ala Thr Cys Lys Pro Arg Gln Ala Met Arg His Val Leu Asp
            515                 520                 525

Gln Leu
    530

<210> SEQ ID NO 20
<211> LENGTH: 520
<212> TYPE: PRT
<213> ORGANISM: Oryza

<400> SEQUENCE: 20

Met Lys Tyr Ser Thr Ser Val Thr Met Asp Lys Ala Tyr Ile Ala Val
1               5                   10                  15

Phe Ser Ile Val Ile Leu Phe Leu Leu Val Asp Tyr Leu Arg Arg Leu
            20                  25                  30

Arg Gly Gly Gly Thr Ser Asn Gly Lys Asn Lys Gly Met Arg Leu Pro
        35                  40                  45

Pro Gly Leu Pro Ala Val Pro Ile Ile Gly His Leu His Leu Val Lys
50                  55                  60

Lys Pro Met His Ala Thr Leu Ser Arg Leu Ala Ala Arg His Gly Pro
65                  70                  75                  80

Val Phe Ser Leu Arg Leu Gly Ser Arg Arg Ala Val Val Val Ser Ser
                85                  90                  95

Pro Gly Cys Ala Arg Glu Cys Phe Thr Glu His Asp Val Ala Phe Ala
            100                 105                 110

Asn Arg Pro Arg Phe Glu Ser Gln Leu Leu Met Ser Phe Asp Gly Thr
        115                 120                 125

Ala Leu Ala Met Ala Ser Tyr Gly Pro His Trp Arg Asn Leu Arg Arg
130                 135                 140

Val Ala Ala Val Gln Leu Leu Ser Ala Arg Arg Val Gly Leu Met Ser
145                 150                 155                 160

Gly Leu Ile Ala Gly Glu Val Arg Ala Met Val Arg Ser Leu Cys Arg
                165                 170                 175

Arg Pro Ala Ala Ala Pro Val Gln Leu Lys Arg Arg Leu Phe Glu
            180                 185                 190

Leu Ser Leu Ser Val Leu Met Glu Thr Ile Ala Gln Ser Lys Ala Thr
        195                 200                 205

Arg Pro Glu Thr Thr Asp Thr Asp Thr Asp Met Ser Met Glu Ala Gln
210                 215                 220

Glu Tyr Lys Gln Val Val Glu Glu Ile Leu Glu Arg Ile Gly Thr Gly
225                 230                 235                 240

Asn Leu Cys Asp Tyr Leu Pro Ala Leu Arg Trp Phe Asp Val Phe Gly
```

```
                    245                 250                 255
Val Arg Asn Arg Ile Leu Ala Ala Val Ser Arg Arg Asp Ala Phe Leu
            260                 265                 270

Arg Arg Leu Ile Tyr Ala Ala Arg Trp Arg Met Asp Asp Gly Glu Lys
            275                 280                 285

Lys Ser Met Ile Ala Val Leu Leu Thr Leu Gln Lys Thr Gln Pro Glu
            290                 295                 300

Val Tyr Thr Asp Asn Met Ile Thr Ala Leu Cys Ser Asn Leu Leu Gly
305                 310                 315                 320

Ala Gly Thr Glu Thr Thr Ser Thr Thr Ile Glu Trp Ala Met Ser Leu
                325                 330                 335

Leu Leu Asn His Pro Glu Thr Leu Lys Lys Ala Gln Ala Glu Ile Asp
                340                 345                 350

Ala Ser Val Gly Asn Ser Arg Leu Ile Thr Ala Asp Asp Val Pro Arg
                355                 360                 365

Ile Thr Tyr Leu Gln Cys Ile Val Arg Glu Thr Leu Arg Leu Tyr Pro
            370                 375                 380

Ala Ala Pro Met Leu Ile Pro His Glu Ser Ser Ala Asp Cys Glu Val
385                 390                 395                 400

Gly Gly Tyr Ser Val Pro Arg Gly Thr Met Leu Leu Val Asn Ala Tyr
                405                 410                 415

Ala Ile His Arg Asp Pro Ala Ala Trp Glu Glu Pro Glu Arg Phe Val
                420                 425                 430

Pro Glu Arg Phe Glu Gly Gly Gly Cys Asp Gly Asn Leu Ser Met Pro
            435                 440                 445

Phe Gly Met Gly Arg Arg Cys Pro Gly Glu Thr Leu Ala Leu His
450                 455                 460

Thr Val Gly Leu Val Leu Gly Thr Leu Ile Gln Cys Phe Asp Trp Glu
465                 470                 475                 480

Arg Val Asp Gly Val Glu Val Asp Met Ala Glu Gly Gly Leu Thr
                485                 490                 495

Met Pro Lys Val Val Pro Leu Glu Ala Val Cys Arg Pro Arg Asp Ala
            500                 505                 510

Met Gly Gly Val Leu Arg Glu Leu
            515                 520

<210> SEQ ID NO 21
<211> LENGTH: 512
<212> TYPE: PRT
<213> ORGANISM: Oryza

<400> SEQUENCE: 21

Met Asp Lys Ala Tyr Ile Ala Val Phe Ser Ile Val Ile Leu Phe Leu
1               5                   10                  15

Leu Val Asp Tyr Leu Arg Arg Leu Arg Gly Gly Gly Thr Ser Asn Gly
                20                  25                  30

Lys Asn Lys Gly Met Arg Leu Pro Pro Gly Leu Pro Ala Val Pro Ile
            35                  40                  45

Ile Gly His Leu His Leu Val Lys Lys Pro Met His Ala Thr Leu Ser
        50                  55                  60

Arg Leu Ala Ala Arg His Gly Pro Val Phe Ser Leu Arg Leu Gly Ser
65              70                  75                  80

Arg Arg Ala Val Val Val Ser Ser Pro Gly Cys Ala Arg Glu Cys Phe
                85                  90                  95
```

```
Thr Glu His Asp Val Ala Phe Ala Asn Arg Pro Arg Phe Glu Ser Gln
            100                 105                 110

Leu Leu Met Ser Phe Asp Gly Thr Ala Leu Ala Met Ala Ser Tyr Gly
        115                 120                 125

Pro His Trp Arg Asn Leu Arg Arg Val Ala Ala Val Gln Leu Leu Ser
    130                 135                 140

Ala Arg Arg Val Gly Leu Met Ser Gly Leu Ile Ala Gly Glu Val Arg
145                 150                 155                 160

Ala Met Val Arg Ser Leu Cys Arg Pro Ala Ala Ala Pro Val
                165                 170                 175

Gln Leu Lys Arg Arg Leu Phe Glu Leu Ser Leu Ser Val Leu Met Glu
            180                 185                 190

Thr Ile Ala Gln Ser Lys Ala Thr Arg Pro Glu Thr Thr Asp Thr Asp
            195                 200                 205

Thr Asp Met Ser Met Glu Ala Gln Glu Tyr Lys Gln Val Val Glu Glu
    210                 215                 220

Ile Leu Glu Arg Ile Gly Thr Gly Asn Leu Cys Asp Tyr Leu Pro Ala
225                 230                 235                 240

Leu Arg Trp Phe Asp Val Phe Gly Val Arg Asn Arg Ile Leu Ala Ala
                245                 250                 255

Val Ser Arg Arg Asp Ala Phe Leu Arg Arg Leu Ile Tyr Ala Ala Arg
            260                 265                 270

Trp Arg Met Asp Asp Gly Glu Lys Ser Met Ile Ala Val Leu Leu
                275                 280                 285

Thr Leu Gln Lys Thr Gln Pro Glu Val Tyr Thr Asp Asn Met Ile Thr
    290                 295                 300

Ala Leu Cys Ser Asn Leu Leu Gly Ala Gly Thr Glu Thr Thr Ser Thr
305                 310                 315                 320

Thr Ile Glu Trp Ala Met Ser Leu Leu Leu Asn His Pro Glu Thr Leu
                325                 330                 335

Lys Lys Ala Gln Ala Glu Ile Asp Ala Ser Val Gly Asn Ser Arg Leu
            340                 345                 350

Ile Thr Ala Asp Asp Val Pro Arg Ile Thr Tyr Leu Gln Cys Ile Val
        355                 360                 365

Arg Glu Thr Leu Arg Leu Tyr Pro Ala Ala Pro Met Leu Ile Pro His
370                 375                 380

Glu Ser Ser Ala Asp Cys Glu Val Gly Gly Tyr Ser Val Pro Arg Gly
385                 390                 395                 400

Thr Met Leu Leu Val Asn Ala Tyr Ala Ile His Arg Asp Pro Ala Ala
                405                 410                 415

Trp Glu Glu Pro Glu Arg Phe Val Pro Glu Arg Phe Glu Gly Gly Gly
            420                 425                 430

Cys Asp Gly Asn Leu Ser Met Pro Phe Gly Met Gly Arg Arg Cys
        435                 440                 445

Pro Gly Glu Thr Leu Ala Leu His Thr Val Gly Leu Val Leu Gly Thr
    450                 455                 460

Leu Ile Gln Cys Phe Asp Trp Glu Arg Val Asp Gly Val Glu Val Asp
465                 470                 475                 480

Met Ala Glu Gly Gly Leu Thr Met Pro Lys Val Val Pro Leu Glu
                485                 490                 495

Ala Val Cys Arg Pro Arg Asp Ala Met Gly Gly Val Leu Arg Glu Leu
            500                 505                 510
```

<210> SEQ ID NO 22
<211> LENGTH: 512
<212> TYPE: PRT
<213> ORGANISM: Sorghum

<400> SEQUENCE: 22

```
Met Asp Lys Ala Tyr Val Ala Ile Leu Ser Val Thr Phe Leu Phe Leu
1               5                   10                  15

Leu His Tyr Leu Met Gly His Ala Ala Val Gly Gly Lys Arg Lys Arg
            20                  25                  30

Leu Pro Pro Ser Pro Leu Ala Ile Pro Phe Ile Gly His Leu His Leu
        35                  40                  45

Val Lys Thr Pro Phe His Ser Ala Leu Val Arg Leu Ala Ala Arg His
    50                  55                  60

Gly Pro Val Phe Ser Met Arg Met Gly His Arg Arg Ala Val Val Val
65                  70                  75                  80

Ser Ser Pro Glu Cys Ala Lys Ala Cys Phe Thr Glu Tyr Asp Gln Ser
                85                  90                  95

Phe Ala Asn Arg Pro His Phe Gln Ser Met Arg Leu Val Ser Phe Asp
            100                 105                 110

Gly Ala Met Leu Ser Val Ser Ser Tyr Gly Pro Tyr Trp Arg Asn Leu
        115                 120                 125

Arg Arg Val Ala Ala Val Gln Leu Leu Ser Ala His Arg Val Ala Cys
    130                 135                 140

Met Ser Pro Val Ile Ala Ala Glu Val Arg Ala Met Val Arg Arg Met
145                 150                 155                 160

Asn Arg Leu Ala Ala Thr Ser Pro Gly Gly Ala Ala Arg Val Gln Leu
                165                 170                 175

Arg Arg Arg Leu Phe Glu Leu Ser Leu Ser Val Leu Met Glu Thr Ile
            180                 185                 190

Ala Gln Thr Lys Thr Ser Arg Ser Glu Ala Tyr Ala Asp Thr Asp Ile
        195                 200                 205

Ser Pro Glu Ala Asn Glu Leu Thr Gln Ile Ser Gln Glu Ile Met Pro
    210                 215                 220

Tyr Leu Gly Thr Ala Asn Leu Trp Asp Tyr Leu Pro Phe Leu Arg Trp
225                 230                 235                 240

Phe Asp Val Phe Gly Val Arg Asn Lys Leu Met Ala Ala Val Arg Trp
                245                 250                 255

Arg Asp Ala Phe Leu Arg Arg Leu Ile Asp Ala Glu Arg Arg Arg Leu
            260                 265                 270

Asp Asp Ala Gly Asp Ser Glu Lys Ser Met Leu Ala Val Leu Leu
        275                 280                 285

Ser Leu Gln Lys Ser Glu Pro Glu Leu Tyr Thr Asp Thr Met Ile Met
    290                 295                 300

Ala Leu Cys Gly Asp Met Phe Gly Ala Gly Thr Glu Thr Thr Ser Ser
305                 310                 315                 320

Thr Thr Glu Trp Ala Met Ser Leu Leu Leu Asn His Pro Glu Ala Leu
                325                 330                 335

Asn Lys Ala Arg Ala Glu Ile Asp Ala Val Val Gly Ser Ser Arg Leu
            340                 345                 350

Ile Thr Pro Asp Asp Val Pro Arg Leu Gly Tyr Leu His Cys Val Ile
        355                 360                 365

Asn Glu Thr Leu Arg Met Tyr Pro Ala Ala Pro Leu Leu Leu Pro His
    370                 375                 380
```

```
Glu Ser Ser Ala Asp Cys Asn Val Gly Gly Tyr Asp Val Pro Arg Gly
385                 390                 395                 400

Thr Leu Leu Ile Val Asn Ala Tyr Ala Ile His Arg Asp Pro Ala Val
                405                 410                 415

Trp Glu Asp Pro Ala Glu Phe Arg Pro Glu Arg Phe Glu Asp Gly Lys
            420                 425                 430

Ala Glu Gly Arg Leu Leu Met Pro Phe Gly Met Gly Arg Arg Lys Cys
        435                 440                 445

Pro Gly Glu Thr Leu Ala Leu Arg Thr Val Gly Leu Val Leu Gly Thr
    450                 455                 460

Leu Ile Gln Cys Phe Asp Trp Asp Arg Val Asp Gly Val Glu Ile Asp
465                 470                 475                 480

Met Thr Glu Ala Gly Gly Leu Thr Met Pro Arg Ala Val Pro Leu Glu
                485                 490                 495

Ala Thr Cys Lys Pro Arg Ala Ala Val Ser Asp Val Leu Lys Gln Leu
            500                 505                 510

<210> SEQ ID NO 23
<211> LENGTH: 519
<212> TYPE: PRT
<213> ORGANISM: Sorghum

<400> SEQUENCE: 23

Met Glu Pro Ala Tyr Val Ala Ile Leu Ser Phe Val Phe Leu Phe Leu
1               5                   10                  15

Leu His Arg Leu Phe Gly Arg His Arg Arg Ile Asn Gly Lys Asn
            20                  25                  30

Asn Arg Ala Gln Leu Pro Pro Ser Pro Pro Ala Ile Pro Val Leu Gly
        35                  40                  45

His Leu His Leu Leu Gly Lys Lys Pro Ile His Ala Ala Leu Ala Arg
    50                  55                  60

Leu Ala Glu Arg Tyr Gly Pro Val Phe Ser Leu Arg Leu Gly Ser Arg
65                  70                  75                  80

Glu Ala Val Val Val Ser Ser Ala Ala Cys Ala Thr Glu Cys Phe Thr
                85                  90                  95

Glu Asn Asp Val Cys Phe Ala Asn Arg Pro Arg Phe Pro Thr Leu Leu
            100                 105                 110

Leu Val Ser Phe Gly Gly Ala Thr Leu Pro Met Cys Arg Tyr Gly Pro
        115                 120                 125

Tyr Trp Arg Ser Ile Arg Arg Val Ala Thr Val His Leu Leu Ser Ala
130                 135                 140

His Arg Val Ser Cys Met Leu Pro Val Ile Ser Ala Glu Val Arg Ala
145                 150                 155                 160

Met Ala Arg Arg Met Tyr Arg Ser Ala Ala Gly Gly Ala Ala Arg
                165                 170                 175

Val Glu Leu Lys Arg Arg Leu Phe Glu Leu Ser Leu Ser Ala Leu Met
            180                 185                 190

Glu Thr Ile Ala Arg Thr Lys Met Ser Arg Ala Val Ala Asp Asp Asp
        195                 200                 205

Thr Asp Met Ser Pro Glu Ala Gln Glu Phe Met Lys Ala Leu Asp Val
    210                 215                 220

Leu Leu Arg Leu Leu Ser Ala Ala Asn Ser Trp Asp Tyr Leu Pro Val
225                 230                 235                 240

Leu Arg Trp Leu Asp Met Phe Gly Val Arg Asn Lys Ile Leu Ala Ala
                245                 250                 255
```

Val Ser Ala Arg Asp Ala Phe Leu Arg Arg Leu Ile Asp Ala Glu Arg
            260                 265                 270

Arg Arg Leu Glu Glu Gly Glu Gly Glu Asn Asp Glu Lys Lys Ser
        275                 280                 285

Met Ile Gly Val Leu Leu Ser Leu Gln Lys Ser Glu Pro Glu Val Tyr
290                 295                 300

Thr Asp Thr Thr Ile Met Ala Leu Cys Ser Ser Met Phe Ala Gly Gly
305                 310                 315                 320

Ser Glu Thr Thr Ala Thr Thr Ala Glu Trp Ala Met Ser Leu Leu Leu
                325                 330                 335

Ser His Pro Asp Val Leu Lys Lys Ala Gln Ala Glu Ile Asp Ala Ser
            340                 345                 350

Val Gly His Ser Arg Leu Leu Gly Ala Asp Asp Val Pro Arg Leu Gly
                355                 360                 365

Tyr Leu Gln Cys Ile Val Thr Glu Thr Leu Arg Leu Tyr Pro Val Val
            370                 375                 380

Pro Thr Leu Val Pro His Glu Ser Thr Ala Asp Cys Thr Val Gly Gly
385                 390                 395                 400

His His Val Pro Ser Gly Thr Met Leu Leu Val Asn Val Tyr Ala Ile
                405                 410                 415

His Arg Asp Pro Ala Thr Trp Ala Asp Pro Ala Ala Phe Arg Pro Glu
            420                 425                 430

Arg Phe Glu Asp Gly Gly Arg Ala Gln Gly Leu Phe Met Met Pro Phe
        435                 440                 445

Gly Met Gly Arg Arg Lys Cys Pro Gly Glu Ala Leu Ala Leu Arg Thr
450                 455                 460

Leu Gly Leu Val Leu Gly Thr Leu Ile Gln Cys Phe Asp Trp Glu Thr
465                 470                 475                 480

Val Gly Gly Ala Glu Val Asp Met Ala Glu Gly Val Gly Ile Thr Leu
                485                 490                 495

Pro Arg Ala Val Pro Leu Glu Ala Ile Cys Lys Pro Arg His Ala Met
            500                 505                 510

Leu Glu Val Leu Lys Gly Leu
        515

<210> SEQ ID NO 24
<211> LENGTH: 513
<212> TYPE: PRT
<213> ORGANISM: Zea

<400> SEQUENCE: 24

Met Asp Lys Ala Tyr Val Ala Ala Leu Ser Val Ala Phe Leu Phe Leu
1               5                   10                  15

Val His Tyr Leu Val Gly Arg Ala Ala Ala Gly Gly Lys Gly Arg
            20                  25                  30

Lys Arg Leu Pro Pro Ser Pro Leu Ala Ile Pro Phe Leu Gly His Leu
        35                  40                  45

His Leu Val Lys Thr Pro Phe His Ser Ala Leu Gly Arg Leu Ala Glu
    50                  55                  60

Arg His Gly Pro Val Phe Ser Leu Arg Met Gly Cys Arg Arg Ala Val
65                  70                  75                  80

Val Val Ser Ser Pro Glu Cys Ala Arg Ala Cys Phe Thr Glu His Asp
                85                  90                  95

Met Ser Phe Ala Asn Arg Pro Arg Phe Glu Ser Met Arg Leu Val Ser

```
                100                 105                 110
Phe Asp Gly Ala Met Leu Ser Val Ser Ser Tyr Gly Pro Tyr Trp Arg
            115                 120                 125

Thr Leu Arg Arg Val Ala Ala Val Gln Leu Leu Ser Ala His Arg Val
            130                 135                 140

Ala Cys Met Ser Pro Val Ile Cys Ala Glu Val Arg Ala Met Val Arg
145                 150                 155                 160

Arg Met Ala Arg Leu Ala Ala Gly Gly Ala Ala Arg Val Gln Leu Arg
                165                 170                 175

Arg Arg Leu Phe Glu Leu Ser Leu Gly Val Leu Met Glu Thr Ile Ala
            180                 185                 190

Arg Thr Lys Thr Ser Arg Ser Glu Ala Cys Ala Ala Asp Thr Asp Val
            195                 200                 205

Ser Pro Glu Ala Ser Glu Leu Thr Arg Ile Ser Glu Glu Ile Met Pro
    210                 215                 220

Tyr Leu Gly Thr Ala Asn Leu Trp Asp Tyr Leu Pro Phe Leu Arg Trp
225                 230                 235                 240

Phe Asp Val Phe Gly Val Arg Asn Lys Leu Met Ala Ala Val Arg Trp
                245                 250                 255

Arg Asp Ala Phe Leu Arg Arg Leu Ile Asp Ala Glu Arg Arg Arg Met
            260                 265                 270

Asp Gly Asp Gly Asp Gly Glu Lys Lys Ser Met Ile Ala Val Leu Leu
            275                 280                 285

Ser Leu Gln Lys Ser Glu Pro Glu Leu Tyr Thr Asp Thr Met Ile Met
    290                 295                 300

Ala Leu Cys Gly Asp Leu Phe Gly Ala Gly Thr Glu Thr Thr Ser Val
305                 310                 315                 320

Thr Thr Glu Trp Ala Met Ser Leu Leu Leu Ser His Pro Glu Ala Leu
                325                 330                 335

Lys Lys Ala Gln Ala Glu Ile Asp Ala Val Val Gly Asn Ser Arg Arg
            340                 345                 350

Leu Ile Thr Ala Asp Asp Val Pro Arg Leu Gly Tyr Leu His Cys Val
            355                 360                 365

Ile Asn Glu Thr Leu Arg Met Tyr Pro Ala Ala Pro Leu Leu Leu Pro
    370                 375                 380

His Glu Ser Ala Ala Asp Cys Lys Val Gly Gly Tyr Asp Val Pro Arg
385                 390                 395                 400

Gly Thr Leu Leu Ile Val Asn Ala Tyr Ala Ile His Arg Asp Pro Ala
                405                 410                 415

Val Trp Glu Asp Pro Gly Ser Phe Leu Pro Glu Arg Phe Glu Asp Gly
            420                 425                 430

Lys Ala Glu Gly Arg Leu Leu Met Pro Phe Gly Met Gly Arg Arg Lys
            435                 440                 445

Cys Pro Gly Glu Thr Leu Ala Leu Arg Thr Val Gly Leu Val Leu Ala
    450                 455                 460

Thr Leu Leu Gln Cys Phe Asp Trp Asp Thr Val Asp Gly Ala Glu Val
465                 470                 475                 480

Asp Met Thr Glu Ser Gly Gly Leu Thr Met Pro Arg Ala Val Pro Leu
                485                 490                 495

Glu Ala Met Cys Lys Pro Arg Ala Ala Met Cys Asp Val Leu Arg Glu
            500                 505                 510

Leu
```

```
<210> SEQ ID NO 25
<211> LENGTH: 517
<212> TYPE: PRT
<213> ORGANISM: Zea

<400> SEQUENCE: 25
```

| | | | | | | | | | | | | | | |
|---|---|---|---|---|---|---|---|---|---|---|---|---|---|---|
| Met | Asp | Lys | Ala | Tyr | Ile | Ala | Ala | Leu | Ser | Ala | Ala | Leu | Phe | Leu |
| 1 | | | | 5 | | | | | 10 | | | | | 15 |
| Leu | His | Tyr | Leu | Leu | Gly | Arg | Arg | Ala | Gly | Gly | Glu | Gly | Lys | Thr | Lys |
| | | | 20 | | | | | 25 | | | | | 30 | | |
| Gly | Ser | Gln | Arg | Arg | Leu | Pro | Pro | Ser | Pro | Pro | Ala | Ile | Pro | Phe | Leu |
| | | | 35 | | | | | 40 | | | | | 45 | | |
| Gly | His | Leu | His | Leu | Val | Lys | Ala | Pro | Phe | His | Ala | Ala | Leu | Ala | Arg |
| | | 50 | | | | | 55 | | | | | 60 | | | |
| Leu | Ala | Ala | Arg | His | Gly | Pro | Val | Phe | Ser | Met | Arg | Leu | Gly | Thr | Arg |
| 65 | | | | | 70 | | | | | 75 | | | | | 80 |
| Arg | Ala | Val | Val | Val | Ser | Ser | Pro | Asp | Cys | Ala | Arg | Glu | Cys | Phe | Thr |
| | | | | 85 | | | | | 90 | | | | | 95 | |
| Glu | His | Asp | Val | Asn | Phe | Ala | Asn | Arg | Pro | Leu | Phe | Pro | Ser | Met | Arg |
| | | | 100 | | | | | 105 | | | | | 110 | | |
| Leu | Ala | Ser | Phe | Asp | Gly | Ala | Met | Leu | Ser | Val | Ser | Ser | Tyr | Gly | Pro |
| | | | 115 | | | | | 120 | | | | | 125 | | |
| Tyr | Trp | Arg | Asn | Leu | Arg | Arg | Val | Ala | Ala | Val | Gln | Leu | Leu | Ser | Ala |
| | | 130 | | | | | 135 | | | | | 140 | | | |
| His | Arg | Val | Ala | Cys | Met | Ala | Pro | Ala | Ile | Glu | Ala | Gln | Val | Arg | Ala |
| 145 | | | | | 150 | | | | | 155 | | | | | 160 |
| Met | Val | Arg | Arg | Met | Asp | Arg | Ala | Ala | Ala | Gly | Gly | Gly | Gly | Ala |
| | | | | 165 | | | | | 170 | | | | | 175 | |
| Ala | Arg | Val | Gln | Leu | Lys | Arg | Arg | Leu | Phe | Glu | Leu | Ser | Leu | Ser | Val |
| | | | 180 | | | | | 185 | | | | | 190 | | |
| Leu | Met | Glu | Thr | Ile | Ala | His | Thr | Lys | Thr | Ser | Arg | Ala | Glu | Ala | Asp |
| | | | 195 | | | | | 200 | | | | | 205 | | |
| Ala | Asp | Ser | Asp | Met | Ser | Pro | Glu | Ala | His | Glu | Phe | Lys | Gln | Ile | Val |
| | | 210 | | | | | 215 | | | | | 220 | | | |
| Asp | Glu | Leu | Val | Pro | Tyr | Ile | Gly | Thr | Ala | Asn | Arg | Trp | Asp | Tyr | Leu |
| 225 | | | | | 230 | | | | | 235 | | | | | 240 |
| Pro | Val | Leu | Arg | Trp | Phe | Asp | Val | Phe | Gly | Val | Arg | Asn | Lys | Ile | Leu |
| | | | | 245 | | | | | 250 | | | | | 255 | |
| Asp | Ala | Val | Gly | Arg | Arg | Asp | Ala | Phe | Leu | Arg | Arg | Leu | Ile | Asp | Gly |
| | | | 260 | | | | | 265 | | | | | 270 | | |
| Glu | Arg | Arg | Arg | Leu | Asp | Ala | Gly | Asp | Asp | Ser | Glu | Ser | Lys | Ser | Met |
| | | | 275 | | | | | 280 | | | | | 285 | | |
| Ile | Ala | Val | Leu | Leu | Thr | Leu | Gln | Lys | Ser | Glu | Pro | Glu | Val | Tyr | Thr |
| | | 290 | | | | | 295 | | | | | 300 | | | |
| Asp | Thr | Val | Ile | Thr | Ala | Leu | Cys | Ala | Asn | Leu | Phe | Gly | Ala | Gly | Thr |
| 305 | | | | | 310 | | | | | 315 | | | | | 320 |
| Glu | Thr | Thr | Ser | Thr | Thr | Glu | Trp | Ala | Met | Ser | Leu | Leu | Leu | Asn |
| | | | | 325 | | | | | 330 | | | | | 335 | |
| His | Arg | Glu | Ala | Leu | Lys | Lys | Ala | Gln | Ala | Glu | Ile | Asp | Ala | Ala | Val |
| | | | 340 | | | | | 345 | | | | | 350 | | |
| Gly | Thr | Ser | Arg | Leu | Val | Thr | Ala | Asp | Val | Pro | His | Leu | Thr | Tyr |
| | | | 355 | | | | | 360 | | | | | 365 | | |
| Leu | Gln | Cys | Ile | Val | Asp | Glu | Thr | Leu | Arg | Leu | His | Pro | Ala | Ala | Pro |
| | | 370 | | | | | 375 | | | | | 380 | | | |

Leu Leu Leu Pro His Glu Ser Ala Ala Asp Cys Thr Val Gly Gly Tyr
385                 390                 395                 400

Asp Val Pro Arg Gly Thr Met Leu Leu Val Asn Val His Ala Val His
                405                 410                 415

Arg Asp Pro Ala Val Trp Asp Pro Asp Arg Phe Val Pro Glu Arg
            420                 425                 430

Phe Glu Gly Gly Lys Ala Glu Gly Arg Leu Leu Met Pro Phe Gly Met
                435                 440                 445

Gly Arg Arg Lys Cys Pro Gly Glu Thr Leu Ala Leu Arg Thr Val Gly
                450                 455                 460

Leu Val Leu Gly Thr Leu Leu Gln Cys Phe Asp Trp Asp Thr Val Asp
465                 470                 475                 480

Gly Ala Gln Val Asp Met Lys Ala Ser Gly Gly Leu Thr Met Pro Arg
                485                 490                 495

Ala Val Pro Leu Glu Ala Met Cys Arg Pro Arg Thr Ala Met Arg Asp
                500                 505                 510

Val Leu Lys Arg Leu
            515

<210> SEQ ID NO 26
<211> LENGTH: 515
<212> TYPE: PRT
<213> ORGANISM: Brachypodium

<400> SEQUENCE: 26

Met Asp Lys Ala Tyr Ile Ala Val Leu Ser Leu Ala Phe Leu Phe Leu
1               5                   10                  15

Val His Tyr Leu Leu Gly Lys Ile Asn Gly Asn Lys Gln Lys Thr Ser
                20                  25                  30

Lys Leu Gln Leu Pro Pro Ser Pro Ala Ile Pro Phe Leu Gly His
            35                  40                  45

Leu His Leu Val Glu Thr Pro Phe His Leu Ala Leu Arg Arg Leu Ala
        50                  55                  60

Ala Arg His Gly Pro Val Phe Tyr Leu Arg Leu Gly Ser Arg Arg Ala
65                  70                  75                  80

Val Val Val Ser Ser Ala Ala Cys Ala Arg Glu Cys Phe Thr Glu His
                85                  90                  95

Asp Val Thr Phe Ala Asn Arg Pro Gln Phe Pro Ser Gln Gln Leu Val
            100                 105                 110

Ser Phe Asp Gly Ala Gly Leu Ala Gln Ser Ser Tyr Gly Pro His Trp
        115                 120                 125

Arg Asn Leu Arg Arg Val Ala Ala Val Gln Leu Leu Ser Ala His Arg
130                 135                 140

Val Ala Cys Met Ser Gly Val Ile Ser Ala Glu Val Arg Ala Met Ala
145                 150                 155                 160

Arg Arg Leu Phe Arg Ala Ser Ser Ala Pro Ala Arg Val Gln Leu
            165                 170                 175

Lys Arg Arg Leu Phe Glu Leu Ser Leu Ser Val Leu Met Glu Thr Ile
            180                 185                 190

Ala Arg Thr Lys Gly Thr Arg Pro Glu Ala Asp Ala Asp Val Asp Met
            195                 200                 205

Ser Val Glu Ala Gln Glu Phe Lys Lys Leu Val Asp Glu Ile Val Pro
        210                 215                 220

His Leu Gly Thr Ala Asn Leu Trp Asp Tyr Leu Pro Leu Leu Arg Trp

```
            225                 230                 235                 240
        Phe Asp Val Met Gly Val Arg Asn Lys Ile Leu Lys Leu Val Arg Arg
                        245                 250                 255

Arg Asp Val Phe Leu Gly Arg Leu Ile Asp Ala Glu Arg Arg Arg Leu
                        260                 265                 270

Asp Glu Gly Gly Asp Gly Asp Lys Lys Ser Met Ile Ser Val Met
                    275                 280                 285

Leu Thr Leu Gln Lys Thr Glu Pro Glu Leu Tyr Thr Asp Thr Met Ile
                290                 295                 300

Lys Ser Leu Cys Ala Asn Leu Phe Gly Ala Gly Thr Glu Thr Thr Ser
        305                 310                 315                 320

Thr Thr Thr Glu Trp Ala Met Ser Leu Leu Leu Asn His Pro Glu Val
                        325                 330                 335

Leu Lys Lys Ala Gln Ala Glu Met Asp Ser Cys Val Gly Thr Ser Arg
                        340                 345                 350

Leu Val Ser Phe Asp Asp Val Pro Arg Leu Ala Tyr Leu Gln Cys Val
                        355                 360                 365

Leu Ser Glu Thr Leu Arg Leu Tyr Pro Ala Ala Pro Leu Leu Leu Pro
                370                 375                 380

His His Ser Ser Ala Asp Thr Lys Val Gly Gly Tyr Asp Val Pro Ala
        385                 390                 395                 400

Asp Thr Met Leu Ile Val Asn Ala Tyr Ala Ile His Arg Glu Pro Ala
                        405                 410                 415

Gly Ala Trp Gly Glu Arg Pro Glu Glu Phe Arg Pro Glu Arg Phe Glu
                        420                 425                 430

Asp Gly Lys Ala Glu Gly Ala Phe Met Ile Pro Phe Gly Met Gly Arg
                    435                 440                 445

Arg Arg Cys Pro Gly Glu Thr Leu Ala Leu Arg Thr Val Gly Met Val
                    450                 455                 460

Leu Ala Thr Leu Val Gln Cys Phe Asp Trp Glu Arg Val Asp Gly Leu
        465                 470                 475                 480

Glu Val Asp Met Ala Glu Gly Gly Leu Thr Met Pro Lys Val Val
                        485                 490                 495

Pro Leu Glu Ala Val Cys Thr Pro Arg Gly Thr Met Leu Arg Val Leu
                        500                 505                 510

Arg Glu Leu
                515

<210> SEQ ID NO 27
<211> LENGTH: 544
<212> TYPE: PRT
<213> ORGANISM: Oryza

<400> SEQUENCE: 27

Met Val Ala Gly Gly Gly Asn Gly Gly Ala Ala Val Leu Val Gly Ile
        1               5                   10                  15

Thr Val Leu Leu Phe Val Val Val Val Val Val Leu Val Arg
                        20                  25                  30

Trp Trp Ser Gly Gly Glu Gly Gly Ala Ala Pro Ser Pro Pro Ala Leu
                        35                  40                  45

Pro Val Leu Gly His Leu His Leu Leu Lys Pro Leu His Arg Ser
                    50                  55                  60

Leu Ala Ala Val Ala Ala Gly Val Gly Ala Pro Val Val Ser Leu Arg
        65                  70                  75                  80
```

-continued

```
Leu Gly Ala Arg Arg Ala Leu Val Val Ser Thr His Ala Ala Ala Glu
             85                  90                  95

Glu Cys Phe Thr Ala Cys Asp Ala Ala Leu Ala Gly Arg Pro Arg Thr
        100                 105                 110

Leu Ala Gly Glu Ile Leu Gly Tyr Asp His Thr Ile Val Leu Trp Thr
    115                 120                 125

Pro His Gly Asp His Trp Arg Ala Leu Arg Arg Phe Leu Ala Val Glu
130                 135                 140

Leu Leu Ser Ala Pro Arg Leu Ala Ala Leu Ala Ala Asp Arg His Ala
145                 150                 155                 160

Glu Ala Ala Ser Leu Val Asp Ala Ile Leu Arg Asp Ala Ala Gly Gly
                165                 170                 175

Ala Lys Val Thr Leu Arg Pro Arg Leu Phe Glu Leu Val Leu Asn Val
            180                 185                 190

Met Leu Arg Ala Ala Thr Thr Arg Arg His Ala Ser Val Asp Ala
        195                 200                 205

Arg Lys Leu Gln Glu Ile Ile Glu Glu Thr Phe Ser Val Asn Gly Thr
    210                 215                 220

Pro Ser Val Gly Asp Phe Phe Pro Ala Leu Arg Trp Val Asp Arg Leu
225                 230                 235                 240

Arg Gly Lys Val Gly Ser Leu Lys Lys Leu Gln Ala Arg Arg Asp Ala
                245                 250                 255

Met Val Thr Gly Leu Ile Asp Asp His Arg Gln Trp Arg Ser Gly Ser
            260                 265                 270

Ala Gly Asp Gly Asp Gln Asp Lys Glu Lys Lys Gly Val Ile Asp Ala
        275                 280                 285

Leu Leu Ala Leu Gln Glu Thr Asp Pro Asp His Tyr Thr Asp Asn Val
    290                 295                 300

Val Lys Gly Ile Ile Leu Phe Ser Ile Thr Val Pro Leu Leu His Phe
305                 310                 315                 320

Tyr Ser Ile Val Ile Asn Met Tyr Asn Gly Phe Asp His Gly Val Gln
                325                 330                 335

Ser Leu Leu Phe Ala Gly Thr Asp Thr Ser Ala Leu Thr Ile Glu Trp
            340                 345                 350

Ala Met Ala Gln Leu Val Thr His Pro Glu Thr Met Lys Lys Ala Arg
        355                 360                 365

Ala Glu Ile Asp Ala Asn Val Gly Thr Ala Arg Leu Val Glu Glu Ala
    370                 375                 380

Asp Met Ala Asn Leu Pro Tyr Ile Gln Cys Val Ile Lys Glu Thr Leu
385                 390                 395                 400

Arg Leu Arg Thr Ala Gly Pro Val Ile Pro Ala His Glu Ala Met Glu
                405                 410                 415

Asp Thr Thr Val Gly Gly Phe Arg Val Ala Arg Gly Thr Lys Val Leu
            420                 425                 430

Val Asn Ala Trp Ala Ile His Arg Asp Gly Asp Val Trp Asp Ala Pro
        435                 440                 445

Glu Glu Phe Arg Pro Glu Arg Phe Val Asp Ser Asp Ala Gly Gly Ala
    450                 455                 460

Val Thr Ala Pro Met Met Pro Phe Gly Leu Gly Arg Arg Arg Cys Pro
465                 470                 475                 480

Gly Glu Gly Leu Ala Val Arg Val Val Gly Val Ser Val Ala Ala Leu
                485                 490                 495

Val Gln Cys Phe Asp Trp Glu Val Gly Asp Asp Asp Val Val Asp Met
```

```
                500               505               510
Thr Glu Gly Gly Gly Leu Thr Met Pro Met Ala Thr Pro Leu Ala Ala
            515               520               525
Val Cys Arg Pro Arg Glu Phe Val Lys Thr Ile Leu Ser Thr Ser Met
            530               535               540

<210> SEQ ID NO 28
<211> LENGTH: 516
<212> TYPE: PRT
<213> ORGANISM: Bambus

<400> SEQUENCE: 28

Met Asp Lys Thr Tyr Val Ala Ile Leu Ser Phe Ala Phe Leu Leu Leu
1               5                   10                  15
Leu His Tyr Leu Val Gly Arg Ser Gly Gly Asn Ser Asn Val Lys Lys
            20                  25                  30
Lys Asp Val Gln Leu Pro Pro Ser Pro Ala Ala Ile Pro Phe Leu Gly
            35                  40                  45
His Leu His Leu Val Glu Lys Pro Phe His Ala Ala Leu Ser Arg Leu
    50                  55                  60
Ala Ala Arg His Gly Pro Val Phe Ser Leu Arg Leu Gly Ser Arg Asn
65                  70                  75                  80
Thr Val Val Val Ser Ser Pro Ala Cys Ala Arg Glu Cys Phe Thr Glu
                85                  90                  95
His Asp Val Ser Phe Ala Asn Arg Pro Leu Phe Pro Ser Gln Leu Leu
            100                 105                 110
Val Ser Phe Asn Gly Thr Ala Leu Ala Ala Ser Ser Tyr Gly Pro Tyr
            115                 120                 125
Trp Arg Asn Leu Arg Arg Ile Ala Thr Val Gln Leu Leu Ser Ala His
        130                 135                 140
Arg Val Ser Cys Met Ser Gly Val Ile Ser Ala Glu Val Arg Ala Met
145                 150                 155                 160
Val Leu Arg Met Tyr Arg Ala Ala Ala Ala Pro Gly Ser Ala Ala
                165                 170                 175
Arg Ile Leu Leu Lys Arg Arg Leu Leu Glu Leu Ser Leu Ser Val Leu
            180                 185                 190
Met Glu Thr Ile Ala Lys Thr Lys Ala Thr Arg Pro Glu Ala Asp Ala
            195                 200                 205
Asp Thr Asp Met Ser Val Glu Ala Gln Glu Phe Lys Lys Met Ser Asp
        210                 215                 220
Glu Ile Ile Pro Gln Leu Gly Thr Ala Asn Leu Trp Asp Tyr Leu Pro
225                 230                 235                 240
Val Leu Arg Trp Phe Asp Val Phe Gly Val Arg Asn Lys Val Leu Asp
                245                 250                 255
Ala Val Arg Arg Arg Asp Ala Phe Leu Arg Arg Leu Ile Asp Ala Glu
            260                 265                 270
Arg Gln Arg Leu Asp Asp Gly Ser Glu Ser Glu Lys Ser Ser Met Ile
        275                 280                 285
Ala Val Leu Leu Thr Leu Gln Arg Thr Glu Pro Glu Val Tyr Thr Asp
    290                 295                 300
Ala Met Ile Thr Ala Leu Cys Gly Asn Leu Phe Gly Ala Gly Thr Glu
305                 310                 315                 320
Thr Ile Ser Ile Thr Thr Glu Trp Ala Met Ser Leu Leu Leu Asn His
                325                 330                 335
```

```
Pro Glu Thr Leu Arg Lys Ala Gln Ala Glu Ile Asp Ala Ser Val Gly
            340                 345                 350

Ser Ser Arg Leu Val Ser Ala Asp Asp Met Pro Arg Leu Ser Tyr Leu
        355                 360                 365

Gln Cys Ile Val Ser Glu Thr Leu Arg Leu Tyr Pro Ala Ala Pro Leu
    370                 375                 380

Leu Leu Pro His Glu Ser Ser Thr Asp Cys Lys Val Gly Gly Tyr Asn
385                 390                 395                 400

Ile Pro Ser Gly Thr Met Leu Leu Val Asn Ala Tyr Ala Ile Gln Arg
                405                 410                 415

Asp Pro Thr Val Trp Glu Glu Pro Thr Lys Phe Lys Pro Glu Arg Phe
            420                 425                 430

Glu Asp Gly Lys Ala Glu Gly Leu Phe Met Ile Pro Phe Gly Met Gly
        435                 440                 445

Arg Arg Lys Cys Pro Gly Glu Thr Leu Ala Leu Arg Thr Ile Gly Leu
    450                 455                 460

Val Leu Gly Thr Leu Ile Gln Cys Phe Asp Trp Asp Thr Val Asp Gly
465                 470                 475                 480

Val Glu Val Asp Met Thr Glu Ser Gly Gly Ile Ser Met Pro Lys Ala
                485                 490                 495

Val Pro Leu Glu Ala Ile Cys Lys Pro Arg Ala Ala Met Tyr Gly Val
            500                 505                 510

Leu Gln Asn Leu
        515

<210> SEQ ID NO 29
<211> LENGTH: 517
<212> TYPE: PRT
<213> ORGANISM: Lolium

<400> SEQUENCE: 29

Met Asp Lys Ala Tyr Ile Ala Ile Leu Ser Cys Ala Phe Leu Phe Leu
1               5                   10                  15

Val His Tyr Val Leu Gly Lys Val Ser Asp Gly Arg Arg Gly Lys Lys
            20                  25                  30

Gly Ala Val Gln Leu Pro Pro Ser Pro Pro Ala Val Pro Phe Leu Gly
        35                  40                  45

His Leu His Leu Val Asp Lys Pro Ile His Ala Thr Met Cys Arg Leu
    50                  55                  60

Ala Ala Arg Leu Gly Pro Val Phe Ser Leu Arg Leu Gly Ser Arg Arg
65                  70                  75                  80

Ala Val Val Val Ser Ser Ser Glu Cys Ala Arg Glu Cys Phe Thr Glu
                85                  90                  95

His Asp Val Thr Phe Ala Asn Arg Pro Lys Phe Pro Ser Gln Leu Leu
            100                 105                 110

Val Ser Phe Asn Gly Thr Ala Leu Val Thr Ser Ser Tyr Gly Pro His
        115                 120                 125

Trp Arg Asn Leu Arg Arg Val Ala Thr Val Gln Leu Leu Ser Ala His
    130                 135                 140

Arg Val Ala Cys Met Ser Gly Val Ile Ala Ala Glu Val Arg Ala Met
145                 150                 155                 160

Ala Arg Arg Leu Phe His Ala Thr Glu Ala Ser Pro Asp Gly Ala Ala
                165                 170                 175

Arg Val Gln Leu Lys Arg Arg Leu Phe Glu Leu Ser Leu Ser Val Leu
            180                 185                 190
```

```
Met Glu Thr Ile Ala Gln Thr Lys Ala Thr Arg Ser Glu Ala Asp Ala
    195                 200                 205

Asp Thr Asp Met Ser Val Glu Ala Gln Glu Phe Lys Glu Val Val Asp
    210                 215                 220

Lys Leu Ile Pro His Leu Gly Ala Ala Asn Met Trp Asp Tyr Leu Pro
225                 230                 235                 240

Val Met Arg Trp Phe Asp Val Phe Gly Val Arg Asn Lys Ile Leu His
                245                 250                 255

Ala Val Ser Arg Arg Asp Ala Phe Leu Arg Arg Leu Ile Asp Ala Glu
            260                 265                 270

Arg Arg Arg Leu Ala Asp Gly Gly Ser Asp Gly Asp Lys Lys Ser Met
        275                 280                 285

Ile Ala Val Leu Leu Thr Leu Gln Lys Thr Glu Pro Lys Val Tyr Thr
    290                 295                 300

Asp Thr Met Ile Thr Ala Leu Cys Ala Asn Leu Phe Gly Ala Gly Thr
305                 310                 315                 320

Glu Thr Thr Ser Thr Thr Thr Glu Trp Ala Met Ser Leu Leu Leu Asn
                325                 330                 335

His Pro Ala Ala Leu Lys Lys Ala Gln Ala Glu Ile Asp Ala Ser Val
            340                 345                 350

Gly Thr Ser Arg Leu Val Ser Val Asp Asp Val Pro Ser Leu Ala Tyr
        355                 360                 365

Leu Gln Cys Ile Val Ser Glu Thr Leu Arg Leu Tyr Pro Ala Ala Pro
    370                 375                 380

Leu Leu Leu Pro His Glu Ser Ser Ala Asp Cys Lys Val Gly Gly Tyr
385                 390                 395                 400

Asn Val Pro Ala Asp Thr Met Leu Ile Val Asn Ala Tyr Ala Ile His
                405                 410                 415

Arg Asp Pro Ala Ala Trp Glu Asp Pro Leu Glu Phe Arg Pro Glu Arg
            420                 425                 430

Phe Glu Asp Gly Lys Ala Glu Gly Leu Phe Met Ile Pro Phe Gly Met
        435                 440                 445

Gly Arg Arg Arg Cys Pro Gly Glu Thr Leu Ala Leu Arg Thr Ile Gly
    450                 455                 460

Met Val Leu Ala Thr Leu Val Gln Cys Phe Asp Trp Glu Pro Val Asp
465                 470                 475                 480

Gly Val Lys Val Asp Met Thr Glu Gly Gly Phe Thr Ile Pro Lys
                485                 490                 495

Ala Val Pro Leu Glu Ala Val Cys Arg Pro Arg Ala Val Met Arg Asp
            500                 505                 510

Val Leu Gln Asn Leu
        515

<210> SEQ ID NO 30
<211> LENGTH: 576
<212> TYPE: PRT
<213> ORGANISM: Brachypodium

<400> SEQUENCE: 30

Met Glu Phe Lys Pro Thr Val Leu Tyr Gly Cys Val Trp Pro Lys Ser
1               5                   10                  15

Gly Arg Arg Ala Glu Lys Ala Leu Lys Asn Thr Thr Pro Lys Thr Thr
            20                  25                  30

Ala Arg Val Ala Ala Gly Trp Arg His Ser His Arg His Pro Asn Gln
```

```
            35                  40                  45
Pro Val Asn Leu Ile Met Asp Asn Ala Tyr Ile Ala Ala Leu Ser Leu
 50                  55                  60

Ala Phe Val Phe Leu Leu His Tyr Leu Leu Lys Gly Lys Arg Ser Asn
 65                  70                  75                  80

Gly Gly Asn Leu Pro Pro Ser Pro Pro Ala Ile Pro Ile Leu Gly His
                 85                  90                  95

Leu His Leu Val Glu Lys Pro Leu His Ala Ala Leu Trp Arg Leu Ala
                100                 105                 110

Gly Arg Leu Gly Pro Val Phe Ser Leu Arg Leu Gly Ser Arg Pro Val
            115                 120                 125

Val Val Val Ser Ser Pro Glu Leu Ala Lys Glu Cys Phe Thr Glu His
130                 135                 140

Asp Val Thr Phe Ala Asp Arg Pro Gln Phe Pro Ser Gln Leu Leu Val
145                 150                 155                 160

Ser Phe Gly Gly Thr Ala Leu Ala Thr Ala Ser Tyr Gly Pro His Trp
                165                 170                 175

Arg Asn Leu Arg Arg Val Ala Ala Val His Leu Leu Ser Ala His Arg
                180                 185                 190

Val Ala Ala Met Ser Ser Gly Val Ile Ser Ala Glu Val Arg Ala Met
            195                 200                 205

Ala Arg Arg Leu Phe Arg Ala Ser Ala Asp Gly Ser Gly Gly Ala Arg
210                 215                 220

Val Gln Leu Lys Arg Arg Leu Phe Glu Leu Ser Leu Ser Val Leu Met
225                 230                 235                 240

Glu Ala Ile Ala Gln Thr Lys Ala Thr Arg Pro Asp Asp Ala Asp Gly
                245                 250                 255

Asp Asp Thr Asp Met Ser Val Glu Ala Gln Glu Phe Lys Lys Val Val
                260                 265                 270

Asp Glu Ile Ile Pro His Leu Gly Thr Ala Asn Leu Trp Asp Tyr Leu
            275                 280                 285

Pro Val Leu Arg Trp Phe Asp Val Phe Gly Val Arg Asn Lys Ile Leu
290                 295                 300

Ala Ala Val Arg Arg Asp Ala Phe Leu Gly Arg Leu Ile Glu Ala
305                 310                 315                 320

Glu Arg Arg Arg Leu Glu Glu Glu Gly Gly Glu Gly Asp Gln Gln
                325                 330                 335

Gly Glu Lys Thr Ser Met Ile Ala Val Leu Leu Thr Leu Gln Lys Thr
            340                 345                 350

Glu Pro Glu Val Tyr Thr Asp Thr Met Ile Thr Ala Leu Cys Ala Asn
                355                 360                 365

Leu Phe Gly Ala Gly Thr Glu Thr Thr Ser Thr Thr Thr Glu Trp Ala
            370                 375                 380

Met Ser Leu Leu Leu Asn His Pro Glu Val Leu Lys Lys Ala Gln Ala
385                 390                 395                 400

Glu Met Asp Ala Ser Val Gly Thr Ser Arg Leu Val Thr Ala Asp Asp
                405                 410                 415

Val Ala His Arg Leu Pro Tyr Leu Gln His Ile Val Ser Glu Thr Leu
                420                 425                 430

Arg Leu Tyr Pro Ala Ala Pro Met Leu Leu Pro His Gln Ser Ser Ala
            435                 440                 445

Asp Cys Lys Ile Gly Gly Tyr Thr Val Pro Arg Gly Thr Met Leu Leu
450                 455                 460
```

```
Val Asn Ala Tyr Ala Ile His Arg Asp Pro Ala Ala Trp Gly Pro Ala
465                 470                 475                 480

Pro Glu Glu Phe Arg Pro Glu Arg Phe Glu Asp Ala Ser Asn Lys Gly
            485                 490                 495

Glu Glu Leu Pro Leu Met Leu Pro Phe Gly Met Gly Arg Arg Lys Cys
        500                 505                 510

Pro Gly Glu Thr Leu Ala Leu Arg Thr Val Gly Met Val Leu Gly Thr
    515                 520                 525

Leu Val Gln Cys Phe Glu Trp Glu Arg Val Gly Gly Val Glu Val Asp
530                 535                 540

Met Thr Gln Gly Thr Gly Leu Thr Met Pro Lys Ala Val Pro Leu Glu
545                 550                 555                 560

Ala Val Cys Arg Pro Arg Ala Ala Met Arg Asp Val Leu Gln Lys Leu
                565                 570                 575

<210> SEQ ID NO 31
<211> LENGTH: 1731
<212> TYPE: DNA
<213> ORGANISM: Brachypodium

<400> SEQUENCE: 31
atggaattta aacccactgt cctctacggc tgcgtctggc ccaagagcgg aagaagagca      60
gagaaggctc tcaagaacac cactccgaaa acaacagccc gagttgcagc aggatggcgg     120
cacagtcaca gacatccaaa tcaaccagtt aaccttatca tggataacgc ttacattgcc     180
gccctctcct tggccttcgt cttcctgctc cactaccttc tcaagggcaa gaggagcaat     240
ggcggcaacc tgccgccgag cccgcctgcc atcccgatcc tgggccacct ccacctggtc     300
gagaagccgc tccacgcggc cctctggcgc tcgcgggcc gtctcggccc ggtcttctcc      360
cttcgtctcg gctcccggcc agtcgtggtc gtctcctccc ggagctcgc caaggagtgc      420
ttcacggagc acgacgtgac cttcgccgac cggccccagt tcccgtcgca gctgctcgtg     480
tccttcggcg gcaccgcgct cgccacggcc agctacggcc gcactggcg caacctccgc      540
cgcgtcgccg ccgtgcacct gctctccgcg caccgcgtcg ccgccatgtc ctccggcgtc     600
atctccgccg aggtccgcgc catggcgcgc cgcctcttcc gcgcctccgc cgacggcagt     660
ggcggcgcca gggtgcagct gaagcggcgg ctgttcgagc tgtccctgag cgtgctcatg     720
gaggccatcg cgcagaccaa ggcgacgcgc ccggacgatg ccgacggcga cgacacggac     780
atgtccgtgg aggcgcagga gttcaagaag gtggtggacg agatcatccc gcacctcggg     840
accgccaacc tctgggatta cctgccggtc ttgcggtggt tcgacgtgtt cggggtgagg     900
aacaagatcc tggctgcggt taggagacgg acgcgttcc tgggccggct gattgaagcg      960
gagcgaagga ggcttgagga ggaaggcggc ggagaagggg atcagcaagg ggagaagacg    1020
agcatgatcg ccgtgctgct cactttgcag aagacggagc cggaggtgta caccgatacc    1080
atgatcacgg ctctctgtgc gaatctattc ggggccggga cggagacgac ctcgacgacg    1140
acggaatggg ccatgtcgct gctcctgaac cacccagagg tcctcaagaa agcgcaggcc    1200
gagatggacg cctccgtggg cacctccggc ctcgtcaccg ccgacgacgt ggcccaccgg    1260
ctcccgtacc tgcagcacat cgtgagcgag acgctccggc tctacccggc ggcgccgatg    1320
ctgctgccgc accagtcctc ggccgactgc aagatcggcg gctacaccgt cccgcgcggc    1380
acgatgctgc tggtgaacgc gtacgccatc cacaggacc ccgccgcctg ggcccggcg      1440
ccggaggagt tcaggccgga gaggttcgag gacgcgagta ataagggcga ggagttgcct    1500
```

```
ttgatgctgc cgttcgggat ggggcggcgc aagtgccccg gcgagacgct ggcgctgcgg      1560
acggtgggga tggtgctggg cacgctggtg cagtgcttcg agtgggagag ggtgggggga      1620
gtggaggtgg acatgacgca ggggaccggg ctcaccatgc ccaaggccgt gccgctcgag      1680
gccgtctgcc ggccgcgcgc cgccatgcgt gacgtgcttc agaagctcta g              1731

<210> SEQ ID NO 32
<211> LENGTH: 1572
<212> TYPE: DNA
<213> ORGANISM: Brachypodium

<400> SEQUENCE: 32
atggataacg cttatattgc tgctctctcc ctcgctttcg tgttccttct tcattacctt        60
ctcaagggca agaggtctaa cggtggaaac cttccaccat ctccaccagc tattccaatt       120
cttggacatc ttcacctcgt tgagaagcca cttcatgctg cactttggag acttgctggt       180
agacttggac cagtgttctc tcttaggctt ggatctagac cagttgtggt tgtttcttca       240
ccagagcttg ccaaagaatg cttcaccgag catgatgtta ctttcgctga taggccacag       300
ttcccatctc agcttttggt ttctttcgga ggaactgctc ttgctactgc ttcttatgga       360
ccacattgga ggaaccttag aagagttgct gctgtgcatc ttttgtctgc tcatagagtt       420
gccgctatgt cctctggtgt tatttctgct gaagttaggg ctatggccag aaggcttttc       480
agagcttctg ctgatggatc tggtggtgct agagttcaac ttaagagaag gctgttcgag       540
ttgtcccttt ccgttctcat ggaagctatt gctcaaacta aggctaccag gccagatgat       600
gctgatggtg atgataccga tatgtccgtt gaagcccaag agttcaagaa agtggtggat       660
gagattatcc cacaccttgg aactgctaac ctttgggatt accttccagt gctcagatgg       720
ttcgatgttt tcggagtgag gaacaagatt ctcgctgctg ttagaagaag ggatgctttc       780
cttggaaggc ttattgaggc tgagagaaga aggcttgaag aggaaggtgg cggagaaggc       840
gatcaacaag gtgaaaagac ttctatgatt gccgtgcttc tcacccttca aaagactgaa       900
ccagaggttt acaccgatac catgattact gctttgtgcg ctaacttgtt cggagctgga       960
actgagacta cttctactac tactgagtgg gctatgtccc ttttgcttaa ccatcctgag      1020
gtgctcaaga aagctcaggc tgaaatggat gcttctgttg aacttctag gcttgtgacc       1080 gctgatgatg ttgctcatag gcttccatac cttcagcaca ttgtgtctga gactcttagg      1140
ttgtatccag ctgctccaat gcttcttcca catcagtcat ctgctgattg caagattgga      1200
ggatacactg ttccaagggg tactatgctt cttgtgaacg cttacgctat tcacagagat      1260
cctgctgctt ggggaccagc tccagaagaa ttcagaccag aaagattcga ggacgcttct      1320
aacaagggtg aggaacttcc acttatgctc ccattcggta tgggtagaag aaagtgccca      1380
ggtgaaactc ttgctcttag gactgttgga atggtgcttg aactcttgt tcaatgcttc       1440 gagtgggaaa gggttggagg tgttgaagtt gatatgactc agggaactgg actcactatg      1500
ccaaaggctg tgccacttga agctgtgtgc agaccaagag ctgctatgag agatgttctt      1560
cagaagctgt ga                                                          1572
```

PLANTS HAVING INCREASED TOLERANCE TO HERBICIDES

This application is a National Stage application of International Application No. PCT/IB2014/063876, filed Aug. 12, 2014, which claims the benefit of U.S. Provisional Application No. 61/864,671, filed Aug. 12, 2013, U.S. Provisional Application No. 61/864,672, filed Aug. 12, 2013, and U.S. Provisional Application No. 61/866,067, filed Aug. 15, 2013, the entire contents of which are hereby incorporated herein by reference in their entirety.

REFERENCE TO SEQUENCE LISTING SUBMITTED VIA EFS-WEB

This amendment was filed electronically via EFS-Web and includes an electronically submitted sequence listing in .txt format. The .txt file contains a sequence listing entitled "75866_Seqlisting.txt" created on Feb. 8, 2016, and is 133,417 bytes in size. The sequence listing contained in this .txt file is part of the specification and is hereby incorporated by reference herein in its entirety.

FIELD OF THE INVENTION

The present invention relates in general to methods for conferring on plants agricultural level tolerance to a herbicide. Particularly, the invention refers to plants having an increased tolerance to PPO-inhibiting herbicides. More specifically, the present invention relates to methods and plants obtained by mutagenesis and cross-breeding and transformation that have an increased tolerance to PPO-inhibiting herbicides.

BACKGROUND OF THE INVENTION

Herbicides that inhibit protoporphyrinogen oxidase (hereinafter referred to as Protox or PPO; EC:1.3.3.4), a key enzyme in the biosynthesis of protoporphyrin IX, have been used for selective weed control since the 1960s. PPO catalyzes the last common step in chlorophyll and heme biosynthesis which is the oxidation of protoporphyrinogen IX to protoporphyrin IX. (Matringe et al. 1989. Biochem. 1. 260: 231). PPO-inhibiting herbicides include many different structural classes of molecules (Duke et al. 1991. Weed Sci. 39: 465; Nandihalli et al. 1992. Pesticide Biochem. Physiol. 43: 193; Matringe et al. 1989. FEBS Lett. 245: 35; Yanase and Andoh. 1989. Pesticide Biochem. Physiol. 35: 70). These herbicidal compounds include the diphenylethers {e.g. lactofen, (+−)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobenzoic acid; its methyl ester; or oxyfluorfen, 2-chloro-1-(3-ethoxy-4-nitrophenoxy)-4-(trifluorobenzene)}, oxidiazoles, (e.g. oxidiazon, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its 0-phenylpyrrolidino- and piperidinocarbamate analogs. Many of these compounds competitively inhibit the normal reaction catalyzed by the enzyme, apparently acting as substrate analogs.

Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death (Lee et al. 1993. Plant Physiol. 102: 881).

Cytochrome P450 monooxygenases ("CYP450s") form a large diverse gene family with about 246 isoforms in *Arabidopsis* and 372 identified in rice. CYP450s are hemoproteins that convert a broad range of substrates to more or less bioactive products. The reaction cycle catalyzed by CYP450s requires the sequential input of two reducing equivalents (i.e., two electrons and two protons). The reducing equivalents for the CYP450-catalyzed reaction are supplied by either NADPH or NADH, depending on the type of redox system concerned, and electron transfer is mediated by two co-factors, one of which is FAD; the other being either FMN or an iron-sulfur $Fe_2S_2$ redoxin (ferredoxin) or, in the microsomal system, cytochrome b5. In particular, the majority of bacterial CYP450s utilize an electron transport chain which consists of an FAD-containing NADH-dependent oxidoreductase, and reduction is mediated by ferredoxin. The mitochondrial system in mammalia bears many similarities with the prokaryotic P450 electron transport chain, except that NADPH is the source of reducing equivalents, and both systems are generally referred to as Class I (see Lewis and Hlavica, Biochimica et Biophysica Acta 1460 (2000) 353-374, as well as references contained therein).

CYP450s are critical in numerous metabolic pathways, including lignin and pigment biosynthesis, detoxification of harmful compounds, and are considered important in the evolution of land plants. Inhibitors of CYP450 activity include 1-aminobenzo-triazole, tetcyclacis, piperonyl butoxide, cinnamonic acid, and tridiphane.

It is believed that PPO-inhibiting herbicides such as, e.g. Saflufenacil inhibits the pigment biosynthesis pathway at PPO, which causes an accumulation of photodynamic, toxic compounds that rapidly damage cell membranes and results in cell death. Herbicidal compositions comprising PPO-inhibiting herbicides have been labeled for pre-plant or pre-emergence treatment in corn, sorghum, wheat, barley, oats, rye, triticale, soybean, and tree/nut/vine cropping systems. PPO inhibitor-containing herbicidal compositions have good foliar and residual activity on broadleaf weeds in both no-till and tilled cropping systems. However, application of PPO-inhibiting herbicides after emergence can result in rapid and significant crop injury. Thus, interest has been gained in the enzymatic degradation or modification of PPO-inhibiting herbicides, both due to concern about the environmental fate of the molecule and as an additional complementation to the systems for engineering herbicide-tolerant plants by augmenting PPO levels in the plant, or replacing the native PPO with a modified PPO conferring tolerance to PPO-inhibiting herbicides.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor. The third strategy was described for successfully obtaining plants which were tolerant to PPO inhibitors (see e.g. U.S. Pat. Nos. 5,767,373 or 5,939,602, and patent family members thereof.). In addition, US 2010/0100988 and WO 2007/024739 discloses nucleotide sequences encoding amino acid sequences having enzymatic activity such that the amino acid sequences are resistant to PPO inhibitor herbicidal chemicals, in particular 3-phenyluracil inhibitor specific PPO mutants.

WO 2012/080975 discloses plants the tolerance of which to a PPO-inhibiting herbicide had been increased by transforming said plants with nucleic acids encoding mutated PPO (mutated PPO) enzymes. In particular, WO 2012/080975 discloses that the introduction of nucleic acids which code for a mutated PPO of an *Amaranthus* type II PPO in which the Arginine at position 128 had been replaced by a leucine, alanine, or valine, and the phenylalanine at position 420 had been replaced by a methionine, cysteine, isoleucine, leucine, or threonine, confers increased tolerance/resistance to a benzoxazinone-derivative herbicide ((1, 5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione). The inventors of the present invention have now surprisingly found that the co-expression of a wildtype and mutated type II PPO together with a cytochrome P450 monooxygenase from *Brachypodium distachyon* (BRADI CYP450; bradi_1g07930.1) confer increased tolerance/resistance of plants to a wide variety of PPO inhibitors including, but not limited to a "benzoxazinone-derivative" herbicide ((1,5-dimethyl-6-thioxo-3-(2,2, 7-trifluoro-3-oxo-4-(prop-2-ynyl)-3,4-dihydro-2H-benzo[b][1,4]oxazin-6-yl)-1,3,5-triazinane-2,4-dione) described in WO 2012/080975.

SUMMARY OF THE INVENTION

In one aspect, the present invention provides a plant or plant part comprising (i) a recombinant polynucleotide encoding a wildtype or mutated PPO polypeptide, and (ii) a recombinant polynucleotide encoding a CYP450 polypeptide, the expression of said polynucleotides (i) and (ii) confers to the plant or plant part tolerance to PPO-inhibiting herbicides.

In some aspects, the present invention provides a seed capable of germination into a plant comprising in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to PPO-inhibiting herbicides.

In one aspect, the present invention provides a plant cell of or capable of regenerating a plant comprising in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to PPO-inhibiting herbicides, wherein the plant cell comprises the recombinant polynucleotide (i) and (ii) operably linked to a promoter.

In another aspect, the present invention provides a plant cell comprising (i) a recombinant polynucleotide operably linked to a promoter operable a cell, the promoter capable of expressing a CYP450 polypeptide encoded by the polynucleotide, and (ii) a recombinant polynucleotide operably linked to a promoter operable in a cell, the promoter capable of expressing a wildtype or mutated PPO polypeptide encoded by the polynucleotide, the expression of the wildtype or mutated PPO and the CYP450 polypeptide conferring to the plant tolerance to PPO-inhibiting herbicides.

In other aspects, the present invention provides a plant product prepared from a plant or plant part comprising in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to PPO-inhibiting herbicides.

In some aspects, the present invention provides a progeny or descendant plant derived from a plant comprising in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, wherein the progeny or descendant plant comprises in at least some of its cells the recombinant polynucleotide (i) and (ii) operably linked to the promoter, the expression of the wildtype or mutated PPO and the CYP450 polypeptide conferring to the progeny or descendant plant tolerance to the PPO-inhibiting herbicides.

In other aspects, the present invention provides a method for controlling weeds at a locus for growth of a plant, the method comprising: (a) applying an herbicide composition comprising PPO-inhibiting herbicides to the locus; and (b) planting a seed at the locus, wherein the seed is capable of producing a plant that comprises in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to PPO-inhibiting herbicides.

In some aspects, the present invention provides a method for controlling weeds at a locus for growth of a plant, the method comprising: applying an herbicidal composition comprising PPO-inhibiting herbicides to the locus; wherein said locus is: (a) a locus that contains: a plant or a seed capable of producing said plant; or (b) a locus that is to be after said applying is made to contain the plant or the seed; wherein the plant or the seed comprises in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to PPO-inhibiting herbicides.

In one aspect, step (a) occurs before, after, or concurrently with step (b).

In other aspects, the present invention provides a method of producing a plant having tolerance to PPO-inhibiting herbicides, the method comprising regenerating a plant from a plant cell transformed with (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to PPO-inhibiting herbicides.

In one aspect, the present invention provides a method of producing a progeny plant having tolerance to PPO-inhibiting herbicides, the method comprising: crossing a first PPO-inhibiting herbicides-tolerant plant with a second plant to produce a PPO-inhibiting herbicides-tolerant progeny plant, wherein the first plant and the progeny plant comprise in at least some of their cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to PPO-inhibiting herbicides.

In still further aspects, the present invention provides a plant or plant part comprising in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to PPO-inhibiting herbicides, wherein the plant or plant part further exhibits a second or third herbicide-tolerant trait.

In another embodiment, the invention refers to a method of producing a transgenic plant cell with an increased resistance to a PPO-inhibiting herbicide as compared to a wild type variety of the plant cell comprising, transforming the plant cell with an expression cassette comprising a (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide.

In another embodiment, the invention refers to a method of producing a transgenic plant comprising, (a) transforming a plant cell with an expression cassette comprising a (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, and (b) generating a plant with an increased resistance to PPO-inhibiting herbicide from the plant cell.

Preferably, the expression cassette further comprises a transcription initiation regulatory region and a translation initiation regulatory region that are functional in the plant.

1=non-transgenic; 2=AMATU_PPO2_L397D_F420V; 3=AMATU_PPO2_L397D_F420V+Bradi01g07930; A=untreated control, B=75 g/ha saflufenacil+120 g/ha carfentrazone, C=50 g/ha saflufenacil+60 g/ha carfentrazone, D=25 g/ha saflufenacil+30 g/ha carfentrazone.

Figure 4A:
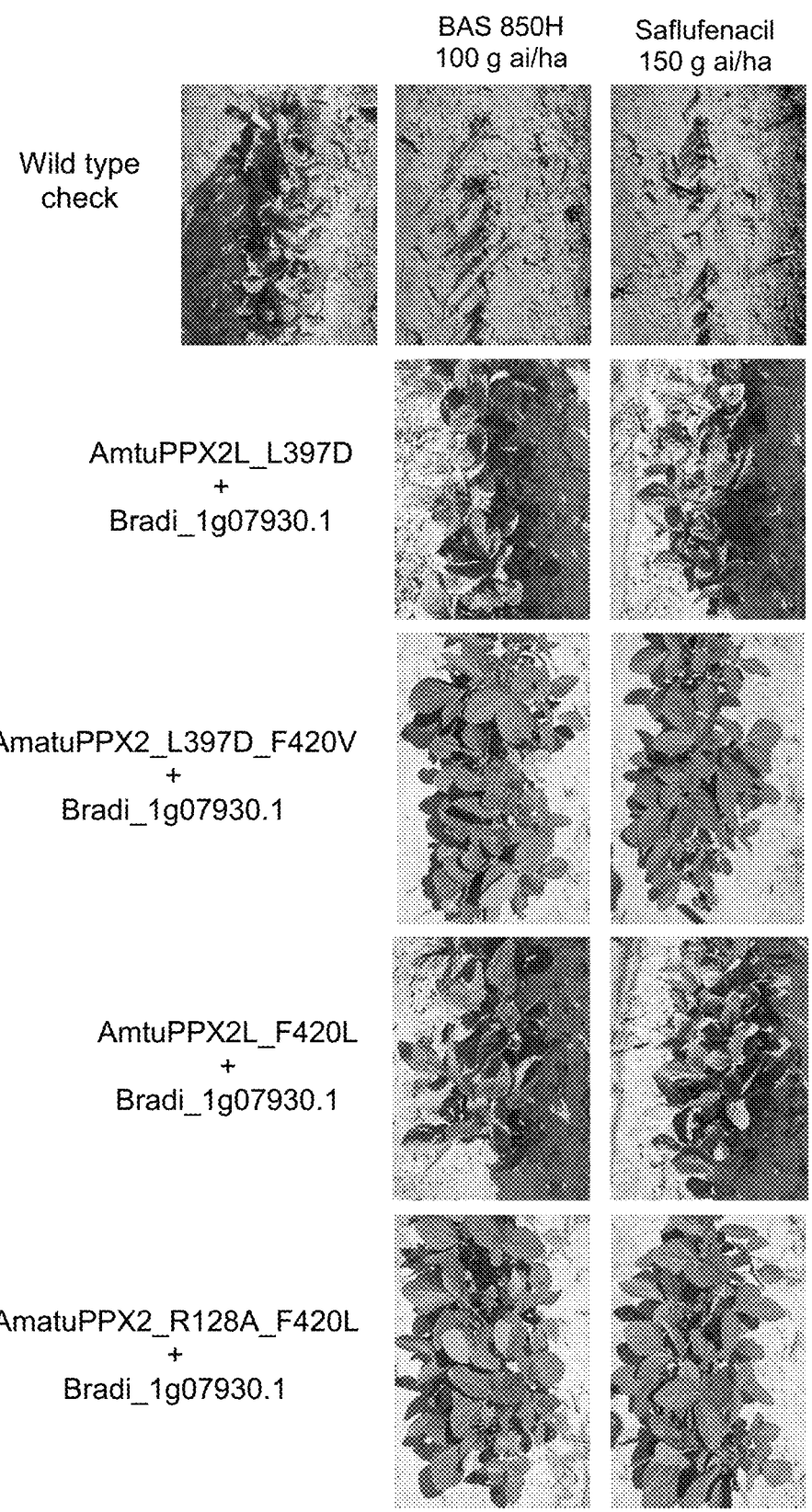

FIG. 4a shows T1 transformed soybean plants expressing the indicated gene-of-interest(s) were sprayed in the field with the indicated herbicide and rate+1% (v/v) MSO. Plants were sprayed at the V2-V3 stage. Pictures were taken 20 days after treatment.

Figure 4B:
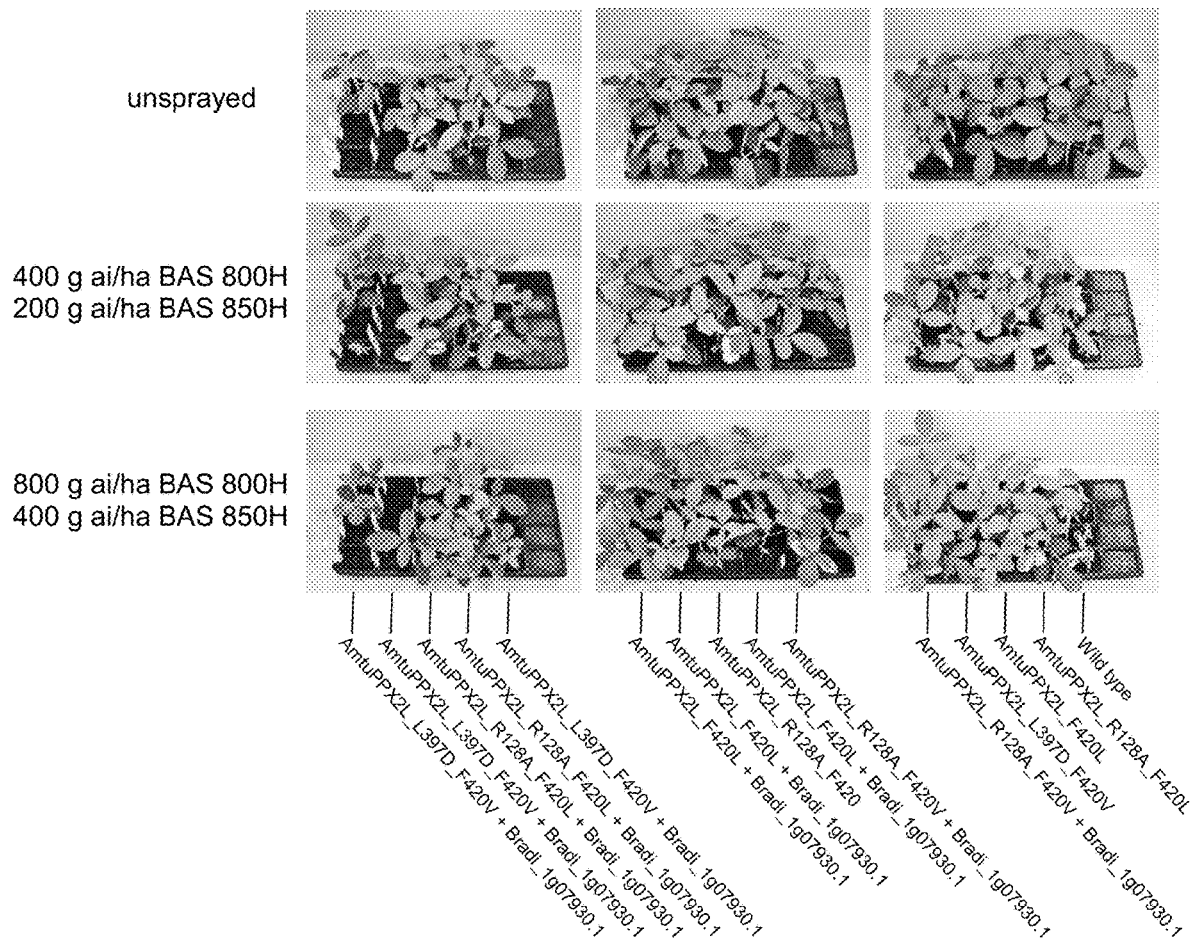

FIG. 4B shows T2 Transformed soybean 14 days after the indicated treatment. Plants were sprayed at the V2-V3 stage. Treatments contained 1% (v/v) MSO. Each row of plants is an independent event.

Figure 4C:
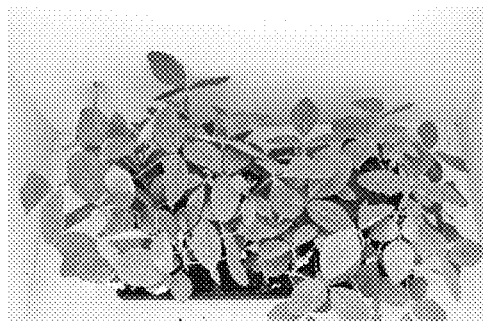
Figure 4C:
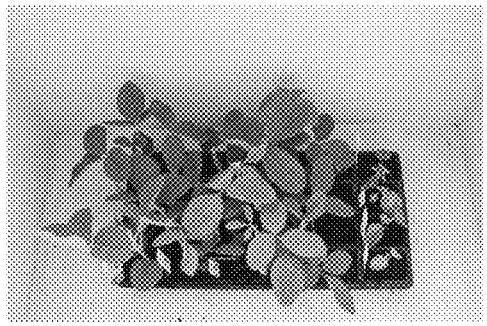
Figure 4C:
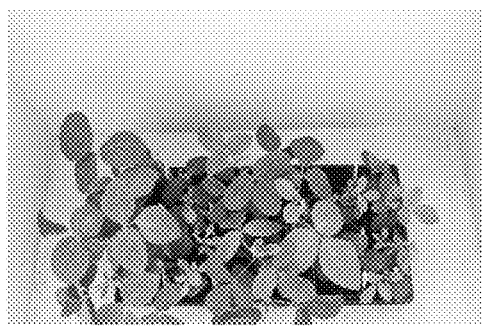
Figure 4C:
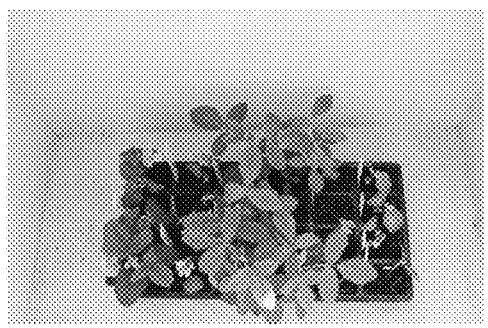
Figure 4C:
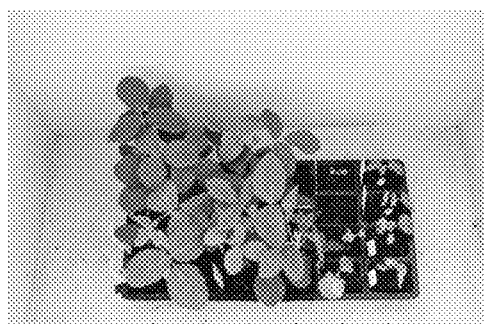

FIG. 4c shows T2 Transformed soybean 14 days after the indicated treatment. Plants were sprayed at the V2-V3 stage. Treatments contained 1% (v/v) MSO. Each row of plants is an independent event.

Figure 4:
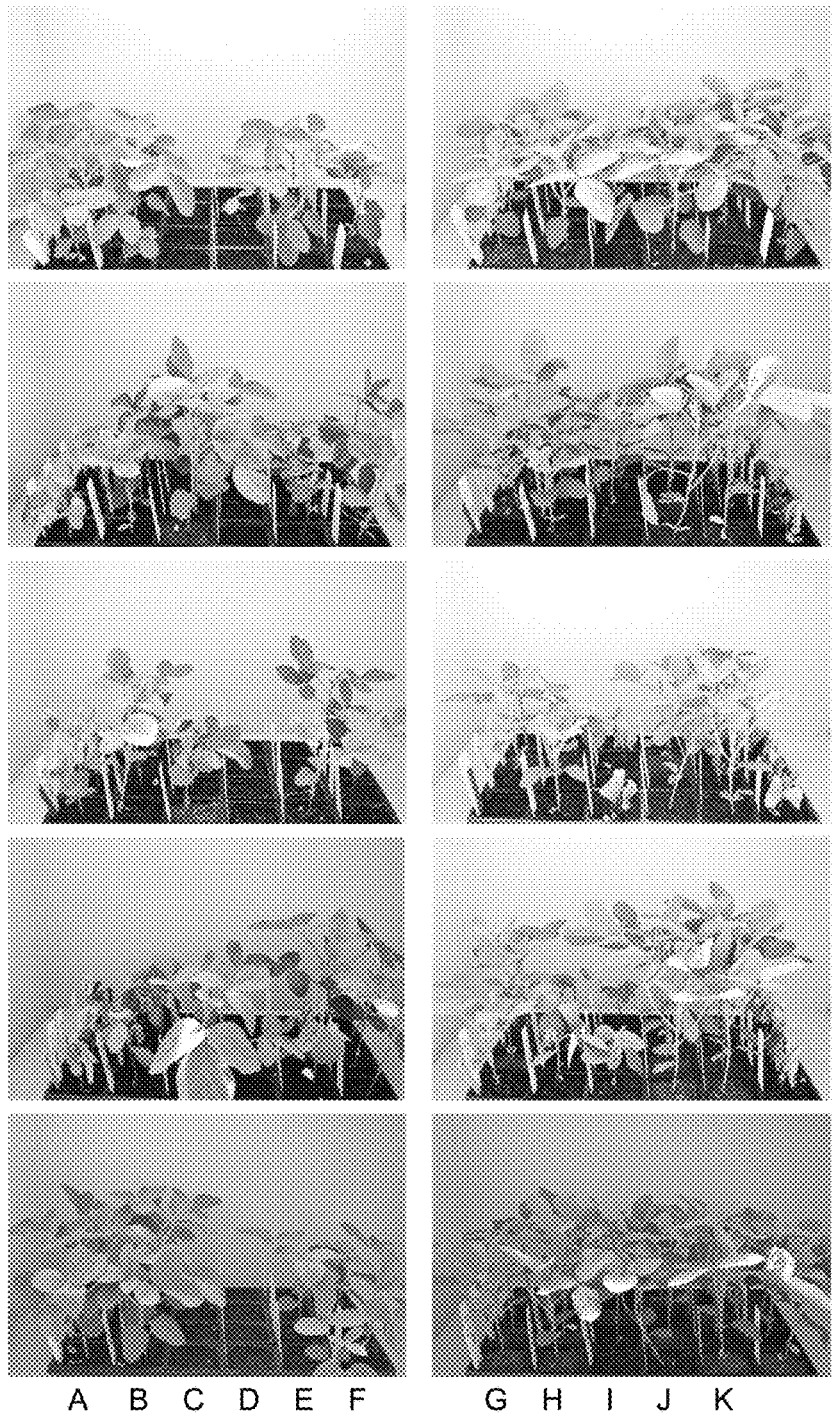

A. Bradi_1g07930.1
B. AmtuPPX2L_R128A_F420V
C. AmtuPPX2L_R128A_F420V+Bradi_1g07930.1
D. AmtuPPX2L_R128A_F420V+Bradi_1g07930.1
E. AmtuPPX2L_R128A_F420V
F. Wild type FIG. 4 D shows T2 Transformed soybean 7 days after the indicated treatment. Plants were sprayed at the V2-V3 stage. Treatments contained 1% (v/v) MSO. Each row of plants is an independent event.

A. Bradi_1g07930.1
B. AmtuPPX2L_R128A_F420V
C. AmtuPPX2L_R128A_F420V+Bradi_1g07930.1

D. AmtuPPX2L_L397D_F420V
E. AmtuPPX2L_L397D_F420V
F. AmtuPPX2L_L397D_F420V+Brad i_1g07930.1
G. AmtuPPX2L_L397D_F420V+Bradi_1g07930.1
H. AmtuPPX2L_R128A_F420L
I. AmtuPPX2L_R128A_F420L
J. AmtuPPX2L_R128A_F420VL+Bradi_1g07930.1
K. AmtuPPX2L_R128A_F420VL+Bradi_1g07930.1
L. Wild type

KEY TO SEQUENCE LISTING

TABLE 1

| SEQ. ID NO: | Description | Organism | Gene | Accession No: Gene locus |
|---|---|---|---|---|
| 1 | PPO nucleic acid | Amaranthus tuberculatum | PPO2 | |
| 2 | PPO amino acid | Amaranthus tuberculatum | PPO2 | |
| 3 | PPO nucleic acid | Alopecurus myosuroides | PPO2 | |
| 4 | PPO amino acid | Alopecurus myosuroides | PPO2 | |
| 5 | CYP450 nucleic acid | Brachypodium distachyon | | Bradi_1g07930.1 |
| 6 | CYP450 amino acid | Brachypodium distachyon | | Bradi_1g07930.1 |
| 7 | CYP450 amino acid | Oryza | | |
| 8 | CYP450 amino acid | Zea | | |
| 9 | CYP450 amino acid | Sorghum | | |
| 10 | CYP450 amino acid | Oryza | | |
| 11 | CYP450 amino acid | Zea | | |
| 12 | CYP450 amino acid | Zea | | |
| 13 | CYP450 amino acid | Oryza | | |
| 14 | CYP450 amino acid | Oryza | | |
| 15 | CYP450 amino acid | Oryza | | |
| 16 | CYP450 amino acid | Lolium | | |
| 17 | CYP450 amino acid | Oryza | | |
| 18 | CYP450 amino acid | Oryza | | |
| 19 | CYP450 amino acid | Sorghum | | |
| 20 | CYP450 amino acid | Oryza | | |
| 21 | CYP450 amino acid | Oryza | | |
| 22 | CYP450 amino acid | Sorghum | | |
| 23 | CYP450 amino acid | Sorghum | | |
| 24 | CYP450 amino acid | Zea | | |
| 25 | CYP450 amino acid | Zea | | |
| 26 | CYP450 amino acid | Brachypodium | | |
| 27 | CYP450 amino acid | Oryza | | |
| 28 | CYP450 amino acid | Bambus | | |
| 29 | CYP450 amino acid | Lolium | | |
| 30 | CYP450 amino acid | Brachypodium distachyon | | |
| 31 | CYP450 nucleic acid | Brachypodium distachyon | | |
| 32 | CYP450 nucleic acid | Brachypodium distachyon | | |

DETAILED DESCRIPTION

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The term "control of undesired vegetation or weeds" is to be understood as meaning the killing of weeds and/or otherwise retarding or inhibiting the normal growth of the weeds. Weeds, in the broadest sense, are understood as meaning all those plants which grow in locations where they are undesired. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsi-* cum spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera), Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max), Gossypium hirsutum, Helianthus* spp. (e.g. *Helianthus annuus), Hemerocallis fulva, Hibiscus* spp., *Hordeum* spp. (e.g. *Hordeum vulgare), Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme), Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia), Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum), Sorghum bicolor, Spinacia* spp., *Syzygium* spp., *Tagetes* spp., *Tamarindus* indica, *Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare), Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferably, the plant is a monocotyledonous plant, such as sugarcane. Further preferably, the plant is a cereal, such as rice, maize, wheat, barley, millet, rye, sorghum or oats.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by herbicides useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope. As used herein, in regard to an herbicidal composition useful in various embodiments hereof, terms such as PPO-inhibiting herbicides, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

When used in reference to a particular mutant enzyme or polypeptide, terms such as herbicide-tolerant and herbicide-tolerance refer to the ability of such enzyme or polypeptide to perform its physiological activity in the presence of an amount of an herbicide A.I. that would normally inactivate or inhibit the activity of the wild-type (non-mutant) version of said enzyme or polypeptide. For example, when used specifically in regard to an PPO enzyme, it refers specifically to the ability to tolerate a PPO-inhibitor. By "herbicide-tolerant wildtype or mutated PPO protein" or "herbicide-resistant wildtype or mutated PPO protein", it is intended that such a PPO protein displays higher PPO activity, relative to the PPO activity of a wild-type PPO protein, when in the presence of at least one herbicide that is known to interfere with PPO activity and at a concentration or level of the herbicide that is known to inhibit the PPO activity of the wild-type or mutated PPO protein. Furthermore, the PPO activity of such a herbicide-tolerant or herbicide-resistant wildtype or mutated PPO protein may be referred to herein as "herbicide-tolerant" or "herbicide-resistant" PPO activity.

As used herein, "recombinant," when referring to nucleic acid or polypeptide, indicates that such material has been altered as a result of human application of a recombinant technique, such as by polynucleotide restriction and ligation, by polynucleotide overlap-extension, or by genomic insertion or transformation. A gene sequence open reading frame is recombinant if that nucleotide sequence has been removed from it natural text and cloned into any type of artificial nucleic acid vector. The term recombinant also can refer to an organism having a recombinant material, e.g., a plant that comprises a recombinant nucleic acid can be considered a recombinant plant.

The term "transgenic plant" refers to a plant that comprises a heterologous polynucleotide.

Preferably, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been so altered by the presence of heterologous nucleic acid including those transgenic organisms or cells initially so altered, as well as those created by crosses or asexual propagation from the initial transgenic organism or cell. In some embodiments, a "recombinant" organism is a "transgenic" organism. The term "transgenic" as used herein is not intended to encompass the alteration of the genome (chromosomal or extrachromosomal) by conventional plant breeding methods (e.g., crosses) or by naturally occurring events such as, e.g., self-fertilization, random cross-fertilization, non-recombinant viral infection, non-recombinant bacterial transformation, non-recombinant transposition, or spontaneous mutation.

As used herein, "mutagenized" refers to an organism or DNA thereof having alteration(s) in the biomolecular sequence of its native genetic material as compared to the sequence of the genetic material of a corresponding wild-type organism or DNA, wherein the alteration(s) in genetic material were induced and/or selected by human action. Examples of human action that can be used to produce a mutagenized organism or DNA include, but are not limited to, as illustrated in regard to herbicide tolerance: tissue culture of plant cells (e.g., calli) and selection thereof with herbicides (e.g., PPO-inhibiting herbicides), treatment of plant cells with a chemical mutagen and subsequent selection with herbicide(s); or by treatment of plant cells with x-rays and subsequent selection with herbicide(s). Any method known in the art can be used to induce mutations. Methods of inducing mutations can induce mutations in random positions in the genetic material or can induce mutations in specific locations in the genetic material (i.e., can be directed mutagenesis techniques), such as by use of a genoplasty technique.

As used herein, a "genetically modified organism" (GMO) is an organism whose genetic characteristics contain alteration(s) that were produced by human effort causing transfection that results in transformation of a target organism with genetic material from another or "source" organism, or with synthetic or modified-native genetic material, or an organism that is a descendant thereof that retains the inserted genetic material. The source organism can be of a different type of organism (e.g., a GMO plant can contain bacterial genetic material) or from the same type of organism (e.g., a GMO plant can contain genetic material from another plant). As used herein in regard to plants and other organisms, "recombinant," "transgenic," and "GMO" are considered synonyms and indicate the presence of genetic material from a different source; in contrast, "mutagenized" is used to refer to a plant or other organism, or the DNA thereof, in which no such transgenic material is present, but in which the native genetic material has become mutated so as to differ from a corresponding wild-type organism or DNA.

As used herein, "wild-type" or "corresponding wild-type plant" means the typical form of an organism or its genetic material, as it normally occurs, as distinguished from, e.g., mutagenized and/or recombinant forms. Similarly, by "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

As used herein, "descendant" refers to any generation plant. In some embodiments, a descendant is a first, second, third, fourth, fifth, sixth, seventh, eight, ninth, or tenth generation plant.

As used herein, "progeny" refers to a first generation plant.

The term "seed" comprises seeds of all types, such as, for example, true seeds, caryopses, achenes, fruits, tubers, seedlings and similar forms. In the context of *Brassica* and *Sinapis* species, "seed" refers to true seed(s) unless otherwise specified. For example, the seed can be seed of transgenic plants or plants obtained by traditional breeding methods. Examples of traditional breeding methods can include cross-breeding, selfing, back-crossing, embryo rescue, in-crossing, out-crossing, inbreeding, selection, asexual propagation, and other traditional techniques as are known in the art.

Although exemplified with reference to specific plants or plant varieties and their hybrids, in various embodiments, the presently described methods using PPO-inhibiting herbicides can be employed with a variety of commercially valuable plants. PPO-inhibiting herbicides-tolerant plant lines described as useful herein can be employed in weed control methods either directly or indirectly, i. e. either as crops for herbicide treatment or as PPO-inhibiting herbicides-tolerance trait donor lines for development, as by traditional plant breeding, to produce other varietal and/or hybrid crops containing such trait or traits. All such resulting variety or hybrids crops, containing the ancestral PPO-inhibiting herbicides-tolerance trait or traits can be referred to herein as progeny or descendant of the ancestral, PPO-inhibiting herbicides-tolerant line(s). Such resulting plants can be said to retain the "herbicide tolerance characteristic (s)" of the ancestral plant, i.e. meaning that they possess and express the ancestral genetic molecular components responsible for the trait.

In one aspect, the present invention provides a plant or plant part comprising (i) a recombinant polynucleotide encoding a wildtype or mutated PPO polypeptide, and (ii) a recombinant polynucleotide encoding a CYP450 polypeptide, the expression of said polynucleotides (i) and (ii) confers to the plant or plant part tolerance to PPO-inhibiting herbicides.

In another embodiment, the recombinant polynucleotide encoding the wildtype or mutated PPO polypeptide comprises the nucleic acid sequence set forth in SEQ ID NO:1, or 3, a variant or derivative thereof.

In another embodiment, the recombinant polynucleotide encoding the CYP450 polypeptide comprises the nucleic acid sequence set forth in SEQ ID NO: 5, a variant or derivative thereof.

In other embodiments, the wildtype or mutated PPO polypeptide for use according to the present invention is a functional variant having, over the full-length of the variant, at least about 80%, illustratively, at least about 80%, 90%, 95%, 98%, 99% or more amino acid sequence identity to SEQ ID NO: 2 or 4.

In other embodiments, the CYP450 for use according to the present invention is a functional variant having, over the full-length of the variant, at least about 80%, illustratively, at least about 80%, 90%, 95%, 98%, 99% or more amino acid sequence identity to SEQ ID NO: 6.

In other embodiments, the CYP450 for use according to the present invention is a functional variant having, over the full-length of the variant, at least about 80%, illustratively, at least about 80%, 90%, 95%, 98%, 99% or more amino acid sequence identity to SEQ ID 7, 8, 9, 10, 11, 12, 13, 14, 15, 16, 17, 18, 19, 20, 21, 22, 23, 24, 25, 26, 27, 28, 29, or 30.

In another embodiment, the wildtype or mutated PPO polypeptide for use according to the present invention is a functional fragment of a polypeptide having the amino acid sequence set forth in SEQ ID NO: 2 or 4. In another embodiment, the CYP450 polypeptide for use according to the present invention is a functional fragment of a polypeptide having the amino acid sequence set forth in SEQ ID NO: 6. In another embodiment, the CYP450 polypeptide for use according to the present invention is a functional fragment of a polypeptide having the amino acid sequence set forth in SEQ ID 7, 8, 9, 10, 11, 12, 13, 14, 15, 16, 17, 18, 19, 20, 21, 22, 23, 24, 25, 26, 27, 28, 29, or 30.

It is recognized that the PPO and CYP450 polynucleotide molecules and PPO and CYP450 polypeptides of the invention encompass polynucleotide molecules and polypeptides comprising a nucleotide or an amino acid sequence that is sufficiently identical to nucleotide sequences set forth in SEQ ID Nos: 1, 3, or 5, or to the amino acid sequences set forth in SEQ ID Nos: 2, 4, or 6. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

Generally, "sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. As the skilled addressee would be aware, an isolated polynucleotide can be an exogenous polynucleotide present in, for example, a transgenic organism which does not naturally comprise the polynucleotide. Furthermore, the terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

The term "mutated PPO nucleic acid" refers to a PPO nucleic acid having a sequence that is mutated from a wild-type PPO nucleic acid and that confers increased PPO-inhibiting herbicide tolerance to a plant in which it is expressed. Furthermore, the term "mutated protoporphyrinogen oxidase (mutated PPO)" refers to the replacement of an amino acid of the wild-type primary sequences SEQ ID NO: 2, or a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

Furthermore, it will be understood by the person skilled in the art that the PPO nucleotide sequences encompass homologues, paralogues and orthologues of SEQ ID NO: 1, or 3, as defined hereinafter.

Furthermore, it will be understood by the person skilled in the art that the CYP450 nucleotide sequences encompass homologues, paralogues and orthologues of SEQ ID NO: 5, as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein comprising the sequence of SEQ ID NO: 2, 4, or 6, as well as those that encode a polypeptide having amino acid substitutions relative to the native protein, e.g. the mutated PPO according to the present invention as disclosed herein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO: 1, 3, or 5. The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

In a preferred embodiment, the nucleotide sequence variant of SEQ ID NO: 5 comprises the nucleotide sequence set forth in SEQ ID NO: 31, or 32.

Polypeptides

By "substantially purified polypeptide" or "purified" a polypeptide is meant that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. As the skilled addressee will appreciate, the purified polypeptide can be a recombinantly produced polypeptide. The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

With regard to a defined polypeptide, it will be appreciated that % identity figures higher than those provided above will encompass preferred embodiments. Thus, where applicable, in light of the minimum % identity figures, it is preferred that the PPO polypeptide of the invention comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 2, or 4.

Furthermore, it is preferred that the CYP450 polypeptide of the invention comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 6, 7, 8, 9, 10, 11, 12, 13, 14, 15, 16, 17, 18, 19, 20, 21, 22, 23, 24, 25, 26, 27, 28, 29, or 30.

By "variant" polypeptide is intended a polypeptide derived from the protein of SEQ ID NO: 2, 4 or, 6, by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. Thus, functional variants and fragments of the PPO and CYP450 polypeptides, and nucleic acid molecules encoding them, also are within the scope of the present invention, and unless specifically described otherwise, irrespective of the origin of said polypeptide and irrespective of whether it occurs naturally. Various assays for functionality of a PPO or CYP450 polypeptide can be employed. For example, a functional variant or fragment of the PPO or CYP450 polypeptide can be assayed to determine its ability to confer PPO-inhibiting herbicides detoxification. By way of illustration, a PPO-inhibiting herbicides detoxification rate can be defined as a catalytic rate sufficient to provide a determinable increase in tolerance to PPO-inhibiting herbicides in a plant or plant part comprising a recombinant polynucleotide encoding the variant or fragment of the PPO or CYP450 polypeptide, wherein the plant or plant part expresses the variant or fragment at up to about 0.5%, illustratively, about 0.05 to about 0.5%, about 0.1 to about 0.4%, and about 0.2 to about 0.3%, of the total cellular protein relative to a similarly treated control plant that does not express the variant or fragment.

In a preferred embodiment, the wildtype or mutated PPO polypeptide is a functional variant or fragment of a protoporphyrinogen oxidase having the amino acid sequence set forth in SEQ ID NO:2, wherein the functional variant or fragment has at least about 80% amino acid sequence identity to SEQ ID NO:2.

In a preferred embodiment, the wildtype or mutated PPO polypeptide is a functional variant or fragment of a protoporphyrinogen oxidase having the amino acid sequence set forth in SEQ ID NO:4, wherein the functional variant or fragment has at least about 80% amino acid sequence identity to SEQ ID NO:4.

In another preferred embodiment, the CYP450 polypeptide is a functional variant or fragment of a cytochrome P450 monooxygenase having the amino acid sequence set forth in SEQ ID NO:6, wherein the functional variant or fragment has at least about 80% amino acid sequence identity to SEQ ID NO:6.

In another preferred embodiment, the functional variant of the CYP450 is a cytochrome P450 monooxygenase comprising the amino acid sequence set forth in SEQ ID NO: 7, 8, 9, 10, 11, 12, 13, 14, 15, 16, 17, 18, 19, 20, 21, 22, 23, 24, 25, 26, 27, 28, 29, or 30.

In other embodiments, the functional variant or fragment further has a PPO-inhibiting herbicides detoxification rate defined as a catalytic rate sufficient to provide a determinable increase in tolerance to PPO-inhibiting herbicides in a plant or plant part comprising a recombinant polynucleotide encoding the variant or fragment, wherein the plant or plant part expresses the variant or fragment at up to about 0.5% of the total cellular protein to a similarly treated control plant that does not express the variant or fragment.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

In addition, one of ordinary skill in the art will further appreciate that changes can be introduced by mutation into the nucleotide sequences of the invention thereby leading to changes in the amino acid sequence of the encoded proteins without altering the biological activity of the proteins. Thus, for example, an isolated polynucleotide molecule encoding a mutated PPO polypeptide having an amino acid sequence that differs from that of SEQ ID NO: 2 can be created by introducing one or more nucleotide substitutions, additions, or deletions into the corresponding nucleotide sequence, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention. For example, preferably, conservative amino acid substitutions may be made at one or more predicted preferably nonessential amino acid residues. A "nonessential" amino acid residue is a residue that can be altered from the wild-type sequence of a protein without altering the biological activity, whereas an "essential" amino acid residue is required for biological activity.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif. Conservative substitution tables are well known in the art (see for example Creighton (1984) Proteins. W.H. Freeman and Company (Eds).

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art.

For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

It is well-known in the art that paralogues and orthologues may share distinct domains harboring suitable amino acid residues at given sites, such as binding pockets for particular substrates or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The proteins of the invention may be altered in various ways including amino acid substitutions, deletions, truncations, and insertions. Methods for such manipulations are generally known in the art. For example, amino acid sequence variants can be prepared by mutations in the DNA. Methods for mutagenesis and nucleotide sequence alterations are well known in the art. See, for example, Kunkel (1985) PNAS, 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be preferable.

Alternatively, variant nucleotide sequences can be made by introducing mutations randomly along all or part of a coding sequence, such as by saturation mutagenesis, and the resultant mutants can be screened to identify mutants that encode proteins that retain activity. For example, following mutagenesis, the encoded protein can be expressed recombinantly, and the activity of the protein can be determined using standard assay techniques.

The inventors of the present invention have found that by substituting one or more of the key amino acid residues of the PPO enzyme of SEQ ID NO:2, e.g. by employing one of the above described methods to mutate the PPO encoding nucleic acids, the tolerance or resistance to particular PPO-inhibiting herbicides could be remarkably increased when co-expressed with a recombinant nucleic acid encoding a CYP450 polypeptide as compared to the activity of the wild type PPO enzymes with SEQ ID NO: 2. Preferred substitutions of mutated PPO are those that increase the herbicide tolerance of the plant, but leave the biological activity of the oxidase activity substantially unaffected.

Thus, in a particularly preferred embodiment, the variant or derivative of the mutated PPO refers to SEQ ID NO: 2, wherein the amino acid sequence differs from an amino acid sequence of a PPO of SEQ ID NO: 2 at one or more of the following positions corresponding to positions: 128, 204, 208, 397, 400, 420, 457.

Examples of differences at these amino acid positions include, but are not limited to, one or more of the following:
the amino acid at or corresponding to positionamino acid at or corresponding to position 128 is other than Arginine;
the amino acid at or corresponding to positionamino acid at or corresponding to position 204 is other than Phenylalanine;
the amino acid at or corresponding to positionamino acid at or corresponding to position 208 is other than Threonine;
the amino acid at or corresponding to positionamino acid at or corresponding to position 397 is other than Leucine,
the amino acid at or corresponding to positionamino acid at or corresponding to position 400 is other than Leucine,
the amino acid at or corresponding to positionamino acid at or corresponding to position 420 is other than Phenylalanine,
the amino acid at or corresponding to positionamino acid at or corresponding to position 457 is other than Phenylalanine.

In some embodiments, the mutated PPO enzyme of SEQ ID NO: 2 comprises one or more of the following:
the amino acid at or corresponding to positionamino acid at or corresponding to position 128 is Leu, Ala, Val, or Ile;
the amino acid at or corresponding to positionamino acid at or corresponding to position 204 is Ala, Leu, Ile, or Val;
the amino acid at or corresponding to positionamino acid at or corresponding to position 208 is Ser;
the amino acid at or corresponding to positionamino acid at or corresponding to position 397 is Gly, Ala, Ser, Thr, Cys, Val, Ile, Met, Pro, Phe, Tyr, Trp, His, Lys, Arg, Asn, Asp, Glu, or Gln;
the amino acid at or corresponding to positionamino acid at or corresponding to position 400 is Ala, Ile, Val, or Met;
the amino acid at or corresponding to positionamino acid at or corresponding to position 420 is Val, Met, Ala, Ile, or Leu;
the amino acid at or corresponding to positionamino acid at or corresponding to position 457 is Met, Ala, Leu, Ile, Val;

Furthermore, the inventors of the present invention have found that by substituting one or more of the key amino acid residues of the PPO enzyme of SEQ ID NO: 4, e.g. by employing one of the above described methods to mutate the PPO encoding nucleic acids, the tolerance or resistance to particular PPO-inhibiting herbicides could be remarkably increased when co-expressed with a recombinant nucleic acid encoding a CYP450 polypeptide as compared to the activity of the wild type PPO enzymes with SEQ ID NO: 4. Preferred substitutions of mutated PPO are those that increase the herbicide tolerance of the plant, but leave the biological activity of the oxidase activity substantially unaffected.

Thus, in a particularly preferred embodiment, the variant or derivative of the mutated PPO refers to a polypeptide of SEQ ID NO: 4, wherein the amino acid sequence differs from an amino acid sequence of SEQ ID NO: 4 at position 137, 415, and/or position 438.

Examples of differences at these amino acid positions include, but are not limited to, one or more of the following:
the amino acid at or corresponding to positionamino acid at or corresponding to position 137 is other than Arginine;
the amino acid at or corresponding to positionamino acid at or corresponding to position 415 is other than Leucine
the amino acid at or corresponding to positionamino acid at or corresponding to position 438 is other than Phenylalanine.

In some embodiments, the mutated PPO enzyme of SEQ ID NO: 2 comprises one or more of the following:
the amino acid at or corresponding to positionamino acid at or corresponding to position 137 is Leu, Ala, Val, Ile, Met, Tyr, Gly, Asn, Cys, Phe, Ser, Thr, Gln, or His;
the amino acid at or corresponding to positionamino acid at or corresponding to position 415 is Ala, Arg, Val, Ile, Met, His, Lys, Asp, Glu, Ser, Thr, Asn, Gln, Cys, Gly, Pro, Phe, Tyr, or Trp
the amino acid at or corresponding to positionamino acid at or corresponding to position 438 is Ala, Leu, Val, Ile, Met, His, Lys, Asp, Glu, Ser, Thr, Asn, Gln, Cys, Gly, Pro, Arg, Tyr, or Trp.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is Leu, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is Leu, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is Leu, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is Leu, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is Leu, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is Ala, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is Ala, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is Ala, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ala, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ala, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Val, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Val, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Val, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Val, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Val, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ile, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ile, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ile, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ile, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ile, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Met, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Met, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Met, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Met, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Met, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Tyr, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Tyr, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Tyr, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Tyr, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Tyr, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Gly, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Gly, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Gly, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Gly, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Gly, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Asn, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Asn, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Asn, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Asn, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Asn, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Cys, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Cys, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Cys, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Cys, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Cys, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Phe, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Phe, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Phe, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Phe, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Phe, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ser, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ser, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ser, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ser, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Ser, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Thr, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Thr, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Thr, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Thr, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Thr, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Gln, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Gln, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Gln, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Gin, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which: the amino acid at or corresponding to positionamino acid at or corresponding to position 128 is Gln, and the amino acid at or corresponding to positionamino acid at or corresponding to position 420 is Met.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is His, and the amino acid at or corresponding to positionamino acid at or corresponding to position 420 is Ala.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is His, and the amino acid at or corresponding to positionamino acid at or corresponding to position 420 is Leu.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is His, and the amino acid at or corresponding to positionamino acid at or corresponding to position 420 is Val.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is His, and the amino acid at or corresponding to positionamino acid at or corresponding to position 420 is Ile.

In another preferred embodiment, the mutated PPO comprises a sequence of SEQ ID NO: 2, a variant, derivative, orthologue, paralogue or homologue thereof, in which:
the amino acid at or corresponding to positionamino acid at or corresponding to position 128 is His, and the amino acid at or corresponding to positionamino acid at or corresponding to position 420 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Gly, Ala, Ser, Thr, Cys, Val, Ile, Met, Pro, Tyr, Trp, Asp, Glu, Asn, Gln, His, Lys, or Arg, and the amino acid at or corresponding to position 420 is Met, Ala, Leu, Ile, or Val.

In another preferred embodiment, the mut-PPO comprises a sequence of SEQ ID NO: 2, a variant, derivative, orthologue, paralogue or homologue thereof, in which:
the amino acid at or corresponding to position 397 is Gly, and the amino acid at or corresponding to position 420 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Gly, and the amino acid at or corresponding to position 420 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Gly, and the amino acid at or corresponding to position 420 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Gly, and the amino acid at or corresponding to position 420 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Gly, and the amino acid at or corresponding to position 420 is Val.

In another preferred embodiment, the mut-PPO comprises a sequence of SEQ ID NO: 2, a variant, derivative, orthologue, paralogue or homologue thereof, in which:
the amino acid at or corresponding to position 397 is Ala, and the amino acid at or corresponding to position 420 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Ala, and the amino acid at or corresponding to position 420 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Ala, and the amino acid at or corresponding to position 420 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Ala, and the amino acid at or corresponding to position 420 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Ala, and the amino acid at or corresponding to position 420 is Val.

In another preferred embodiment, the mut-PPO comprises a sequence of SEQ ID NO: 2, a variant, derivative, orthologue, paralogue or homologue thereof, in which:
the amino acid at or corresponding to position 397 is Ser, and the amino acid at or corresponding to position 420 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Ser, and the amino acid at or corresponding to position 420 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Ser, and the amino acid at or corresponding to position 420 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Ser, and the amino acid at or corresponding to position 420 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Ser, and the amino acid at or corresponding to position 420 is Val.

In another preferred embodiment, the mut-PPO comprises a sequence of SEQ ID NO: 2, a variant, derivative, orthologue, paralogue or homologue thereof, in which:

the amino acid at or corresponding to position 397 is Thr, and the amino acid at or corresponding to position 420 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Thr, and the amino acid at or corresponding to position 420 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Thr, and the amino acid at or corresponding to position 420 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Thr, and the amino acid at or corresponding to position 420 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Thr, and the amino acid at or corresponding to position 420 is Val.

In another preferred embodiment, the mut-PPO comprises a sequence of SEQ ID NO: 2, a variant, derivative, orthologue, paralogue or homologue thereof, in which:
the amino acid at or corresponding to position 397 is Cys, and the amino acid at or corresponding to position 420 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Cys, and the amino acid at or corresponding to position 420 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Cys, and the amino acid at or corresponding to position 420 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Cys, and the amino acid at or corresponding to position 420 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Cys, and the amino acid at or corresponding to position 420 is Val.

In another preferred embodiment, the mut-PPO comprises a sequence of SEQ ID NO: 2, a variant, derivative, orthologue, paralogue or homologue thereof, in which:
the amino acid at or corresponding to position 397 is Val, and the amino acid at or corresponding to position 420 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Val, and the amino acid at or corresponding to position 420 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Val, and the amino acid at or corresponding to position 420 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Val, and the amino acid at or corresponding to position 420 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Val, and the amino acid at or corresponding to position 420 is Val.

In another preferred embodiment, the mut-PPO comprises a sequence of SEQ ID NO: 2, a variant, derivative, orthologue, paralogue or homologue thereof, in which:
the amino acid at or corresponding to position 397 is Ile, and the amino acid at or corresponding to position 420 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Ile, and the amino acid at or corresponding to position 420 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Ile, and the amino acid at or corresponding to position 420 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Ile, and the amino acid at or corresponding to position 420 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Ile, and the amino acid at or corresponding to position 420 is Val.

In another preferred embodiment, the mut-PPO comprises a sequence of SEQ ID NO: 2, a variant, derivative, orthologue, paralogue or homologue thereof, in which:
the amino acid at or corresponding to position 397 is Met, and the amino acid at or corresponding to position 420 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Met, and the amino acid at or corresponding to position 420 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Met, and the amino acid at or corresponding to position 420 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Met, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Met, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is Pro, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 397 is Pro, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Pro, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 397 is Pro, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Pro, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is Tyr, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 397 is Tyr, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Tyr, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 397 is Tyr, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Tyr, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is Trp, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 397 is Trp, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Trp, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 397 is Trp, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Trp, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is Asp, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 397 is Asp, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Asp, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 397 is Asp, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Asp, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is Glu, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 397 is Glu, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Glu, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 397 is Glu, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Glu, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is Asn, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 397 is Asn, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Asn, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 397 is Asn, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Asn, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is Gln, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 397 is Gln, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Gln, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 397 is Gln, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Gln, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is His, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 397 is His, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 397 is His, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 397 is His, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is His, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is Lys, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 397 is Lys, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Lys, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 397 is Lys, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Lys, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is Arg, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 397 is Arg, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Arg, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 397 is Arg, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Arg, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 397 is Asp, Glu, Gln, Asn, and the amino acid at or corresponding to position 400 is Ala, Ile, Val, Met.

In another preferred embodiment, the mut-PPO comprises a sequence of SEQ ID NO: 2, a variant, derivative, orthologue, paralogue or homologue thereof, in which: the amino acid at or corresponding to position 397 is Asp, and the amino acid at or corresponding to position 400 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Asp, and the amino acid at or corresponding to position 400 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Asp, and the amino acid at or corresponding to position 400 is Val.

In another preferred embodiment, the mut-PPO comprises a sequence of SEQ ID NO: 2, a variant, derivative, orthologue, paralogue or homologue thereof, in which: the amino acid at or corresponding to position 397 is Asp, and the amino acid at or corresponding to position 400 is Met.

In another preferred embodiment, the mut-PPO comprises a sequence of SEQ ID NO: 2, a variant, derivative, orthologue, paralogue or homologue thereof, in which: the amino acid at or corresponding to position 397 is Glu, and the amino acid at or corresponding to position 400 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Glu, and the amino acid at or corresponding to position 400 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Glu, and the amino acid at or corresponding to position 400 is Val.

In another preferred embodiment, the mut-PPO comprises a sequence of SEQ ID NO: 2, a variant, derivative, orthologue, paralogue or homologue thereof, in which: the amino acid at or corresponding to position 397 is Glu, and the amino acid at or corresponding to position 400 is Met.

In another preferred embodiment, the mut-PPO comprises a sequence of SEQ ID NO: 2, a variant, derivative, orthologue, paralogue or homologue thereof, in which: the amino acid at or corresponding to position 397 is Gln, and the amino acid at or corresponding to position 400 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Gln, and the amino acid at or corresponding to position 400 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Gln, and the amino acid at or corresponding to position 400 is Val.

In another preferred embodiment, the mut-PPO comprises a sequence of SEQ ID NO: 2, a variant, derivative, orthologue, paralogue or homologue thereof, in which: the amino acid at or corresponding to position 397 is Gln, and the amino acid at or corresponding to position 400 is Met.

In another preferred embodiment, the mut-PPO comprises a sequence of SEQ ID NO: 2, a variant, derivative, orthologue, paralogue or homologue thereof, in which: the amino acid at or corresponding to position 397 is Asn, and the amino acid at or corresponding to position 400 is Ala.

In another preferred embodiment, the mut-PPO comprises a sequence of SEQ ID NO: 2, a variant, derivative, orthologue, paralogue or homologue thereof, in which: the amino acid at or corresponding to position 397 is Asn, and the amino acid at or corresponding to position 400 is Ile.

In another preferred embodiment, the mut-PPO comprises a sequence of SEQ ID NO: 2, a variant, derivative, orthologue, paralogue or homologue thereof, in which: the amino acid at or corresponding to position 397 is Asn, and the amino acid at or corresponding to position 400 is Val.

In another preferred embodiment, the mut-PPO comprises a sequence of SEQ ID NO: 2, a variant, derivative, orthologue, paralogue or homologue thereof, in which: the amino acid at or corresponding to position 397 is Asn, and the amino acid at or corresponding to position 400 is Met.

In another preferred embodiment, the mut-PPO comprises a sequence of SEQ ID NO: 2, a variant, derivative, orthologue, paralogue or homologue thereof, in which: the amino acid at or corresponding to position 397 is Asp, Glu, Gln, Asn, and the amino acid at or corresponding to position 457 is Met, Ala, Leu, Ile, Val.

In another preferred embodiment, the mut-PPO comprises a sequence of SEQ ID NO: 2, a variant, derivative, orthologue, paralogue or homologue thereof, in which:
the amino acid at or corresponding to position 397 is Asp, and the amino acid at or corresponding to position 457 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Asp, and the amino acid at or corresponding to position 457 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Asp, and the amino acid at or corresponding to position 457 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Asp, and the amino acid at or corresponding to position 457 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Asp, and the amino acid at or corresponding to position 457 is Val.

In another preferred embodiment, the mut-PPO comprises a sequence of SEQ ID NO: 2, a variant, derivative, orthologue, paralogue or homologue thereof, in which:
the amino acid at or corresponding to position 397 is Glu, and the amino acid at or corresponding to position 457 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Glu, and the amino acid at or corresponding to position 457 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Glu, and the amino acid at or corresponding to position 457 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Glu, and the amino acid at or corresponding to position 457 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Glu, and the amino acid at or corresponding to position 457 is Val.

In another preferred embodiment, the mut-PPO comprises a sequence of SEQ ID NO: 2, a variant, derivative, orthologue, paralogue or homologue thereof, in which:
the amino acid at or corresponding to position 397 is Gln, and the amino acid at or corresponding to position 457 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Gln, and the amino acid at or corresponding to position 457 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Gln, and the amino acid at or corresponding to position 457 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Gln, and the amino acid at or corresponding to position 457 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Gln, and the amino acid at or corresponding to position 457 is Val.

In another preferred embodiment, the mut-PPO comprises a sequence of SEQ ID NO: 2, a variant, derivative, orthologue, paralogue or homologue thereof, in which:
the amino acid at or corresponding to position 397 is Asn, and the amino acid at or corresponding to position 457 is Met.

In another preferred embodiment, the mut-PPO comprises a sequence of SEQ ID NO: 2, a variant, derivative, orthologue, paralogue or homologue thereof, in which:
the amino acid at or corresponding to position 397 is Asn, and the amino acid at or corresponding to position 457 is Ala.

In another preferred embodiment, the mut-PPO comprises a sequence of SEQ ID NO: 2, a variant, derivative, orthologue, paralogue or homologue thereof, in which:
the amino acid at or corresponding to position 397 is Asn, and the amino acid at or corresponding to position 457 is Leu.

In another preferred embodiment, the mut-PPO comprises a sequence of SEQ ID NO: 2, a variant, derivative, orthologue, paralogue or homologue thereof, in which:
the amino acid at or corresponding to position 397 is Asn, and the amino acid at or corresponding to position 457 is Ile.

In another preferred embodiment, the mut-PPO comprises a sequence of SEQ ID NO: 2, a variant, derivative, orthologue, paralogue or homologue thereof, in which:
the amino acid at or corresponding to position 397 is Asn, and the amino acid at or corresponding to position 457 is Val.

In another preferred embodiment, the mut-PPO comprises a sequence of SEQ ID NO: 2, a variant, derivative, orthologue, paralogue or homologue thereof, in which:
the amino acid at or corresponding to position 204 is Ala, Leu, Ile, Val, and the amino acid at or corresponding to position 397 is Asp, Glu, Gln, Asn.

In another preferred embodiment, the mut-PPO comprises a sequence of SEQ ID NO: 2, a variant, derivative, orthologue, paralogue or homologue thereof, in which:
the amino acid at or corresponding to position 204 is Ala, and the amino acid at or corresponding to position 397 is Asp.

In another preferred embodiment, the mut-PPO comprises a sequence of SEQ ID NO: 2, a variant, derivative, orthologue, paralogue or homologue thereof, in which:
the amino acid at or corresponding to position 204 is Ala, and the amino acid at or corresponding to position 397 is Glu.

In another preferred embodiment, the mut-PPO comprises a sequence of SEQ ID NO: 2, a variant, derivative, orthologue, paralogue or homologue thereof, in which:
the amino acid at or corresponding to position 204 is Ala, and the amino acid at or corresponding to position 397 is Gln.

In another preferred embodiment, the mut-PPO comprises a sequence of SEQ ID NO: 2, a variant, derivative, orthologue, paralogue or homologue thereof, in which:
the amino acid at or corresponding to position 204 is Ala, and the amino acid at or corresponding to position 397 is Asn.

In another preferred embodiment, the mut-PPO comprises a sequence of SEQ ID NO: 2, a variant, derivative, orthologue, paralogue or homologue thereof, in which:
the amino acid at or corresponding to position 204 is Leu, and the amino acid at or corresponding to position 397 is Asp.

In another preferred embodiment, the mut-PPO comprises a sequence of SEQ ID NO: 2, a variant, derivative, orthologue, paralogue or homologue thereof, in which:
the amino acid at or corresponding to position 204 is Leu, and the amino acid at or corresponding to position 397 is Glu.

In another preferred embodiment, the mut-PPO comprises a sequence of SEQ ID NO: 2, a variant, derivative, orthologue, paralogue or homologue thereof, in which:
the amino acid at or corresponding to position 204 is Leu, and the amino acid at or corresponding to position 397 is Gln.

In another preferred embodiment, the mut-PPO comprises a sequence of SEQ ID NO: 2, a variant, derivative, orthologue, paralogue or homologue thereof, in which:
the amino acid at or corresponding to position 204 is Leu, and the amino acid at or corresponding to position 397 is Asn.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 397 is Asp.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 397 is Glu.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 397 is Gln.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 397 is Asn.

In another preferred embodiment, the mut-PPO comprises a sequence of SEQ ID NO: 2, a variant, derivative, orthologue, paralogue or homologue thereof, in which:
the amino acid at or corresponding to position 204 is Val, and the amino acid at or corresponding to position 397 is Asp.

In another preferred embodiment, the mut-PPO comprises a sequence of SEQ ID NO: 2, a variant, derivative, orthologue, paralogue or homologue thereof, in which:
the amino acid at or corresponding to position 204 is Val, and the amino acid at or corresponding to position 397 is Glu.

In another preferred embodiment, the mut-PPO comprises a sequence of SEQ ID NO: 2, a variant, derivative, orthologue, paralogue or homologue thereof, in which:
the amino acid at or corresponding to position 204 is Val, and the amino acid at or corresponding to position 397 is Gln.

In another preferred embodiment, the mut-PPO comprises a sequence of SEQ ID NO: 2, a variant, derivative, orthologue, paralogue or homologue thereof, in which:
the amino acid at or corresponding to position 204 is Val, and the amino acid at or corresponding to position 397 is Asn.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 400 is Ala, Ile, Val, Met.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 400 is Ala.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 400 is Ile.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 400 is Val.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 400 is Met.

In another preferred embodiment, the mut-PPO comprises a sequence of SEQ ID NO: 2, a variant, derivative, orthologue, paralogue or homologue thereof, in which:
the amino acid at or corresponding to position 400 is Ala, and the amino acid at or corresponding to position 457 is Met, Ala, Leu, Ile, Val.

In another preferred embodiment, the mut-PPO comprises a sequence of SEQ ID NO: 2, a variant, derivative, orthologue, paralogue or homologue thereof, in which:
the amino acid at or corresponding to position 400 is Ala, and the amino acid at or corresponding to position 457 is Met.

In another preferred embodiment, the mut-PPO comprises a sequence of SEQ ID NO: 2, a variant, derivative, orthologue, paralogue or homologue thereof, in which:
the amino acid at or corresponding to position 400 is Ala, and the amino acid at or corresponding to position 457 is Ala.

In another preferred embodiment, the mut-PPO comprises a sequence of SEQ ID NO: 2, a variant, derivative, orthologue, paralogue or homologue thereof, in which:

the amino acid at or corresponding to position 400 is Ala, and the amino acid at or corresponding to position 457 is Leu.

In another preferred embodiment, the mut-PPO comprises a sequence of SEQ ID NO: 2, a variant, derivative, orthologue, paralogue or homologue thereof, in which:
the amino acid at or corresponding to position 400 is Ala, and the amino acid at or corresponding to position 457 is Ile.

In another preferred embodiment, the mut-PPO comprises a sequence of SEQ ID NO: 2, a variant, derivative, orthologue, paralogue or homologue thereof, in which:
the amino acid at or corresponding to position 400 is Ala, and the amino acid at or corresponding to position 457 is Val.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 400 is Ala, Ile, Val, Met.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 400 is Ala.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 400 is Ile.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 400 is Val.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 400 is Met.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 457 is Met, Ala, Leu, Ile, Val.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 457 is Met.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 457 is Ala.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 457 is Leu.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 457 is Ile.

In another preferred embodiment, the mut-PPO comprises a sequence of SEQ ID NO: 2, a variant, derivative, orthologue, paralogue or homologue thereof, in which:
the amino acid at or corresponding to position 208 is Ser, and the amino acid at or corresponding to position 457 is Val.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 208 is Ser.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 208 is Ser.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 457 is Met, Ala, Leu, Ile, Val.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 457 is Met.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 457 is Ala.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 457 is Leu.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 457 is Ile.

In another preferred embodiment, the mut-PPO comprises a sequence of SEQ ID NO: 2, a variant, derivative, orthologue, paralogue or homologue thereof, in which:
the amino acid at or corresponding to position 204 is Ile, and the amino acid at or corresponding to position 457 is Val.

In another preferred embodiment, the mut-PPO comprises a sequence of SEQ ID NO: 2, a variant, derivative, orthologue, paralogue or homologue thereof, in which:
the amino acid at or corresponding to position 400 is Ala, Ile, Val, or Met, and the amino acid at or corresponding to position 420 is Met, Ala, Leu, Ile, or Val.

In another preferred embodiment, the mut-PPO comprises a sequence of SEQ ID NO: 2, a variant, derivative, orthologue, paralogue or homologue thereof, in which:
the amino acid at or corresponding to position 400 is Ala, and the amino acid at or corresponding to position 420 is Met.

In another preferred embodiment, the mut-PPO comprises a sequence of SEQ ID NO: 2, a variant, derivative, orthologue, paralogue or homologue thereof, in which:
the amino acid at or corresponding to position 400 is Ala, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 400 is Ala, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 400 is Ala, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 400 is Ala, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 400 is Ile, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 400 is Ile, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 400 is Ile, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 400 is Ile, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 400 is Ile, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 400 is Val, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 400 is Val, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 400 is Val, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 400 is Val, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 400 is Val, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 400 is Met, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 400 is Met, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 400 is Met, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 400 is Met, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 400 is Met, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 204 is Ile, and the amino acid at or corresponding to position 420 is Met, Ala, Leu, Ile, Val.

In another preferred embodiment, the mut-PPO comprises a sequence of SEQ ID NO: 2, a variant, derivative, orthologue, paralogue or homologue thereof, in which: the amino acid at or corresponding to position 204 is Ile, and the amino acid at or corresponding to position 420 is Met.

In another preferred embodiment, the mut-PPO comprises a sequence of SEQ ID NO: 2, a variant, derivative, orthologue, paralogue or homologue thereof, in which: the amino acid at or corresponding to position 204 is Ile, and the amino acid at or corresponding to position 420 is Ala.

In another preferred embodiment, the mut-PPO comprises a sequence of SEQ ID NO: 2, a variant, derivative, orthologue, paralogue or homologue thereof, in which: the amino acid at or corresponding to position 204 is Ile, and the amino acid at or corresponding to position 420 is Leu.

In another preferred embodiment, the mut-PPO comprises a sequence of SEQ ID NO: 2, a variant, derivative, orthologue, paralogue or homologue thereof, in which: the amino acid at or corresponding to position 204 is Ile, and the amino acid at or corresponding to position 420 is Ile.

In another preferred embodiment, the mut-PPO comprises a sequence of SEQ ID NO: 2, a variant, derivative, orthologue, paralogue or homologue thereof, in which: the amino acid at or corresponding to position 204 is Ile, and the amino acid at or corresponding to position 420 is Val.

In another preferred embodiment, the mut-PPO comprises a sequence of SEQ ID NO: 2, a variant, derivative, orthologue, paralogue or homologue thereof, in which: the amino acid at or corresponding to position 420 is Met, Ala, Leu, Ile, Val, and the amino acid at or corresponding to position 457 is Met, Ala, Leu, Ile, Val.

In another preferred embodiment, the mut-PPO comprises a sequence of SEQ ID NO: 2, a variant, derivative, orthologue, paralogue or homologue thereof, in which: the amino acid at or corresponding to position 420 is Met, and the amino acid at or corresponding to position 457 is Met.

In another preferred embodiment, the mut-PPO comprises a sequence of SEQ ID NO: 2, a variant, derivative, orthologue, paralogue or homologue thereof, in which: the amino acid at or corresponding to position 420 is Met, and the amino acid at or corresponding to position 457 is Ala.

In another preferred embodiment, the mut-PPO comprises a sequence of SEQ ID NO: 2, a variant, derivative, orthologue, paralogue or homologue thereof, in which: the amino acid at or corresponding to position 420 is Met, and the amino acid at or corresponding to position 457 is Leu.

In another preferred embodiment, the mut-PPO comprises a sequence of SEQ ID NO: 2, a variant, derivative, orthologue, paralogue or homologue thereof, in which: the amino acid at or corresponding to position 420 is Met, and the amino acid at or corresponding to position 457 is Ile.

In another preferred embodiment, the mut-PPO comprises a sequence of SEQ ID NO: 2, a variant, derivative, orthologue, paralogue or homologue thereof, in which: the amino acid at or corresponding to position 420 is Met, and the amino acid at or corresponding to position 457 is Val.

In another preferred embodiment, the mut-PPO comprises a sequence of SEQ ID NO: 2, a variant, derivative, orthologue, paralogue or homologue thereof, in which: the amino acid at or corresponding to position 420 is Ala, and the amino acid at or corresponding to position 457 is Met.

In another preferred embodiment, the mut-PPO comprises a sequence of SEQ ID NO: 2, a variant, derivative, orthologue, paralogue or homologue thereof, in which: the amino acid at or corresponding to position 420 is Ala, and the amino acid at or corresponding to position 457 is Ala.

In another preferred embodiment, the mut-PPO comprises a sequence of SEQ ID NO: 2, a variant, derivative, orthologue, paralogue or homologue thereof, in which: the amino acid at or corresponding to position 420 is Ala, and the amino acid at or corresponding to position 457 is Leu.

In another preferred embodiment, the mut-PPO comprises a sequence of SEQ ID NO: 2, a variant, derivative, orthologue, paralogue or homologue thereof, in which: the amino acid at or corresponding to position 420 is Ala, and the amino acid at or corresponding to position 457 is Ile.

In another preferred embodiment, the mut-PPO comprises a sequence of SEQ ID NO: 2, a variant, derivative, orthologue, paralogue or homologue thereof, in which: the amino acid at or corresponding to position 420 is Ala, and the amino acid at or corresponding to position 457 is Val.

In another preferred embodiment, the mut-PPO comprises a sequence of SEQ ID NO: 2, a variant, derivative, orthologue, paralogue or homologue thereof, in which: the amino acid at or corresponding to position 420 is Leu, and the amino acid at or corresponding to position 457 is Met.

In another preferred embodiment, the mut-PPO comprises a sequence of SEQ ID NO: 2, a variant, derivative, orthologue, paralogue or homologue thereof, in which: the amino acid at or corresponding to position 420 is Leu, and the amino acid at or corresponding to position 457 is Ala.

In another preferred embodiment, the mut-PPO comprises a sequence of SEQ ID NO: 2, a variant, derivative, orthologue, paralogue or homologue thereof, in which: the amino acid at or corresponding to position 420 is Leu, and the amino acid at or corresponding to position 457 is Leu.

In another preferred embodiment, the mut-PPO comprises a sequence of SEQ ID NO: 2, a variant, derivative, orthologue, paralogue or homologue thereof, in which: the amino acid at or corresponding to position 420 is Leu, and the amino acid at or corresponding to position 457 is Ile.

In another preferred embodiment, the mut-PPO comprises a sequence of SEQ ID NO: 2, a variant, derivative, orthologue, paralogue or homologue thereof, in which: the amino acid at or corresponding to position 420 is Leu, and the amino acid at or corresponding to position 457 is Val.

In another preferred embodiment, the mut-PPO comprises a sequence of SEQ ID NO: 2, a variant, derivative, orthologue, paralogue or homologue thereof, in which: the amino acid at or corresponding to position 420 is Ile, and the amino acid at or corresponding to position 457 is Met.

In another preferred embodiment, the mut-PPO comprises a sequence of SEQ ID NO: 2, a variant, derivative, orthologue, paralogue or homologue thereof, in which: the amino acid at or corresponding to position 420 is Ile, and the amino acid at or corresponding to position 457 is Ala.

In another preferred embodiment, the mut-PPO comprises a sequence of SEQ ID NO: 2, a variant, derivative, orthologue, paralogue or homologue thereof, in which: the amino acid at or corresponding to position 420 is Ile, and the amino acid at or corresponding to position 457 is Leu.

In another preferred embodiment, the mut-PPO comprises a sequence of SEQ ID NO: 2, a variant, derivative, orthologue, paralogue or homologue thereof, in which: the amino acid at or corresponding to position 420 is Ile, and the amino acid at or corresponding to position 457 is Ile.

In another preferred embodiment, the mut-PPO comprises a sequence of SEQ ID NO: 2, a variant, derivative, orthologue, paralogue or homologue thereof, in which: the amino acid at or corresponding to position 420 is Ile, and the amino acid at or corresponding to position 457 is Val.

In another preferred embodiment, the mut-PPO comprises a sequence of SEQ ID NO: 2, a variant, derivative, orthologue, paralogue or homologue thereof, in which: the amino acid at or corresponding to position 420 is Val, and the amino acid at or corresponding to position 457 is Met.

In another preferred embodiment, the mut-PPO comprises a sequence of SEQ ID NO: 2, a variant, derivative, orthologue, paralogue or homologue thereof, in which: the amino acid at or corresponding to position 420 is Val, and the amino acid at or corresponding to position 457 is Ala.

In another preferred embodiment, the mut-PPO comprises a sequence of SEQ ID NO: 2, a variant, derivative, orthologue, paralogue or homologue thereof, in which:

the amino acid at or corresponding to position 420 is Val, and the amino acid at or corresponding to position 457 is Leu.

In another preferred embodiment, the mut-PPO comprises a sequence of SEQ ID NO: 2, a variant, derivative, orthologue, paralogue or homologue thereof, in which:
the amino acid at or corresponding to position 420 is Val, and the amino acid at or corresponding to position 457 is Ile.

In another preferred embodiment, the mut-PPO comprises a sequence of SEQ ID NO: 2, a variant, derivative, orthologue, paralogue or homologue thereof, in which:
the amino acid at or corresponding to position 420 is Val, and the amino acid at or corresponding to position 457 is Val.

In another preferred embodiment, the mut-PPO comprises a sequence of SEQ ID NO: 2, a variant, derivative, orthologue, paralogue or homologue thereof, in which:
the amino acid at or corresponding to position 128 is Ala, Leu, Ile, Val, and the amino acid at or corresponding to position 397 is Asp, Glu, Gln, Asn.

In another preferred embodiment, the mut-PPO comprises a sequence of SEQ ID NO: 2, a variant, derivative, orthologue, paralogue or homologue thereof, in which:
the amino acid at or corresponding to position 128 is Ala, and the amino acid at or corresponding to position 397 is Asp.

In another preferred embodiment, the mut-PPO comprises a sequence of SEQ ID NO: 2, a variant, derivative, orthologue, paralogue or homologue thereof, in which:
the amino acid at or corresponding to position 128 is Ala, and the amino acid at or corresponding to position 397 is Glu.

In another preferred embodiment, the mut-PPO comprises a sequence of SEQ ID NO: 2, a variant, derivative, orthologue, paralogue or homologue thereof, in which:
the amino acid at or corresponding to position 128 is Ala, and the amino acid at or corresponding to position 397 is Gln.

In another preferred embodiment, the mut-PPO comprises a sequence of SEQ ID NO: 2, a variant, derivative, orthologue, paralogue or homologue thereof, in which:
the amino acid at or corresponding to position 128 is Ala, and the amino acid at or corresponding to position 397 is Asn.

In another preferred embodiment, the mut-PPO comprises a sequence of SEQ ID NO: 2, a variant, derivative, orthologue, paralogue or homologue thereof, in which:
the amino acid at or corresponding to position 128 is Leu, and the amino acid at or corresponding to position 397 is Asp.

In another preferred embodiment, the mut-PPO comprises a sequence of SEQ ID NO: 2, a variant, derivative, orthologue, paralogue or homologue thereof, in which:
the amino acid at or corresponding to position 128 is Leu, and the amino acid at or corresponding to position 397 is Glu.

In another preferred embodiment, the mut-PPO comprises a sequence of SEQ ID NO: 2, a variant, derivative, orthologue, paralogue or homologue thereof, in which:
the amino acid at or corresponding to position 128 is Leu, and the amino acid at or corresponding to position 397 is Gln.

In another preferred embodiment, the mut-PPO comprises a sequence of SEQ ID NO: 2, a variant, derivative, orthologue, paralogue or homologue thereof, in which:
the amino acid at or corresponding to position 128 is Leu, and the amino acid at or corresponding to position 397 is Asn.

In another preferred embodiment, the mut-PPO comprises a sequence of SEQ ID NO: 2, a variant, derivative, orthologue, paralogue or homologue thereof, in which:
the amino acid at or corresponding to position 128 is Ile, and the amino acid at or corresponding to position 397 is Asp.

In another preferred embodiment, the mut-PPO comprises a sequence of SEQ ID NO: 2, a variant, derivative, orthologue, paralogue or homologue thereof, in which:
the amino acid at or corresponding to position 128 is Ile, and the amino acid at or corresponding to position 397 is Glu.

In another preferred embodiment, the mut-PPO comprises a sequence of SEQ ID NO: 2, a variant, derivative, orthologue, paralogue or homologue thereof, in which:
the amino acid at or corresponding to position 128 is Ile, and the amino acid at or corresponding to position 397 is Gln.

In another preferred embodiment, the mut-PPO comprises a sequence of SEQ ID NO: 2, a variant, derivative, orthologue, paralogue or homologue thereof, in which:
the amino acid at or corresponding to position 128 is Ile, and the amino acid at or corresponding to position 397 is Asn.

In another preferred embodiment, the mut-PPO comprises a sequence of SEQ ID NO: 2, a variant, derivative, orthologue, paralogue or homologue thereof, in which:
the amino acid at or corresponding to position 128 is Val, and the amino acid at or corresponding to position 397 is Asp.

In another preferred embodiment, the mut-PPO comprises a sequence of SEQ ID NO: 2, a variant, derivative, orthologue, paralogue or homologue thereof, in which:
the amino acid at or corresponding to position 128 is Val, and the amino acid at or corresponding to position 397 is Glu.

In another preferred embodiment, the mut-PPO comprises a sequence of SEQ ID NO: 2, a variant, derivative, orthologue, paralogue or homologue thereof, in which:
the amino acid at or corresponding to position 128 is Val, and the amino acid at or corresponding to position 397 is Gln.

In another preferred embodiment, the mut-PPO comprises a sequence of SEQ ID NO: 2, a variant, derivative, orthologue, paralogue or homologue thereof, in which:
the amino acid at or corresponding to position 128 is Val, and the amino acid at or corresponding to position 397 is Asn.

In other aspects, the present invention encompasses a progeny or a descendant of a PPO-inhibiting herbicides-tolerant plant of the present invention as well as seeds derived from the PPO-inhibiting herbicides-tolerant plants of the invention and cells derived from the PPO-inhibiting herbicides-tolerant plants of the invention.

In some embodiments, the present invention provides a progeny or descendant plant derived from a plant comprising in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, wherein the progeny or descendant plant comprises in at least some of its cells the recombinant polynucleotide (i) and (ii) operably linked to the promoter, the expression of the wildtype or mutated PPO and the CYP450 polypeptide conferring to the progeny or descendant plant tolerance to the PPO-inhibiting herbicides.

In one embodiment, seeds of the present invention preferably comprise the PPO-inhibiting herbicides-tolerance characteristics of the PPO-inhibiting herbicides-tolerant plant. In other embodiments, a seed is capable of germination into a plant comprising in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the progeny or descendant plant tolerance to the PPO-inhibiting herbicides.

In some embodiments, plant cells of the present invention are capable of regenerating a plant or plant part. In other embodiments, plant cells are not capable of regenerating a plant or plant part. Examples of cells not capable of regenerating a plant include, but are not limited to, endosperm, seed coat (testa & pericarp), and root cap.

In another embodiment, the present invention provides a plant cell of or capable of regenerating a plant comprising in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to the PPO-inhibiting herbicides, wherein the plant cell comprises the recombinant polynucleotide (i) and (ii) operably linked to a promoter.

In other embodiments, the present invention provides a plant cell comprising (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the cell tolerance to the PPO-inhibiting herbicides.

In some aspects, the present invention provides a plant product prepared from the PPO-inhibiting herbicides-tolerant plants hereof. In some embodiments, examples of plant products include, without limitation, grain, oil, and meal. In one embodiment, a plant product is plant grain (e.g., grain suitable for use as feed or for processing), plant oil (e.g., oil suitable for use as food or biodiesel), or plant meal (e.g., meal suitable for use as feed).

In one embodiment, a plant product prepared from a plant or plant part is provided, wherein the plant or plant part comprises in at least some of its (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the a plant or plant part tolerance to the PPO-inhibiting herbicides.

In another embodiment, the invention refers to a method of producing a transgenic plant cell with an increased resistance to a PPO-inhibiting herbicide as compared to a wild type variety of the plant cell comprising, transforming the plant cell with an expression cassette comprising (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide.

In another embodiment, the invention refers to a method of producing a transgenic plant comprising, (a) transforming a plant cell with an expression cassette comprising a (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, and (b) generating a plant with an increased resistance to PPO-inhibiting herbicide from the plant cell.

In some aspects, the present invention provides a method for producing a PPO-inhibiting herbicides-tolerant plant. In one embodiment, the method comprises: regenerating a plant from a plant cell transformed with (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to the PPO-inhibiting herbicides.

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the PPO-inhibiting herbicide derivative herbicide of the present invention, it will be understood that the at least one nucleic acid is "over-expressed" by methods and means known to the person skilled in the art.

The term "increased expression" or "overexpression" as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

Where appropriate, nucleic acid sequences may be optimized for increased expression in a transformed plant. For example, coding sequences that comprise plant-preferred codons for improved expression in a plant can be provided. See, for example, Campbell and Gowri (1990) Plant Physiol., 92: 1-11 for a discussion of host-preferred codon usage. Methods also are known in the art for preparing plant-preferred genes. See, for example, U.S. Pat. Nos. 5,380,831, and 5,436,391, and Murray et al. (1989) Nucleic Acids Res. 17:477-498, herein incorporated by reference.

Consequently, wildtype/mutated PPO and CYP450 nucleic acids of the invention are provided in expression cassettes for expression in the plant of interest. The cassette will include regulatory sequences operably linked to a mutated PPO nucleic acid sequence of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the wildtype/mutated PPO or CYP450 nucleic acid sequence to be under the transcriptional regulation of the regulatory regions. The expression cassette may additionally contain selectable marker genes. The expression cassette of the present invention will include in the 5'-3' direction of transcription, a transcriptional and translational initiation region (i.e., a promoter), a wildtype/ mutated PPO or CYP450 encoding nucleic acid sequence of the invention, and a transcriptional and translational termination region (i.e., termination region) functional in plants. The promoter may be native or analogous, or foreign or heterologous, to the plant host and/or to the wildtype/ mutated PPO or CYP450 nucleic acid sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the wildtype/mutated PPO or CYP450 nucleic acid sequence of the invention, it is intended that the promoter is not the native or naturally occurring promoter for the operably linked wildtype/mutated PPO or CYP450 nucleic acid sequence of the invention. As used herein, a chimeric gene comprises a coding sequence operably linked to a transcription initiation region that is heterologous to the coding sequence. While it may be preferable to express the wildtype/mutated PPO or CYP450 nucleic acids of the invention using heterologous promoters, the native promoter sequences may be used. Such constructs would change expression levels of the wildtype/mutated PPO or CYP450 protein in the plant or plant cell. Thus, the phenotype of the plant or plant cell is altered.

The termination region may be native with the transcriptional initiation region, may be native with the operably linked wildtype/mutated PPO or CYP450 sequence of interest, may be native with the plant host, or may be derived from another source (i.e., foreign or heterologous to the promoter, the wildtype/mutated PPO or CYP450 nucleic acid sequence of interest, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas et al. (1989) Nucleic Acids Res. 17:7891-7903; and Joshi et al. (1987) Nucleic Acid Res. 15:9627-9639. Where appropriate, the gene(s) may be optimized for increased expression in the transformed plant. That is, the genes can be synthesized using plant-preferred codons for improved expression. See, for example, Campbell and Gown (1990) Plant Physiol. 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

While the polynucleotides of the invention may find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairn et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595; Kleinschnidt et al (1988) Biochemistry 27: 1094-1104; Bonin (1993) Ph.D. Thesis, University of Heidelberg; Gossen et al (1992) Proc. Natl Acad. ScL USA 89:5547-5551; Oliva et al (1992) Antimicrob. Agents Chemother. 36:913-

919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention.

Further, additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. Also, if desired, sequences can be readily modified to avoid predicted hairpin secondary mRNA structures. Nucleotide sequences for enhancing gene expression can also be used in the plant expression vectors. These include, for example, introns of the maize Adh gene Adh1-S intron 1, 2, and 6 (Callis et al. Genes and Development 1: 1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize gene expression, the plant expression vectors of the invention also may contain DNA sequences containing matrix attachment regions (MARs). Plant cells transformed with such modified expression systems, then, may exhibit overexpression or constitutive expression of a nucleotide sequence of the invention.

The invention further provides an isolated recombinant expression vector comprising the expression cassette containing a wildtype/mutated PPO nucleic acid and/or the CYP nucleic acid as described above, wherein expression of the vector in a host cell results in increased tolerance to a PPO-inhibiting herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mutated PPO polypeptides, fusion polypeptides, etc.)

Expression vectors may additionally contain 5' leader sequences in the expression construct. Such leader sequences can act to enhance translation. Translation leaders are known in the art and include: picornavirus leaders, for example, EMCV leader (Encephalomyo carditis 5' noncoding region) (Elroy-Stein et al. (1989) PNAS, 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968.

Other methods known to enhance translation also can be utilized, for example, introns, and the like. In preparing an expression vector, the various nucleic acid fragments may be manipulated, so as to provide for the nucleic acid sequences in the proper orientation and, as appropriate, in the proper reading frame. Toward this end, adapters or linkers may be employed to join the nucleic acid fragments or other manipulations may be involved to provide for convenient restriction sites, removal of superfluous nucleic acid, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984)

EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression within a particular plant tissue. Such tissue-preferred promoters include, but are not limited to, leaf-preferred promoters, root-preferred promoters, seed-preferred promoters, and stem-preferred promoters. Some examples of tissue-preferred promoters are described by, e.g., Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al. (1997) Transgenic Res. 6(2): 157-168; Rinehart et al. (1996) Plant Physiol. 1 12(3): 1331-1341; Van Camp et al. (1996) Plant Physiol. 112(2):525-535; Canevascini et al. (1996) Plant Physiol. 1 12(2):513-524; Yamamoto et al. (1994) Plant Cell Physiol. 35(5):773-778; Lam (1994) Results Probl. Cell Differ. 20:181-196; Orozco et al. (1993) Plant Mol Biol. 23(6): 1 129-1138; Matsuoka et al. (1993) Voc Natl. Acad. ScL USA 90(20):9586-9590; and Guevara-Garcia et al. (1993) Plant J 4(3):495-505. Promoters can be modified, if necessary, for weak expression.

In some embodiments, the nucleic acids of interest can be targeted to the chloroplast for expression. In this manner, where the nucleic acid of interest is not directly inserted into the chloroplast, the expression vector will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the desired coding sequence of the invention such that the two sequences are contiguous and in the same reading frame. See, for example, Von Heijne et al. (1991) Plant Mol. Biol. Rep. 9: 104-126; Clark et al. (1989) J Biol. Chem. 264: 17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481. For example, a chloroplast transit peptide known in the art can be fused to the amino acid sequence of a PPO or CYP450 polypeptide of the invention by operably linking a choloroplast-targeting sequence to the 5'-end of a nucleotide sequence encoding the PPO or CYP450 polypeptide.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J Biol. Chem. 266(5):3335-3342); EPSPS (Archer et al. (1990) J Bioenerg. Biomemb. 22(6):789-810); tryptophan synthase (Zhao et al. (1995) J Biol. Chem. 270(11):6081-6087); plastocyanin (Lawrence et al. (1997) J Biol. Chem. 272(33):20357-20363); chorismate synthase (Schmidt et al. (1993) J Biol. Chem. 268(36):27447-27457); and the light harvesting chlorophyll a/b binding protein (LHBP) (Lamppa et al. (1988) J Biol. Chem. 263: 14996-14999). See also Von Heijne et al. (1991) Plant Mol. Biol. Rep. 9: 104-126; Clark et al. (1989) J Biol. Chem. 264: 17544-17550; Della-Cioppa et al. (1987) Plant Physiol. 84:965-968; Romer et al. (1993) Biochem Biophys. Res. Commun. 196: 1414-1421; and Shah et al. (1986) Science 233:478-481.

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Numerous plant transformation vectors and methods for transforming plants are available. See, for example, An, G. et al. (1986) Plant PysioL, 81:301-305; Fry, J., et al. (1987) Plant Cell Rep. 6:321-325; Block, M. (1988) Theor. Appl. Genet 0.16: 161-1 1 A; Hinchee, et al. (1990) Stadler. Genet. Symp. 2032\2.203-2\2; Cousins, et al. (1991) Aust. J. Plant Physiol. 18:481-494; Chee, P. P. and Slightom, J. L. (1992) Gene.I I 8:255-260; Christou, et al. (1992) Trends. Biotechnol. 10:239-246; Halluin, et al. (1992) Bio/Technol. 10:309-314; Dhir, et al. (1992) Plant Physiol. 99:81-88; Casas et al. (1993) Proc. Nat. Acad Sd. USA 90: 1 1212-1 1216; Christou, P. (1993) In Vitro Cell. Dev. Biol.-Plant; 29P. 119-124; Davies, et al. (1993) Plant Cell Rep. 12: 180-183; Dong, J. A. and Mchughen, A. (1993) Plant ScL 91: 139-148; Franklin, C. I. and Trieu, T. N. (1993) Plant. Physiol. 102: 167; Golovkin, et al. (1993) Plant ScL 90:41-52; Guo Chin ScL Bull. 38:2072-2078; Asano, et al. (1994) Plant Cell Rep. 13; Ayeres N. M. and Park, W. D. (1994) Crit. Rev. Plant. Sci. 13:219-239; Barcelo, et al. (1994) Plant. J. 5:583-592; Becker, et al. (1994) Plant. J. 5:299-307; Borkowska et al. (1994) Acta. Physiol Plant. 16:225-230; Christou, P. (1994) Agro. Food. Ind. Hi Tech. 5: 17-27; Eapen et al. (1994) Plant Cell Rep. 13:582-586; Hartman, et al. (1994) Bio-Technology 12: 919923; Ritala, et al. (1994) Plant. Mol. Biol. 24:317-325; and Wan, Y. C. and Lemaux, P. G. (1994) Plant Physiol. 104:3748.

In some embodiments, the methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods. The term "introduction" or "transformation" as referred to herein further means the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

By "stable transformation" is intended that the polynucleotide construct introduced into a plant integrates into the genome of the plant and is capable of being inherited by descendent thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed. In an embodiment of the invention, the encoding nucleotide sequence is operably linked to a plant promoter, e.g. a promoter known in the art for high-level expression in a plant cell, and this construct is then introduced into a plant cell that is susceptible to PPO-inhibiting herbicides; and a transformed plant is regenerated. In some embodiments, the transformed plant is tolerant to exposure to a level of PPO-inhibiting herbicides that would kill or significantly injure a plant regenerated from an untransformed cell. This method can be applied to any plant species or crops.

Methodologies for constructing plant expression vectors and introducing foreign nucleic acids into plants are generally known in the art. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al (1991) Gene 100: 247-250; Scheid et al., (1991) MoL Gen. Genet., 228: 104-1 12; Guerche et al., (1987) Plant Science 52: 1 1 1-1 16; Neuhause et al., (1987) Theor. Appl Genet. 75: 30-36; Klein et al., (1987) Nature 327: 70-73; Howell et al., (1980) Science 208: 1265; Horsch et al., (1985) Science 227: 1229-1231; DeBlock et al., (1989) Plant Physiology 91: 694-701; Methods for Plant Molecular Biology (Weissbach and Weissbach, eds.) Academic Press, Inc. (1988) and Methods in Plant Molecular Biology (Schuler and Zielinski, eds.) Academic Press, Inc. (1989).

Other suitable methods of introducing nucleotide sequences into plant cells include microinjection as described by, e.g., Crossway et al. (1986) Biotechniques 4:320-334, electroporation as described by e.g., Riggs et al. (1986) Proc. Natl. Acad. ScL USA 83:5602-5606, Agrobacterium-mediated transformation as described by e.g., Townsend et al., U.S. Pat. No. 5,563,055, Zhao et al., U.S. Pat. No. 5,981,840, direct gene transfer as described by, e.g., Paszkowski et al. (1984) EMBO J. 3:2717-2722, and ballistic particle acceleration as described by, e.g., U.S. Pat. Nos. 4,945,050; 5,879,918; 5,886,244; and 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); McCabe et al. (1988) Biotechnology 6:923-926); and Led transformation (WO 00/28058). Also see, Weissinger et al., (1988) Ann. Rev. Genet. 22:421-477; Sanford et al, (1987) Particulate Science and Technology 5:27-37 (onion); Christou et al, (1988) Plant Physiol. 87:671-674 (soybean); McCabe et al., (1988) Bio/Technology 6:923-926 (soybean); Finer and McMullen (1991) In Vitro Cell Dev. Biol. 27P: 175-182 (soybean); Singh et al, (1998) Theor. Appl. Genet. 96:319-324 (soybean); Datta et al., (1990) Biotechnology 8:736-740 (rice); Klein et al., (1988) PNAS, 85:4305-4309 (maize); Klein et al., (1988) Biotechnology 6:559-563 (maize); U.S. Pat. Nos. 5,240,855; 5,322,783; and 5,324,646; Tomes et al., (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al., (1988) Plant Physiol. 91:440-444 (maize); Fromm et al., (1990) Biotechnology 8:833-839 (maize); Hooykaas-Van Slogteren et al., (1984) Nature (London) 31 1:763-764; Bowen et al, U.S. Pat. No. 5,736,369 (cereals); Bytebier et al, (1987) PNAS 84:5345-5349 (Liliaceae); De Wet et al., (1985) in The Experimental Manipulation of Ovule Tissues, ed. Chapman et al, (Longman, N.Y.), pp. 197-209 (pollen); Kaeppler et al., (1990) Plant Cell Reports 9:415-418 and Kaeppler et al., (1992) Theor. Apph Genet. 84:560-566 (whisker-mediated transformation); D'Halluin et al., (1992) Plant Cell 4: 1495-1505 (electroporation); Li et al., (1993) Plant Cell Reports 12:250-255 and Christou and Ford (1995) Annals of Botany 75:407-413 (rice); Osjoda et al, (1996) Nature Biotechnology 14:745-750 (maize via *Agrobacterium tumefaciens*); each of which is herein incorporated by reference.

Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

One transformation method known to those of skill in the art is the dipping of a flowering plant into an Agrobacteria solution, wherein the Agrobacteria contains the PPO and CYP nucleic acid, followed by breeding of the transformed gametes. *Agrobacterium* mediated plant transformation can be performed using for example the GV3101(pMP90) (Koncz and Schell, 1986, Mol. Gen. Genet. 204:383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

In some embodiments, polynucleotides of the present invention may be introduced into plants by contacting plants with a virus or viral nucleic acids. Generally, such methods involve incorporating a polynucleotide construct of the invention within a viral DNA or RNA molecule. It is recognized that the polypeptides of the invention may be initially synthesized as part of a viral polyprotein, which later may be processed by proteolysis in vivo or in vitro to produce the desired recombinant polypeptide. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866, 785, 5,589,367 and 5,316,931; herein incorporated by reference. The cells that have been transformed may be grown into plants in accordance with conventional ways. See, for example, McCormick et a (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, monocots and dicots. Examples of plant species of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet e.g., pearl millet (*Pennisetum glaucum*), proso millet (*Panicum miliaceum*), foxtail millet (*Setaria italica*), finger millet (*Eleusine coracana*)), sunflower (*Helianthus annu*), safflower (*Carthamus tinctorius*), wheat (*Triticum aestivum, T. Turgidum* ssp. *durum*), soybean (*Glycine max*), tobacco (*Nicotiana tabacum*), potato (*Solarium tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Preferably, plants of the present invention are crop plants (for example, sunflower, *Brassica* sp., cotton, sugar, beet, soybean, peanut, alfalfa, safflower, tobacco, corn, rice, wheat, rye, barley triticale, sorghum, millet, etc.).

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the expression of the nucleic acid in the plant results in the plant's increased resistance to PPO-inhibiting herbicide as compared to a wild type variety of the plant.

In other aspects, PPO-inhibiting herbicides-tolerant plants of the present invention can be employed as PPO-inhibiting herbicides-tolerance trait donor lines for development, as by traditional plant breeding, to produce other varietal and/or hybrid crops containing such trait or traits. All such resulting variety or hybrids crops, containing the ancestral PPO-inhibiting herbicides-tolerance trait or traits can be referred to herein as progeny or descendant of the ancestral, PPO-inhibiting herbicides-tolerant line(s).

In other embodiments, the present invention provides a method for producing a PPO-inhibiting herbicides-tolerant plant. The method comprises: crossing a first PPO-inhibiting herbicides-tolerant plant with a second plant to produce a PPO-inhibiting herbicides-tolerant progeny plant, wherein the first plant and the progeny plant comprise in at least some of their cells (i) a recombinant polynucleotide operably linked to a promoter operable in plant cells, the recombinant polynucleotide being effective in the cells of the first plant to express a CYP450 polypeptide encoded by the polynucleotide, and (ii) a recombinant polynucleotide operably linked to a promoter operable in plant cells, the recombinant polynucleotide being effective in the cells of the first plant to express a wildtype or mutated PPO polypeptide encoded by the polynucleotide, the expression of the wildtype or mutated PPO and the CYP450 polypeptide conferring to the plant tolerance to PPO-inhibiting herbicides.

In some embodiments, traditional plant breeding is employed whereby the PPO-inhibiting herbicides-tolerant trait is introduced in the progeny plant resulting therefrom. In one embodiment, the present invention provides a method for producing a PPO-inhibiting herbicides-tolerant progeny plant, the method comprising: crossing a parent plant with a PPO-inhibiting herbicides-tolerant plant to introduce the PPO-inhibiting herbicides-tolerance characteristics of the PPO-inhibiting herbicides-tolerant plant into the germplasm of the progeny plant, wherein the progeny plant has increased tolerance to the PPO-inhibiting herbicides relative to the parent plant. In other embodiments, the method further comprises the step of introgressing the PPO-inhibiting herbicides-tolerance characteristics through traditional plant breeding techniques to obtain a descendent plant having the PPO-inhibiting herbicides-tolerance characteristics.

In other aspects, plants of the invention include those plants which, in addition to being PPO-inhibiting herbicides-tolerant, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil) herbicides as a result of conventional methods of breeding or genetic engineering, Thus, PPO-inhibiting herbicides-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, PPO-inhibiting herbicides-tolerant plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other PPO inhibitors; and to GS inhibitors, such as glufosinate.

In addition to these classes of inhibitors, PPO-inhibiting herbicides-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype HPPD proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins other than the CYP450s of the present invention having an herbicide-degrading activity. PPO-inhibiting herbicides-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, PPO-inhibiting herbicides-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA(b), CryIIIA, CryIIIB(bI) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda).

In some embodiments, expression of one or more protein toxins (e.g., insecticidal proteins) in the PPO-inhibiting herbicides-tolerant plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes bicolor*); the grain beetle *Ahasverus advena*; the summer schafer *Amphimallon solstitialis*; the furniture beetle *Anobium punctatum*; *Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera virgifera*, and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata*; Lyctus beetles {*Lyctus* spp., the pollen beetle *Meligethes aeneus*; the common cockshafer *Melolontha melolontha*; the American spider beetle *Mezium americanum*; the golden spider beetle *Niptus hololeuc* s; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala*; *Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicronyx fulvus*; the drugstore beetle *Stegobium paniceum*; the yellow mealworm beetle *Tenebrio molitor*, the flour beetles *Tribolium castaneum* and *Tribolium confusum*; warehouse and cabinet beetles {*Trogoderma* spp.); the sunflower beetle *Zygogramma exclamationis*; Dermaptera (earwigs) such as the European earwig *Forficula auricularia* and the striped earwig *Labidura riparia*; Dictyoptera such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); Isoptera (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear psylla *Cacopsylla pyricola*; the currant aphid *Cryptomyzus ribis*; the grape phylloxera *Daktulosphaira vitifoliae*; the citrus psylla *Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae*; Lepidoptera such as *Adoxophyes orana* (summer fruit tortrix moth); *Archips podana* (fruit tree tortrix moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis vires cens* (tobacco budworm), *Homeosoma electellum* (sunflower moth); *Homona magnanima* (oriental tea tree tortrix moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armywonn); *Spodoptera littoralis* (cotton leafworm); *Sylepta derogata* (cotton leaf roller); *Trichoplusia ni* (cabbage looper); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differ entialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria*; Symphyla such as the garden symphylan *Scutigerella immaculate*; Thysanoptera such as the tobacco thrips *Frankliniella fusca*, the flower thrips *Frankliniella intonsa*, the western flower thrips *Frankliniella occidentalism* the cotton bud thrips *Frankliniella schultzei*, the banded greenhouse thrips *Hercinothrips femoralis*, the soybean thrips *Neohydatothrips variabilis*, Kelly's citrus thrips *Pezothrips kellyanus*, the avocado thrips *Scirtothrips perseae*, the melon thrips *Thrips palmi*, and the onion thrips *Thrips tabaci*; and the like, and combinations comprising one or more of the foregoing organisms.

In some embodiments, expression of one or more protein toxins (e.g., insecticidal proteins) in the PPO-inhibiting herbicides-tolerant plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the PPO-inhibiting herbicides-tolerant plants is effective for controlling cabbage seedpod weevil, the Bertha armyworm, Lygus bugs, or the diamondback moth.

Furthermore, in one embodiment, PPO-inhibiting herbicides-tolerant plants are also covered which are, e.g. by the use of recombinant DNA techniques and/or by breeding and/or otherwise selected for such traits, rendered able to synthesize one or more proteins to increase the resistance or tolerance of those plants to bacterial, viral or fungal pathogens. The methods for producing such genetically modified plants are generally known to the person skilled in the art.

Furthermore, in another embodiment, PPO-inhibiting herbicides-tolerant plants are also covered which are, e.g. by the use of recombinant DNA techniques and/or by breeding and/or otherwise selected for such traits, rendered able to synthesize one or more proteins to increase the productivity (e.g. oil content), tolerance to drought, salinity or other growth-limiting environmental factors or tolerance to pests and fungal, bacterial or viral pathogens of those plants.

Furthermore, in other embodiments, PPO-inhibiting herbicides-tolerant plants are also covered which are, e.g. by the use of recombinant DNA techniques and/or by breeding and/or otherwise selected for such traits, altered to contain a modified amount of one or more substances or new substances, for example, to improve human or animal nutrition, e.g. oil crops that produce health-promoting long-chain omega-3 fatty acids or unsaturated omega-9 fatty acids (e.g. Nexera(R) rape, Dow Agro Sciences, Canada).

Furthermore, in some embodiments, PPO-inhibiting herbicides-tolerant plants are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, PPO-inhibiting herbicides-tolerant plants of the present invention, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), I-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, I,2'-disinapoyl-2-feruloylgentiobiose, 3-0-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, PPO-inhibiting herbicides-tolerant plants of the present invention, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g. genistein, daidzein, and glycitein; resorcyclic acid lactones; organosulphur compounds; phytosterols; terpenoids such as carnosol, rosmarinic acid, glycyrrhizin and saponins; chlorophyll; chlorphyllin, sugars, anthocyanins, and vanilla.

In other embodiments, PPO-inhibiting herbicides-tolerant plants of the present invention, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

In other aspects, a method for treating a plant of the present invention is provided.

In some embodiments, the method comprises contacting the plant with an agronomically acceptable composition. In one embodiment, the agronomically acceptable composition comprises an auxinic herbicide A. I.

In another aspect, the present invention provides a method for preparing a descendent seed. The method comprises planting a seed of or capable of producing a plant of the present invention. In one embodiment, the method further comprises growing a descendent plant from the seed; and harvesting a descendant seed from the descendent plant. In other embodiments, the method further comprises applying a PPO-inhibiting herbicides herbicidal composition to the descendent plant.

In another embodiment, the invention refers to harvestable parts of the transgenic plant according to the present invention. Preferably, the harvestable parts comprise the PPO nucleic acid or PPO protein of the present invention. The harvestable parts may be seeds, roots, leaves and/or flowers comprising the PPO nucleic acid or PPO protein or parts thereof. Preferred parts of soy plants are soy beans comprising the PPO nucleic acid or PPO protein.

In another embodiment, the invention refers to products derived from a transgenic plant according to the present invention, parts thereof or harvestable parts thereof. A preferred plant product is fodder, seed meal, oil, or seed-treatment-coated seeds. Preferably, the meal and/or oil comprises the PPO/CYP450 nucleic acids or PPO/CYP450 proteins.

In another embodiment, the invention refers to a method for the production of a product, which method comprises
a) growing the plants of the invention or obtainable by the methods of invention and
b) producing said product from or by the plants of the invention and/or parts, e.g. seeds, of these plants.

In a further embodiment the method comprises the steps
a) growing the plants of the invention,
b) removing the harvestable parts as defined above from the plants and
c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Herbicides

Generally, if the PPO-inhibiting herbicides (also referred to as compounds A hereinafter) and/or the herbicidal compounds B as described herein, which can be employed in the context of the present invention, are capable of forming geometrical isomers, for example E/Z isomers, it is possible to use both, the pure isomers and mixtures thereof, in the compositions useful for the present the invention. If the PPO-inhibiting herbicides A and/or the herbicidal compounds B as described herein have one or more centers of chirality and, as a consequence, are present as enantiomers or diastereomers, it is possible to use both, the pure enantiomers and diastereomers and their mixtures, in the compositions according to the invention. If the PPO-inhibiting herbicides A and/or the herbicidal compounds B as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds. Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethyl-ammonium (olamine salt), 2-(2-hydroxyeth-1-oxy) eth-1-ylammonium (diglycolamine salt), di(2-hydroxyeth-1-yl)ammonium (diolamine salt), tris(2-hydroxyethyl) ammonium (trolamine salt), tris(2-hydroxypropyl) ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri (C$_1$-C$_4$-alkyl)sulfoxonium, and finally the salts of polybasic amines such as N,N-bis-(3-aminopropyl)methylamine and diethylenetriamine. Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of C$_1$-C$_4$-alkanoic acids, preferably formate, acetate, propionate and butyrate.

The PPO-inhibiting herbicides A and/or the herbicidal compounds B as described herein having a carboxyl group can be employed in the form of the acid, in the form of an agriculturally suitable salt as mentioned above or else in the form of an agriculturally acceptable derivative, for example as amides, such as mono- and di-C$_1$-C$_6$-alkylamides or arylamides, as esters, for example as allyl esters, propargyl esters, C$_1$-C$_{10}$-alkyl esters, alkoxyalkyl esters, tefuryl ((tetrahydrofuran-2-yl)methyl) esters and also as thioesters, for example as C$_1$-C$_{10}$-alkylthio esters. Preferred mono- and di-C$_1$-C$_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred C$_1$-C$_4$-alkoxy-C$_1$-C$_4$-alkyl esters are the straight-chain or branched C$_1$-C$_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched C$_1$-C$_{10}$-alkylthio ester is the ethylthio ester.

Examples of PPO inhibiting herbicides which can be used according to the present invention are acifluorfen, acifluorfen-sodium, aclonifen, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, chlornitrofen, flumipropyn, fluoronitrofen, flupropacil, furyloxyfen, nitrofluorfen, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), N-ethyl-3-2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4), and uracils of formula III

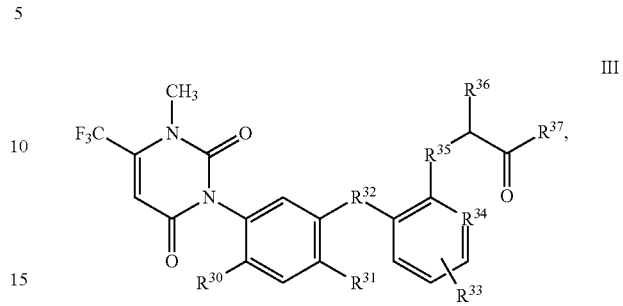

wherein
R$^{30}$ and R$^{31}$ independently of one another are F, Cl or CN;
R$^{32}$ is O or S;
R$^{33}$ is H, F, Cl, CH$_3$ or OCH$_3$;
R$^{34}$ is CH or N;
R$^{35}$ is O or S;
R$^{36}$ is H, CN, CH$_3$, CF$_3$, OCH$_3$, OC$_2$H$_5$, SCH$_3$, SC$_2$H$_5$, (CO)OC$_2$H$_5$ or CH$_2$R$^{38}$,
wherein R$^{38}$ is F, Cl, OCH$_3$, SCH$_3$, SC$_2$H$_5$, CH$_2$F, CH$_2$Br or CH$_2$OH;
and
R$^{37}$ is (C$_1$-C$_6$-alkyl)amino, (C$_1$-C$_6$-dialkyl)amino, (NH) OR$^{39}$, OH, OR$^{40}$ or SR$^{40}$
wherein R$^{39}$ is CH$_3$, C$_2$H$_5$ or phenyl; and
R$^{40}$ is independently of one another C$_1$-C$_6$-alkyl, C$_2$-C$_6$-alkenyl, C$_3$-C$_6$-alkynyl, C$_1$-C$_6$-haloalkyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, C$_2$-C$_6$-cyanoalkyl, C$_1$-C$_4$-alkoxy-carbonyl-C$_1$-C$_4$-alkyl, C$_1$-C$_4$-alkyl-carbonyl-amino, C$_1$-C$_6$-alkylsulfinyl-C$_1$-C$_6$-alkyl, C$_1$-C$_6$-alkyl-sulfonyl-C$_1$-C$_6$-alkyl, C$_1$-C$_6$-di-alkoxy-C$_1$-C$_6$-alkyl, C$_1$-C$_6$-alkyl-carbonyloxy-C$_1$-C$_6$-alkyl, phenyl-carbonyl-C$_1$-C$_6$-alkyl, tri(C$_1$-C$_3$-alkyl)-silyl-C$_1$-C$_6$-alkyl, tri(C$_1$-C$_3$-alkyl)-silyl-C$_1$-C$_6$-alkenyl, tri(C$_1$-C$_3$-alkyl)-silyl-C$_1$-C$_6$-alkynyl, tri(C$_1$-C$_3$-alkyl)-silyl-C$_1$-C$_6$-alkoxy-C$_1$-C$_6$-alkyl, dimethylamino, tetra-hydropyranyl, tetrahydrofuranyl-C$_1$-C$_3$-alkyl, phenyl-C$_1$-C$_6$-alkoxy-C$_1$-C$_6$-alkyl, phenyl-C$_1$-C$_3$-alkyl, pyridyl-C$_1$-C$_3$-alkyl, pyridyl, phenyl,
which pyridyls and phenyls independently of one another are substituted by one to five substituents selected from the group consisting of halogen, C$_1$-C$_3$-alkyl or C$_1$-C$_2$-haloalkyl;
C$_3$-C$_6$-cycloalkyl or C$_3$-C$_6$-cycloalkyl-C$_1$-C$_4$-alkyl,
which cycloalkyls independently of one another are unsubstituted or substituted by one to five substituents selected from the group consisting of halogen, C$_1$-C$_3$-alkyl and C$_1$-C$_2$-haloalkyl;
including their agriculturally acceptable alkali metal salts or ammonium salts.

Preferred PPO-inhibiting herbicides that can be used according to the present invention are: Acifluorfen, acifluorfen-sodium, azafenidin, bencarbazone, benzfendizone, butafenacil, carfentrazone-ethyl, cinidon-ethyl, flufenpyr-ethyl, flumiclorac-pentyl, flumioxazin, fluoroglycofen-ethyl, fluthiacet-methyl, fomesafen, lactofen, oxadiargyl, oxadiazon, oxyfluorfen, pentoxazone, pyraflufen-ethyl, saflufenacil, sulfentrazone, ethyl [3-[2-chloro-4-fluoro-5-(1-methyl-6-trifluoromethyl-2,4-dioxo-1,2,3,4-tetrahydropyrimidin-3- yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0); 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4)
uracils of formula III.1 (corresponding to uracils of formula III, wherein $R^{30}$ is F, $R^{31}$ is Cl, $R^{32}$ is O; $R^{33}$ is H; $R^{34}$ is CH; $R^{35}$ is O and $R^{37}$ is $OR^{40}$)

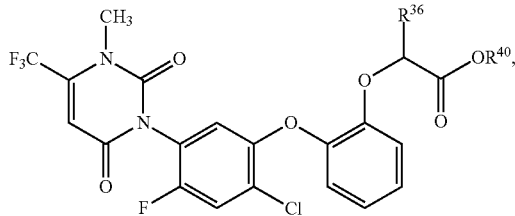

III.1 wherein
$R^{36}$ is $OCH_3$, $OC_2H_5$, $SCH_3$ or $SC_2H_5$;
and
$R^{40}$ is $C_1$-$C_6$-alkyl, $C_2$-$C_6$-alkenyl, $C_3$-$C_6$-alkynyl, $C_1$-$C_6$-haloalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_3$-cyanoalkyl, phenyl-$C_1$-$C_3$-alkyl, pyridyl-$C_1$-$C_3$-alkyl, $C_3$-$C_6$-cycloalkyl or $C_3$-$C_6$-cycloalkyl-$C_1$-$C_4$-alkyl,
which cycloalkyls are unsubstituted or substituted by one to five substituents selected from the group consisting of halogen, $C_1$-$C_3$-alkyl and $C_1$-$C_2$-haloalkyl;
and
uracils of formula III.2 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is $OR^{40}$ with $R^{40}$ is $C_1$-$C_6$-alkyl)

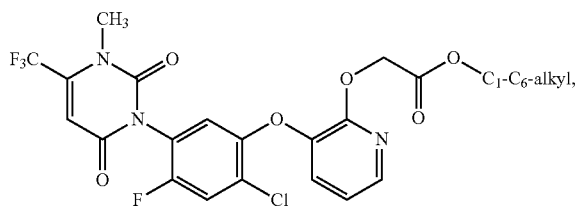

III.2

Particularly preferred PPO-inhibiting herbicides that can be used according to the present invention are:
acifluorfen, acifluorfen-sodium, butafenacil, carfentrazone-ethyl, cinidon-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0),
uracils of formula III.1.1 (corresponding to uracils of formula III, wherein $R^{30}$ is F, $R^{31}$ is Cl, $R^{32}$ is O; $R^{33}$ is H; $R^{34}$ is CH; $R^{35}$ is O, $R^{36}$ is $OCH_3$ and $R^{37}$ is $OR^{40}$)

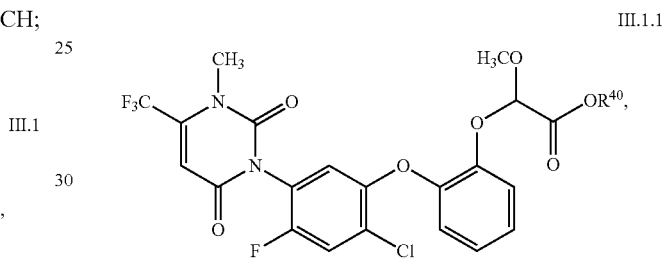

III.1.1 wherein
$R^{40}$ is $C_1$-$C_6$-alkyl, $C_2$-$C_6$-alkenyl, $C_3$-$C_6$-alkynyl, $C_1$-$C_6$-haloalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_3$-cyanoalkyl, phenyl-$C_1$-$C_3$-alkyl, pyridyl-$C_1$-$C_3$-alkyl, $C_3$-$C_6$-cycloalkyl or $C_3$-$C_6$-cycloalkyl-$C_1$-$C_4$-alkyl,
which cycloalkyls are unsubstituted or substituted by one to five substituents selected from the group consisting of halogen, $C_1$-$C_3$-alkyl and $C_1$-$C_2$-haloalkyl;
is preferably $CH_3$, $CH_2CH_2OC_2H_5$, $CH_2CHF_2$, cyclohexyl, (1-methylcyclopropyl)methyl or $CH_2$(pyridine-4-yl);
uracils of formula III.2.1 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is $OR^{40}$ with $R^{40}$ is $CH_3$)

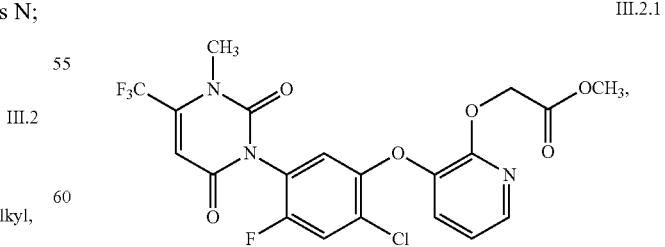

III.2.1 and
uracils of formula III.2.2 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is $OR^{40}$ with $R^{40}$ is $C_2H5$)

III.2.2

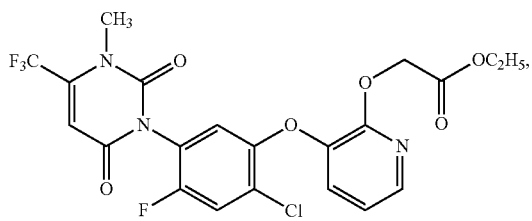

Especially preferred PPO-inhibiting herbicides are the PPO-inhibiting herbicides.1 to A.14 listed below in table A:

TABLE A

| | |
|---|---|
| A.1 | acifluorfen |
| A.2 | butafenacil |
| A.3 | carfentrazone-ethyl |
| A.4 | cinidon-ethyl |
| A.5 | flumioxazin |
| A.6 | fluthiacet-methyl |
| A.7 | fomesafen |
| A.8 | lactofen |
| A.9 | oxadiargyl |
| A.10 | oxyfluorfen |
| A.11 | saflufenacil |
| A.12 | sulfentrazone |
| A.13 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) |
| A.14 | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) |

The PPO-inhibiting herbicides described above that are useful to carry out the present invention are often best applied in conjunction with one or more other herbicides to obtain control of a wider variety of undesirable vegetation. For example, PPO-inhibiting herbicides may further be used in conjunction with additional herbicides to which the crop plant is naturally tolerant, or to which it is resistant via expression of one or more additional transgenes as mentioned supra. When used in conjunction with other targeting herbicides, the PPO-inhibiting herbicides, to which the plant of the present invention had been made resistant or tolerant, can be formulated with the other herbicide or herbicides, tank mixed with the other herbicide or herbicides, or applied sequentially with the other herbicide or herbicides.

Suitable components for mixtures are, for example, selected from the herbicides of class b1) to b15)
B) herbicides of class b1) to b15):
  b1) lipid biosynthesis inhibitors;
  b2) acetolactate synthase inhibitors (ALS inhibitors);
  b3) photosynthesis inhibitors;
  b4) protoporphyrinogen-IX oxidase inhibitors,
  b5) bleacher herbicides;
  b6) enolpyruvyl shikimate 3-phosphate synthase inhibitors (EPSP inhibitors);
  b7) glutamine synthetase inhibitors;
  b8) 7,8-dihydropteroate synthase inhibitors (DHP inhibitors);
  b9) mitosis inhibitors;
  b10) inhibitors of the synthesis of very long chain fatty acids (VLCFA inhibitors);
  b11) cellulose biosynthesis inhibitors;
  b12) decoupler herbicides;
  b13) auxinic herbicides;
  b14) auxin transport inhibitors; and
  b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives.

Examples of herbicides B which can be used in combination with the PPO-inhibiting herbicides according to the present invention are:
b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-Z-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-Z-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;
b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4); b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)-pyrimidine (CAS 180608-33-7), HPPD inhibitors: benzobicyclon, benzofenap, clomazone, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the group of the EPSP synthase inhibitors:
glyphosate, glyphosate-isopropylammonium, glyposate-potassium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitosis inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide and napropamide, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

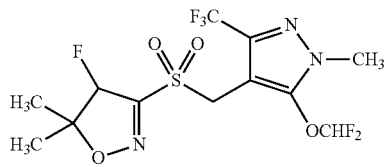

II.1

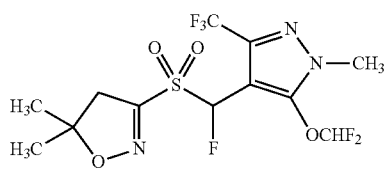

II.2

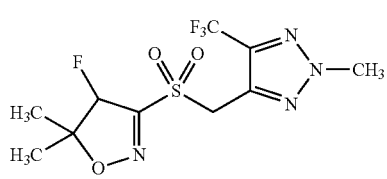

II.3

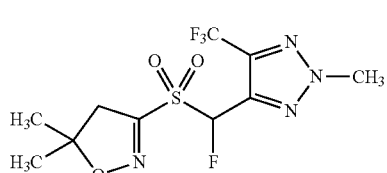

II.4

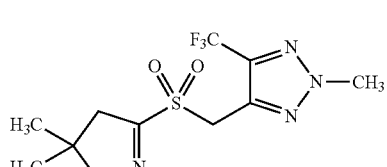

II.5

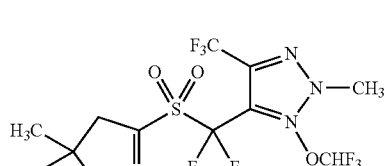

II.6

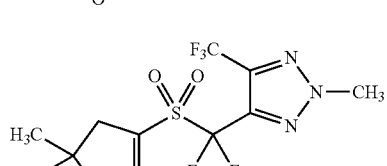

II.7

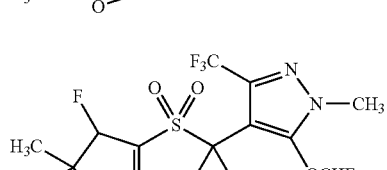

II.8

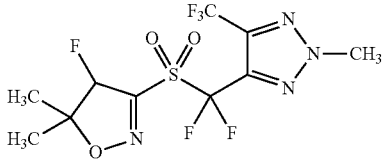

II.9 the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors: chlorthiamid, dichlobenil, flupoxam, indaziflam, triaziflam, isoxaben and 1-Cyclohexyl-5-pentafluorphenyloxy-1$^4$-[1,2,4,6]thiatriazin-3-ylamine;

b12) from the group of the decoupler herbicides: dinoseb, dinoterb and DNOC and its salts;

b13) from the group of the auxinic herbicides:
2,4-D and its salts and esters such as clacyfos, 2,4-DB and its salts and esters, aminocyclopyrachlor and its salts and esters, aminopyralid and its salts such as aminopyralid-tris (2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, MCPP and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam and tridiphane.

Preferred herbicides B that can be used in combination with the PPO-inhibiting herbicides according to the present invention are:

b1) from the group of the lipid biosynthesis inhibitors: clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1, 1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors:
amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors:
ametryn, amicarbazone, atrazine, bentazone, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors:
acifluorfen, acifluorfen-sodium, azafenidin, bencarbazone, benzfendizone, butafenacil, carfentrazone-ethyl, cinidon-ethyl, flufenpyr-ethyl, flumiclorac-pentyl, flumioxazin, fluoroglycofen-ethyl, fluthiacet-methyl, fomesafen, lactofen, oxadiargyl, oxadiazon, oxyfluorfen, pentoxazone, pyraflufen-ethyl, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione; 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
aclonifen, beflubutamid, benzobicyclon, clomazone, diflufenican, flurochloridone, flurtamone, isoxaflutole, mesotrione, norflurazon, picolinafen, pyrasulfotole, pyrazolynate, sulcotrione, tefuryltrione, tembotrione, topramezone, bicyclopyrone, 4-(3-trifluoromethylphenoxy)-2-(4-trifluoromethylphenyl)pyrimidine (CAS 180608-33-7), amitrole and flumeturon;

b6) from the group of the EPSP synthase inhibitors:
glyphosate, glyphosate-isopropylammonium, glyphosate-potassium and glyphosate-trimesium (sulfosate);

b7) from the group of the glutamine synthase inhibitors:
glufosinate, glufosinate-P, glufosinate-ammonium;

b8) from the group of the DHP synthase inhibitors: asulam;

b9) from the group of the mitosis inhibitors:
benfluralin, dithiopyr, ethalfluralin, oryzalin, pendimethalin, thiazopyr and trifluralin;

b10) from the group of the VLCFA inhibitors:
acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors:
dichlobenil, flupoxam, isoxaben and 1-Cyclohexyl-5-pentafluorphenyloxy-1$^4$-[1,2,4,6]thiatriazin-3-ylamine;

b13) from the group of the auxinic herbicides:
2,4-D and its salts and esters, aminocyclopyrachlor and its salts and esters, aminopyralid and its salts such as aminopyralid-tris(2-hydroxypropyl)ammonium and its esters, clopyralid and its salts and esters, dicamba and its salts and esters, dichlorprop-P and its salts and esters, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac and triclopyr and its salts and esters;

b14) from the group of the auxin transport inhibitors:
diflufenzopyr and diflufenzopyr-sodium;

b15) from the group of the other herbicides: bromobutide, cinmethylin, cumyluron, cyclopyrimorate (CAS 499223-49-3) and its salts and esters, dalapon, difenzoquat, difenzoquat-metilsulfate, DSMA, dymron (=daimuron), flamprop, flamprop-isopropyl, flamprop-methyl, flamprop-M-isopropyl, flamprop-M-methyl, indanofan, indaziflam, metam, methylbromide, MSMA, oxaziclomefone, pyributicarb, triaziflam and tridiphane. Particularly preferred herbicides B that can be used in combination with the PPO-inhibiting herbicides according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3 (6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors: acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

b5) from the group of the bleacher herbicides: clomazone, diflufenican, flurochloridone, isoxaflutole, mesotrione, picolinafen, sulcotrione, tefuryltrione, tembotrione, topramezone, bicyclopyrone, amitrole and flumeturon;

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: isoxaben;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, fluroxypyr-meptyl, quinclorac and quinmerac;

b14) from the group of the auxin transport inhibitors: diflufenzopyr and diflufenzopyr-sodium, b15) from the group of the other herbicides: dymron (=daimuron), indanofan, indaziflam, oxaziclomefone and triaziflam.

Moreover, it may be useful to apply the PPO-inhibiting herbicides, when used in combination with a compound B described SUPRA, in combination with safeners. Safeners are chemical compounds which prevent or reduce damage on useful plants without having a major impact on the herbicidal action of herbicides towards unwanted plants. They can be applied either before sowings (e.g. on seed treatments, shoots or seedlings) or in the pre-emergence application or post-emergence application of the useful plant.

Furthermore, the safeners C, the PPO-inhibiting herbicides and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3) and 2,2,5-trimethyl-3-(dichloroacetyl)-1,3-oxazolidine (R-29148, CAS 52836-31-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C are benoxacor, cloquintocet, cyprosulfamide, dichlormid, fenchlorazole, fenclorim, furilazole, isoxadifen, mefenpyr, naphthalic anhydride, 4-(dichloroacetyl)-1-oxa-4-azaspiro[4.5]decane (MON4660, CAS 71526-07-3), and 2,2,5-trimethyl-3-(dichloroacetyl)-1,3-oxazolidine (R-29148, CAS 52836-31-4).

Also preferred safeners C are benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C, which, as component C, are constituent of the composition according to the invention are the safeners C as defined above; in particular the safeners C.1-C.12 listed below in table C:

TABLE C

| | Safener C |
|---|---|
| C.1 | benoxacor |
| C.2 | cloquintocet |
| C.3 | cyprosulfamide |
| C.4 | dichlormid |
| C.5 | fenchlorazole |
| C.6 | fenclorim |
| C.7 | furilazole |
| C.8 | isoxadifen |
| C.9 | mefenpyr |
| C.10 | naphtalic acid anhydride |
| C.11 | 4-(dichloroacetyl)-1-oxa-4-azaspiro[4.5]decane (MON4660, CAS 71526-07-3) |
| C.12 | 2,2,5-trimethyl-3-(dichloro-acetyl)-1,3-oxazolidine (R-29148, CAS 52836-31-4) |

The PPO-inhibiting herbicides (compounds A) and the active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloro-acetyl)-1,3-oxazolidine [CAS No. 52836-31-4] is also referred to as R-29148. 4-(Dichloroacetyl)-1-oxa-4-azaspiro [4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl. Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanol-ammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethyl-ammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium.

Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium and aminopyralid-tris(2-hydroxypropyl) ammonium.

Suitable salts of glyphosate are for example glyphosate-ammonium, glyphosate-diammonium, glyphosate-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

The preferred embodiments of the invention mentioned herein below have to be understood as being preferred either independently from each other or in combination with one another.

According to a preferred embodiment of the invention, the composition comprises as component B at least one, preferably exactly one herbicide B.

According to another preferred embodiment of the invention, the composition comprises at least two, preferably exactly two, herbicides B different from each other.

According to another preferred embodiment of the invention, the composition comprises at least three, preferably exactly three, herbicides B different from each other.

According to another preferred embodiment of the invention, the composition comprises as component A at least one, preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100; 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and as component B at least one, preferably exactly one, herbicide B.

According to another preferred embodiment of the invention, the composition comprises as component A at least one, preferably exactly preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and at least two, preferably exactly two, herbicides B different from each other.

According to another preferred embodiment of the invention, the composition comprises as component A at least one, preferably exactly preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) and at least three, preferably exactly three, herbicides B different from each other.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b1), in particular selected from the group consisting of clethodim, clodinafop-propargyl, cycloxydim, cyhalofop-butyl, fenoxaprop-P-ethyl, fluazifop, pinoxaden, profoxydim, quizalofop, sethoxydim, tepraloxydim, tralkoxydim, esprocarb, prosulfocarb, thiobencarb and triallate.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b2), in particular selected from the group consisting of bensulfuron-methyl, bispyribac-sodium, cloransulam-methyl, cyclosulfamuron, diclosulam, flumetsulam, flupyrsulfuron-methyl-sodium, foramsulfuron, halosulfuron-methyl, imazamox, imazapic, imazapyr, imazaquin, imazethapyr, imazosulfuron, iodosulfuron, iodosulfuron-methyl-sodium, mesosulfuron-methyl, metazosulfuron, nicosulfuron, penoxsulam, propoxycarbazon-sodium, pyrazosulfuron-ethyl, pyrithiobac-sodium, pyroxsulam, rimsulfuron, sulfosulfuron, thiencarbazon-methyl, thifensulfuron-methyl, trifloxysulfuron and tritosulfuron.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b3), in particular selected from the group consisting of ametryn, atrazine, bentazon, bromoxynil, diuron, fluometuron, hexazinone, isoproturon, linuron, metribuzin, paraquat, paraquat-dichloride, prometryne, propanil, terbutryn and terbuthylazine.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b4), in particular selected from the group consisting of acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4).

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b5), in particular selected from the group consisting of clomazone, diflufenican, flurochloridone, isoxaflutole, mesotrione, picolinafen, sulcotrione, tefuryltrione, tembotrione, topramezone, bicyclopyrone, amitrole and flumeturon.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2, 4-dione (CAS 1258836-72-4), at least one and especially exactly one herbicidally active compound from group b6), in particular selected from the group consisting of glyphosate, glyphosate-isopropylammonium and glyphosate-trimesium (sulfosate).

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b7), in particular selected from the group consisting of glufosinate, glufosinate-P and glufosinate-ammonium.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b9), in particular selected from the group consisting of pendimethalin and trifluralin.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4)), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b13), in particular selected from the group consisting of 2,4-D and its salts and esters, aminocyclopyrachlor and its salts and esters, aminopyralid and its salts such as aminopyralid-tris(2-hydroxypropyl)ammonium and its esters, clopyralid and its salts and esters, dicamba and its salts and esters, fluroxypyr-meptyl, quinclorac and quinmerac.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b14), in particular selected from the group consisting of diflufenzopyr and diflufenzopyr-sodium.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2, 4-dione (CAS 1258836-72-4), at least one and especially exactly one herbicidally active compound from group b15), in particular selected from the group consisting of dymron (=daimuron), indanofan, indaziflam, oxaziclomefone and triaziflam.

Here and below, the term "binary compositions" includes compositions comprising one or more, for example 1, 2 or 3, active compounds of the PPO-inhibiting herbicide and either one or more, for example 1, 2 or 3, herbicides B.

In binary compositions comprising at least one PPO-inhibiting herbicide as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

Particularly preferred herbicides B are the herbicides B as defined above; in particular the herbicides B.1-B.229 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | fluazifop |
| B.8 | metamifop |
| B.9 | pinoxaden |
| B.10 | profoxydim |
| B.11 | quizalofop |
| B.12 | sethoxydim |
| B.13 | tepraloxydim |
| B.14 | tralkoxydim |
| B.15 | esprocarb |
| B.16 | ethofumesate |
| B.17 | molinate |
| B.18 | prosulfocarb |
| B.19 | thiobencarb |
| B.20 | triallate |
| B.21 | bensulfuron-methyl |
| B.22 | bispyribac-sodium |
| B.23 | cloransulam-methyl |
| B.24 | chlorsulfuron |
| B.25 | clorimuron |
| B.26 | cyclosulfamuron |
| B.27 | diclosulam |
| B.28 | florasulam |
| B.29 | flumetsulam |
| B.30 | flupyrsulfuron-methyl-sodium |
| B.31 | foramsulfuron |
| B.32 | halosulfuron-methyl |
| B.33 | imazamox |
| B.34 | imazamox-ammonium |
| B.35 | imazapic |
| B.36 | imazapic-ammonium |
| B.37 | imazapic-isopropylammonium |
| B.38 | imazapyr |
| B.39 | imazapyr-ammonium |
| B.40 | imazapyr-isopropylammonium |
| B.41 | imazaquin |
| B.42 | imazaquin-ammonium |
| B.43 | imazethapyr |
| B.44 | imazethapyr-ammonium |
| B.45 | imazethapyr-isopropylammonium |
| B.46 | imazosulfuron |
| B.47 | iodosulfuron-methyl-sodium |
| B.48 | iofensulfuron |
| B.49 | iofensulfuron-sodium |
| B.50 | mesosulfuron-methyl |
| B.51 | metazosulfuron |
| B.52 | metsulfuron-methyl |

TABLE B-continued

| | Herbicide B |
|---|---|
| B.53 | metosulam |
| B.54 | nicosulfuron |
| B.55 | penoxsulam |
| B.56 | propoxycarbazon-sodium |
| B.57 | pyrazosulfuron-ethyl |
| B.58 | pyribenzoxim |
| B.59 | pyriftalid |
| B.60 | pyrithiobac-sodium |
| B.61 | pyroxsulam |
| B.62 | propyrisulfuron |
| B.63 | rimsulfuron |
| B.64 | sulfosulfuron |
| B.65 | thiencarbazone-methyl |
| B.66 | thifensulfuron-methyl |
| B.67 | tribenuron-methyl |
| B.68 | trifloxysulfuron |
| B.69 | tritosulfuron |
| B.70 | triafamone |
| B.71 | ametryne |
| B.72 | atrazine |
| B.73 | bentazon |
| B.74 | bromoxynil |
| B.75 | bromoxynil-octanoate |
| B.76 | bromoxynil-heptanoate |
| B.77 | bromoxynil-potassium |
| B.78 | diuron |
| B.79 | fluometuron |
| B.80 | hexazinone |
| B.81 | isoproturon |
| B.82 | linuron |
| B.83 | metamitron |
| B.84 | metribuzin |
| B.85 | prometryne |
| B.86 | propanil |
| B.87 | simazin |
| B.88 | terbuthylazine |
| B.89 | terbutryn |
| B.90 | paraquat-dichloride |
| B.91 | acifluorfen |
| B.92 | acifluorfen-sodium |
| B.93 | azafenidin |
| B.94 | bencarbazone |
| B.95 | benzfendizone |
| B.96 | bifenox |
| B.97 | butafenacil |
| B.98 | carfentrazone |
| B.99 | carfentrazone-ethyl |
| B.100 | chlomethoxyfen |
| B.101 | cinidon-ethyl |
| B.102 | fluazolate |
| B.103 | flufenpyr |
| B.104 | flufenpyr-ethyl |
| B.105 | flumiclorac |
| B.106 | flumiclorac-pentyl |
| B.107 | flumioxazin |
| B.108 | fluoroglycofen |
| B.109 | fluoroglycofen-ethyl |
| B.110 | fluthiacet |
| B.111 | fluthiacet-methyl |
| B.112 | fomesafen |
| B.113 | halosafen |
| B.114 | lactofen |
| B.115 | oxadiargyl |
| B.116 | oxadiazon |
| B.117 | oxyfluorfen |
| B.118 | pentoxazone |
| B.119 | profluazol |
| B.120 | pyraclonil |
| B.121 | pyraflufen |
| B.122 | pyraflufen-ethyl |
| B.123 | saflufenacil |
| B.124 | sulfentrazone |
| B.125 | thidiazimin |
| B.126 | tiafenacil |
| B.127 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl- |

TABLE B-continued

| | Herbicide B |
|---|---|
| B.128 | oxy]acetate (CAS 353292-31-6) 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione (CAS 1258836-72-4) |
| B.129 | N-ethyl-3-(2,6-dichloro-4-trifluoromethylphenoxy)-5-methyl-1H-pyrazole-1-carboxamide (CAS 452098-92-9) |
| B.130 | N-tetrahydrofurfuryl-3-(2,6-dichloro-4-trifluoromethylphenoxy)-5-methyl-1H-pyrazole-1-carboxamide (CAS 915396-43-9) |
| B.131 | N-ethyl-3-(2-chloro-6-fluoro-4-trifluoromethylphenoxy)-5-methyl-1H-pyrazole-1-carboxamide (CAS 452099-05-7) |
| B.132 | N-tetrahydrofurfuryl-3-(2-chloro-6-fluoro-4-trifluoro-methylphenoxy)-5-methyl-1H-pyrazole-1-carboxamide (CAS 452100-03-7) |
| B.133 | 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione |
| B.134 | 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione |
| B.135 | 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione |
| B.136 | methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3] |
| B.137 | 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4) |
| B.138 | benzobicyclon |
| B.139 | clomazone |
| B.140 | diflufenican |
| B.141 | flurochloridone |
| B.142 | isoxaflutole |
| B.143 | mesotrione |
| B.144 | norflurazon |
| B.145 | picolinafen |
| B.146 | sulcotrione |
| B.147 | tefuryltrione |
| B.148 | tembotrione |
| B.149 | topramezone |
| B.150 | topramezone-sodium |
| B.151 | bicyclopyrone |
| B.152 | amitrole |
| B.153 | fluometuron |
| B.154 | glyphosate |
| B.155 | glyphosate-ammonium |
| B.156 | glyphosate-dimethylammonium |
| B.157 | glyphosate-isopropylammonium |
| B.158 | glyphosate-trimesium (sulfosate) |
| B.159 | glyphosate-potassium |
| B.160 | glufosinate |
| B.161 | glufosinate-ammonium |
| B.162 | glufosinate-P |
| B.163 | glufosinate-P-ammonium |
| B.164 | pendimethalin |
| B.165 | trifluralin |
| B.166 | acetochlor |
| B.167 | butachlor |
| B.168 | cafenstrole |
| B.169 | dimethenamid-P |
| B.170 | fentrazamide |
| B.171 | flufenacet |
| B.172 | mefenacet |
| B.173 | metazachlor |
| B.174 | metolachlor |
| B.175 | S-metolachlor |
| B.176 | pretilachlor |
| B.177 | fenoxasulfone |
| B.178 | isoxaben |
| B.179 | ipfencarbazone |
| B.180 | pyroxasulfone |
| B.181 | 2,4-D |
| B.182 | 2,4-D-isobutyl |
| B.183 | 2,4-D-dimethylammonium |
| B.184 | 2,4-D-N,N,N-trimethylethanolammonium |
| B.185 | aminopyralid |
| B.186 | aminopyralid-methyl |
| B.187 | aminopyralid-tris(2-hydroxypropyl)ammonium |
| B.188 | clopyralid |
| B.189 | clopyralid-methyl |
| B.190 | clopyralid-olamine |
| B.191 | dicamba |
| B.192 | dicamba-butotyl |
| B.193 | dicamba-diglycolamine |
| B.194 | dicamba-dimethylammonium |
| B.195 | dicamba-diolamine |
| B.196 | dicamba-isopropylammonium |
| B.197 | dicamba-potassium |
| B.198 | dicamba-sodium |
| B.199 | dicamba-trolamine |
| B.200 | dicamba-N,N-bis-(3-aminopropyl)methylamine |
| B.201 | dicamba-diethylenetriamine |
| B.202 | fluroxypyr |
| B.203 | fluroxypyr-meptyl |
| B.204 | MCPA |
| B.205 | MCPA-2-ethylhexyl |
| B.206 | MCPA-dimethylammonium |
| B.207 | quinclorac |
| B.208 | quinclorac-dimethylammonium |
| B.209 | quinmerac |
| B.210 | quinmerac-dimethylammonium |
| B.211 | aminocyclopyrachlor |
| B.212 | aminocyclopyrachlor-potassium |
| B.213 | aminocyclopyrachlor-methyl |
| B.214 | diflufenzopyr |
| B.215 | diflufenzopyr-sodium |
| B.216 | dymron |
| B.217 | indanofan |
| B.218 | indaziflam |
| B.219 | oxaziclomefone |
| B.220 | triaziflam |
| B.221 | II.1 |
| B.222 | II.2 |
| B.223 | II.3 |
| B.224 | II.4 |
| B.225 | II.5 |
| B.226 | II.6 |
| B.227 | II.7 |
| B.228 | II.8 |
| B.229 | II.9 |

Particularly preferred are compositions 1.1 to 1.229, comprising acifluorfen and the substance(s) as defined in the respective row of table B-1:

TABLE B-1

(compositions 1.1 to 1.229):

| comp. no. | herbicide B |
|---|---|
| 1.1 | B.1 |
| 1.2 | B.2 |
| 1.3 | B.3 |
| 1.4 | B.4 |
| 1.5 | B.5 |
| 1.6 | B.6 |
| 1.7 | B.7 |
| 1.8 | B.8 |
| 1.9 | B.9 |
| 1.10 | B.10 |
| 1.11 | B.11 |
| 1.12 | B.12 |
| 1.13 | B.13 |
| 1.14 | B.14 |
| 1.15 | B.15 |
| 1.16 | B.16 |
| 1.17 | B.17 |
| 1.18 | B.18 |
| 1.19 | B.19 |
| 1.20 | B.20 |
| 1.21 | B.21 |
| 1.22 | B.22 |
| 1.23 | B.23 |
| 1.24 | B.24 |
| 1.25 | B.25 |
| 1.26 | B.26 |
| 1.27 | B.27 |
| 1.28 | B.28 |
| 1.29 | B.29 |
| 1.30 | B.30 |
| 1.31 | B.31 |
| 1.32 | B.32 |
| 1.33 | B.33 |
| 1.34 | B.34 |
| 1.35 | B.35 |
| 1.36 | B.36 |
| 1.37 | B.37 |
| 1.38 | B.38 |
| 1.39 | B.39 |
| 1.40 | B.40 |
| 1.41 | B.41 |
| 1.42 | B.42 |
| 1.43 | B.43 |
| 1.44 | B.44 |
| 1.45 | B.45 |
| 1.46 | B.46 |
| 1.47 | B.47 |
| 1.48 | B.48 |
| 1.49 | B.49 |
| 1.50 | B.50 |
| 1.51 | B.51 |
| 1.52 | B.52 |
| 1.53 | B.53 |
| 1.54 | B.54 |
| 1.55 | B.55 |
| 1.56 | B.56 |
| 1.57 | B.57 |
| 1.58 | B.58. |
| 1.59 | B.59 |
| 1.60 | B.60 |
| 1.61 | B.61 |
| 1.62 | B.62 |
| 1.63 | B.63 |
| 1.64 | B.64 |
| 1.65 | B.65 |
| 1.66 | B.66 |
| 1.67 | B.67 |
| 1.68 | B.68 |
| 1.69 | B.69 |
| 1.70 | B.70 |
| 1.71 | B.71 |
| 1.72 | B.72 |
| 1.73 | B.73 |
| 1.74 | B.74 |
| 1.75 | B.75 |
| 1.76 | B.76 |
| 1.77 | B.77 |
| 1.78 | B.78 |
| 1.79 | B.79 |
| 1.80 | B.80 |
| 1.81 | B.81 |
| 1.82 | B.82 |
| 1.83 | B.83 |
| 1.84 | B.84 |
| 1.85 | B.85 |
| 1.86 | B.86 |
| 1.87 | B.87 |
| 1.88 | B.88 |
| 1.89 | B.89 |
| 1.90 | B.90 |
| 1.91 | B.91 |
| 1.92 | B.92 |
| 1.93 | B.93 |
| 1.94 | B.94 |
| 1.95 | B.95 |
| 1.96 | B.96 |
| 1.97 | B.97 |
| 1.98 | B.98 |
| 1.99 | B.99 |
| 1.100 | B.100 |
| 1.101 | B.101 |
| 1.102 | B.102 |
| 1.103 | B.103 |
| 1.104 | B.104 |
| 1.105 | B.105 |
| 1.106 | B.106 |
| 1.107 | B.107 |
| 1.108 | B.108 |
| 1.109 | B.109 |
| 1.110 | B.110 |
| 1.111 | B.111 |
| 1.112 | B.112 |
| 1.113 | B.113 |
| 1.114 | B.114 |
| 1.115 | B.115 |
| 1.116 | B.116 |
| 1.117 | B.117 |
| 1.118 | B.118 |
| 1.119 | B.119 |
| 1.120 | B.120 |
| 1.121 | B.121 |
| 1.122 | B.122 |
| 1.123 | B.123 |
| 1.124 | B.124 |
| 1.125 | B.125 |
| 1.126 | B.126 |
| 1.127 | B.127 |
| 1.128 | B.128 |
| 1.129 | B.129 |
| 1.130 | B.130 |
| 1.131 | B.131 |
| 1.132 | B.132 |
| 1.133 | B.133 |
| 1.134 | B.134 |
| 1.135 | B.135 |
| 1.136 | B.136 |
| 1.137 | B.137 |
| 1.138 | B.138 |
| 1.139 | B.139 |
| 1.140 | B.140 |
| 1.141 | B.141 |
| 1.142 | B.142 |
| 1.143 | B.143 |
| 1.144 | B.144 |
| 1.145 | B.145 |
| 1.146 | B.146 |
| 1.147 | B.147 |
| 1.148 | B.148 |
| 1.149 | B.149 |
| 1.150 | B.150 |

TABLE B-1-continued (compositions 1.1 to 1.229):

| comp. no. | herbicide B |
|---|---|
| 1.151 | B.151 |
| 1.152 | B.152 |
| 1.153 | B.153 |
| 1.154 | B.154 |
| 1.155 | B.155 |
| 1.156 | B.156 |
| 1.157 | B.157 |
| 1.158 | B.158 |
| 1.159 | B.159 |
| 1.160 | B.160 |
| 1.161 | B.161 |
| 1.162 | B.162 |
| 1.163 | B.163 |
| 1.164 | B.164 |
| 1.165 | B.165 |
| 1.166 | B.166 |
| 1.167 | B.167 |
| 1.168 | B.168 |
| 1.169 | B.169 |
| 1.170 | B.170 |
| 1.171 | B.171 |
| 1.172 | B.172 |
| 1.173 | B.173 |
| 1.174 | B.174 |
| 1.175 | B.175 |
| 1.176 | B.176 |
| 1.177 | B.177 |
| 1.178 | B.178 |
| 1.179 | B.179 |
| 1.180 | B.180 |
| 1.181 | B.181 |
| 1.182 | B.182 |
| 1.183 | B.183 |
| 1.184 | B.184 |
| 1.185 | B.185 |
| 1.186 | B.186 |
| 1.187 | B.187 |
| 1.188 | B.188 |
| 1.189 | B.189 |
| 1.190 | B.190 |
| 1.191 | B.191 |
| 1.192 | B.192 |
| 1.193 | B.193 |
| 1.194 | B.194 |
| 1.195 | B.195 |
| 1.196 | B.196 |
| 1.197 | B.197 |
| 1.198 | B.198 |
| 1.199 | B.199 |
| 1.200 | B.200 |
| 1.201 | B.201 |
| 1.202 | B.202 |
| 1.203 | B.203 |
| 1.204 | B.204 |
| 1.205 | B.205 |
| 1.206 | B.206 |
| 1.207 | B.207 |
| 1.208 | B.208 |
| 1.209 | B.209 |
| 1.210 | B.210 |
| 1.211 | B.211 |
| 1.212 | B.212 |
| 1.213 | B.213 |
| 1.214 | B.214 |
| 1.215 | B.215 |
| 1.216 | B.216 |
| 1.217 | B.217 |
| 1.218 | B.218 |
| 1.219 | B.219 |
| 1.220 | B.220 |
| 1.221 | B.221 |
| 1.222 | B.222 |
| 1.223 | B.223 |
| 1.224 | B.224 |
| 1.225 | B.225 |
| 1.226 | B.226 |
| 1.227 | B.227 |
| 1.228 | B.228 |
| 1.229 | B.229 |

Also especially preferred are compositions 2.1. to 2.229 which differ from the corresponding compositions 1.1 to 1.229 only in that they comprise as component A acifluorfen-sodium.

Also especially preferred are compositions 3.1. to 3.229 which differ from the corresponding compositions 1.1 to 1.229 only in that they comprise as component A azafenidin.

Also especially preferred are compositions 4.1. to 4.229 which differ from the corresponding compositions 1.1 to 1.229 only in that they comprise as component A bencarbazone.

Also especially preferred are compositions 5.1. to 5.229 which differ from the corresponding compositions 1.1 to 1.229 only in that they comprise as component A benzfendizone.

Also especially preferred are compositions 6.1. to 6.229 which differ from the corresponding compositions 1.1 to 1.229 only in that they comprise as component A bifenox.

Also especially preferred are compositions 7.1. to 7.229 which differ from the corresponding compositions 1.1 to 1.227 only in that they comprise as component A butafenacil.

Also especially preferred are compositions 8.1. to 8.229 which differ from the corresponding compositions 1.1 to 1.229 only in that they comprise as component A carfentrazone.

Also especially preferred are compositions 9.1. to 9.229 which differ from the corresponding compositions 1.1 to 1.229 only in that they comprise as component A carfentrazone-ethyl.

Also especially preferred are compositions 10.1. to 10.229 which differ from the corresponding compositions 1.1 to 1.229 only in that they comprise as component A chlomethoxyfen.

Also especially preferred are compositions 11.1. to 11.229 which differ from the corresponding compositions 1.1 to 1.229 only in that they comprise as component A cinidon-ethyl.

Also especially preferred are compositions 12.1. to 12.229 which differ from the corresponding compositions 1.1 to 1.229 only in that they comprise as component A fluazolate.

Also especially preferred are compositions 13.1. to 13.229 which differ from the corresponding compositions 1.1 to 1.229 only in that they comprise as component A flufenpyr.

Also especially preferred are compositions 14.1. to 14.229 which differ from the corresponding compositions 1.1 to 1.229 only in that they comprise as component A flufenpyr-ethyl.

Also especially preferred are compositions 15.1. to 15.229 which differ from the corresponding compositions 1.1 to 1.229 only in that they comprise as component A flumiclorac.

Also especially preferred are compositions 16.1. to 16.229 which differ from the corresponding compositions 1.1 to 1.229 only in that they comprise as component A flumiclorac-pentyl.

Also especially preferred are compositions 17.1. to 17.229 which differ from the corresponding compositions 1.1 to 1.229 only in that they comprise as component A flumioxazin.

Also especially preferred are compositions 18.1. to 18.229 which differ from the corresponding compositions 1.1 to 1.229 only in that they comprise as component A fluoroglycofen.

Also especially preferred are compositions 19.1. to 19.229 which differ from the corresponding compositions 1.1 to 1.229 only in that they comprise as component A fluoroglycofen-ethyl.

Also especially preferred are compositions 20.1. to 20.229 which differ from the corresponding compositions 1.1 to 1.229 only in that they comprise as component A fluthiacet.

Also especially preferred are compositions 21.1. to 21.229 which differ from the corresponding compositions 1.1 to 1.229 only in that they comprise as component A fluthiacet-methyl.

Also especially preferred are compositions 22.1. to 22.229 which differ from the corresponding compositions 1.1 to 1.229 only in that they comprise as component A fomesafen.

Also especially preferred are compositions 23.1. to 23.229 which differ from the corresponding compositions 1.1 to 1.229 only in that they comprise as component A halosafen.

Also especially preferred are compositions 24.1. to 24.229 which differ from the corresponding compositions 1.1 to 1.229 only in that they comprise as component A lactofen.

Also especially preferred are compositions 25.1. to 25.229 which differ from the corresponding compositions 1.1 to 1.229 only in that they comprise as component A oxadiargyl.

Also especially preferred are compositions 26.1. to 26.229 which differ from the corresponding compositions 1.1 to 1.229 only in that they comprise as component A oxadiazon.

Also especially preferred are compositions 27.1. to 27.229 which differ from the corresponding compositions 1.1 to 1.229 only in that they comprise as component A oxyfluorfen.

Also especially preferred are compositions 28.1. to 28.229 which differ from the corresponding compositions 1.1 to 1.229 only in that they comprise as component A pentoxazone.

Also especially preferred are compositions 29.1. to 29.229 which differ from the corresponding compositions 1.1 to 1.229 only in that they comprise as component A profluazol.

Also especially preferred are compositions 30.1. to 30.229 which differ from the corresponding compositions 1.1 to 1.229 only in that they comprise as component A pyraclonil.

Also especially preferred are compositions 31.1. to 31.229 which differ from the corresponding compositions 1.1 to 1.229 only in that they comprise as component A pyraflufen.

Also especially preferred are compositions 32.1. to 32.229 which differ from the corresponding compositions 1.1 to 1.229 only in that they comprise as component A pyraflufen-ethyl.

Also especially preferred are compositions 33.1. to 33.229 which differ from the corresponding compositions 1.1 to 1.229 only in that they comprise as component A saflufenacil.

Also especially preferred are compositions 34.1. to 34.229 which differ from the corresponding compositions 1.1 to 1.229 only in that they comprise as component A sulfentrazone.

Also especially preferred are compositions 35.1. to 35.229 which differ from the corresponding compositions 1.1 to 1.229 only in that they comprise as component A thidiazimin.

Also especially preferred are compositions 36.1. to 36.229 which differ from the corresponding compositions 1.1 to 1.229 only in that they comprise as component A tiafenacil.

Also especially preferred are compositions 37.1. to 37.229 which differ from the corresponding compositions 1.1 to 1.229 only in that they comprise as component A ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100).

Also especially preferred are compositions 38.1. to 38.229 which differ from the corresponding compositions 1.1 to 1.229 only in that they comprise as component A 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4)

Also especially preferred are compositions 39.1. to 39.229 which differ from the corresponding compositions 1.1 to 1.229 only in that they comprise as component A N-ethyl-3-(2,6-dichloro-4-trifluoromethylphenoxy)-5-methyl-1H-pyrazole-1-carboxamide (CAS 452098-92-9).

Also especially preferred are compositions 40.1. to 40.229 which differ from the corresponding compositions 1.1 to 1.229 only in that they comprise as component A N-tetrahydrofurfuryl-3-(2,6-dichloro-4-trifluoromethylphenoxy)-5-methyl-1H-pyrazole-1-carboxamide (CAS 915396-43-9).

Also especially preferred are compositions 41.1. to 41.229 which differ from the corresponding compositions 1.1 to 1.229 only in that they comprise as component A N-ethyl-3-(2-chloro-6-fluoro-4-trifluoromethylphenoxy)-5-methyl-1H-pyrazole-1-carboxamide (CAS 452099-05-7).

Also especially preferred are compositions 42.1. to 42.229 which differ from the corresponding compositions 1.1 to 1.229 only in that they comprise as component A N-tetrahydrofurfuryl-3-(2-chloro-6-fluoro-4-trifluoromethylphenoxy)-5-methyl-1H-pyrazole-1-carboxamide (CAS 452100-03-7).

Also especially preferred are compositions 43.1. to 43.229 which differ from the corresponding compositions 1.1 to 1.229 only in that they comprise as component A 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione.

Also especially preferred are compositions 44.1. to 44.229 which differ from the corresponding compositions 1.1 to 1.229 only in that they comprise as component A methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3).

Also especially preferred are compositions 45.1. to 45.229 which differ from the corresponding compositions 1.1 to 1.229 only in that they comprise as component A 3-[7-Chloro-5-fluoro-2-(trifluoromethyl)-1H-benzimidazol-4-yl]-1-methyl-6-(trifluoromethyl)-1 H-pyrimidine-2,4-dione (CAS 212754-02-4).

Also especially preferred are compositions 46.1. to 46.229 which differ from the corresponding compositions 1.1 to 1.229 only in that they comprise as component A 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione.

Also especially preferred are compositions 47.1. to 47.229 which differ from the corresponding compositions 1.1 to 1.229 only in that they comprise as component A 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione Also especially preferred are compositions 48.1. to 48.229 which differ from the corresponding compositions 1.1 to 1.229 only in that they additionally comprise benoxacor as safener C.

Also especially preferred are compositions 49.1. to 49.229 which differ from the corresponding compositions 1.1 to 1.229 only in that they additionally comprise cloquintocet as safener C.

Also especially preferred are compositions 50.1. to 50.229 which differ from the corresponding compositions 1.1 to 1.229 only in that they additionally comprise cyprosulfamide as safener C.

Also especially preferred are compositions 51.1. to 51.229 which differ from the corresponding compositions 1.1 to 1.229 only in that they additionally comprise dichlormid as safener C.

Also especially preferred are compositions 52.1. to 52.229 which differ from the corresponding compositions 1.1 to 1.229 only in that they additionally comprise fenchlorazole as safener C.

Also especially preferred are compositions 53.1. to 53.229 which differ from the corresponding compositions 1.1 to 1.229 only in that they additionally comprise fenclorim as safener C.

Also especially preferred are compositions 54.1. to 54.229 which differ from the corresponding compositions 1.1 to 1.229 only in that they additionally comprise furilazole as safener C.

Also especially preferred are compositions 55.1. to 55.229 which differ from the corresponding compositions 1.1 to 1.229 only in that they additionally comprise isoxadifen as safener C.

Also especially preferred are compositions 56.1. to 56.229 which differ from the corresponding compositions 1.1 to 1.229 only in that they additionally comprise mefenpyr as safener C.

Also especially preferred are compositions 57.1. to 57.229 which differ from the corresponding compositions 1.1 to 1.229 only in that they additionally comprise 4-(dichloroacetyl)-1-oxa-4-azaspiro[4.5]decane (MON4660, CAS 71526-07-3) as safener C.

Also especially preferred are compositions 58.1. to 58.229 which differ from the corresponding compositions 1.1 to 1.229 only in that they additionally comprise 2,2,5-trimethyl-3-(dichloroacetyl)-1,3-oxazolidine (R-29148, CAS 52836-31-4) as safener C.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

As described above, the present invention teaches compositions and methods for increasing the PPO-inhibiting tolerance of a crop plant or seed as compared to a wild-type variety of the plant or seed. In a preferred embodiment, the PPO-inhibiting tolerance of a crop plant or seed is increased such that the plant or seed can withstand a PPO-inhibiting herbicide application of preferably approximately 1-1000 g ai ha$^{-1}$, more preferably 1-200 g ai ha$^{-1}$, even more preferably 5-150 g ai ha$^{-1}$, and most preferably 10-100 g ai ha$^{-1}$. As used herein, to "withstand" a PPO-inhibiting herbicide application means that the plant is either not killed or only moderately injured by such application. It will be understood by the person skilled in the art that the application rates may vary, depending on the environmental conditions such as temperature or humidity, and depending on the chosen kind of herbicide (active ingredient ai).

Post-emergent weed control methods useful in various embodiments hereof utilize about >0.3× application rates of PPO-inhibiting herbicides; in some embodiments, this can be about, for example, >0.3×, >0.4×, >0.5×, >0.6×, >0.7×, >0.8×, >0.9×, or >1× of PPO-inhibiting herbicides. In one embodiment, PPO-inhibiting herbicides-tolerant plants of the present invention have tolerance to a post-emergant application of a PPO-inhibiting herbicides at an amount of about 25 to about 200 g ai/ha. In some embodiments, wherein the PPO-inhibiting herbicides-tolerant plant is a dicot (e.g., soy, cotton), the post-emergant application of the PPO-inhibiting herbicides is at an amount of about 50 g ai/ha. In another embodiment, wherein the PPO-inhibiting herbicides-tolerant plant is a monocot (e.g., maize, rice, sorghum), the post-emergant application of the PPO-inhibiting herbicides is at an amount of about 200 g ai/ha. In other embodiments, wherein the PPO-inhibiting herbicides-tolerant plant is a *Brassica* (e.g., canola), the post-emergant application of the PPO-inhibiting herbicides is at an amount of about 25 g ai/ha. In post-emergent weed control methods hereof, in some embodiments, the method can utilize PPO-inhibiting herbicides application rates at about 7 to 10 days post-emergent. In another embodiment, the application rate can exceed 1× PPO-inhibiting herbicides; in some embodiments, the rate can be up to 4× PPO-inhibiting herbicides, though more typically it will be about 2.5× or less, or about 2× or less, or about 1× or less.

Furthermore, the present invention provides methods that involve the use of at least one PPO-inhibiting herbicide, optionally in combination with one or more herbicidal compounds B, and, optionally, a safener C, as described in detail supra.

In these methods, the PPO-inhibiting herbicide can be applied by any method known in the art including, but not limited to, seed treatment, soil treatment, and foliar treatment. Prior to application, the PPO-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to PPO-inhibiting herbicide, a wide variety of formulations can be employed for protecting plants from weeds, so as to enhance plant growth and reduce competition for nutrients. A PPO-inhibiting herbicide can be used by itself for pre-emergence, post-emergence, pre-planting, and at-planting control of weeds in areas surrounding the crop plants described herein, or a PPO-inhibiting herbicide formulation can be used that contains other additives. The PPO-inhibiting herbicide can also be used as a seed treatment. Additives found in a PPO-inhibiting herbicide formulation include other herbicides, detergents, adjuvants, spreading agents, sticking agents, stabilizing agents, or the like. The PPO-inhibiting herbicide formulation can be a wet or dry preparation and can include, but is not limited to, flowable powders, emulsifiable concentrates, and liquid concentrates. The PPO-inhibiting herbicide and herbicide formulations can be applied in accordance with conventional methods, for example, by spraying, irrigation, dusting, or the like.

Suitable formulations are described in detail in PCT/EP2009/063387 and PCT/EP2009/063386, which are incorporated herein by reference.

Herbicide-tolerant plants of the invention can be used in conjunction with an herbicide to which they are tolerant. Herbicides can be applied to the plants of the invention using any techniques known to those skilled in the art. Herbicides can be applied at any point in the plant cultivation process. For example, herbicides can be applied pre-planting, at planting, pre-emergence, post-emergence or combinations thereof. Herbicides may be applied to seeds and dried to form a layer on the seeds.

In some embodiments, seeds are treated with a safener, followed by a post-emergent application of a PPO-inhibiting herbicides. In one embodiment, the post-emergent application of the PPO-inhibiting herbicides is about 7 to 10 days following planting of safener-treated seeds. In some embodiments, the safener is cloquintocet, dichlormid, fluxofenim, or combinations thereof.

Methods of Controlling Weeds or Undesired Vegetation

In other aspects, the present invention provides a method for controlling weeds at a locus for growth of a plant or plant part thereof, the method comprising: applying a composition comprising a PPO-inhibiting herbicides to the locus.

In some aspects, the present invention provides a method for controlling weeds at a locus for growth of a plant, the method comprising: applying an herbicide composition comprising PPO-inhibiting herbicides to the locus; wherein said locus is: (a) a locus that contains: a plant or a seed capable of producing said plant; or (b) a locus that is to be after said applying is made to contain the plant or the seed; wherein the plant or the seed comprises in at least some of its cells (i) a recombinant polynucleotide operably linked to a promoter operable in plant cells, the promoter capable of expressing a CYP450 polypeptide encoded by the polynucleotide, and (ii) a recombinant polynucleotide operably linked to a promoter operable in plant cells, the promoter capable of expressing a wildtype or mutated PPO polypeptide encoded by the polynucleotide, the expression of the wildtype or mutated PPO and the CYP450 polypeptide conferring to the plant tolerance to PPO-inhibiting herbicides.

Herbicide compositions hereof can be applied, e.g., as foliar treatments, soil treatments, seed treatments, or soil drenches. Application can be made, e.g., by spraying, dusting, broadcasting, or any other mode known useful in the art.

In one embodiment, herbicides can be used to control the growth of weeds that may be found growing in the vicinity of the herbicide-tolerant plants invention. In embodiments of this type, an herbicide can be applied to a plot in which herbicide-tolerant plants of the invention are growing in vicinity to weeds. An herbicide to which the herbicide-tolerant plant of the invention is tolerant can then be applied to the plot at a concentration sufficient to kill or inhibit the growth of the weed. Concentrations of herbicide sufficient to kill or inhibit the growth of weeds are known in the art and are disclosed above.

In other embodiments, the present invention provides a method for controlling weeds in the vicinity of a PPO-inhibiting herbicides-tolerant plant of the invention. The method comprises applying an effective amount of a PPO-inhibiting herbicides to the weeds and to the auxinic herbicide-tolerant plant, wherein the plant has increased tolerance to auxinic herbicide when compared to a wild-type plant. In some embodiments, the PPO-inhibiting herbicides-tolerant plants of the invention are preferably crop plants, including, but not limited to, sunflower, alfalfa, *Brassica* sp., soybean, cotton, safflower, peanut, tobacco, tomato, potato, wheat, rice, maize, sorghum, barley, rye, millet, and sorghum.

In other aspects, herbicide(s) (e.g., PPO-inhibiting herbicides) can also be used as a seed treatment. In some embodiments, an effective concentration or an effective amount of herbicide(s), or a composition comprising an effective concentration or an effective amount of herbicide(s) can be applied directly to the seeds prior to or during the sowing of the seeds. Seed Treatment formulations may additionally comprise binders and optionally colorants.

Binders can be added to improve the adhesion of the active materials on the seeds after treatment. In one embodiments, suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol(R), Polymin(R)), polyethers, polyurethans, polyvinylacetate, tylose and copolymers derived from these polymers. Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15: 1, pigment blue 80, pigment yellow 1, pigment yellow 13, pigment red 1 12, pigment red 48:2, pigment red 48: 1, pigment red 57: 1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The term seed treatment comprises all suitable seed treatment techniques known in the art, such as seed dressing, seed coating, seed dusting, seed soaking, and seed pelleting. In one embodiment, the present invention provides a method of treating soil by the application, in particular into the seed drill: either of a granular formulation containing the PPO-inhibiting herbicides as a composition/formulation (e.g., a granular formulation), with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising PPO-inhibiting herbicides and at least one other herbicide such as, e.g., an AHAS-inhibitor selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

In some embodiments, the seed treatment application with PPO-inhibiting herbicides or with a formulation comprising the PPO-inhibiting herbicides is carried out by spraying or dusting the seeds before sowing of the plants and before emergence of the plants.

In other embodiments, in the treatment of seeds, the corresponding formulations are applied by treating the seeds with an effective amount of PPO-inhibiting herbicides or a formulation comprising the PPO-inhibiting herbicides.

In other aspects, the present invention provides a method for combating undesired vegetation or controlling weeds comprising contacting the seeds of the PPO-inhibiting herbicides-tolerant plants of the present invention before sowing and/or after pregermination with PPO-inhibiting herbicides. The method can further comprise sowing the seeds, for example, in soil in a field or in a potting medium in greenhouse. The method finds particular use in combating undesired vegetation or controlling weeds in the immediate vicinity of the seed. The control of undesired vegetation is understood as the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: *Sinapis, Lepiclium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solarium, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*.

In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

In other embodiments, in the treatment of seeds, the corresponding formulations are applied by treating the seeds with an effective amount of PPO-inhibiting herbicides or a formulation comprising the PPO-inhibiting herbicides.

A method for growing the plant according to the present invention, while controlling weeds in the vicinity of said plant, said method comprising the steps of:

a) growing said plant; and
b) applying a herbicide composition comprising a PPO-inhibiting herbicide to the plant and weeds, wherein the herbicide normally inhibits the PPO enzyme, at a level of the herbicide that would inhibit the growth of a corresponding wild-type plant.

A combination useful for weed control, comprising (a) a recombinant polynucleotide operably linked to a promoter operable in plant cells, the promoter capable of expressing a CYP450 polypeptide encoded by the polynucleotide, and (b) a recombinant polynucleotide operably linked to a promoter operable in plant cells, the promoter capable of expressing a wildtype or mutated PPO polypeptide encoded by the polynucleotide and having at least 60%, at least 80%, 90%, 95%, 98%, 99% or more amino acid sequence identity to SEQ ID NO: 2 or 4; and (c) a PPO inhibiting herbicide.

A process for preparing a combination useful for weed control, (a) providing a recombinant polynucleotide operably linked to a promoter operable in plant cells, the promoter capable of expressing a CYP450 polypeptide encoded by the polynucleotide, and (b) providing a recombinant polynucleotide operably linked to a promoter operable in plant cells, the promoter capable of expressing a wildtype or mutated PPO polypeptide encoded by the polynucleotide and having at least 60%, at least 80%, 90%, 95%, 98%, 99% or more amino acid sequence identity to SEQ ID NO: 2 or 4; and (c) providing a PPO inhibiting herbicide.

In a preferred embodiment, said step of providing a recombinant polynucleotide as defined above comprises providing a plant containing said polynucleotide.

In another preferred embodiment said step of providing a recombinant polynucleotide as defined above comprises providing a seed containing the polynucleotide.

In another preferred embodiment, said process further comprises a step of applying the PPO inhibiting herbicide to the seed.

Use of a combination comprising (a) a recombinant polynucleotide operably linked to a promoter operable in plant cells, the promoter capable of expressing a CYP450 polypeptide encoded by the polynucleotide, and (b) a recombinant polynucleotide operably linked to a promoter operable in plant cells, the promoter capable of expressing a wildtype or mutated PPO polypeptide encoded by the polynucleotide and having at least 60%, at least 80%, 90%, 95%, 98%, 99% or more amino acid sequence identity to SEQ ID NO: 2 or 4; and (c) a PPO inhibiting herbicide, to control weeds at a plant cultivation site.

In still further aspects, treatment of loci, plants, plant parts, or seeds of the present invention comprises application of an agronomically acceptable composition that does not contain an A.I. In one embodiment, the treatment comprises application of an agronomically acceptable composition that does not contain a PPO-inhibiting herbicides A.I. In some embodiments, the treatment comprises application of an agronomically acceptable composition that does not contain a PPO-inhibiting herbicides A.L, wherein the composition comprises one or more of agronomically-acceptable carriers, diluents, excipients, plant growth regulators, and the like. In other embodiments, the treatment comprises application of an agronomically acceptable composition that does not contain a PPO-inhibiting herbicides A.I., wherein the composition comprises an adjuvant. In one embodiment, the adjuvant is a surfactant, a spreader, a sticker, a penetrant, a drift-control agent, a crop oil, an emulsifier, a compatibility agent, or combinations thereof.

It should also be understood that the foregoing relates to preferred embodiments of the present invention and that

EXAMPLES

Example 1

Site-Directed Mutagenesis of PPO

All nucleic acid coding sequence and all single and double mutants based on SEQ ID NO: 1, or 3, were synthesized and cloned by Geneart (Geneart AG, Regensburg, Germany). Rational design mutants were synthesized by Geneart. Random PPO gene libraries were synthesized by Geneart. Plasmids were isolated from E. coli TOP10 by performing a plasmid minpreparation and confirmed by DNA sequencing.

Example 2

Expression and Purification of Recombinant Wildtype and Mutant PPO (Taken from: Franck E. Dayan, Pankaj R. Daga, Stephen O. Duke, Ryan M. Lee, Patrick J. Tranel, Robert J. Doerksen. Biochemical and structural consequences of a glycine deletion in the α-8 helix of protoporphyrinogen oxidase. Biochimica et Biophysica Acta 1804 (2010), 1548-56) Clones in pRSET vector were transformed into BL21 (DE3)-pLysS strain of E. coli. Cells were grown in 250 mL of LB with 100 µgmL-1 of carbenicillin, shaking overnight at 37° C. Cultures were diluted in 1 L of LB with antibiotic and grown at 37° C. shaking for 2 h, induced with 1 mM IPTG and grown at 25° C. shaking for 5 more hours. The cells were harvested by centrifugation at 1600×g, washed with 0.09% NaCl, and stored at −80° C. Cells were lysed using a French press at 140 MPa in 50 mM sodium phosphate pH 7.5, 1 M NaCl, 5 mM imidazole, 5% glycerol, and 1 µg mL-1 leupeptin. Following lysis, 0.5 U of benzonase (Novagen, EMD Chemicals, Inc., Gibbstown, N.J.) and PMSF (final concentration of 1 mM) were added. Cell debris was removed by centrifugation at 3000×g. His-tagged PPO proteins were purified on a nickel activated Hitrap Chelating HP column (GE Healthcare Bio-Sciences Corp., Piscataway, N.J.) equilibrated with 20 mM sodium phosphate pH 8.0, 50 mM NaCl, 5 mM imidazole, 5 mM MgCl2, 0.1 mM EDTA, and 17% glycerol. PPO is eluted with 250 mM imidazole. The active protein was desalted on a PD-10 column (GE Healthcare Bio-Sciences Corp., Piscataway, N.J.) equilibrated with a 20 mM sodium phosphate buffer, pH 7.5, 5 mM MgCl2, 1 mM EDTA and 17% glycerol. Each litre of culture provided approximately 10 mg of pure PPO, which was stored at −20° C. until being used in assays.

Example 3

PPO Enzyme Assay (Non-Recombinant)

PPO protein (EC 1.3.3.4) was extracted from coleoptiles or shoots (150 g fresh weight) of dark-grown corn, black nightshade, morning glory, and velvetleaf seedlings as described previously (Grossmann et al. 2010). Before harvesting, the seedlings were allowed to green for 2 hours in the light in order to achieve the highest specific enzyme activities in the thylakoid fractions at low chlorophyll concentrations. At high chlorophyll concentrations significant quenching of fluorescence occurs, which limits the amount of green thylakoids that can be used in the test. Plant materials were homogenized in the cold with a Braun blender using a fresh-weight-to-volume ratio of 1:4. Homogenization buffer consisted of tris(hydroxymethyl) aminomethane (Tris)-HCl (50 mM; pH 7.3), sucrose (0.5 M), magnesium chloride (1 mM), ethylenediaminetetraacetic acid (EDTA) (1 mM) and bovine serum albumin (2 g $L^{-1}$). After filtration through four layers of Miracloth, crude plastid preparations were obtained after centrifugation at 10 000×g for 5 min and resuspension in homogenization buffer before centrifugation at 150×g for 2 min to remove crude cell debris. The supernatant was centrifuged at 4000×g for 15 min and the pellet fraction was resuspended in 1 ml of a buffer containing Tris-HCl (50 mM; pH 7.3), EDTA (2 mM), leupeptin (2 µM), pepstatin (2 µM) and glycerol (200 ml $L^{-1}$) and stored at −80° C. until use. Protein was determined in the enzyme extract with bovine serum albumin as a standard. PPO activity was assayed fluorometrically by monitoring the rate of Proto formation from chemically reduced protoporphyrinogen IX under initial velocity conditions. The assay mixture consisted of Tris-HCl (100 mM; pH 7.3), EDTA (1 mM), dithiothreitol (5 mM), Tween 80 (0.085%), protoporphyrinogen IX (2 µM), and 40 µg extracted protein in a total volume of 200 µl. The reaction was initiated by addition of substrate protoporphyrinogen IX at 22° C. saflufenacil, 1,5-dimethyl-6-thioxo-3-(2,2,7-trifluoro-3-oxo-4-(prop-2-ynyl)-3,4-dihydro-2H-benzo[b][1,4] oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control were prepared in dimethyl sulfoxide (DMSO) solution (0.1 mM concentration of DMSO in the assay) and added to the assay mixture in concentrations of 0.005 µM to 5 µM before incubation. Fluorescence was monitored directly from the assay mixture using a POLARstar Optima/Galaxy (BMG) with excitation at 405 nm and emission monitored at 630 nm. Non-enzymatic activity in the presence of heat-inactivated extract was negligible. Inhibition of enzyme activity induced by the herbicide was expressed as percentage inhibition relative to untreated controls. Molar concentrations of compound required for 50% enzyme inhibition (1050 values) were calculated by fitting the values to the dose-response equation using non-linear regression analysis.

Example 4

PPO Enzyme Assay (Recombinant)

Proto was purchased from Sigma-Aldrich (Milwaukee, Wis.). Protogen was prepared according to Jacobs and Jacobs (N. J. Jacobs, J. M. Jacobs, Assay for enzymatic protoporphyrinogen oxidation, a late step in heme synthesis, Enzyme 28 (1982) 206-219). Assays were conducted in 100 mM sodium phosphate pH 7.4 with 0.1 mM EDTA, 0.1% Tween 20, 5 µM FAD, and 500 mM imidazole. Dose-response curves with the PPO inhibitors saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control, and MC-15608 were obtained in the presence of 150 μM Protogen. The excitation and emission bandwidths were set at 1.5 and 30 nm, respectively. All assays were made in duplicates or triplicates and measured using a POLARstar Optima/Galaxy (BMG) with excitation at 405 nm and emission monitored at 630 nm. Molar concentrations of compound required for 50% enzyme inhibition (1050 values) were calculated by fitting the values to the dose-response equation using non-linear regression analysis. The results are shown in Tables 4A-C.

TABLE 4A

IC$_{50}$ (M) values for wild type and amino acid substituted PPO enzyme, preferably comprising a substitution at position L397 of SEQ ID NO: 2, for the inhibitors saflufenacil and 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione.

| Amino Acid Substitution | Relative Ezyme Activity (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|
| PPO herbicide sensitive PPO2 WC | 1000 | 1.86E−09 | 5.17E−10 |
| PPO herbicide sensitive PPO2 AC | 800 | 1.78E−10 | 5.96E−11 |
| R128L | 700 | 2.22E−07 | 7.73E−10 |
| R128A, L397D | 100 | 1.00E−05 | 5.90E−09 |
| R128L, L397D | ND | | ND |
| F204I, T208S | 745 | 5.89E−11 | 1.29E−10 |
| F204I, L397D | ND | | ND |
| F204I, L400A | 150 | | 4.57E−11 |
| F204I, F420V | 265 | | 4.69E−09 |
| F204I, F457M | 200 | 1.89E−11 | 7.52E−11 |
| T208S, L397D | 150 | 4.08E−07 | 1.25E−10 |
| T208S, L400A | ND | | ND |
| T208S, F420V | 520 | 8.48E−07 | 2.34E−09 |
| T208S, F457M | 550 | 1.02E−10 | 1.95E−10 |
| L397D, L400A | ND | | ND |
| L397R, F420M | ND | | ND |
| L397N, F420M | 90 | | 1.63E−08 |
| L397D, F420M | 120 | >0.00001 | 2.95E−08 |
| L397A, F420V | ND | | ND |
| L397R, F420V | ND | | ND |
| L397N, F420V | ND | | ND |
| L397Q, F420V | 90 | >0.00001 | 1.01E−07 |
| L397K, F420V | ND | | ND |
| L397F, F420V | ND | | ND |
| L397P, F420V | ND | | ND |
| L397W, F420V | ND | | ND |
| L397V, F420V | 150 | | 1.21E−08 |
| L397H, F420V | ND | | ND |
| L397I, F420M | 410 | | 1.98E−10 |
| L397M, F420K | ND | | ND |
| L397M, F420M | 250 | | 2.32E−10 |
| L397F, F420M | ND | | ND |
| L397S, F420M | 210 | | 3.33E−09 |
| L397W, F420M | ND | | ND |
| L397Y, F420M | ND | | ND |
| L397I, F420V | 100 | | 4.09E−09 |
| L397A, F420M | 150 | | 4.53E−09 |
| L397C, F420M | 370 | | 1.79E−09 |
| L397D, F420V | 60 | >0.00001 | 1.16E−06 |
| L397C, F420V | 150 | | 5.54E−08 |
| L397E, F420V | 105 | >0.00001 | 1.41E−07 |
| L397G, F420V | ND | | ND |
| L397H, F420V | ND | | ND |

TABLE 4A-continued

IC$_{50}$ (M) values for wild type and amino acid substituted PPO enzyme, preferably comprising a substitution at position L397 of SEQ ID NO: 2, for the inhibitors saflufenacil and 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione.

| Amino Acid Substitution | Relative Ezyme Activity (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|
| L397M, F420V | 140 | | 8.79E−09 |
| L397S, F420V | 110 | | 4.26E−08 |
| L397T, F420V | 150 | | 1.31E−08 |
| L397Q, F420M | 110 | 1.00E−06 | 5.41E−09 |
| L397E, F420M | 340 | 1.00E−06 | 6.03E−09 |
| L397G, F420M | 80 | | 6.06E−08 |
| L397P, F420M | ND | | ND |
| L397T, F420M | ND | | ND |
| L397V, F420M | 400 | | 1.05E−09 |
| L397D, F457M | ND | | ND |
| L400A, F420V | ND | | ND |
| L400A, F457M | 160 | | 1.35E−11 |
| F420V, F457M | 105 | | 1.02E−09 |

TABLE 4B

IC$_{50}$ (M) values for wild type and amino acid substituted PPO enzyme, preferably comprising a substitution at positions R128 and/or F420 of SEQ ID NO: 2, for the inhibitors saflufenacil and 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione.

| Amino Acid Substitution | Relative Ezyme Activity (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|
| PPO herbicide sensitive PPO2 WC | 1000 | 1.86E−09 | 5.17E−10 |
| PPO herbicide sensitive PPO2 AC | 800 | 1.78E−10 | 5.96E−11 |
| dG210 | 80 | 1.60E−06 | 2.12E−09 |
| R128L | 700 | 2.22E−07 | 7.73E−10 |
| R128L | 700 | 2.22E−07 | 7.73E−10 |
| R128A | 730 | 1.29E−07 | 1.40E−10 |
| R128C | 515 | 5.57E−07 | 1.16E−10 |
| R128D | ND | ND | ND |
| R128E | ND | ND | ND |
| R128F | 280 | 5.25E−07 | 2.21E−10 |
| R128G | 440 | 9.91E−07 | 4.71E−11 |
| R128H | 640 | 1.02E−08 | 6.15E−11 |
| R128I | 250 | 3.65E−07 | 9.80E−11 |
| R128K | 180 | 9.65E−11 | ND |
| R128L | 280 | 3.88E−07 | 1.01E−10 |
| R128M | 200 | 6.97E−07 | 3.56E−11 |
| R128N | 420 | 5.79E−07 | 4.33E−11 |
| R128P | ND | ND | ND |
| R128Q | 480 | 1.94E−07 | 1.09E−11 |
| R128S | 490 | 2.46E−07 | 1.12E−11 |
| R128T | 510 | 2.11E−07 | 3.79E−11 |
| R128V | 600 | 2.49E−07 | 6.70E−11 |
| R128W | ND | ND | ND |
| R128Y | 230 | 2.19E−06 | 5.77E−11 |
| F420A | ND | ND | ND |
| F420V | 200 | 1.59E−06 | 1.61E−09 |

TABLE 4B-continued

IC$_{50}$ (M) values for wild type and amino acid substituted PPO enzyme, preferably comprising a substitution at positions R128 and/or F420 of SEQ ID NO: 2, for the inhibitors saflufenacil and 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione.

| Amino Acid Substitution | Relative Ezyme Activity (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|
| F420V | 330 | | 1.61E-09 |
| F420M | 350 | 6.77E-07 | 2.75E-10 |
| F420M | 700 | | 2.18E-10 |
| F420L | 200 | 7.20E-06 | 9.93E-10 |
| F420I | 200 | 9.19E-07 | 4.95E-10 |
| R128A, F420V | 510 | >0.00001 | 2.50E-08 |
| R128A + F420M | 400 | >0.00001 | 6.24E-09 |
| R128A + F420L | 300 | >0.00001 | 1.62E-08 |
| R128A + F420I | 330 | >0.00001 | 2.46E-08 |
| R128A_F420A | ND | ND | ND |
| R128L_F420A | ND | ND | ND |
| R128L_F420L | 300 | >0.00001 | 1.71E-06 |
| R128L_F420I | 450 | >0.00001 | 1.23E-06 |
| R128L_F420V | 300 | >0.00001 | 1.51E-06 |
| R128L_F420M | 400 | >0.00001 | 2.46E-07 |
| R128I_F420A | ND | ND | ND |
| R128I_F420L | 200 | >0.00001 | 4.66E-07 |
| R128I_F420I | 100 | >0.00001 | 4.33E-07 |
| R128I_F420V | 470 | >0.00001 | 4.24E-07 |
| R128I_F420M | 500 | >0.00001 | 5.82E-08 |
| R128V_F420A | ND | ND | ND |
| R128V_F420L | 370 | >0.00001 | 4.41E-07 |
| R128V_F420I | 300 | >0.00001 | 2.23E-07 |
| R128V_F420V | 300 | >0.00001 | 4.46E-07 |
| R128V_F420M | 460 | >0.00001 | 4.27E-08 |
| R128M_F420A | ND | ND | ND |
| R128M_F420L | 300 | >0.00001 | 6.95E-07 |
| R128M_F420I | 350 | >0.00001 | 4.45E-07 |
| R128M_F420V | 270 | >0.00001 | 7.04E-07 |
| R128M_F420M | 480 | >0.00001 | 7.05E-08 |

TABLE 4C

IC$_{50}$ (M) values for wild type and amino acid substituted PPO enzyme, preferably comprising a substitution at positions R137 and/or F438 of SEQ ID NO: 4 (Alopecurus mysuriodes; ALOMY), for the inhibitors saflufenacil and 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione.

| Amino Acid Substitution | SEQ. ID NO. | Species | Relative Ezyme Activity (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|---|---|
| PPO herbicide sensitive PPO2 | 4 | ALOMY | 530 | 2.11E-07 | 3.64E-11 |
| PPO herbicide sensitive PPO2 WC | | AMARE | 1000 | 1.86E-09 | 5.17E-10 |
| PPO herbicide sensitive PPO2 AC | | AMARE | 800 | 1.78E-10 | 5.96E-11 |
| dG210 | | AMARE | 80 | 1.60E-06 | 2.12E-09 |
| R137I | 4 | ALOMY | 780 | 1.81E-06 | 1.30E-09 |
| R128I | | AMARE | 250 | 3.65E-07 | |
| R137V | 4 | ALOMY | 1060 | 1.93E-06 | 5.99E-10 |
| R128V | | AMARE | 600 | 2.49E-07 | |
| R137A | 4 | ALOMY | 700 | 2.08E-06 | 4.01E-11 |
| R128A | | AMARE | 730 | 1.29E-07 | 1.40E-10 |
| R137L | 4 | ALOMY | 420 | 6.73E-06 | 3.56E-09 |
| R128L | | AMARE | 700 | 2.22E-07 | 7.73E-10 |
| R137M | 4 | ALOMY | 1200 | >>0.00001 | 8.25E-10 |
| R128M | | AMARE | 200 | 6.97E-07 | |
| F438L | 4 | ALOMY | 905 | >0.00001 | 8.71E-08 |
| F420L | | AMARE | 200 | 7.20E-06 | 9.93E-10 |
| F438V | 4 | ALOMY | 1300 | >0.00001 | 3.64E-08 |
| F420V | | AMARE | 200 | 1.59E-06 | 1.61E-09 |
| F438M | 4 | ALOMY | 460 | >0.00001 | 2.23E-09 |
| F420M | | AMARE | 350 | 6.77E-07 | 2.75E-10 |
| R137A, F438M | 4 | ALOMY | 405 | >>0.00001 | 9.44E-08 |
| R128A, F420M | | AMARE | 400 | >0.00001 | 6.24E-09 |
| R137A, F438V | 4 | ALOMY | 220 | >>0.00001 | 5.37E-07 |
| R128A, F420V | | AMARE | 510 | >0.00001 | 2.50E-08 |
| F438I | 4 | ALOMY | 910 | >>0.00001 | 6.01E-08 |

TABLE 4C-continued

IC$_{50}$ (M) values for wild type and amino acid substituted PPO enzyme, preferably compr TABLE 4D-continued IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| FOMESAFEN | | R128A, F420V | 478 | 1.61E−06 | |
| FOMESAFEN | | R128I, F420L | 202 | ≥1.00E−05 | 38 |
| FOMESAFEN | | R128I, F420V | 292 | 2.79E−06 | |
| FOMESAFEN | | R128V, F420M | 413 | ≥1.00E−05 | 47 |
| FOMESAFEN | | R128M, F420M | 289 | ≥1.00E−05 | 48 |
| FOMESAFEN | | R128Y, F420I | 99 | 2.15E−05 | |
| FOMESAFEN | | R128Y, F420M | 174 | ≥1.00E−05 | 28 |
| FOMESAFEN | | R128N, F420M | 153 | 1.07E−05 | |
| FOMESAFEN | | R128C, F420L | 192 | 1.00E−05 | 42 |
| FOMESAFEN | | R128C, F420V | 160 | 2.36E−06 | |
| FOMESAFEN | | R128C, F420M | 277 | 1.10E−05 | |
| FOMESAFEN | | R128H, F420M | 184 | 2.91E−06 | |
| LACTOFEN | (2-ethoxy-1-methyl-2-oxo-ethyl) 5-[2-chloro-4-(trifluoromethyl)phenoxy]-2-nitro-benzoate | WT | 650 | 2.93E−10 | |
| LACTOFEN | (2-ethoxy-1-methyl-2-oxo-ethyl) 5-[2-chloro-4-(trifluoromethyl)phenoxy]-2-nitro-benzoate | R128A, F420M | 362 | 4.57E−08 | |
| LACTOFEN | (2-ethoxy-1-methyl-2-oxo-ethyl) 5-[2-chloro-4-(trifluoromethyl)phenoxy]-2-nitro-benzoate | R128A, F420L | 316 | 6.88E−08 | |
| LACTOFEN | (2-ethoxy-1-methyl-2-oxo-ethyl) 5-[2-chloro-4-(trifluoromethyl)phenoxy]-2-nitro-benzoate | R128A, F420V | 478 | 8.45E−09 | |
| LACTOFEN | (2-ethoxy-1-methyl-2-oxo-ethyl) 5-[2-chloro-4-(trifluoromethyl)phenoxy]-2-nitro-benzoate | R128I, F420L | 202 | 1.30E−07 | |
| LACTOFEN | (2-ethoxy-1-methyl-2-oxo-ethyl) 5-[2-chloro-4-(trifluoromethyl)phenoxy]-2-nitro-benzoate | R128I, F420V | 292 | 1.40E−08 | |
| LACTOFEN | (2-ethoxy-1-methyl-2-oxo-ethyl) 5-[2-chloro-4-(trifluoromethyl)phenoxy]-2-nitro-benzoate | R128V, F420M | 413 | 9.41E−08 | |
| LACTOFEN | (2-ethoxy-1-methyl-2-oxo-ethyl) 5-[2-chloro-4-(trifluoromethyl)phenoxy]-2-nitro-benzoate | R128M, F420M | 289 | 1.31E−07 | |
| LACTOFEN | (2-ethoxy-1-methyl-2-oxo-ethyl) 5-[2-chloro-4-(trifluoromethyl)phenoxy]-2-nitro-benzoate | R128Y, F420I | 99 | 4.80E−08 | |
| LACTOFEN | (2-ethoxy-1-methyl-2-oxo-ethyl) 5-[2-chloro-4-(trifluoromethyl)phenoxy]-2-nitro-benzoate | R128Y, F420M | 174 | 1.43E−07 | |
| LACTOFEN | (2-ethoxy-1-methyl-2-oxo-ethyl) 5-[2-chloro-4-(trifluoromethyl)phenoxy]-2-nitro-benzoate | R128N, F420M | 153 | 1.67E−07 | |
| LACTOFEN | (2-ethoxy-1-methyl-2-oxo-ethyl) 5-[2-chloro-4-(trifluoromethyl)phenoxy]-2-nitro-benzoate | R128C, F420L | 192 | 1.42E−07 | |
| LACTOFEN | (2-ethoxy-1-methyl-2-oxo-ethyl) 5-[2-chloro-4-(trifluoromethyl)phenoxy]-2-nitro-benzoate | R128C, F420V | 160 | 1.50E−08 | |
| LACTOFEN | (2-ethoxy-1-methyl-2-oxo-ethyl) 5-[2-chloro-4-(trifluoromethyl)phenoxy]-2-nitro-benzoate | R128C, F420M | 277 | 6.39E−08 | |
| LACTOFEN | (2-ethoxy-1-methyl-2-oxo-ethyl) 5-[2-chloro-4-(trifluoromethyl)phenoxy]-2-nitro-benzoate | R128H, F420M | 184 | 6.13E−08 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| BUTAFENACIL | | WT | 650 | 1.38E−10 | |
| BUTAFENACIL | | R128A, F420M | 362 | 1.40E−08 | |
| BUTAFENACIL | | R128A, F420L | 316 | 9.17E−08 | |
| BUTAFENACIL | | R128A, F420V | 478 | 2.51E−08 | |
| BUTAFENACIL | | R128I, F420L | 202 | 8.02E−08 | |
| BUTAFENACIL | | R128I, F420V | 292 | 2.56E−08 | |
| BUTAFENACIL | | R128V, F420M | 413 | 1.05E−08 | |
| BUTAFENACIL | | R128M, F420M | 289 | 4.38E−08 | |
| BUTAFENACIL | | R128Y, F420I | 99 | 5.47E−08 | |
| BUTAFENACIL | | R128Y, F420M | 174 | 5.04E−08 | |
| BUTAFENACIL | | R128N, F420M | 153 | 2.84E−08 | |
| BUTAFENACIL | | R128C, F420L | 192 | 1.10E−07 | |
| BUTAFENACIL | | R128C, F420V | 160 | 6.69E−08 | |
| BUTAFENACIL | | R128C, F420M | 277 | 2.31E−08 | |
| BUTAFENACIL | | R128H, F420M | 184 | 1.28E−08 | |
| CARFENTRAZONE-ETHYL | | WT | 650 | 1.03E−09 | |
| CARFENTRAZONE-ETHYL | | R128A, F420M | 362 | 6.72E−08 | |
| CARFENTRAZONE-ETHYL | | R128A, F420L | 316 | 4.29E−07 | |
| CARFENTRAZONE-ETHYL | | R128A, F420V | 478 | 7.97E−07 | |
| CARFENTRAZONE-ETHYL | | R128I, F420L | 202 | 1.61E−07 | |
| CARFENTRAZONE-ETHYL | | R128I, F420V | 292 | 2.07E−07 | |
| CARFENTRAZONE-ETHYL | | R128V, F420M | 413 | 2.29E−08 | |
| CARFENTRAZONE-ETHYL | | R128M, F420M | 289 | 7.86E−08 | |
| CARFENTRAZONE-ETHYL | | R128Y, F420I | 99 | 2.82E−07 | |
| CARFENTRAZONE-ETHYL | | R128Y, F420M | 174 | 8.52E−08 | |
| CARFENTRAZONE-ETHYL | | R128N, F420M | 153 | 1.88E−07 | |
| CARFENTRAZONE-ETHYL | | R128C, F420L | 192 | 3.08E−07 | |
| CARFENTRAZONE-ETHYL | | R128C, F420V | 160 | 3.96E−07 | |
| CARFENTRAZONE-ETHYL | | R128C, F420M | 277 | 2.99E−08 | |
| CARFENTRAZONE-ETHYL | | R128H, F420M | 184 | 1.21E−07 | |
| ACIFLUORFEN | 5-(2-CHLORO-4-TRIFLUOROMETHYL-PHENOXY)-2-NITRO-BENZOIC ACID | WT | 650 | 3.36E−08 | |
| ACIFLUORFEN | 5-(2-CHLORO-4-TRIFLUOROMETHYL-PHENOXY)-2-NITRO-BENZOIC ACID | R128A, F420M | 362 | ≥1.00E−05 | 27 |
| ACIFLUORFEN | 5-(2-CHLORO-4-TRIFLUOROMETHYL-PHENOXY)-2-NITRO-BENZOIC ACID | R128A, F420L | 316 | ≥1.00E−05 | 20 |
| ACIFLUORFEN | 5-(2-CHLORO-4-TRIFLUOROMETHYL-PHENOXY)-2-NITRO-BENZOIC ACID | R128A, F420V | 478 | 6.67E−06 | |
| ACIFLUORFEN | 5-(2-CHLORO-4-TRIFLUOROMETHYL-PHENOXY)-2-NITRO-BENZOIC ACID | R128I, F420L | 202 | ≥1.00E−05 | 16 |
| ACIFLUORFEN | 5-(2-CHLORO-4-TRIFLUOROMETHYL-PHENOXY)-2-NITRO-BENZOIC ACID | R128I, F420V | 292 | 1.21E−05 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| ACIFLUORFEN | 5-(2-CHLORO-4-TRIFLUOROMETHYL-PHENOXY)-2-NITRO-BENZOIC ACID | R128V, F420M | 413 | ≥1.00E−05 | 17 |
| ACIFLUORFEN | 5-(2-CHLORO-4-TRIFLUOROMETHYL-PHENOXY)-2-NITRO-BENZOIC ACID | R128M, F420M | 289 | ≥1.00E−05 | 21 |
| ACIFLUORFEN | 5-(2-CHLORO-4-TRIFLUOROMETHYL-PHENOXY)-2-NITRO-BENZOIC ACID | R128Y, F420I | 99 | ≥1.00E−05 | 21 |
| ACIFLUORFEN | 5-(2-CHLORO-4-TRIFLUOROMETHYL-PHENOXY)-2-NITRO-BENZOIC ACID | R128Y, F420M | 174 | ≥1.00E−05 | 15 |
| ACIFLUORFEN | 5-(2-CHLORO-4-TRIFLUOROMETHYL-PHENOXY)-2-NITRO-BENZOIC ACID | R128Y, F420M | 153 | ≥1.00E−05 | 39 |
| ACIFLUORFEN | 5-(2-CHLORO-4-TRIFLUOROMETHYL-PHENOXY)-2-NITRO-BENZOIC ACID | R128C, F420L | 192 | ≥1.00E−05 | 17 |
| ACIFLUORFEN | 5-(2-CHLORO-4-TRIFLUOROMETHYL-PHENOXY)-2-NITRO-BENZOIC ACID | R128C, F420V | 160 | 6.72E−06 | |
| ACIFLUORFEN | 5-(2-CHLORO-4-TRIFLUOROMETHYL-PHENOXY)-2-NITRO-BENZOIC ACID | R128C, F420M | 277 | ≥1.00E−05 | 33 |
| ACIFLUORFEN | 5-(2-CHLORO-4-TRIFLUOROMETHYL-PHENOXY)-2-NITRO-BENZOIC ACID | R128H, F420M | 184 | ≥1.00E−05 | 48 |
| FLUMIOXAZIN | 2-(7-fluoro-3-oxo-4-prop-2-ynyl-1,4-benzoxazin-6-yl)-4,5,6,7-tetrahydroisoindole-1,3-dione | WT | 650 | 9.58E−11 | |
| FLUMIOXAZIN | 2-(7-fluoro-3-oxo-4-prop-2-ynyl-1,4-benzoxazin-6-yl)-4,5,6,7-tetrahydroisoindole-1,3-dione | R128A, F420M | 362 | 8.43−06 | |
| FLUMIOXAZIN | 2-(7-fluoro-3-oxo-4-prop-2-ynyl-1,4-benzoxazin-6-yl)-4,5,6,7-tetrahydroisoindole-1,3-dione | R128A, F420L | 316 | ≥1.00E−05 | −8 |
| FLUMIOXAZIN | 2-(7-fluoro-3-oxo-4-prop-2-ynyl-1,4-benzoxazin-6-yl)-4,5,6,7-tetrahydroisoindole-1,3-dione | R128A, F420V | 478 | 6.34E−06 | |
| FLUMIOXAZIN | 2-(7-fluoro-3-oxo-4-prop-2-ynyl-1,4-benzoxazin-6-yl)-4,5,6,7-tetrahydroisoindole-1,3-dione | R128I, F420L | 202 | ≥1.00E−05 | 9 |
| FLUMIOXAZIN | 2-(7-fluoro-3-oxo-4-prop-2-ynyl-1,4-benzoxazin-6-yl)-4,5,6,7-tetrahydroisoindole-1,3-dione | R128I, F420V | 292 | ≥1.00E−05 | 41 |
| FLUMIOXAZIN | 2-(7-fluoro-3-oxo-4-prop-2-ynyl-1,4-benzoxazin-6-yl)-4,5,6,7-tetrahydroisoindole-1,3-dione | R128V, F420M | 413 | ≥1.00E−05 | 34 |
| FLUMIOXAZIN | 2-(7-fluoro-3-oxo-4-prop-2-ynyl-1,4-benzoxazin-6-yl)-4,5,6,7-tetrahydroisoindole-1,3-dione | R128M, F420M | 289 | ≥1.00E−05 | 21 |
| FLUMIOXAZIN | 2-(7-fluoro-3-oxo-4-prop-2-ynyl-1,4-benzoxazin-6-yl)-4,5,6,7-tetrahydroisoindole-1,3-dione | R128Y, F420I | 99 | ≥1.00E−05 | 19 |
| FLUMIOXAZIN | 2-(7-fluoro-3-oxo-4-prop-2-ynyl-1,4-benzoxazin-6-yl)-4,5,6,7-tetrahydroisoindole-1,3-dione | R128Y, F420M | 174 | ≥1.00E−05 | −2 |
| FLUMIOXAZIN | 2-(7-fluoro-3-oxo-4-prop-2-ynyl-1,4-benzoxazin-6-yl)-4,5,6,7-tetrahydroisoindole-1,3-dione | R128N, F420M | 153 | 6.15E−06 | |
| FLUMIOXAZIN | 2-(7-fluoro-3-oxo-4-prop-2-ynyl-1,4-benzoxazin-6-yl)-4,5,6,7-tetrahydroisoindole-1,3-dione | R128C, F420L | 192 | ≥1.00E−05 | −11 |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| FLUMIOXAZIN | 2-(7-fluoro-3-oxo-4-prop-2-ynyl-1,4-benzoxazin-6-yl)-4,5,6,7-tetrahydroisoindole-1,3-dione | R128C, F420V | 160 | 7.28E−06 | |
| FLUMIOXAZIN | 2-(7-fluoro-3-oxo-4-prop-2-ynyl-1,4-benzoxazin-6-yl)-4,5,6,7-tetrahydroisoindole-1,3-dione | R128C, F420M | 277 | ≥1.00E−05 | 48 |
| FLUMIOXAZIN | 2-(7-fluoro-3-oxo-4-prop-2-ynyl-1,4-benzoxazin-6-yl)-4,5,6,7-tetrahydroisoindole-1,3-dione | R128H, F420M | 184 | ≥1.00E−05 | 30 |
| CINIDON-ETHYL | ethyl (Z)-2-chloro-3-[2-chloro-5-(1,3-dioxo-4,5,6,7-tetrahydroisoindol-2-yl)phenyl]prop-2-enoate | WT | 650 | 6.69E−10 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128A, F420M | 362 | 1.60E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128A, F420L | 316 | ≥1.00E−05 | 48 |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128A, F420V | 478 | 5.43E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128I, F420L | 202 | 9.51E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128I, F420V | 292 | 4.72E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128V, F420M | 413 | 1.78E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128M, F420M | 289 | 3.84E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128Y, F420I | 99 | ≥1.00E−05 | 38 |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128Y, F420M | 174 | 1.08E−05 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128N, F420M | 153 | ≥1.00E−05 | 48 |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128C, F420L | 192 | ≥1.00E−05 | 42 |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128C, F420V | 160 | 9.43E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128C, F420M | 277 | 2.45E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | R128H, F420M | 184 | ≥1.00E−05 | 41 |
| OXIFLUORFEN | 2-CHLORO-1-(3-ETHOXY-4-NITROPHENOXY)-4-(TRIFLUOROMETHYL)BENZENE | WT | 650 | 1.04E−09 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| OXIFLUORFEN | 2-CHLORO-1-(3-ETHOXY-4-NITROPHENOXY)-4-(TRIFLUOROMETHYL)BENZENE | R128A, F420M | 365 | 2.17E−07 | |
| OXIFLUORFEN | 2-CHLORO-1-(3-ETHOXY-4-NITROPHENOXY)-4-(TRIFLUOROMETHYL)BENZENE | R128A, F420L | 343 | 5.58E−07 | |
| OXIFLUORFEN | 2-CHLORO-1-(3-ETHOXY-4-NITROPHENOXY)-4-(TRIFLUOROMETHYL)BENZENE | R128A, F420V | 550 | 2.35E−08 | |
| OXIFLUORFEN | 2-CHLORO-1-(3-ETHOXY-4-NITROPHENOXY)-4-(TRIFLUOROMETHYL)BENZENE | R128I, F420L | 196 | 4.21E−06 | |
| OXIFLUORFEN | 2-CHLORO-1-(3-ETHOXY-4-NITROPHENOXY)-4-(TRIFLUOROMETHYL)BENZENE | R128I, F420V | 326 | 1.98E−07 | |
| OXIFLUORFEN | 2-CHLORO-1-(3-ETHOXY-4-NITROPHENOXY)-4-(TRIFLUOROMETHYL)BENZENE | R128V, F420M | 482 | 1.05E−06 | |
| OXIFLUORFEN | 2-CHLORO-1-(3-ETHOXY-4-NITROPHENOXY)-4-(TRIFLUOROMETHYL)BENZENE | R128M, F420M | 323 | 7.36E−07 | |
| OXIFLUORFEN | 2-CHLORO-1-(3-ETHOXY-4-NITROPHENOXY)-4-(TRIFLUOROMETHYL)BENZENE | R128Y, F420I | 75 | 1.17E−06 | |
| OXIFLUORFEN | 2-CHLORO-1-(3-ETHOXY-4-NITROPHENOXY)-4-(TRIFLUOROMETHYL)BENZENE | R128Y, F420M | 175 | 1.13E−06 | |
| OXIFLUORFEN | 2-CHLORO-1-(3-ETHOXY-4-NITROPHENOXY)-4-(TRIFLUOROMETHYL)BENZENE | R128N, F420M | 174 | 3.91E−07 | |
| OXIFLUORFEN | 2-CHLORO-1-(3-ETHOXY-4-NITROPHENOXY)-4-(TRIFLUOROMETHYL)BENZENE | R128C, F420L | 188 | 1.49E−06 | |
| OXIFLUORFEN | 2-CHLORO-1-(3-ETHOXY-4-NITROPHENOXY)-4-(TRIFLUOROMETHYL)BENZENE | R128C, F420V | 225 | 6.52E−08 | |
| OXIFLUORFEN | 2-CHLORO-1-(3-ETHOXY-4-NITROPHENOXY)-4-(TRIFLUOROMETHYL)BENZENE | R128C, F420M | 271 | 4.16E−07 | |
| OXIFLUORFEN | 2-CHLORO-1-(3-ETHOXY-4-NITROPHENOXY)-4-(TRIFLUOROMETHYL)BENZENE | R128H, F420M | 196 | 3.68E−07 | |
| OXADIARGYL | | WT | 650 | 3.64E−10 | |
| OXADIARGYL | | R128A, F420M | 365 | 1.97E−08 | |
| OXADIARGYL | | R128A, F420L | 343 | 1.37E−06 | |
| OXADIARGYL | | R128A, F420V | 550 | 4.38E−08 | |
| OXADIARGYL | | R128I, F420L | 196 | 8.64E−07 | |
| OXADIARGYL | | R128I, F420V | 326 | 2.76E−08 | |
| OXADIARGYL | | R128V, F420M | 482 | 3.40E−08 | |
| OXADIARGYL | | R128M, F420M | 323 | 3.33E−08 | |
| OXADIARGYL | | R128Y, F420I | 75 | 1.73E−07 | |
| OXADIARGYL | | R128Y, F420M | 175 | 3.60E−08 | |
| OXADIARGYL | | R128N, F420M | 174 | 1.28E−07 | |
| OXADIARGYL | | R128C, F420L | 188 | 3.01E−06 | |
| OXADIARGYL | | R128C, F420V | 225 | 1.46E−07 | |
| OXADIARGYL | | R128C, F420M | 271 | 6.24E−08 | |
| OXADIARGYL | | R128H, F420M | 196 | 1.32E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | WT | 650 | 1.35E−10 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128A, F420M | 365 | 3.71E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128A, F420L | 343 | 2.77E−07 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128A, F420V | 550 | 4.75E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128I, F420L | 196 | 2.01E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128I, F420V | 326 | 4.38E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128V, F420M | 482 | 3.58E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128M, F420M | 323 | 4.83E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128Y, F420I | 75 | 4.64E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128Y, F420M | 175 | 8.92E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128N, F420M | 174 | 1.92E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128C, F420L | 188 | 6.81E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128C, F420V | 225 | 1.24E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128C, F420M | 271 | 6.95E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | R128H, F420M | 196 | 4.18E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | WT | 650 | ≥1.00E−05 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128A, F420M | 321 | 7.02E−09 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128A, F420M | 362 | 7.95E−09 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128A, F420M | 365 | 6.10E−09 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128A, F420L | 316 | 2.96E−08 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128A, F420L | 343 | 1.56E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128A, F420V | 478 | 4.14E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128A, F420V | 550 | 2.13E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128A, F420V | 555 | 3.99E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128I, F420L | 202 | 4.05E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128I, F420L | 196 | 2.45E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128I, F420I | 95 | 1.38E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128I, F420V | 292 | 2.14E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128I, F420V | 326 | 3.15E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128I, F420M | 328 | 6.10E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128V, F420M | 413 | 6.50E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128V, F420M | 482 | 4.86E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128M, F420M | 235 | 7.69E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128M, F420M | 289 | 7.07E−08 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128M, F420M | 323 | 4.84E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128Y, F420I | 99 | 4.82E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128Y, F420I | 75 | 2.63E−06 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128Y, F420M | 174 | 2.85E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128Y, F420M | 175 | 1.02E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128G, F420M | 153 | 1.26E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128Q, F420M | 432 | 1.07E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128H, F420L | 193 | 7.98E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128H, F420I | 191 | 8.22E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128N, F420M | 153 | 7.12E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128N, F420M | 174 | 4.97E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128C, F420L | 192 | 1.00E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128C, F420L | 188 | 1.83E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128C, F420V | 160 | 1.66E−07 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128C, F420V | 225 | 2.66E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128C, F420M | 277 | 2.53E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128C, F420M | 271 | 2.33E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128F, F420L | 129 | 1.01E−06 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128F, F420M | 136 | 1.21E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128S, F420M | 328 | 2.40E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128T, F420M | 275 | 4.33E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128H, F420V | 95 | 7.63E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128H, F420M | 184 | 2.64E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | R128H, F420M | 196 | 2.13E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397D, F420M | 112 | 4.07E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397V, F420V | 248 | 1.73E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397M, F420M | 399 | 4.23E−09 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397S, F420M | 339 | 1.96E−10 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397A, F420M | 291 | 3.15E−09 | 6 |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397C, F420M | 461 | 2.51E−09 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397C, F420V | 217 | 3.29E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397T, F420V | 295 | 4.10E−09 | 48 |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397Q, F420M | 180 | 2.16E−09 | 32 |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397E, F420M | 192 | 8.10E−09 | 41 |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397G, F420M | 118 | 4.16E−09 | 43 |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) | L397V, F420M | 632 | 9.73E−10 | 11 |
| 850 analogon | 2-(2,2,7-trifluoro-3-oxo-4-prop-2-ynyl-1,4-benzoxazin-6-yl)-4,5,6,7-tetrahydroisoindole-1,3-dione | WT | 650 | 1.46E−10 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128A, F420M | 365 | 6.41E−07 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128A, F420L | 343 | 1.14E−05 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128A, F420V | 550 | 2.74E−07 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128I, F420L | 196 | ≥1.00E−05 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128I, F420V | 326 | 4.32E−06 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128V, F420M | 482 | 3.11E−06 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128M, F420M | 323 | ≥1.00E−05 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128Y, F420I | 75 | ≥1.00E−05 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128Y, F420M | 175 | ≥1.00E−05 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128N, F420M | 174 | ≥1.00E−05 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| 850 analogon | 2-(2,2,7-trifluoro-3-oxo-4-prop-2-ynyl-1,4-benzoxazin-6-yl)-4,5,6,7-tetrahydroisoindole-1,3-dione | R128C, F420L | 188 | ≥1.00E−05 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128C, F420V | 225 | 3.70E−06 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128C, F420M | 271 | 3.57E−06 | |
| 850 analogon | 2-(2,2,7-trifluoro-3-oxo-4-prop-2-ynyl-1,4-benzoxazin-6-yl)-4,5,6,7-tetrahydroisoindole-1,3-dione | R128H, F420M | 196 | 3.07E−06 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | WT | 650 | 3.15E−10 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128A, F420M | 365 | 2.56E−09 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128A, F420L | 343 | 1.62E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128A, F420V | 550 | 6.33E−09 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128I, F420L | 196 | 2.69E−07 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128I, F420V | 326 | 9.01E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128V, F420M | 482 | 4.65E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128M, F420M | 323 | 4.94E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128Y, F420I | 75 | 4.46E−07 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128Y, F420M | 175 | 1.13E−07 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128N, F420M | 174 | 5.94E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128C, F420L | 188 | 6.72E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128C, F420V | 225 | 2.60E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128C, F420M | 271 | 1.11E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | R128H, F420M | 196 | 1.05E−08 | |
| | methyl 2-[2-[2-chloro-4-fluoro-5- | WT | 650 | 4.11E−10 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| | [3-methyl-2,6-dioxo-4-(trifluoromethyl)pyrimidin-1-yl]phenoxy]phenoxy]-2-methoxy-acetate | | | | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420M | 321 | 8.19E−09 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420L | 343 | 4.70E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420V | 555 | 2.32E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420L | 196 | 7.13E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420I | 95 | 2.27E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420V | 326 | 1.71E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420M | 328 | 1.15E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128V, F420M | 482 | 1.49E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128M, F420M | 235 | 1.62E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128Y, F420I | 75 | 2.86E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128G, F420M | 153 | 4.76E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128Q, F420M | 432 | 7.14E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128H, F420L | 193 | 4.47E−08 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128H, F420I | 191 | 7.54E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128N, F420M | 174 | 1.20E−07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128C, F420V | 225 | 1.16E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128C, F420M | 271 | 1.16E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128F, F420L | 129 | 4.84E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128F, F420M | 136 | 2.81E−09 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128S, F420M | 328 | 3.62E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128T, F420M | 275 | 2.79E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128H, F420V | 95 | 6.93E−09 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128H, F420M | 196 | 1.76E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397D, F420M | 112 | 5.88E−06 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397V, F420V | 248 | 2.20E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397M, F420M | 399 | 1.59E−07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397S, F420M | 339 | 2.79E−09 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397A, F420M | 291 | 2.73E−07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397C, F420M | 461 | 5.08E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397C, F420V | 217 | 6.14E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397T, F420V | 295 | 6.33E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397Q, F420M | 180 | 3.59E−07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397E, F420M | 192 | 9.59E−07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397G, F420M | 118 | 2.05E−07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397V, F420M | 632 | 6.32E−09 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | WT | 650 | 3.80E−10 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420M | 321 | 1.51E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420V | 555 | 2.92E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420M | 328 | 1.39E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128M, F420M | 235 | 2.24E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128S, F420M | 328 | 4.68E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128T, F420M | 275 | 2.93E−08 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| | yl]phenoxy]phenoxy]-2-methoxy-acetate | | | | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397A, F420M | 291 | 6.87E−07 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397C, F420M | 461 | 2.01E−07 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397Q, F420M | 180 | 9.33E−07 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397E, F420M | 192 | 4.43E−06 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397V, F420M | 632 | 3.02E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | WT | 650 | 5.23E−10 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420M | 321 | 2.27E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420L | 343 | 9.37E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420V | 555 | 4.16E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420L | 196 | 1.07E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420I | 95 | 1.82E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420V | 326 | 3.78E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420M | 328 | 1.06E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128V, F420M | 482 | 1.49E−08 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at $1 \times 10^{-5}$M |
|---|---|---|---|---|---|
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128M, F420M | 235 | 3.22E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128Y, F420I | 75 | 6.82E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128G, F420M | 153 | 5.14E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128Q, F420M | 432 | 1.72E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128H, F420L | 193 | 6.93E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128H, F420I | 191 | 1.31E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128N, F420M | 174 | 1.48E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128C, F420V | 225 | 1.01E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128C, F420M | 271 | 2.98E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128F, F420L | 129 | 1.18E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128F, F420M | 136 | 6.26E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128S, F420M | 328 | 5.24E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128T, F420M | 275 | 1.17E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128H, F420V | 95 | 9.06E−08 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128H, F420M | 196 | 2.97E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397D, F420M | 112 | ≥1.00E−05 | 26 |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397V, F420V | 248 | 1.11E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397M, F420M | 399 | 1.13E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397S, F420M | 339 | 3.39E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397A, F420M | 291 | 1.66E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397C, F420M | 461 | 2.53E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397C, F420V | 217 | 1.17E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397T, F420V | 295 | 3.06E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397Q, F420M | 180 | 6.42E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397E, F420M | 192 | 8.56E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397G, F420M | 118 | 2.68E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397V, F420M | 632 | 4.42E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | WT | 650 | 4.27E−10 | |
| | 4-pyridylmethyl 2-[2-[2-chloro-4-fluoro-5-[3-methyl-2,6-dioxo-4-(trifluoromethyl)pyrimidin-1- | R128A, F420M | 321 | 1.22E−08 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| | yl]phenoxy]phenoxy]-2-methoxy-acetate | | | | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420V | 555 | 2.61E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420M | 328 | 1.56E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128M, F420M | 235 | 3.34E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128S, F420M | 328 | 5.65E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128T, F420M | 275 | 5.88E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397A, F420M | 291 | 8.78E−07 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397C, F420M | 461 | 1.83E−07 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397Q, F420M | 180 | 9.45E−07 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397E, F420M | 192 | 6.38E−06 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397V, F420M | 632 | 2.70E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | WT | 650 | 4.16E−10 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420M | 321 | 1.19E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420V | 555 | 4.25E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420M | 328 | 1.37E−08 | |

TABLE 4D-continued

IC$_{50}$ (M) values for wild type and amino acid substituted PPO enzymes, for a selection of inhibitors

| Common Name | Name | Mutation | rate (FU/min) | IC50 (M) | inhibition (%) at 1 × 10−5M |
|---|---|---|---|---|---|
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128M, F420M | 235 | 2.47E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128S, F420M | 328 | 6.94E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128T, F420M | 275 | 5.77E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397A, F420M | 291 | 4.04E−07 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397C, F420M | 461 | 1.65E−07 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397Q, F420M | 180 | 4.56E−07 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397E, F420M | 192 | 1.87E−06 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397V, F420M | 632 | 2.87E−08 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | WT | 650 | 4.43E−10 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420M | 321 | 4.93E−08 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128A, F420V | 555 | 6.42E−08 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128I, F420M | 328 | 4.61E−08 | |

TABLE 4D-continued $IC_{50}$ (M) values for wild type and amino acid substituted PPO enzymes, for a selection of inhibitors

| Common Name | Name | Mutation | rate (FU/min) | IC50 (M) | inhibition (%) at 1 × 10–5M |
|---|---|---|---|---|---|
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128M, F420M | 235 | 1.06E–07 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128S, F420M | 328 | 9.94E–08 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | R128T, F420M | 275 | 1.50E–07 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397A, F420M | 291 | 3.28E–07 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397C, F420M | 461 | 1.19E–07 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397Q, F420M | 180 | 3.19E–07 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397E, F420M | 192 | 8.75E–07 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | L397V, F420M | 632 | 1.42E–08 | |

Example 5

Engineering PPO-Derivative Herbicide Tolerant Plants Having Wildtype or Mutated PPO Sequences PPO-derivative herbicide tolerant soybean (*Glycine max*), corn (*Zea mays*), and Canola (*Brassica napus* or *Brassica Rapa* var. or *Brassica campestris* L.) plants are produced by a method as described by Olhoft et al. (US patent 2009/0049567). For transformation of soybean or *Arabidopsis thaliana*, Wildtype or Mutated PPO sequences based on one of the following sequences SEQ ID NO: 1, or 3, are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOD in between ubiquitin promoter (PcUbi) and nopaline synthase terminator (NOS) sequence. For corn transformation, Wildtype or Mutated PPO sequences are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOD in between corn ubiquitin promoter (ZmUbi) and nopaline synthase terminator (NOS) sequence. Binary plasmids are introduced to *Agrobacterium tumefaciens* for plant transformation. Plasmid constructs are introduced into soybean's axillary meristem cells at the primary node of seedling explants via *Agrobacterium*-mediated transformation. After inoculation and co-cultivation with Agrobacteria, the explants are transferred to shoot introduction media without selection for one week. The explants were subsequently transferred to a shoot induction medium with 1-3 μM imazapyr (Arsenal) for 3 weeks to select for transformed cells. Explants with healthy callus/shoot pads at the primary node are then transferred to shoot elongation medium containing 1-3 μM imazapyr until a shoot elongated or the explant died. Transgenic plantlets are rooted, subjected to TaqMan analysis for the presence of the transgene, transferred to soil and grown to maturity in greenhouse. Transformation of corn plants are done by a method described by McElver and Singh (WO 2008/124495). Plant transformation vector constructs containing mutated PPO sequences are introduced into maize immature embryos via *Agrobacterium*-mediated transformation.

Figure 1:
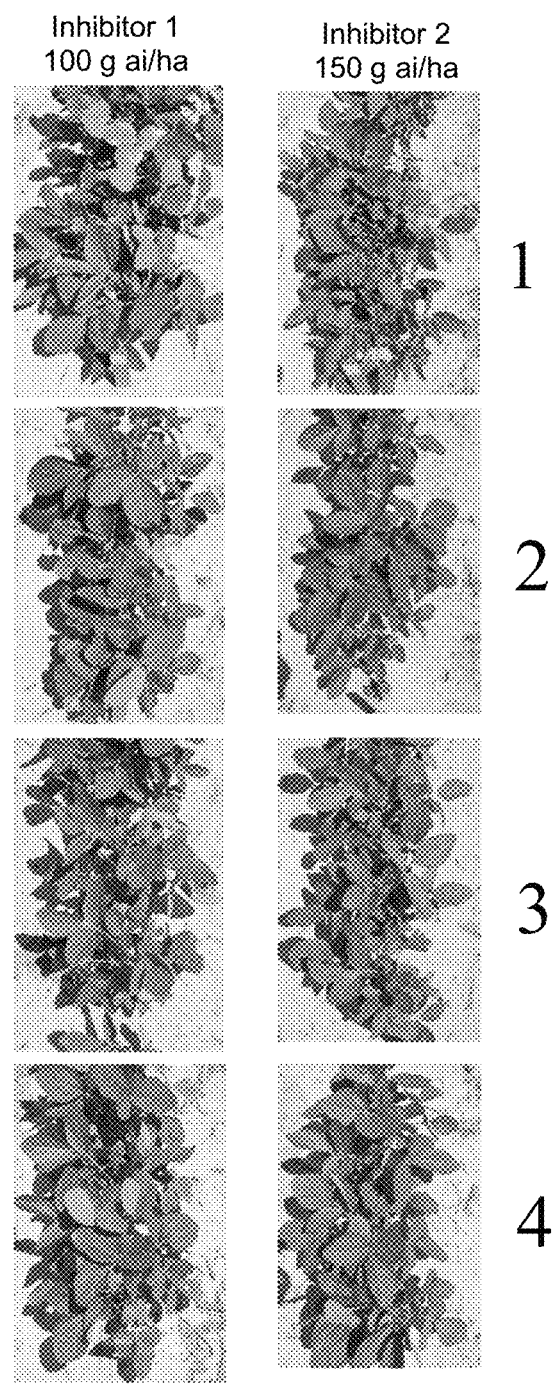
FIG. 1 shows Transgenic T1 soybean plants expressing the indicated constructs (1=AmatuPPX2_L397D_F420V; 2=AmatuPPX2_L397D_F420V+Bradi_1g07930.1_Zm; 3=AmatuPPX2_R128A_F420L; 4=AmatuPPX2_R128A_F420L+Bradi_1g07930.1_Zm were sprayed in the field with the indicated herbicide and rate over the top at the V2-V3 developmental stage. Pictures were taken 20 days after treatment. Inhibitor 1: 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (BAS850); Inhibitor 2: Saflufenacil; Amatu=*Amaranthus tuberculatus* FIG. 2 shows Transgenic T1 soybean plants expressing the indicated gene-of-interest (s) were sprayed in the field with the indicated herbicide and rate over the top at the V2-V3 developmental stage. Pictures were taken 20 days after treatment.
Figure 2:
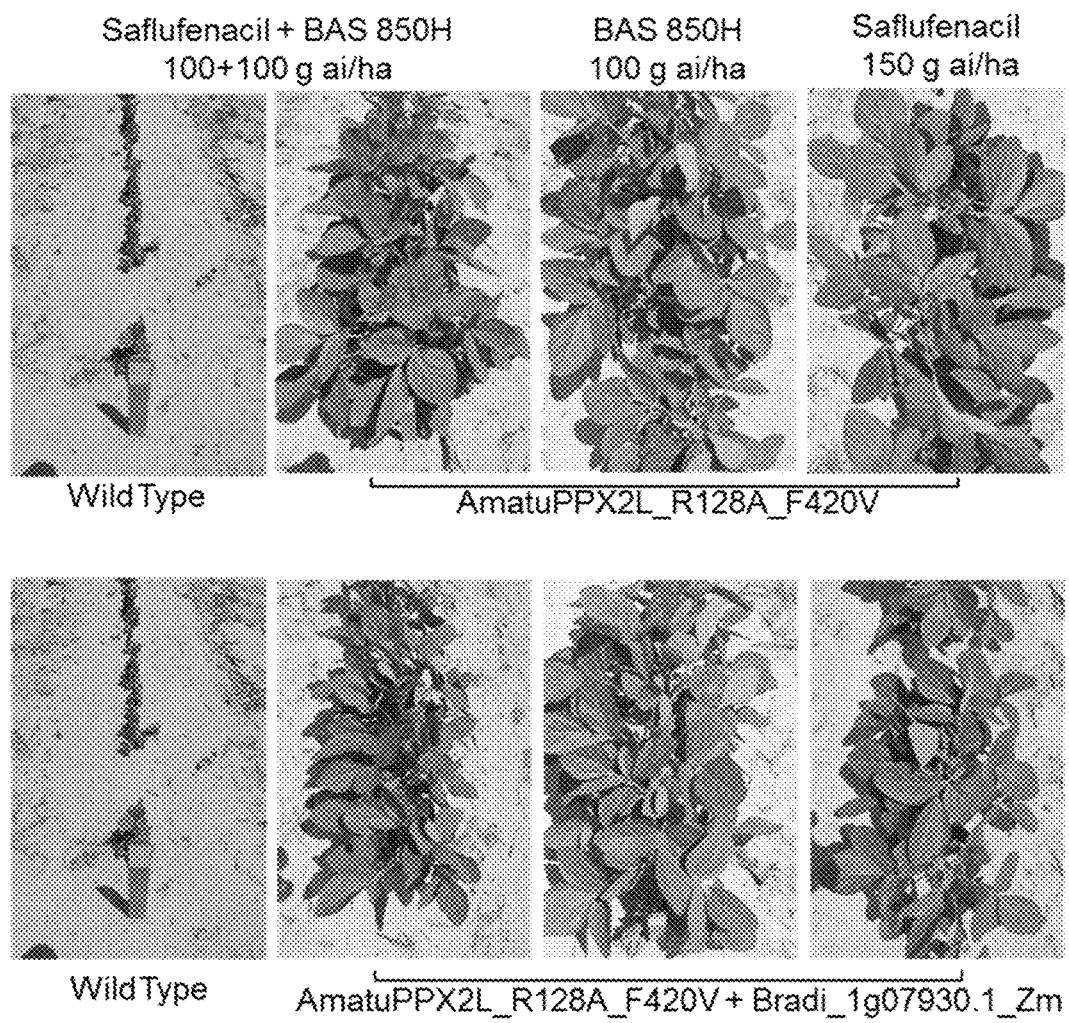
Figure 3:
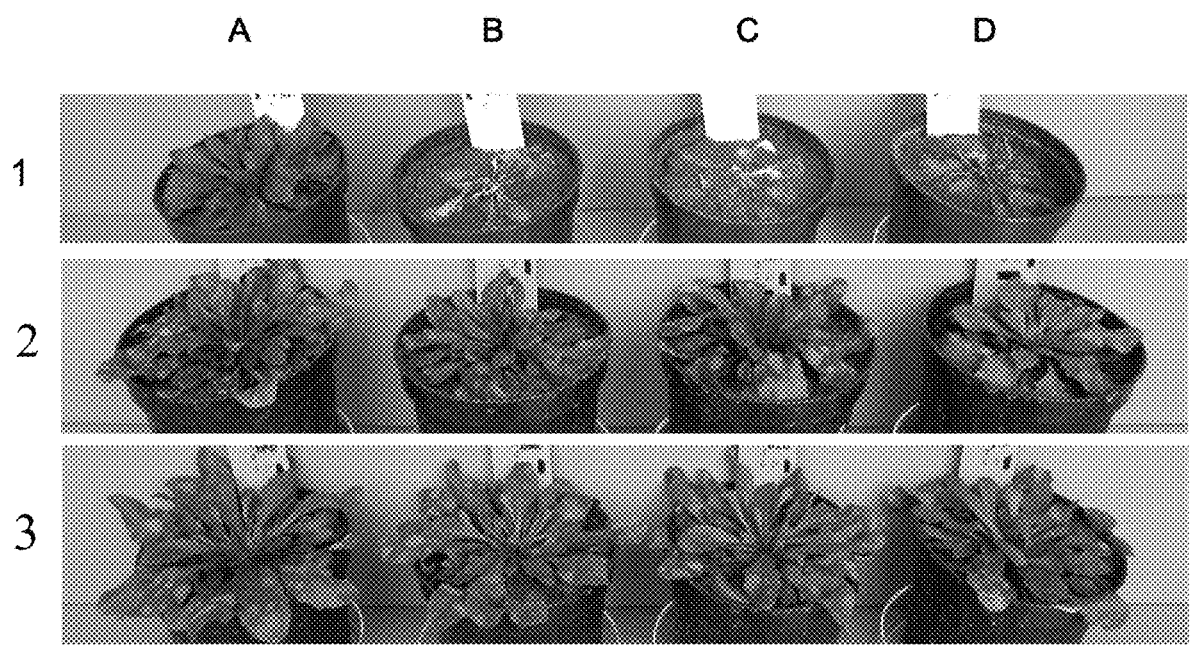
FIG. 3 shows non transgenic and transgenic *Arabidopsis* plants treated with Saflufenacil+Carfentrazone.

Transformed cells were selected in selection media supplemented with 0.5-1.5 μM imazethapyr for 3-4 weeks. Transgenic plantlets were regenerated on plant regeneration media and rooted afterwards. Transgenic plantlets are subjected to TaqMan analysis for the presence of the transgene before being transplanted to potting mixture and grown to maturity in greenhouse. *Arabidopsis thaliana* are transformed with wildtype or mutated PPO sequences by floral dip method as described by McElver and Singh (WO 2008/124495). Transgenic *Arabidopsis* plants were subjected to TaqMan analysis for analysis of the number of integration loci. Transformation of *Oryza sativa* (rice) are done by protoplast transformation as described by Peng et al. (U.S. Pat. No. 6,653,529) T0 or T1 transgenic plant of soybean, corn, and rice containing mutated PPO sequences Additionally, transgenic T2 *Arabidopsis* plants were tested for improved tolerance to PPO-inhibiting herbicides in greenhouse studies with the following PPO-inhibiting herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. The results are shown in Table 5 and FIG. 3

Shown are phytotox values on a scale from 0-100, were 100 is 100% damage.

| compound | event<br>g ai/ha | ARBTH<br>WT | AMATU_PPO2_L397D_F420V<br>O | | AMATU_PPO2_L397D_F420V +<br>Bradi01g07930 | |
|---|---|---|---|---|---|---|
| | | | | P | G | H |
| KIXOR + VALOR | 75 + 400 + 3750 | 100 | 0 | 7 | 3 | 0 |
| (Flumioxazin) + | 50 + 200 + 3750 | 100 | 0 | 7 | 0 | 0 |
| DESTINY HC | 25 + 100 + 3750 | 100 | 0 | 3 | 0 | 0 |
| KIXOR + SPOTLIGHT | 75 + 120 + 3750 | 100 | 15 | 22 | 3 | 0 |
| (Carfentrazone) + DESTINY | 50 + 60 + 3750 | 100 | 5 | 7 | 0 | 0 |
| HC | 25 + 30 + 3750 | 100 | 3 | 3 | 0 | 0 |
| KIXOR + BAS 850 00 H + | 75 + 200 + 3750 | 100 | 13 | 15 | 13 | 13 |
| DESTINY HC | 50 + 100 + 3750 | 100 | 10 | 10 | 8 | 3 |
| | 25 + 50 + 3750 | 100 | 7 | 7 | 3 | 0 |
| BAS 850 00 H + VALOR | 200 + 400 + | 100 | 17 | 17 | 5 | 10 |
| (Flumioxazin) + DESTINY | 3750 | | | | | |
| HC | 100 + 200 + | 100 | 10 | 10 | 3 | 3 |
| | 3750 | | | | | |
| | 50 + 100 + 3750 | 100 | 3 | 0 | 0 | 3 |
| BAS 850 00 H + SPOTLIGHT | 200 + 120 + | 100 | 17 | 20 | 5 | 3 |
| (Carfentrazone) + DESTINY | 3750 | | | | | |
| HC | 100 + 60 + 3750 | 100 | 8 | 7 | 0 | 0 |
| | 50 + 30 + 3750 | 100 | 0 | 3 | 0 | 0 | are tested for improved tolerance to PPO-derived herbicides in greenhouse studies and mini-plot studies with the following PPO-inhibiting herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control.

Transgenic *Arabidopsis thaliana* plants were assayed for improved tolerance to saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) Physiologia Plantarum 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 μmol Phot*m$^{-2}$*s$^{-1}$ with 14:10 h light:dark photoperiod. Growth inhibition is evaluated seven to ten days after seeding in comparison to wild type plants.

Example 6

Tissue Culture Conditions

An in vitro tissue culture mutagenesis assay has been developed to isolate and characterize plant tissue (e.g., maize, rice tissue) that is tolerant to protoporphyrinogen oxidase inhibiting herbicides, (saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control). The assay utilizes the somaclonal variation that is found in in vitro tissue culture. Spontaneous mutations derived from somaclonal variation can be enhanced by chemical mutagenesis and subsequent selection in a stepwise manner, on increasing concentrations of herbicide.

The present invention provides tissue culture conditions for encouraging growth of friable, embryogenic maize or rice callus that is regenerable. Calli were initiated from 4 different maize or rice cultivars encompassing *Zea mays* and *Japonica* (Taipei 309, Nipponbare, Koshihikari) and Indica (Indica 1) varieties, respectively. Seeds were surface sterilized in 70% ethanol for approximately 1 min followed by 20% commercial Clorox bleach for 20 minutes. Seeds were rinsed with sterile water and plated on callus induction media. Various callus induction media were tested. The ingredient lists for the media tested are presented in Table 6.

TABLE 6

| Ingredient | Supplier | R001M | R025M | R026M | R327M | R008M | MS711R |
|---|---|---|---|---|---|---|---|
| B5 Vitamins | Sigma | | | | | 1.0 X | |
| MS salts | Sigma | | | 1.0 X | 1.0 X | 1.0 X | 1.0 X |
| MS Vitamins | Sigma | | | 1.0 X | 1.0 X | | |
| N6 salts | Phytotech | 4.0 g/L | 4.0 g/L | | | | |
| N6 vitamins | Phytotech | 1.0 X | 1.0 X | | | | |
| L-Proline | Sigma | 2.9 g/L | 0.5 g/L | | | | 1.2 g/L |
| Casamino Acids | BD | 0.3 g/L | 0.3 g/L | 2 g/L | | | |
| Casein Hydrolysate | Sigma | | | | | | 1.0 g/L |
| L-Asp Monohydrate | Phytotech | | | | | | 150 mg/L |
| Nicotinic Acid | Sigma | | | | | | 0.5 mg/L |
| Pyridoxine HCl | Sigma | | | | | | 0.5 mg/L |
| Thiamine HCl | Sigma | | | | | | 1.0 mg/L |
| Myo-inositol | Sigma | | | | | | 100 mg/L |
| MES | Sigma | 500 mg/L | 500 mg/L | 500 mg/L | 500 mg/L | 500 mg/L | 500 mg/L |
| Maltose | VWR | 30 g/L | 30 g/L | 30 g/L | 30 g/L | | |
| Sorbitol | Duchefa | | | 30 g/L | | | |
| Sucrose | VWR | | | | | 10 g/L | 30 g/L |
| NAA | Duchefa | | | | | 50 µg/L | |
| 2,4-D | Sigma | 2.0 mg/L | | | | | 1.0 mg/L |
| MgCl$_2$•6H$_2$O | VWR | | | | | 750 mg/L | |
| →pH | | 5.8 | 5.8 | 5.8 | 5.8 | 5.8 | 5.7 |
| Gelrite | Duchefa | 4.0 g/L | | | | 2.5 g/L | |
| Agarose Type1 | Sigma | | 7.0 g/L | 10 g/L | 10 g/L | | |
| →Autoclave | | 15 min | 15 min | 15 min | 15 min | 15 min | 20 min |
| Kinetin | Sigma | | 2.0 mg/L | 2.0 mg/L | | | |
| NAA | Duchefa | | 1.0 mg/L | 1.0 mg/L | | | |
| ABA | Sigma | | 5.0 mg/L | | | | |
| Cefotaxime | Duchefa | | 0.1 g/L | 0.1 g/L | 0.1 g/L | | |
| Vancomycin | Duchefa | | 0.1 g/L | 0.1 g/L | 0.1 g/L | | |
| G418 Disulfate | Sigma | | 20 mg/L | 20 mg/L | 20 mg/L | | |

R001M callus induction media was selected after testing numerous variations. Cultures were kept in the dark at 30° C. Embryogenic callus was subcultured to fresh media after 10-14 days.

Example 7

Selection of Herbicide-Tolerant Calli

Once tissue culture conditions were determined, further establishment of selection conditions were established through the analysis of tissue survival in kill curves with saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. Careful consideration of accumulation of the herbicide in the tissue, as well as its persistence and stability in the cells and the culture media was performed. Through these experiments, a sub-lethal dose has been established for the initial selection of mutated material. After the establishment of the starting dose of saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control in selection media, the tissues were selected in a step-wise fashion by increasing the concentration of the PPO inhibitor with each transfer until cells are recovered that grew vigorously in the presence of toxic doses. The resulting calli were further subcultured every 3-4 weeks to R001M with selective agent. Over 26,000 calli were subjected to selection for 4-5 sub-cultures until the selective pressure was above toxic levels as determined by kill curves and observations of continued culture. Alternatively, liquid cultures initiated from calli in MS711R with slow shaking and weekly subcultures. Once liquid cultures were established, selection agent was added directly to the flask at each subculture. Following 2-4 rounds of liquid selection, cultures were transferred to filters on solid R001M media for further growth.

Example 8

Regeneration of Plants

Tolerant tissue was regenerated and characterized molecularly for PPO gene sequence mutations and/or biochemically for altered PPO activity in the presence of the selective agent. In addition, genes involved directly and/or indirectly in tetrapyrrole biosynthesis and/or metabolism pathways were also sequenced to characterize mutations. Finally, enzymes that change the fate (e.g. metabolism, translocation, transportation) were also sequence to characterized mutations. Following herbicide selection, calli were regenerated using a media regime of R025M for 10-14 days, R026M for ca. 2 weeks, R327M until well formed shoots were developed, and R008S until shoots were well rooted for transfer to the greenhouse. Regeneration was carried out in the light. No selection agent was included during regeneration. Once strong roots were established, M0 regenerants were transplant to the greenhouse in square or round pots. Transplants were maintained under a clear plastic cup until they were adapted to greenhouse conditions. The greenhouse was set to a day/night cycle of 27° C./21° C. (80° F./70° F.) with 600W high pressure sodium lights supplementing light to maintain a 14 hour day length. Plants were watered according to need, depending in the weather and fertilized daily.

Example 9

Sequence Analysis

Leaf tissue was collected from clonal plants separated for transplanting and analyzed as individuals. Genomic DNA was extracted using a Wizard® 96 Magnetic DNA Plant System kit (Promega, U.S. Pat. Nos. 6,027,945 & 6,368,800) as directed by the manufacturer. Isolated DNA was PCR amplified using the appropriate forward and reverse primer.

PCR amplification was performed using Hotstar Taq DNA Polymerase (Qiagen) using touchdown thermocycling program as follows: 96° C. for 15 min, followed by 35 cycles (96° C., 30 sec; 58° C.—0.2° C. per cycle, 30 sec; 72° C., 3 min and 30 sec), 10 min at 72° C. PCR products were verified for concentration and fragment size via agarose gel electrophoresis. Dephosphorylated PCR products were analyzed by direct sequence using the PCR primers (DNA Landmarks, or Entelechon). Chromatogram trace files (.scf) were analyzed for mutation relative to the wild-type gene using Vector NTI Advance 10™ (Invitrogen). Based on sequence information, mutations were identified in several individuals. Sequence analysis was performed on the representative chromatograms and corresponding AlignX alignment with default settings and edited to call secondary peaks.

Example 10

Demonstration of Herbicide-Tolerance

T0 or T1 transgenic plant of soybean, corn, Canola varieties and rice containing PPO1 and or PPO2 sequences are tested for improved tolerance to herbicides in greenhouse studies and mini-plot studies with the following herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides. For post emergence treatment, the test plants are first grown to a height of 3 to 15 cm, depending on the plant habit, and only then treated with the herbicides. For this purpose, the test plants are either sown directly, and grown in the same containers or they are first grown separately and transplanted into the test containers a few days prior to treatment.

For testing of T0 plants, cuttings can be used. In the case of soybean plants, an optimal shoot for cutting is about 7.5 to 10 cm tall, with at least two nodes present. Each cutting is taken from the original transformant (mother plant) and dipped into rooting hormone powder (indole-3-butyric acid, IBA). The cutting is then placed in oasis wedges inside a bio-dome. Wild type cuttings are also taken simultaneously to serve as controls. The cuttings are kept in the bio-dome for 5-7 days and then transplanted to pots and then acclimated in the growth chamber for two more days. Subsequently, the cuttings are transferred to the greenhouse, acclimated for approximately 4 days, and then subjected to spray tests as indicated. Depending on the species, the plants are kept at 10-25° C. or 20-35° C. The test period extends over 3 weeks. During this time, the plants are tended and their response to the individual treatments is evaluated. Herbicide injury evaluations are taken at 2 and 3 weeks after treatment. Plant injury is rated on a scale of 0% to 100%, 0% being no injury and 100% being complete death.

Transgenic *Arabidopsis thaliana* plants were assayed for improved tolerance to saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control, in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) Physiologia Plantarum 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 µmol Phot*$m^{-2}$*$s^{-1}$ with 14:10 h light:dark photoperiod. Growth inhibition is evaluated seven to ten days after seeding in comparison to wild type plants. Additionally, transgenic T1 *Arabidopsis* plants were tested for improved tolerance to herbicides in greenhouse studies with the following herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control.

Example 11

Herbicide Selection Using Tissue Culture

Media was selected for use and kill curves developed as specified above. For selection, different techniques were utilized. Either a step wise selection was applied, or an immediate lethal level of herbicide was applied. In either case, all of the calli were transferred for each new round of selection. Selection was 4-5 cycles of culture with 3-5 weeks for each cycle. Cali were placed onto nylon membranes to facilitate transfer (200 micron pore sheets, Biodesign, Saco, Me.). Membranes were cut to fit 100×20 mm Petri dishes and were autoclaved prior to use 25-35 calli (average weight/calli being 22 mg) were utilized in every plate. In addition, one set of calli were subjected to selection in liquid culture media with weekly subcultures followed by further selection on semi-solid media. Mutant lines were selected using saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. Efficiencies of obtaining mutants was high either based on a percentage of calli that gave rise to a regenerable, mutant line or the number of lines as determined by the gram of tissue utilized.

Example 12

Maize Whole Plant Transformation and PPO Inhibitor Tolerance Testing

Immature embryos were transformed according to the procedure outlined in Peng et al. (WO2006/136596). Plants were tested for the presence of the T-DNA by Taqman analysis with the target being the nos terminator which is present in all constructs. Healthy looking plants were sent to the greenhouse for hardening and subsequent spray testing. The plants were individually transplanted into MetroMix 360 soil in 4" pots. Once in the greenhouse (day/night cycle of 27° C./21° C. with 14 hour day length supported by 600 W high pressure sodium lights), they were allowed to grow for 14 days. They were then sprayed with a treatment of 25 to 200 g ai/ha saflufenacil+1.0% v/v methylated seed oil (MSO) and/or 25-200 g ai/ha 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) plus 1% MSO. Other PPO inhibiting herbicides were also tested in a similar fashion for confirming cross resistance: flumioxazin, butafenacil, acifluorfen, lactofen, bifenox, sulfentrazone, and photosynthesis inhibitor diuron as negative control. Herbicide injury evaluations were taken at 7, 14 and 21 days after treatment. Herbicide injury evaluations were taken 2, 7, 14 and 21 days post-spray to look for injury to new growth points and overall plant health. The top survivors were transplanted into gallon pots filled with MetroMix 360 for seed production.

Example 13

Soybean Transformation and PPO Inhibitor Tolerance Testing

Soybean cv Jake was transformed as previously described by Siminszky et al., Phytochem Rev. 5:445-458 (2006). After regeneration, transformants were transplanted to soil in small pots, placed in growth chambers (16 hr day/8 hr night; 25° C. day/23° C. night; 65% relative humidity; 130-150 microE m-2 s-1) and subsequently tested for the presence of the T-DNA via Taqman analysis. After a few weeks, healthy, transgenic positive, single copy events were transplanted to larger pots and allowed to grow in the growth chamber. An optimal shoot for cutting was about 3-4 inches tall, with at least two nodes present. Each cutting was taken from the original transformant (mother plant) and dipped into rooting hormone powder (indole-3-butyric acid, IBA). The cutting was then placed in oasis wedges inside a bio-dome. The mother plant was taken to maturity in the greenhouse and harvested for seed. Wild type cuttings were also taken simultaneously to serve as negative controls. The cuttings were kept in the bio-dome for 5-7 days and then transplanted to 3 inch pots and then acclimated in the growth chamber for two more days. Subsequently, the cuttings were transferred to the greenhouse, acclimated for approximately 4 days, and then sprayed with a treatment of 0-200 g ai/ha saflufenacil plus 1% MSO and/or 25-200 g ai/ha 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) plus 1% MSO. Other PPO inhibiting herbicides were also tested in a similar fashion for confirming cross resistance: flumioxazin, butafenacil, acifluorfen, lactofen, bifenox, sulfentrazone, and photosynthesis inhibitor diuron as negative control. Other herbicides, such as AHAS (ALS—Acetolactate Synthase) inhibiting herbicides were also tested in a similar fashion for confirming cross resistance to other modes of action: Tritosulfuron, Florasulam, Metsulfuron, Rimsulfuron. Herbicide injury evaluations were taken at 2, 7, 14 and 21 days after treatment. Results are shown in Table 7 and FIG. 4.

TABLE 7A

Greenhouse data - Clones from T0 individuals. Rated for injury (0-9 point scale) 1 week after treatment

| GOI | event | Saflufenacil (g ai/ha) | | | | | |
|---|---|---|---|---|---|---|---|
| | | 0 | 12.5 | 25 | 50 | 100 | 200 |
| wild type | 1 | 0 | 9 | 9 | 9 | * | * |
| | 2 | 0 | * | 9 | 9 | 9 | 9 |
| | 3 | 0 | * | 9 | 8 | 8 | 9 |
| Bradi_1g07930.1_Zm | 1 | 0 | 4 | 6 | 6 | 8 | * |
| | 2 | 0 | 1 | 6 | * | * | * |
| | 3 | 0 | 4 | 6 | * | * | * |
| | 4 | 0 | 6 | 5 | * | * | * |
| | 5 | 0 | 6 | 5 | 6 | 6 | * |
| | 6 | 0 | 6 | 6 | * | * | * |
| | 7 | 0 | 0 | 1 | 5 | * | * |
| | 8 | 0 | 5 | 6 | 8 | 7 | * |
| | 9 | 0 | 6 | 9 | 9 | 9 | * |
| | 10 | 0 | 5 | 6 | 6 | 5 | * |
| | 11 | 1 | 4 | 4 | 5 | 8 | * |
| | 12 | 1 | 5 | 6 | 6 | * | * |
| AmtuPPX2L_F420V | 1 | 3 | * | * | 6 | 6 | * |
| AmtuPPX2L_L397D | 1 | 2 | * | 7 | 9 | 9 | * |
| | 2 | 1 | * | 2 | 4 | 4 | * |
| | 3 | 1 | * | 9 | 9 | 9 | * |
| | 4 | 1 | * | 2 | 3 | 4 | * |
| | 5 | 0 | * | 5 | 6 | 6 | * |
| | 6 | 0 | * | 3 | 5 | 5 | * |
| | 7 | * | * | 2 | 4 | 6 | * |
| AmtuPPX2L_L397D_F420V | 1 | 0 | * | 3 | 6 | 6 | * |
| | 2 | 1 | 1 | 1 | 2 | * | * |
| | 3 | 1 | 0 | 0 | 1 | * | * |
| | 4 | 2 | * | 4 | 6 | 6 | * |
| | 5 | 0 | * | 6 | 7 | 7 | * |
| | 6 | 0 | * | 5 | 4 | 5 | * |
| | 7 | 0 | * | 5 | 4 | 4 | * |
| | 8 | 0 | * | 5 | 5 | 5 | * |
| | 9 | * | * | 8 | 9 | 9 | * |

TABLE 7A-continued

Greenhouse data - Clones from T0 individuals. Rated for injury (0-9 point scale) 1 week after treatment

| | | Saflufenacil (g ai/ha) | | | | | |
|---|---|---|---|---|---|---|---|
| GOI | event | 0 | 12.5 | 25 | 50 | 100 | 200 |
| AmtuPPX2L_F420L | 1 | 1 | * | 9 | 9 | 9 | * |
| | 2 | 0 | 1 | 0 | 0 | * | * |
| | 3 | 1 | 0 | 2 | 2 | * | * |
| | 4 | 1 | 3 | 1 | 1 | * | * |
| | 5 | 0 | * | 2 | 3 | 4 | * |
| | 6 | 0 | * | 2 | 5 | 6 | * |
| | 7 | 0 | * | 2 | 3 | 5 | * |
| AmtuPPX2L_R128A_F420L | 1 | 0 | * | 4 | 6 | 6 | * |
| | 2 | 0 | * | 0 | 1 | 1 | * |
| | 3 | 0 | * | * | * | 9 | 8 |
| | 4 | 0 | * | * | * | 4 | 6 |
| | 5 | 2 | * | * | 3 | 5 | 4 |
| | 6 | 0 | * | * | 6 | 6 | 7 |
| AmtuPPX2L_R128A_F420V | 1 | 1 | * | * | * | 6 | 6 |
| | 2 | * | * | * | * | 2 | 2 |
| | 3 | * | * | * | * | 1 | 3 |
| | 4 | * | * | * | * | 6 | 6 |
| | 5 | * | * | * | * | 6 | 6 |
| | 6 | * | * | * | * | * | 2 |
| | 7 | * | * | * | * | 9 | 9 |
| | 8 | 1 | * | * | * | 4 | 4 |
| | 9 | 0 | * | * | * | 4 | 6 |
| | 10 | 0 | * | * | * | 3 | 6 |
| | 11 | 2 | * | * | * | 2 | 2 |
| | 12 | 0 | * | * | * | 3 | 2 |
| | 13 | 0 | * | * | * | 4 | 4 |
| | 14 | 0 | * | * | * | 9 | 9 |
| AmtuPPX2L_F420V stacked with Bradi_1g07930.1_Zm | 1 | 1 | 0 | 1 | 0 | * | * |
| | 2 | 0 | 2 | 1 | 1 | * | * |
| | 3 | 2 | 0 | 0 | 1 | * | * |
| | 4 | 0 | * | 0 | 0 | 0 | * |
| | 5 | 0 | * | 0 | 1 | 1 | * |
| | 6 | 0 | * | 9 | 9 | 9 | * |
| | 7 | 0 | * | 0 | 2 | 2 | * |
| | 8 | 0 | * | 0 | 0 | 2 | * |
| | 9 | 0 | * | 0 | 0 | 2 | * |
| | 10 | 0 | * | 0 | 1 | 1 | * |
| AmtuPPX2L L397D stacked with Bradi_1g07930.1_Zm | 1 | 0 | * | 1 | 2 | 2 | * |
| | 2 | * | * | 6 | 9 | 9 | * |
| | 3 | 0 | * | 5 | 6 | 7 | * |
| | 4 | 1 | * | 2 | 2 | 5 | * |
| | 5 | 1 | * | 1 | 2 | 3 | * |
| | 6 | 0 | * | 0 | 1 | 1 | * |
| | 7 | 0 | * | 4 | 7 | 9 | * |
| | 8 | 1 | * | 1 | 2 | 3 | * |
| | 9 | * | * | 1 | 1 | 1 | * |
| | 10 | 0 | * | 0 | 1 | 2 | * |
| AmtuPPX2L_L397D_F420V stacked with Bradi_1g07930.1_Zm | 1 | 0 | 1 | 2 | 1 | * | * |
| | 2 | 0 | * | 3 | 3 | 4 | * |
| | 3 | 0 | * | 2 | 3 | 3 | * |
| | 4 | 0 | * | 0 | 0 | 2 | * |
| | 5 | 2 | * | 4 | 5 | 5 | * |
| | 6 | * | * | 5 | 5 | 5 | * |
| | 7 | 4 | * | 6 | 3 | 4 | * |
| | 8 | 3 | * | * | * | 2 | * |
| | 9 | 0 | * | 0 | 1 | 2 | * |
| | 10 | 2 | * | 4 | 4 | 5 | * |
| | 11 | 0 | * | 8 | 9 | 9 | * |
| | 12 | 0 | * | | 3 | 4 | * |
| AmtuPPX2L_F420L stacked with Bradi_1g07930.1_Zm | 1 | 0 | 4 | 4 | 3 | * | * |
| | 2 | 0 | 1 | 1 | 1 | * | * |
| | 3 | 0 | 6 | * | 5 | * | * |
| | 4 | 0 | 5 | 6 | 6 | * | * |
| | 5 | 0 | 0 | 0 | 1 | * | * |
| | 6 | 0 | 1 | 2 | 2 | * | * |
| | 7 | 0 | 0 | 0 | 1 | * | * |
| | 8 | 0 | 1 | 2 | 2 | * | * |
| | 9 | 0 | * | * | 1 | 3 | 2 |
| | 10 | 2 | * | * | 5 | 6 | 6 |
| | 11 | 2 | * | * | 2 | 2 | 2 |

TABLE 7A-continued

Greenhouse data - Clones from T0 individuals. Rated for injury (0-9 point scale) 1 week after treatment

| GOI | event | Saflufenacil (g ai/ha) | | | | | |
|---|---|---|---|---|---|---|---|
| | | 0 | 12.5 | 25 | 50 | 100 | 200 |
| AmtuPPX2L__R128A__F420L stacked with Bradi_1g07930.1_Zm | 1 | * | * | * | * | 0 | 1 |
| | 2 | 1 | * | * | * | 3 | 5 |
| | 3 | 0 | * | * | 1 | 1 | 3 |
| | 4 | 0 | * | * | 1 | 2 | 2 |
| | 5 | 3 | * | * | * | 2 | 2 |
| | 6 | 6 | * | * | * | 6 | 5 |
| | 7 | 0 | * | * | * | 2 | 3 |
| | 8 | 0 | * | * | * | 1 | 0 |
| | 9 | 0 | * | * | * | 1 | 2 |
| | 10 | 3 | * | * | * | 2 | 2 |
| | 11 | 0 | * | * | * | 4 | 4 |
| AmtuPPX2L__R128A__F420V stacked with Bradi_1g07930.1_Zm | 1 | 0 | * | * | 1 | 3 | 2 |
| | 2 | 0 | * | * | * | 0 | 5 |
| | 3 | 1 | * | * | 2 | 1 | 3 |
| | 4 | 1 | * | * | 6 | 7 | 7 |
| | 5 | 4 | * | * | 2 | 2 | 3 |
| | 6 | 4 | * | * | 1 | 3 | 2 |
| | 7 | 1 | * | * | 1 | 3 | 2 |
| | 8 | 1 | * | * | 4 | 3 | 6 |
| | 9 | 0 | * | * | 1 | 3 | 2 |
| | 10 | 0 | * | * | * | 5 | 8 |
| | 11 | 6 | * | * | 3 | 4 | 5 |

TABLE 7B

Field data - T1 generation. Rated for injury (1-5 point scale) 3 days after treatment.

| GOI | Event | 1,5-dimethyl-6-thioxo-3-(2,2,7-trifluoro-3-oxo-4-(prop-2-ynyl)-3,4-dihydro-2H-benzo-[b][1,4]oxazin-6-yl)-1,3,5-triazinane-2,4-dione + Saflufenacil (100 gai/ha + 100 gai/ha) | 1,5-dimethyl-6-thioxo-3-(2,2,7-trifluoro-3-oxo-4-(prop-2-ynyl)-3,4-dihydro-2H-benzo-[b][1,4]oxazin-6-yl)-1,3,5-triazinane-2,4-dione + Saflufenacil (50 gai/ha + 50 gai/ha) | 1,5-dimethyl-6-thioxo-3-(2,2,7-trifluoro-3-oxo-4-(prop-2-ynyl)-3,4-dihydro-2H-benzo[b]-[1,4]oxazin-6-yl)-1,3,5-triazinane-2,4-dione (100 gai/ha) | 1,5-dimethyl-6-thioxo-3-(2,2,7-trifluoro-3-oxo-4-(prop-2-ynyl)-3,4-dihydro-2H-benzo[b]-[1,4]oxazin-6-yl)-1,3,5-triazinane-2,4-dione (50 gai/ha) | Saflufenacil (150 gai/ha) | Saflufenacil (75 gai/ha) |
|---|---|---|---|---|---|---|---|
| | | | | Rating | | | |
| Wild type | 1 | 5 | 5 | 5 | 5 | 5 | 5 |
| | 2 | 5 | 5 | 5 | 5 | 5 | 5 |
| | 3 | 5 | 5 | 5 | 5 | 5 | 5 |
| | 4 | 5 | 5 | 5 | 5 | 5 | 5 |
| | 5 | 5 | 5 | 5 | 5 | 5 | 5 |
| | 6 | 5 | 5 | 5 | 5 | 5 | 5 |
| | 7 | 5 | 5 | 5 | 5 | 5 | 5 |
| | 8 | 5 | 5 | 5 | 5 | 5 | 5 |
| | 9 | 5 | 5 | 5 | 5 | 2 | 5 |
| AmtuPPX2L__F420V stacked with Bradi_1g07930.1_Zm | 1 | * | * | 1 | 2 | 2 | 2 |
| | 2 | * | * | 2 | 1 | 2 | 2 |
| | 3 | * | * | 1 | 1 | 2 | 2 |
| | 4 | 2.5 | 2.5 | 2 | 2.5 | 2 | 2 |
| | 5 | 3 | 3 | 2.5 | 2.5 | 3 | 2.5 |
| | 6 | 2.5 | 2.5 | 2 | 2 | 2 | 2 |
| | 7 | 2.5 | 2.5 | 2 | 2 | 2 | 2 |
| | 8 | 2 | 2 | 2 | 2 | 2 | 2.5 |
| | 9 | 2.5 | 2 | 2 | 2 | 2.5 | 2.5 |
| AmtuPPX2L L397D stacked with Bradi_1g07930.1_Zm | 1 | * | * | 3 | 4 | 2 | 2 |
| | 2 | * | * | 3 | 4 | 2 | 2 |
| | 3 | 3 | 3.5 | 3.5 | 3.5 | 2.5 | 2.5 |
| | 4 | 3.5 | 3.5 | 3.5 | 3.5 | 2.5 | 2.5 |
| | 5 | 3.5 | 3.5 | 3.5 | 3.5 | 2.5 | 2.5 |
| AmtuPPX2L__L397D_F420V | 1 | 3.5 | 3 | 3 | 3.5 | 3 | 3 |
| | 2 | 4 | 3.5 | 3.5 | 3.5 | 3.5 | 3.5 |
| | 3 | 4 | 3.5 | 3 | 3 | 3.5 | 3.5 |

TABLE 7B-continued

Field data - T1 generation. Rated for injury (1-5 point scale) 3 days after treatment.

| GOI | Event | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione + Saflufenacil (100 gai/ha + 100 gai/ha) | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione + Saflufenacil (50 gai/ha + 50 gai/ha) | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (100 gai/ha) | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (50 gai/ha) | Saflufenacil (150 gai/ha) | Saflufenacil (75 gai/ha) |
|---|---|---|---|---|---|---|---|
| AmtuPPX2L_L397D_F420V stacked with Bradi_1g07930.1_Zm | 1 | 2.5 | 3 | 2.5 | 2.5 | 3 | 2.5 |
|  | 2 | 3.5 | 3 | 3.5 | 3.5 | 3 | 3 |
|  | 3 | 3.5 | 3.5 | 3.5 | 3.5 | 3.5 | 3 |
|  | 4 | 3.5 | 3.5 | 3.5 | 3.5 | 3.5 | 3 |
| AmtuPPX2L_F420L | 1 | 2.5 | 2.5 | 2.5 | 2.5 | 2.5 | 2.5 |
|  | 2 | 3 | 3 | 3 | 3 | 2.5 | 2.5 |
|  | 3 | 2.5 | 2.5 | 2.5 | 2 | 2 | 2.5 |
| AmtuPPX2L_F420L stacked with Bradi_1g07930.1_Zm | 1 | * | * | 2 | 2 | 2 | 2 |
|  | 2 | * | * | 2 | 2 | 2 | 2 |
|  | 3 | 2.5 | 2.5 | 2 | 2 | 2 | 2 |
|  | 4 | 2.5 | 2.5 | 2.5 | 2 | 2 | 2 |
|  | 5 | 2 | 2.5 | 2 | 2 | 2 | 2 |
|  | 6 | 2.5 | 2.5 | 2 | 2.5 | 2 | 2 |
| AmtuPPX2L_R128A_F420L | 1 | 3 | 3 | 3 | 3 | 2 | 2 |
|  | 2 | 3.5 | 4 | 4 | 4 | 3.5 | 3 |
| AmtuPPX2L_R128A_F420L stacked with Bradi_1g07930.1_Zm | * | * | * | 1 | 2 | 2 | 2 | 2 |
|  | * | * | * | 2 | 3 | 2 | 2 | 2 |
|  | * | * | * | 3 | 3 | 2 | 2 | 2 |
|  | 4 | 3 | 3 | 2.5 | 2.5 | 2.5 | 2.5 |
|  | 5 | 2.5 | 2.5 | 2 | 2 | 2.5 | 2.5 |
|  | 6 | 2.5 | 2.5 | 2.5 | 2.5 | 2.5 | 2 |
| AmtuPPX2L_R128A_F420V | 1 | * | * | 2 | 3 | 2 | 2 |
|  | 2 | * | * | 2 | 2 | 2 | 2 |
|  | 3 | 2.5 | 2.5 | 2.5 | 2.5 | 2 | 2 |
|  | 4 | 3.5 | 3 | 3 | 3 | 2.5 | 2.5 |
|  | 5 | 3.5 | 3 | 3 | 3 | 2.5 | 2.5 |
| AmtuPPX2L_R128A_F420V stacked with Bradi_1g07930.1_Zm | 1 | * | * | 2 | 2 | 2 | 2 |
|  | 2 | 2.5 | 2.5 | 2 | 2 | 2 | 2 |
|  | 3 | 2.5 | 2.5 | 2 | 2 | 2 | 2.5 |
|  | 4 | 2.5 | 2.5 | 2 | 2 | 2 | 2 |
|  | 5 | 2.5 | 2.5 | 2 | 2 | 2 | 2 |
|  | 6 | 2.5 | 2.5 | 2 | 2.5 | 2 | 2 |

TABLE 7C

Transgenic T2 soybean plants were grown in the greenhouse and treated with the indicated herbicide combination at the V2-V3 developmental stage and scored for injury on a 0-9 point scale (0 = no injury; 9 = death) 1 week after treatment. Data are the average of up to 4 individuals per event tested. BAS 800 H refers to saflufenacil/Kixor; BAS 850 refers to 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

| Herbicide | g ai/ha | WT | Bradi_1g07930.1 | L397D_F420V (Event 1) | L397D_F420V + Bradi_1g07930.1 (Event 1) | L397D_F420V + Bradi_1g07930.1 (Event 2) |
|---|---|---|---|---|---|---|
| BAS 800H + BAS 850H | unsprayed | 0.3 | 0.3 | 3.0 | 0.0 | 1.0 |
|  | 6.25 + 3.125 | 8.3 | 6.8 | 6.0 | 2.0 | 1.3 |
|  | 12.5 + 6.25 | 9.0 | 7.5 | 3.0 | 0.7 | 2.5 |
|  | 25 + 12.5 | 9.0 | 7.5 | 4.5 | 2.0 | 3.8 |
|  | 50 + 25 | 9.0 | 8.0 | 6.0 | 3.0 | 3.3 |
|  | 100 + 50 | 9.0 | 8.8 | 5.3 | 2.0 | 4.0 |
|  | 200 + 100 | 9.0 | 8.8 | 5.5 | 2.0 | 3.8 |
|  | 400 + 200 | 9.0 | 9.0 | 5.7 | 4.3 | 4.0 |
|  | 800 + 400 | 9.0 | 9.0 | 6.0 | 4.0 | 4.0 |

| Herbicide | g ai/ha | R128A_F420L (Event 1) | R128A_F420L (Event 2) | R128A_F420L + Bradi_1g07930.1 (Event 1) | R128A_F420L + Bradi_1g07930.1 (Event 2) | R128A_F420V (Event 1) |
|---|---|---|---|---|---|---|
| BAS 800H + BAS | unsprayed | 0.3 | 1.3 | 0.3 | 1.0 | 2.0 |
|  | 6.25 + 3.125 | 4.0 | 6.0 | 0.3 | 0.3 | 0.5 |
|  | 12.5 + 6.25 | 0.7 | 6.0 | 1.0 | 0.7 | 1.0 |

TABLE 7C-continued

Transgenic T2 soybean plants were grown in the greenhouse and treated with the indicated herbicide combination at the V2-V3 developmental stage and scored for injury on a 0-9 point scale (0 = no injury; 9 = death) 1 week after treatment. Data are the average of up to 4 individuals per event tested. BAS 800 H refers to saflufenacil/Kixor; BAS 850 refers to 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

| | | | | | | |
|---|---|---|---|---|---|---|
| 850H | 25 + 12.5 | 1.5 | 7.5 | 1.0 | 0.0 | 1.7 |
| | 50 + 25 | 2.8 | 7.5 | 1.3 | 0.7 | 1.0 |
| | 100 + 50 | 5.0 | 6.0 | 0.3 | 0.3 | 2.3 |
| | 200 + 100 | 5.0 | 6.7 | 2.8 | 2.0 | 3.5 |
| | 400 + 200 | 4.7 | 8.5 | 3.5 | 4.0 | 3.3 |
| | 800 + 400 | 5.3 | 8.5 | 3.3 | 4.0 | 3.0 |

| Herbicide | g ai/ha | R128A_F420V (Event 2) | R128A_F420V (Event 3) | R128A_F420V + Bradi_1g07930.1 (Event 1) | R128A_F420V + Bradi_1g07930.1 (Event 2) |
|---|---|---|---|---|---|
| BAS 800H + BAS 850H | unsprayed | 0.8 | 1.0 | 2.5 | 1.8 |
| | 6.25 + 3.125 | 0.3 | 0.0 | 1.0 | 1.7 |
| | 12.5 + 6.25 | 0.3 | 1.0 | 0.0 | 0.7 |
| | 25 + 12.5 | 1.0 | 3.5 | 0.7 | 1.0 |
| | 50 + 25 | 2.5 | 2.0 | 0.0 | 1.0 |
| | 100 + 50 | 2.3 | 4.0 | 1.0 | 0.3 |
| | 200 + 100 | 3.5 | 4.5 | 2.3 | 1.7 |
| | 400 + 200 | 2.8 | 4.3 | 3.0 | 2.0 |
| | 800 + 400 | 3.8 | 4.3 | 3.5 | 3.3 |

TABLE 7D

Transgenic T2 soybean plants were grown in the greenhouse and treated with the indicated herbicide combination at the V2-V3 developmental stage and scored for injury on a 0-9 point scale (0 = no injury; 9 = death) 2 week after treatment. Data are the average of up to 4 individuals per event tested.

| Herbicide | g ai/ha | wild type | Bradi_1g07930.1 (Event 1) | R128A_F420V (Event 1) | R128A_F420V (Event 2) | R128A_F420V + Bradi_1g07930.1 (Event 1) | R128A_F420V + Bradi_1g07930.1 (Event 2) |
|---|---|---|---|---|---|---|---|
| none | 0 | 0.3 | 0.3 | 0.8 | 0 | 0.0 | 1 |
| Tritosulfuron | 4.375 | 8.0 | 1.5 | 5.3 | 6.0 | 0.3 | 1.0 |
| | 8.75 | 8.0 | 0.5 | 6.0 | 6.5 | 0.3 | 2.3 |
| | 17.5 | 8.0 | 1.7 | 7.0 | 7.0 | 1.5 | 1.5 |
| | 35 | 8.3 | 2.3 | 7.0 | 7.0 | 2.0 | 1.0 |
| | 70 | 8.3 | 1.5 | 7.0 | 7.0 | 2.7 | 3.0 |
| | 140 | 8.3 | 0.3 | 6.5 | 8.0 | 1.3 | 3.0 |
| Flurasulam | 0.156 | 0.3 | 0.3 | 0.0 | 1.0 | 1.5 | 3.3 |
| | 0.3125 | 3.0 | 0.5 | 3.3 | 1.0 | 2.3 | 3.0 |
| | 0.625 | 4.0 | 2.5 | 3.5 | 3.5 | 3.0 | 3.0 |
| | 1.25 | 5.5 | 3.0 | 4.5 | 5.0 | 3.5 | 3.5 |
| | 2.5 | 6.0 | 1.7 | 6.8 | 6.0 | 3.3 | 3.0 |
| | 5 | 7.5 | 3.3 | 6.5 | 6.0 | 2.5 | 3.5 |
| Rimsulfuron | 1.25 | 8.0 | 6.0 | 6.5 | 6.0 | 4.0 | 3.0 |
| | 2.5 | 8.5 | 6.0 | * | 7.0 | 3.5 | 4.0 |
| | 5 | 8.3 | 6.0 | 7.0 | 7.0 | 3.3 | 4.5 |
| | 10 | 8.5 | 6.0 | 7.5 | 7.0 | 4.3 | 5.0 |
| Metsulfuron | 1.05 | 8.5 | 1.0 | 8.0 | 8.0 | 2.7 | 3.0 |
| | 2.1 | 8.3 | 0.7 | 8.0 | 9.0 | 3.0 | 3.7 |
| | 4.2 | 8.8 | 2.3 | 8.0 | 8.7 | 4.0 | 3.0 |
| | 8.4 | 8.5 | 3.3 | 8.7 | 9.0 | 4.3 | 3.0 |

TABLE 7E

Transgenic T2 soybean plants were grown in the greenhouse and treated with the indicated herbicide combination at the V2-V3 developmental stage and scored for injury on a 0-9 point scale (0 = no injury; 9 = death) 1 week after treatment. Data are the average of up to 4 individuals per event tested.

| Treatment | g ai/ha | WT | CYP | R128A_F420V (Event 1) | R128A_F420V + Bradi_1g07930.1 (Event 1) | L397D_F420V (Event 1) | L397D_F420V (Event 2) |
|---|---|---|---|---|---|---|---|
| unsprayed | 0.0 | 0.5 | 0.5 | 1.5 | * | 3.5 | 0.0 |
| Tritosulfuron | 17.5 | 9.0 | 7.0 | 4.8 | 1.3 | * | 7.0 |
| saflufenacil | 50.0 | | | | | | |
| BAS850H + 1% (v/v) MSO | 25.0 | | | | | | |

TABLE 7E-continued

Transgenic T2 soybean plants were grown in the greenhouse and treated with the indicated herbicide combination at the V2-V3 developmental stage and scored for injury on a 0-9 point scale (0 = no injury; 9 = death) 1 week after treatment. Data are the average of up to 4 individuals per event tested.

| Treatment | g ai/ha | | | | | | |
|---|---|---|---|---|---|---|---|
| Tritosulfuron<br>saflufenacil<br>BAS850H | 35.0<br>50.0<br>25.0 | 9.0 | 8.3 | 7.3 | 0.7 | 7.0 | 8.7 |
| Tritosulfuron<br>saflufenacil<br>BAS850H + 1% (v/v) MSO | 70.0<br>50.0<br>25.0 | 9.0 | 7.0 | 6.7 | 1.0 | 9.0 | 8.0 |
| Florasulam<br>saflufenacil<br>BAS850H + 1% (v/v) MSO | 0.6<br>50.0<br>25.0 | 9.0 | 8.5 | 3.5 | 0.3 | * | 5.8 |
| Florasulam<br>saflufenacil<br>BAS850H + 1% (v/v) MSO | 1.3<br>50.0<br>25.0 | 8.3 | 8.3 | 6.3 | 2.0 | 7.5 | 8.0 |
| Florasulam<br>saflufenacil<br>BAS850H + 1% (v/v) MSO | 2.5<br>50.0<br>25.0 | 9.0 | 8.7 | 8.0 | 3.0 | 8.0 | 8.0 |
| Rimsulfuron<br>saflufenacil<br>BAS850H + 1% (v/v) MSO | 1.3<br>50.0<br>25.0 | 9.0 | 7.8 | 3.5 | 3.0 | * | 5.0 |
| Rimsulfuron<br>saflufenacil<br>BAS850H + 1% (v/v) MSO | 2.5<br>50.0<br>25.0 | 9.0 | 8.5 | 4.8 | 3.3 | 6.0 | 8.0 |
| Rimsulfuron<br>saflufenacil<br>BAS850H + 1% (v/v) MSO | 5.0<br>50.0<br>25.0 | 9.0 | 8.5 | 4.3 | 4.5 | 8.0 | 6.8 |
| Metsulfuron<br>saflufenacil<br>BAS850H + 1% (v/v) MSO | 1.1<br>50.0<br>25.0 | 9.0 | 9.0 | 8.0 | 1.0 | * | 8.5 |
| Metsulfuron<br>saflufenacil<br>BAS850H + 1% (v/v) MSO | 2.1<br>50.0<br>25.0 | 9.0 | 7.8 | 8.3 | 2.0 | 9.0 | 9.0 |
| Metsulfuron<br>saflufenacil<br>BAS850H + 1% (v/v) MSO | 4.2<br>50.0<br>25.0 | 9.0 | 8.5 | 8.3 | 1.0 | 9.0 | 9.0 |
| 1% (v/v) MSO only | 0.0 | 0.5 | 1.0 | 0.3 | * | * | 0.5 |

| Treatment | g ai/ha | WT | CYP | L397D_F420V + Bradi_1g07930.1 (Event 1) | L397D_F420V + Bradi_1g07930.1 (Event 2) | R128A_F420L (Event 1) | R128A_F420L + Bradi_1g07930.1 (Event 1) | R128A_F420L + Bradi_1g07930.1 (Event 2) |
|---|---|---|---|---|---|---|---|---|
| unsprayed | 0.0 | 0.5 | 0.5 | 0.0 | 0.8 | 0.0 | 0.3 | 0.3 |
| Tritosulfuron<br>saflufenacil<br>BAS850H + 1% (v/v) MSO | 17.5<br>50.0<br>25.0 | 9.0 | 7.0 | 2.0 | 0.0 | 5.7 | 0.5 | 1.8 |
| Tritosulfuron<br>saflufenacil<br>BAS850H | 35.0<br>50.0<br>25.0 | 9.0 | 8.3 | 2.0 | 4.5 | 6.5 | 0.5 | 0.3 |
| Tritosulfuron<br>saflufenacil<br>BAS850H + 1% (v/v) MSO | 70.0<br>50.0<br>25.0 | 9.0 | 7.0 | 2.5 | 0.5 | 6.3 | 0.3 | 1.0 |
| Florasulam<br>saflufenacil<br>BAS850H + 1% (v/v) MSO | 0.6<br>50.0<br>25.0 | 9.0 | 8.5 | 2.3 | 1.7 | 4.3 | 1.7 | 1.8 |
| Florasulam<br>saflufenacil<br>BAS850H + 1% (v/v) MSO | 1.3<br>50.0<br>25.0 | 8.3 | 8.3 | 1.3 | 1.3 | 4.0 | 1.3 | 2.7 |
| Florasulam<br>saflufenacil<br>BAS850H + 1% (v/v) MSO | 2.5<br>50.0<br>25.0 | 9.0 | 8.7 | 3.0 | 1.5 | 6.0 | 1.3 | 3.0 |

TABLE 7E-continued

Transgenic T2 soybean plants were grown in the greenhouse and treated with the indicated herbicide combination at the V2-V3 developmental stage and scored for injury on a 0-9 point scale (0 = no injury; 9 = death) 1 week after treatment. Data are the average of up to 4 individuals per event tested.

| | | | | | | | | |
|---|---|---|---|---|---|---|---|---|
| Rimsulfuron<br>saflufenacil<br>BAS850H + 1%<br>(v/v) MSO | 1.3<br>50.0<br>25.0 | 9.0 | 7.8 | 2.0 | 3.0 | 4.0 | 2.3 | 3.3 |
| Rimsulfuron<br>saflufenacil<br>BAS850H + 1%<br>(v/v) MSO | 2.5<br>50.0<br>25.0 | 9.0 | 8.5 | 3.7 | 3.5 | 5.7 | 1.3 | 3.5 |
| Rimsulfuron<br>saflufenacil<br>BAS850H + 1%<br>(v/v) MSO | 5.0<br>50.0<br>25.0 | 9.0 | 8.5 | 4.0 | 3.3 | 4.0 | 3.0 | 4.3 |
| Metsulfuron<br>saflufenacil<br>BAS850H + 1%<br>(v/v) MSO | 1.1<br>50.0<br>25.0 | 9.0 | 9.0 | 2.3 | 2.3 | 8.0 | 0.5 | 0.5 |
| Metsulfuron<br>saflufenacil<br>BAS850H + 1%<br>(v/v) MSO | 2.1<br>50.0<br>25.0 | 9.0 | 7.8 | 3.5 | 3.7 | 7.8 | 2.3 | 0.8 |
| Metsulfuron<br>saflufenacil<br>BAS850H + 1%<br>(v/v) MSO | 4.2<br>50.0<br>25.0 | 9.0 | 8.5 | 3.8 | 2.0 | 8.5 | 1.0 | 0.0 |
| 1% (v/v) MSO only | 0.0 | 0.5 | 1.0 | 1.0 | 0.7 | 0.5 | 0.7 | 0.0 |

Example 14

Detection of Herbicide Degradation by Biochemical Assay

Yeast expression system: The cDNA of CYP450 monooxygenase genes were synthesized with an optimized codon usage for yeast, cloned via unique BamHI-SalI restriction sites in the low copy pESC-ura expression vector (Agilent Technologies). Constructs were transformed into S. cerevisiae wild type strain BJ5459 (MATa ura3-5 hp lys2-801 leu2Δ1 his3Δ200 pep4Δ::HIS3 prb1Δ1.6R can1 GAL cir+; ATCC 208284) using a Yeast Maker Transformation System from Clontech and verified by colony PCR. Positive clones were selected on minimal synthetic-defined media (SD) supplemented with appropriate dropout solution. The strain had no obvious phenotypes. Cells were induced in SG-Ura medium (same composition as SD but with galactose instead of glucose) for 24 h (Pompon et al., Methods in Enzymology 272:51-64 (1996); Urban et al., Eur. J. Biochem. 222:853-850 (1994)). Optimal heterologous protein expression was assayed using Western Blot analysis. Analysis of xenobiotic metabolism: 96 deep well growth plates (STARLAB GmbH) charged with 700 μL SDA medium are inoculated with the respective yeast strains from cryostock and incubated at 30° C., 400 rpm. After 48 h, an aliquot is transferred into a new plate with fresh SDA medium 400 rpm. After 4 h the cultures are spun down, the supernatant discarded and the pellets resuspended in 700 μL pre-warmed SGA media to induce protein expression at 30° C. and 400 rpm. After an incubation time of 24 h, 7 μL herbicide solution (500 μM DMSO stock solution) or solvent control is added to the yeast culture incubated for additional 24 h. The herbicide conversion is stopped by adding 700 μL acetonitrile followed by ultrasonification. The homogenate is prepared for UPLC-MS/MS analysis. The degradation rate was calculated by the determination of the recovery of the herbicide in reference to the control.

Example 15

Engineering Herbicide Tolerant Plants Having Additional Cytochrome P450 Genes Herbicide tolerant soybean (Glycine max) or corn (Zea mays) plants are generated as described by Olhoft et al. (US patent 2009/0049567). For transformation of soybean or Arabidopsis thaliana, CYP450 monooxygenase genes are cloned with standard cloning techniques as described in Sambrook et al. (Molecular cloning (2001) Cold Spring Harbor Laboratory Press) in a binary vector containing resistance marker gene cassette (AHAS) and CYP450 monooxygenase sequence (marked as GOD in between ubiquitin promoter (PcUbi) and nopaline synthase terminator (NOS) sequence. For corn transformation, CYP450 monooxygenase sequences are cloned with standard cloning techniques as described in Sambrook et al. (Molecular cloning (2001) Cold Spring Harbor Laboratory Press) in a binary vector containing resistance marker gene cassette (AHAS) and CYP450 monooxygenase sequence (marked as GOD in between corn ubiquitin promoter (ZmUbi) and nopaline synthase terminator (NOS) sequence. Binary plasmids are introduced to Agrobacterium tumefaciens for plant transformation. Plasmid constructs are introduced into soybean's axillary meristem cells at the primary node of seedling explants via Agrobacterium-mediated transformation. After inoculation and co-cultivation with Agrobacteria, the explants are transferred to shoot introduction media without selection for one week. The explants were subsequently transferred to a shoot induction medium with 1-3 μM imazapyr (Arsenal) for 3 weeks to select for transformed cells. Explants with healthy callus/shoot pads at the primary node are then transferred to shoot elongation medium containing 1-3 μM imazapyr until a shoot elongated or the explant died. Transgenic plantlets are rooted, subjected to TaqMan analysis for the presence of the transgene, transferred to soil and grown to maturity in greenhouse. Transformation of corn plants are done by a method described by McElver and Singh (WO 2008/124495). Plant transformation vector constructs containing CYP450 monooxygenase sequences are introduced into maize immature embryos via *Agrobacterium*-mediated transformation.

Transformed cells were selected in selection media supplemented with 0.5-1.5 µM imazethapyr for 3-4 weeks. Transgenic plantlets were regenerated on plant regeneration media and rooted afterwards. Transgenic plantlets are subjected to TaqMan analysis for the presence of the transgene before being transplanted to potting mixture and grown to maturity in greenhouse. *Arabidopsis thaliana* are transformed with CYP450 monooxygenase sequences by floral dip method as described by McElver and Singh (WO 2008/124495). Transgenic *Arabidopsis* plants were subjected to TaqMan analysis for analysis of the number of integration loci. Transformation of *Oryza sativa* (rice) are done by protoplast transformation as described by Peng et al. (U.S. Pat. No. 6,653,529)

Example 16

Demonstration of Herbicide Tolerance

T0 or T1 transgenic plant of soybean, corn, and rice containing CYP450 monooxygenase sequences are tested for improved tolerance to herbicides in greenhouse studies and mini-plot studies with the following herbicides: saflufenacil or 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione.

For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides. For post emergence treatment, the test plants are first grown to a height of 3 to 15 cm, depending on the plant habit, and only then treated with the herbicides. For this purpose, the test plants are either sown directly and grown in the same containers, or they are first grown separately and transplanted into the test containers a few days prior to treatment.

For testing of T0 plants, cuttings can be used. In the case of soybean plants, an optimal shoot for cutting is about 7.5 to 10 cm tall, with at least two nodes present. Each cutting is taken from the original transformant (mother plant) and dipped into rooting hormone powder (indole-3-butyric acid, IBA). The cutting is then placed in oasis wedges inside a bio-dome. Wild type cuttings are also taken simultaneously to serve as controls. The cuttings are kept in the bio-dome for 5-7 days and then transplanted to pots and then acclimated in the growth chamber for two more days. Subsequently, the cuttings are transferred to the greenhouse, acclimated for approximately 4 days, and then subjected to spray tests as indicated. Depending on the species, the plants are kept at 10-25° C. or 20-35° C. The test period extends over 3 weeks. During this time, the plants are tended and their response to the individual treatments is evaluated. Herbicide injury evaluations are taken at 2 and 3 weeks after treatment. Plant injury is rated on a scale of 0% to 100%, 0% being no injury and 100% being complete death.

Transgenic *Arabidopsis thaliana* plants were assayed for improved tolerance to saflufenacil, benzoxazine-derivative herbicide, flumioxazin, butafenacil, acifluorfen, lactofen, bifenox, diuron, sulfentrazon, tepraloxydim, coumarone-derivative herbicides, azine-derivative herbicides in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) Physiologia Plantarum 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 µmol Phot*$m^{-2}$*$s^{-1}$ with 14:10 h light:dark photoperiod. Growth inhibition is evaluated seven to ten days after seeding in comparison to wild type plants. Additionally, transgenic T1 *Arabidopsis* plants were tested for improved tolerance to herbicides in greenhouse studies with the following herbicides: saflufenacil, benzoxazinone-derivative herbicide, flumioxazin, butafenacil, acifluorfen, lactofen, bifenox, diuron, sulfentrazone, tepraloxydim, coumarone-derivative herbicides, azine-derivative herbicides.

Example 17

Sequence Analysis

Leaf tissue was collected from clonal plants separated for transplanting and analyzed as individuals. Genomic DNA was extracted using a Wizard® 96 Magnetic DNA Plant System kit (Promega, U.S. Pat. Nos. 6,027,945 & 6,368,800) as directed by the manufacturer. Isolated DNA was PCR amplified using the appropriate forward and reverse primer. PCR amplification was performed using Hotstar Taq DNA Polymerase (Qiagen) using touchdown thermocycling program as follows: 96° C. for 15 min, followed by 35 cycles (96° C., 30 sec; 58° C.—0.2° C. per cycle, 30 sec; 72° C., 3 min and 30 sec), 10 min at 72° C. PCR products were verified for concentration and fragment size via agarose gel electrophoresis. Dephosphorylated PCR products were analyzed by direct sequence using the PCR primers (DNA Landmarks, or Entelechon). Chromatogram trace files (.scf) were analyzed for mutation relative to the wild-type gene using Vector NTI Advance 10™ (Invitrogen). Based on sequence information, mutations were identified in several individuals. Sequence analysis was performed on the representative chromatograms and corresponding AlignX alignment with default settings and edited to call secondary peaks.

The following gives a definition of the injury scores measured above:
Score Description of injury
0 No Injury
1 Minimal injury, only a few patches of leaf injury or chlorosis.
2 Minimal injury with slightly stronger chlorosis. Overall growth points remain undamaged.
3 Slightly stronger injury on secondary leaf tissue, but primary leaf and growth points are still undamaged.
4 Overall plant morphology is slightly different, some chlorosis and necrosis in secondary growth points and leaf tissue. Stems are intact. Regrowth is highly probable within 1 week.
5 Overall plant morphology is clearly different, some chlorosis and necrosis on a few leaves and growth points, but primary growth point is intact. Stem tissue is still green. Regrowth is highly probably within 1 week.

6 Strong injury can be seen on the new leaflet growth. Plant has a high probability to survive only through regrowth at different growth points. Most of the leaves are chlorotic/necrotic but stem tissue is still green. May have regrowth but with noticeable injured appearance.
7 Most of the active growth points are necrotic. There may be a single growth point that could survive and may be partially chlorotic or green and partially necrotic. Two leaves may still be chlorotic with some green; the rest of the plant including stem is necrotic.
8 Plant will likely die, and all growth points are necrotic. One leaf may still be chlorotic with some green. The remainder of the plant is necrotic.
9 Plant is dead.
* Not tested

The invention claimed is:

1. A plant or plant part comprising (i) an exogenous polynucleotide encoding a mutated PPO polypeptide, and (ii) an exogenous polynucleotide encoding a CYP450 polypeptide, wherein the expression of said polynucleotides (i) and (ii) confers to the plant or plant part tolerance to PPO-inhibiting herbicides, wherein the mutated PPO polypeptide comprises an amino acid sequence having at least 90% sequence identity to SEQ ID NO: 2 and comprises one or more substitutions at positions corresponding to positions 128, 204, 208, 397, 400, 420, and 457 of SEQ ID NO: 2, and wherein the CYP450 polypeptide comprises an amino acid sequence having at least 90% sequence identity to SEQ ID NO: 6.

2. The plant or plant part of claim 1, wherein the polynucleotide encoding the CYP450 polypeptide comprises the nucleic acid sequence set forth in SEQ ID NO: 5.

3. The plant or plant part of claim 1, wherein the mutated PPO polypeptide has at least 95% amino acid sequence identity to SEQ ID NO: 2.

4. The plant or plant part of claim 1, wherein the CYP450 polypeptide has at least 95% amino acid sequence identity to SEQ ID NO: 6.

5. A seed capable of germination into a plant comprising in at least some of its cells (i) an exogenous polynucleotide encoding a CYP450 polypeptide, the polynucleotide operably linked to a promoter operable in plant cells, the CYP450 polypeptide having at least 90% amino acid sequence identity to SEQ ID NO: 6 and (ii) an exogenous polynucleotide encoding a mutated PPO polypeptide, the polynucleotide operably linked to a promoter operable in plant cells, the mutated PPO polypeptide having at least 90% amino acid sequence identity to SEQ ID NO: 2 and comprising one or more substitutions at positions corresponding to positions 128, 204, 208, 397, 400, 420, and 457 of SEQ ID NO: 2, the expression of the mutated PPO and the CYP450 polypeptide conferring to the plant tolerance to PPO-inhibiting herbicides.

6. A plant cell comprising (i) an exogenous polynucleotide encoding a CYP450 polypeptide, the polynucleotide operably linked to a promoter operable a cell, the CYP450 polypeptide having at least 90% amino acid sequence identity to SEQ ID NO: 6 and (ii) an exogenous polynucleotide encoding a mutated PPO polypeptide, the polynucleotide operably linked to a promoter operable in a cell, the mutated PPO polypeptide having at least 90% amino acid sequence identity to SEQ ID NO: 2 and comprising one or more substitutions at positions corresponding to positions 128, 204, 208, 397, 400, 420, and 457 of SEQ ID NO: 2, the expression of the mutated PPO and the CYP450 polypeptide conferring to the plant tolerance to PPO-inhibiting herbicides.

7. A method for controlling weeds at a locus for growth of a plant, the method comprising: (a) applying an herbicide composition comprising PPO-inhibiting herbicides to the locus; and (b) planting a seed at the locus, wherein the seed is capable of producing a plant that comprises in at least some of its cells (i) an exogenous polynucleotide encoding a CYP450 polypeptide, the polynucleotide operably linked to a promoter operable in plant cells, the CYP450 polypeptide having at least 90% amino acid sequence identity to SEQ ID NO: 6, and (ii) an exogenous polynucleotide encoding a mutated PPO polypeptide, the polynucleotide operably linked to a promoter operable in plant cells, the mutated PPO polypeptide having at least 90% amino acid sequence identity to SEQ ID NO: 2 and comprising one or more substitutions at positions corresponding to positions 128, 204, 208, 397, 400, 420, and 457 of SEQ ID NO: 2, the expression of the mutated PPO and the CYP450 polypeptide conferring to the plant tolerance to PPO-inhibiting herbicides.

8. The method of claim 7, wherein herbicide composition is applied to the weeds and to the plant produced by the seed.

9. The method according to claim 7, wherein the herbicide composition comprising PPO-inhibiting herbicides of (a) is applied in conjunction with one or more other herbicides selected from the group consisting of lipid biosynthesis inhibitors, acetolactate synthase inhibitors (ALS inhibitors), photosynthesis inhibitors, bleacher herbicides, enolpyruvyl shikimate 3-phosphate synthase inhibitors (EPSP inhibitors), glutamine synthetase inhibitors, 7,8-dihydropteroate synthase inhibitors (DHP inhibitors), mitosis inhibitors, inhibitors of the synthesis of very long chain fatty acids (VLCFA inhibitors), cellulose biosynthesis inhibitors, decoupler herbicides, and auxinic herbicides.

10. The method of claim 9, wherein the other herbicide is an ALS inhibitor.

11. A method for producing a plat product from the plant of claim 1, the method comprising processing the plant or a plant part thereof to obtain the plant product.

12. The method of claim 11, wherein the plant product is fodder, seed meal, oil, or seed treatment-coated seeds.

13. The plant product of claim 11, wherein the product is fodder, seed meal, or seed treatment-coated seed, Wherein the plant product comprises the exogenous polynucleotides of claim 1 encoding the mutated PPO polypeptide and the CYP450 polypeptide.

14. A method for growing the plant of claim 1 while controlling weeds in the vicinity of said plant, said method comprising the steps of:
  a) growing said plant; and
  b) applying a herbicide composition comprising a PPO-inhibiting herbicide to the plant and weeds, wherein the herbicide normally inhibits the PPO enzyme, at a level of the herbicide that would inhibit the growth of a corresponding wild-type plant.

15. The plant or plant part of claim 4, wherein the mutated PPO polypeptide has at least 95% amino acid sequence identity to SEQ ID NO: 2.

16. The seed of claim 5, wherein the mutated PPO polypeptide has at least 95% amino acid sequence identity to SEQ ID NO: 2.

17. The seed of claim 16, wherein the CYP450 polypeptide has at least 95% amino acid sequence identity to SEQ ID NO: 6.

18. The plant cell of claim 6, wherein the mutated PPO polypeptide has at least 95% amino acid sequence identity to SEQ ID NO: 2.

19. The plant cell of claim 18, wherein the CYP450 polypeptide has at least 95% amino acid sequence identity to SEQ ID NO: 6.

20. The method of claim 7, wherein the mutated PPO polypeptide has at least 95% amino acid sequence identity to SEQ ID NO: 2.

21. The method of claim 20, wherein the CYP450 polypeptide has at least 95% amino acid sequence identity to SEQ ID NO: 6.

* * * * *